(12) United States Patent
Vendely et al.

(10) Patent No.: US 12,274,444 B2
(45) Date of Patent: Apr. 15, 2025

(54) METHOD OF APPLYING BUTTRESSES TO SURGICALLY CUT AND STAPLED SITES

(71) Applicant: Cilag GmbH International, Zug (CH)

(72) Inventors: Michael J. Vendely, Lebanon, OH (US); Trevor J. Barton, Cincinnati, OH (US); Pamela M. Ridgley, Lebanon, OH (US); Rebecca Spatholt, Cincinnati, OH (US); Christopher J. Hess, Blue Ash, OH (US); Heather Strang, West Chester, OH (US); Mark S. Zeiner, Mason, OH (US); John V. Hunt, Cincinnati, OH (US); Emily A. Scheliin, Cincinnati, OH (US); Frederick E. Shelton, IV, Hillsboro, OH (US); Jason L. Harris, Lebanon, OH (US); David T. Krumanaker, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/439,881

(22) Filed: Feb. 13, 2024

(65) Prior Publication Data

US 2024/0252172 A1    Aug. 1, 2024

Related U.S. Application Data

(63) Continuation of application No. 18/164,665, filed on Feb. 6, 2023, now Pat. No. 12,076,014, which is a
(Continued)

(51) Int. Cl.
*A61B 17/064* (2006.01)
*A61B 17/072* (2006.01)
(Continued)

(52) U.S. Cl.
CPC ...... *A61B 17/07292* (2013.01); *A61B 17/072* (2013.01); *A61B 17/07207* (2013.01);
(Continued)

(58) Field of Classification Search
CPC .................................. A61B 17/07292
See application file for complete search history.

(56) References Cited

U.S. PATENT DOCUMENTS

| 4,805,823 A | 2/1989 | Rothfuss |
| 5,415,334 A | 5/1995 | Williamson, IV et al. |

(Continued)

FOREIGN PATENT DOCUMENTS

| EP | 2008595 A2 | 12/2008 |
| EP | 3135213 A1 | 3/2017 |

(Continued)

OTHER PUBLICATIONS

European Extended Search Report and Written Opinion dated Apr. 1, 2020, for Application No. 19218567.6, 12 pages.
(Continued)

*Primary Examiner* — Eyamindae C Jallow
(74) *Attorney, Agent, or Firm* — Frost Brown Todd LLP

(57) ABSTRACT

A method of applying a buttress to a surgically cut and stapled site uses an end effector with a buttress applier cartridge assembly to load one or more buttress assemblies to the end effector. The buttress assemblies each include a buttress to support a staple formed therein as well an adhesive for adhering to the end effector. The adhesive of the buttress assemblies can include a pattern to assist in both attachment to the end effector and release from the end effector after cutting and stapling a tissue site. The buttress applier cartridge can include features that accommodate end effectors having various tip configurations, including straight tips and curved or bent tips.

20 Claims, 81 Drawing Sheets

Related U.S. Application Data continuation of application No. 17/316,920, filed on May 11, 2021, now Pat. No. 11,602,347, which is a continuation of application No. 16/235,617, filed on Dec. 28, 2018, now Pat. No. 11,033,269.

(51) Int. Cl.
*A61B 17/32* (2006.01)
*A61B 17/00* (2006.01)

(52) U.S. Cl.
CPC ............... *A61B 17/320092* (2013.01); *A61B 2017/00526* (2013.01); *A61B 2017/07257* (2013.01); *A61B 2017/07271* (2013.01); *A61B 2017/07278* (2013.01); *A61B 2017/07285* (2013.01)

(56) References Cited

U.S. PATENT DOCUMENTS

| | | |
|---|---|---|
| 5,465,895 A | 11/1995 | Knodel et al. |
| 5,597,107 A | 1/1997 | Knodel et al. |
| 5,632,432 A | 5/1997 | Schulze et al. |
| 5,673,840 A | 10/1997 | Schulze et al. |
| 5,704,534 A | 1/1998 | Huitema et al. |
| 5,792,135 A | 8/1998 | Madhani et al. |
| 5,814,055 A | 9/1998 | Knodel et al. |
| 5,817,084 A | 10/1998 | Jensen |
| 5,878,193 A | 3/1999 | Wang et al. |
| 6,231,565 B1 | 5/2001 | Tovey et al. |
| 6,364,888 B1 | 4/2002 | Niemeyer et al. |
| 6,783,524 B2 | 8/2004 | Anderson et al. |
| 6,978,921 B2 | 12/2005 | Shelton, IV et al. |
| 6,988,650 B2 | 1/2006 | Schwemberger et al. |
| 7,000,818 B2 | 2/2006 | Shelton, IV et al. |
| 7,134,587 B2 | 11/2006 | Schwemberger et al. |
| 7,143,923 B2 | 12/2006 | Shelton, IV et al. |
| 7,147,139 B2 | 12/2006 | Schwemberger et al. |
| 7,147,140 B2 | 12/2006 | Wukusick et al. |
| 7,204,404 B2 | 4/2007 | Nguyen et al. |
| 7,207,472 B2 | 4/2007 | Wukusick et al. |
| 7,303,108 B2 | 12/2007 | Shelton, IV |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,434,715 B2 | 10/2008 | Shelton, IV et al. |
| 7,524,320 B2 | 4/2009 | Tierney et al. |
| 7,644,848 B2 | 1/2010 | Swayze et al. |
| 7,691,098 B2 | 4/2010 | Wallace et al. |
| 7,721,930 B2 | 5/2010 | McKenna et al. |
| 7,806,891 B2 | 10/2010 | Nowlin et al. |
| 8,141,762 B2 | 3/2012 | Bedi et al. |
| 8,210,411 B2 | 7/2012 | Yates et al. |
| 8,371,491 B2 | 2/2013 | Huitema et al. |
| 8,408,439 B2 | 4/2013 | Huang et al. |
| 8,453,904 B2 | 6/2013 | Eskaros et al. |
| 8,453,914 B2 | 6/2013 | Laurent et al. |
| 8,479,969 B2 | 7/2013 | Shelton, IV |
| 8,573,461 B2 | 11/2013 | Shelton, IV et al. |
| 8,573,465 B2 | 11/2013 | Shelton, IV |
| 8,579,990 B2 | 11/2013 | Priewe |
| 8,602,288 B2 | 12/2013 | Shelton, IV et al. |
| 8,616,431 B2 | 12/2013 | Timm et al. |
| 8,783,541 B2 | 7/2014 | Shelton, IV et al. |
| 8,800,838 B2 | 8/2014 | Shelton, IV |
| 8,801,735 B2 | 8/2014 | Shelton, IV et al. |
| 8,814,025 B2 | 8/2014 | Miller et al. |
| 8,820,605 B2 | 9/2014 | Shelton, IV |
| 8,844,789 B2 | 9/2014 | Shelton, IV et al. |
| 8,899,464 B2 | 12/2014 | Hueil et al. |
| 8,992,060 B2 | 4/2015 | Dassanayake et al. |
| 8,998,060 B2 | 4/2015 | Bruewer et al. |
| 9,101,359 B2 | 8/2015 | Smith et al. |
| 9,186,142 B2 | 11/2015 | Fanelli et al. |
| 9,198,644 B2 | 12/2015 | Balek et al. |
| 9,211,120 B2 | 12/2015 | Scheib et al. |
| 9,301,759 B2 | 4/2016 | Spivey et al. |
| 9,393,018 B2 | 7/2016 | Wang et al. |
| 9,398,911 B2 | 7/2016 | Auld et al. |
| 9,492,170 B2 | 11/2016 | Bear et al. |
| 9,517,065 B2 | 12/2016 | Simms et al. |
| 9,597,082 B2 | 3/2017 | Stokes et al. |
| 9,622,746 B2 | 4/2017 | Simms et al. |
| 9,717,497 B2 | 8/2017 | Zerkle et al. |
| 9,795,379 B2 | 10/2017 | Leimbach et al. |
| 9,808,248 B2 | 11/2017 | Hoffman |
| 9,839,421 B2 | 12/2017 | Zerkle et al. |
| 9,848,871 B2 | 12/2017 | Harris et al. |
| 9,867,615 B2 | 1/2018 | Fanelli et al. |
| 9,913,642 B2 | 3/2018 | Leimbach et al. |
| 9,936,954 B2 | 4/2018 | Shelton, IV et al. |
| 9,999,408 B2 | 6/2018 | Boudreaux et al. |
| 10,045,780 B2 | 8/2018 | Adams et al. |
| 10,085,745 B2 | 10/2018 | Dalessandro et al. |
| 10,092,292 B2 | 10/2018 | Boudreaux et al. |
| D833,010 S | 11/2018 | Harris et al. |
| 10,123,798 B2 | 11/2018 | Baxter, III et al. |
| D836,198 S | 12/2018 | Harris et al. |
| D836,199 S | 12/2018 | Schowalter et al. |
| 10,166,023 B2 | 1/2019 | Vendely et al. |
| 10,314,588 B2 | 6/2019 | Turner et al. |
| 10,349,939 B2 | 7/2019 | Shelton, IV et al. |
| 10,499,918 B2 | 12/2019 | Schellin et al. |
| 10,639,039 B2 * | 5/2020 | Vendely ................ A61B 50/30 |
| D901,686 S | 11/2020 | Barton et al. |
| D903,115 S | 11/2020 | Zeiner et al. |
| 10,856,866 B2 | 12/2020 | Shelton, IV et al. |
| 10,905,424 B2 | 2/2021 | Bakos et al. |
| D922,576 S | 6/2021 | Schellin et al. |
| 11,033,269 B2 | 6/2021 | Vendely et al. |
| D926,317 S | 7/2021 | Posey et al. |
| D926,318 S | 7/2021 | Posey et al. |
| 11,103,243 B2 | 8/2021 | Bakos et al. |
| 11,116,505 B2 | 9/2021 | Vendely et al. |
| D932,621 S | 10/2021 | Ridgley et al. |
| D933,220 S | 10/2021 | Tate et al. |
| 11,166,724 B2 | 11/2021 | McGiveron et al. |
| 11,166,725 B2 | 11/2021 | Vendely et al. |
| 11,202,628 B2 | 12/2021 | Posey et al. |
| 11,272,935 B2 | 3/2022 | Bakos et al. |
| 11,432,817 B2 | 9/2022 | Barton et al. |
| 11,602,347 B2 | 3/2023 | Vendely et al. |
| 11,701,109 B2 | 7/2023 | Posey et al. |
| 12,076,014 B2 | 9/2024 | Vendely et al. |
| 2003/0120284 A1 * | 6/2003 | Palacios ............ A61B 17/07207 606/139 |
| 2005/0119669 A1 * | 6/2005 | Demmy ............. A61B 17/0684 606/139 |
| 2005/0139636 A1 | 6/2005 | Schwemberger et al. |
| 2005/0143759 A1 | 6/2005 | Kelly |
| 2005/0145672 A1 | 7/2005 | Schwemberger et al. |
| 2006/0142786 A1 | 6/2006 | Mathisen et al. |
| 2006/0173470 A1 * | 8/2006 | Oray ................ A61B 17/07207 606/151 |
| 2007/0034669 A1 * | 2/2007 | de la Torre ....... A61B 17/07207 227/180.1 |
| 2008/0169328 A1 | 7/2008 | Shelton |
| 2009/0001122 A1 | 1/2009 | Prommersberger et al. |
| 2009/0095791 A1 * | 4/2009 | Eskaros ............... A61B 17/072 227/175.1 |
| 2009/0205986 A1 * | 8/2009 | Baker .................... A61B 50/30 206/363 |
| 2012/0241493 A1 | 9/2012 | Baxter, III et al. |
| 2012/0312861 A1 * | 12/2012 | Gurumurthy .......... A61B 90/94 227/179.1 |
| 2013/0068816 A1 | 3/2013 | Vasudevan et al. |
| 2013/0075447 A1 | 3/2013 | Weisenburgh et al. |
| 2013/0153635 A1 | 6/2013 | Hodgkinson |
| 2013/0206813 A1 | 8/2013 | Nalagatla |
| 2014/0239037 A1 | 8/2014 | Boudreaux et al. |
| 2015/0351758 A1 | 12/2015 | Shelton, IV et al. |
| 2016/0089146 A1 | 3/2016 | Harris et al. |
| 2016/0278774 A1 | 9/2016 | Shelton, IV et al. |

(56) References Cited

U.S. PATENT DOCUMENTS

| | | |
|---|---|---|
| 2017/0027571 A1 | 2/2017 | Nalagatla et al. |
| 2017/0049444 A1 | 2/2017 | Schellin et al. |
| 2017/0055980 A1 | 3/2017 | Vendely et al. |
| 2017/0055981 A1* | 3/2017 | Vendely ............ A61B 17/07292 |
| 2017/0055982 A1* | 3/2017 | Zeiner ................ A61B 17/0682 |
| 2017/0055986 A1 | 3/2017 | Harris et al. |
| 2017/0056016 A1 | 3/2017 | Barton et al. |
| 2017/0056017 A1 | 3/2017 | Vendely et al. |
| 2017/0056018 A1 | 3/2017 | Zeiner et al. |
| 2017/0086823 A1 | 3/2017 | Leimbach et al. |
| 2017/0086837 A1 | 3/2017 | Vendely et al. |
| 2017/0086842 A1 | 3/2017 | Shelton, IV et al. |
| 2018/0235610 A1 | 8/2018 | Harris et al. |
| 2018/0235611 A1 | 8/2018 | Harris et al. |
| 2018/0235619 A1 | 8/2018 | Harris et al. |
| 2018/0235626 A1 | 8/2018 | Shelton, IV et al. |
| 2019/0000481 A1 | 1/2019 | Harris et al. |
| 2020/0205811 A1 | 7/2020 | Posey et al. |
| 2020/0205822 A1 | 7/2020 | Heupel et al. |
| 2020/0205824 A1 | 7/2020 | Barton et al. |

FOREIGN PATENT DOCUMENTS

| | | |
|---|---|---|
| EP | 3135214 A1 | 3/2017 |
| EP | 3363374 A2 | 8/2018 |

OTHER PUBLICATIONS

European Communication dated Mar. 29, 2023, for Application No. 19218567.6, 7 pages.

International Search Report and Written Opinion dated Apr. 1, 2020, for International Application No. PCT/IB2019/060818, 19 pages.

Japanese First Office Action dated Sep. 19, 2023, for Application No. 2021-537815, 9 pages.

Japanese Second Office Action dated Mar. 12, 2024, for Application No. 2021-537815, 8 pages.

U.S. Appl. No. 62/209,041, entitled "Method and Apparatus for Applying a Buttress to End Effector of a Surgical Stapler," filed Aug. 24, 2015.

* cited by examiner

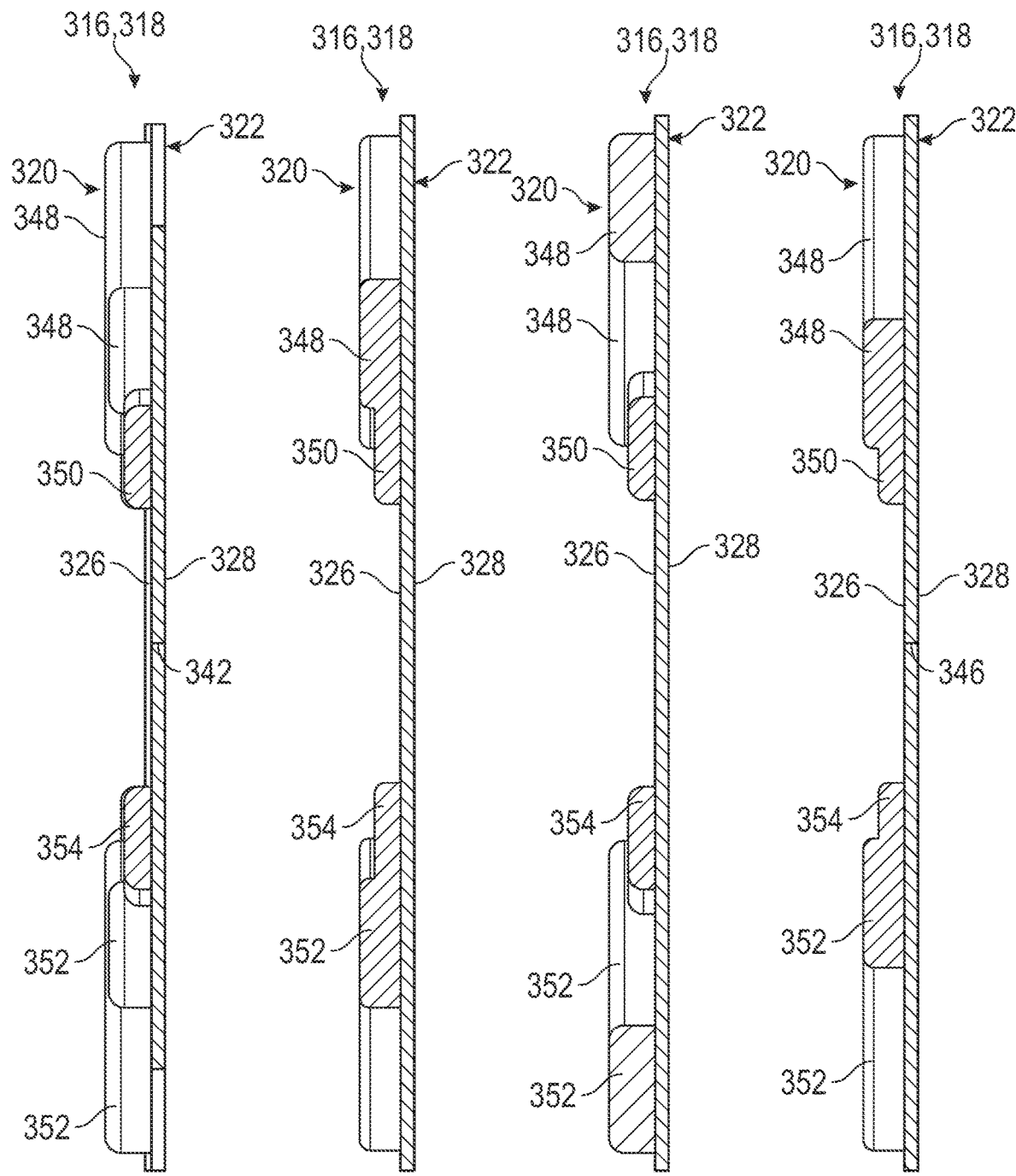

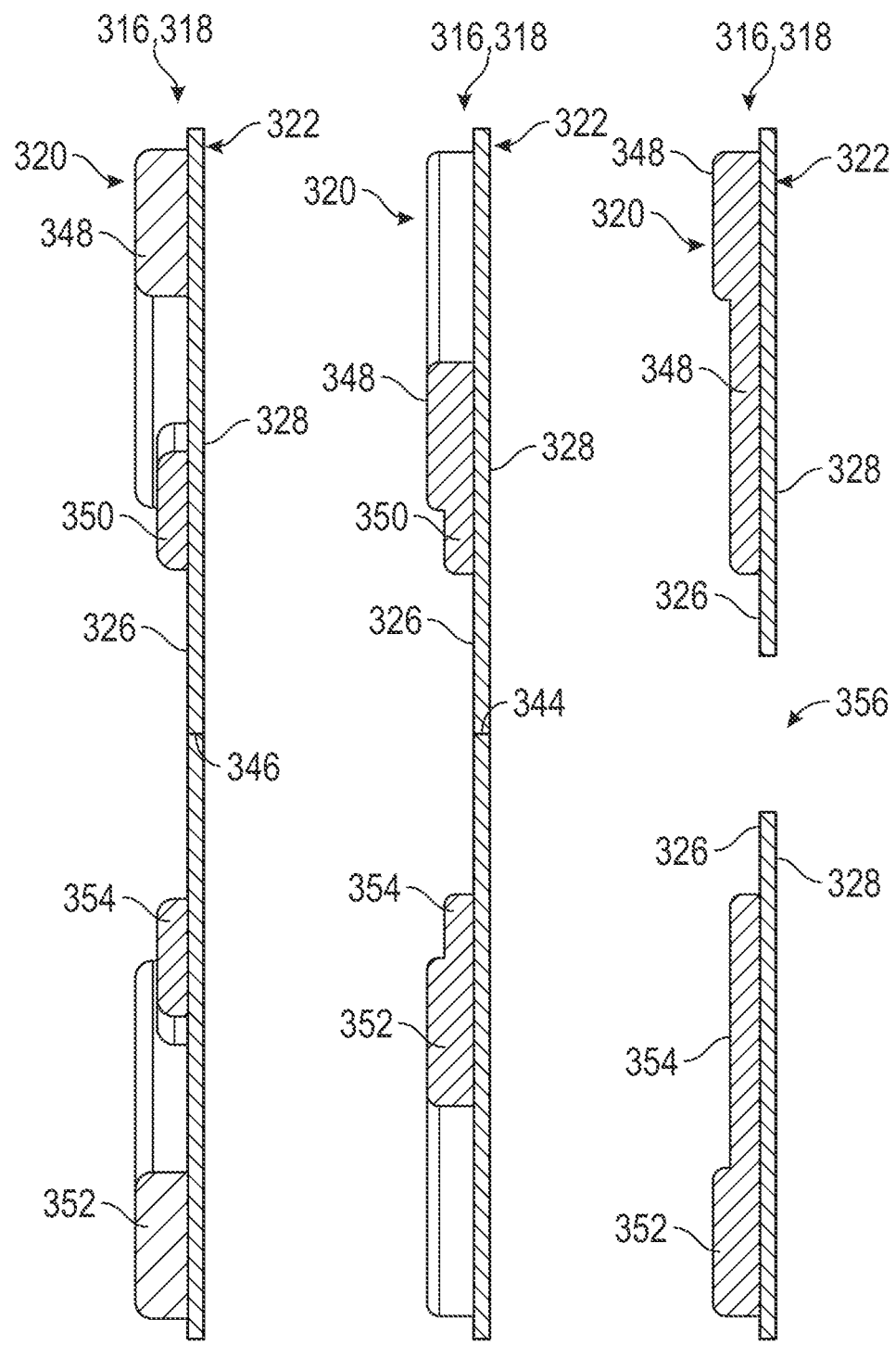

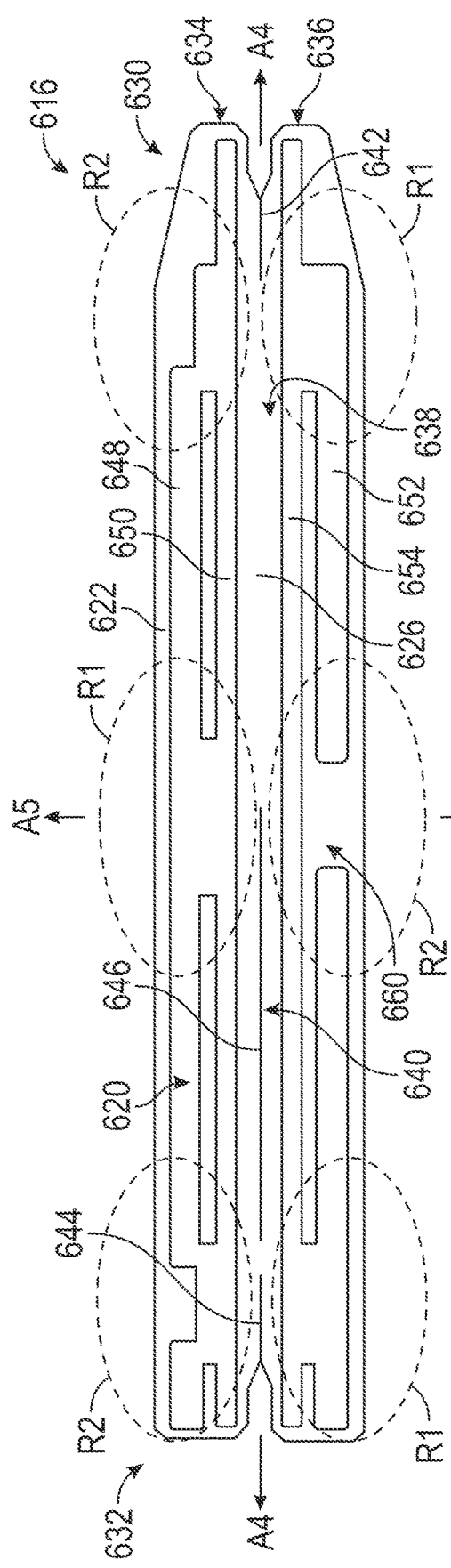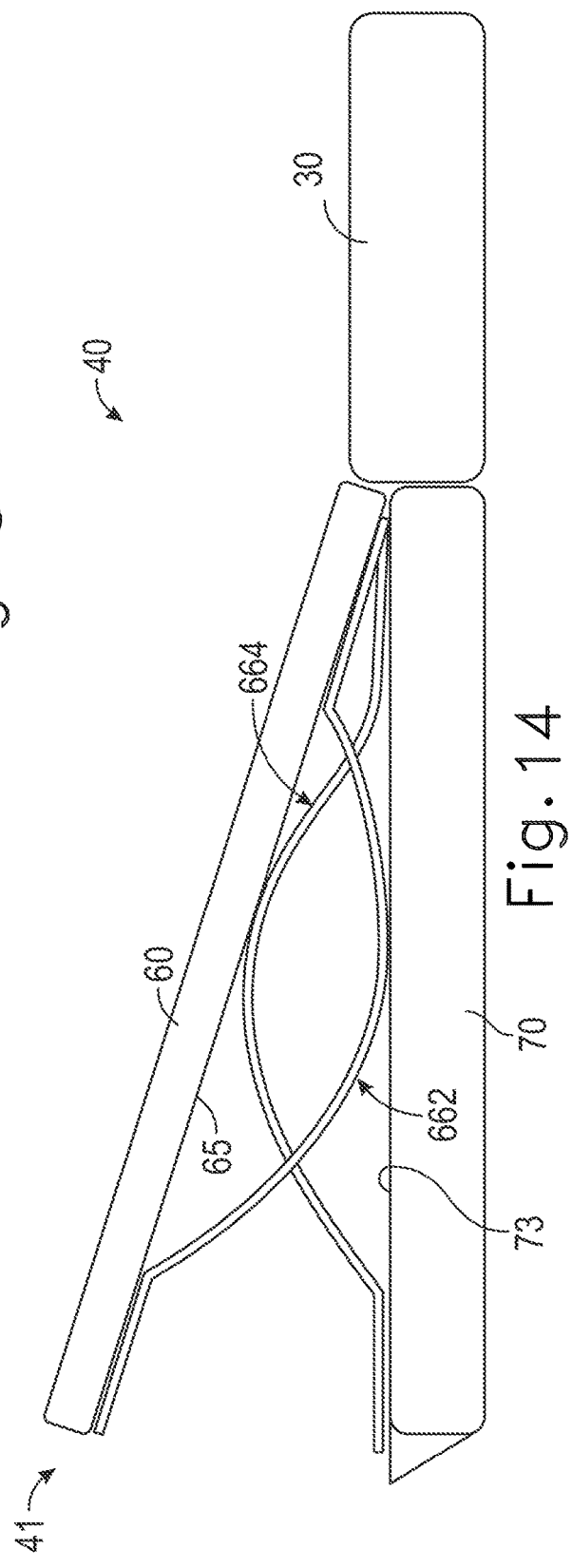

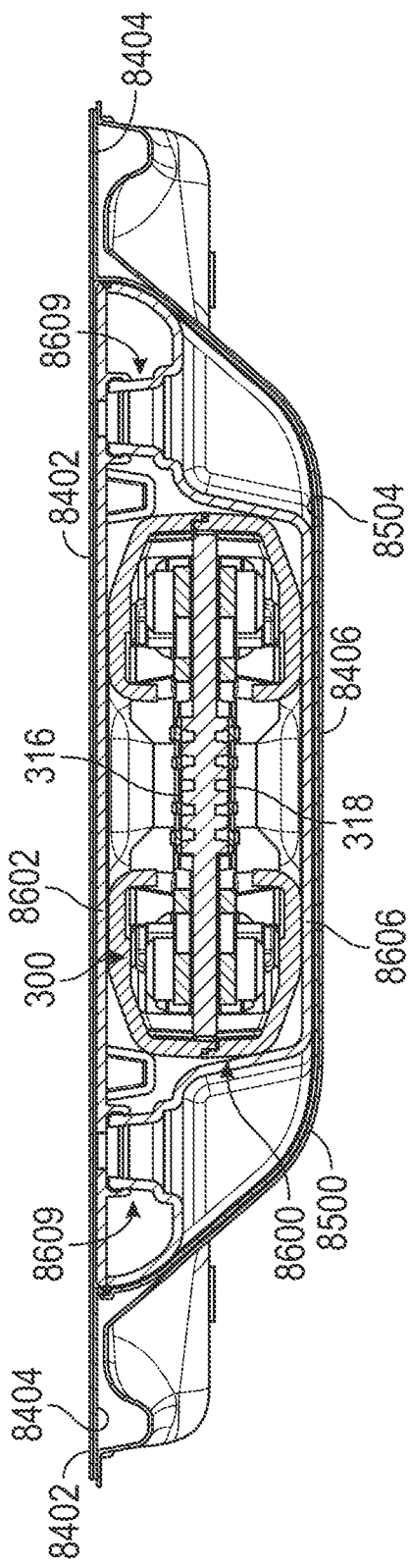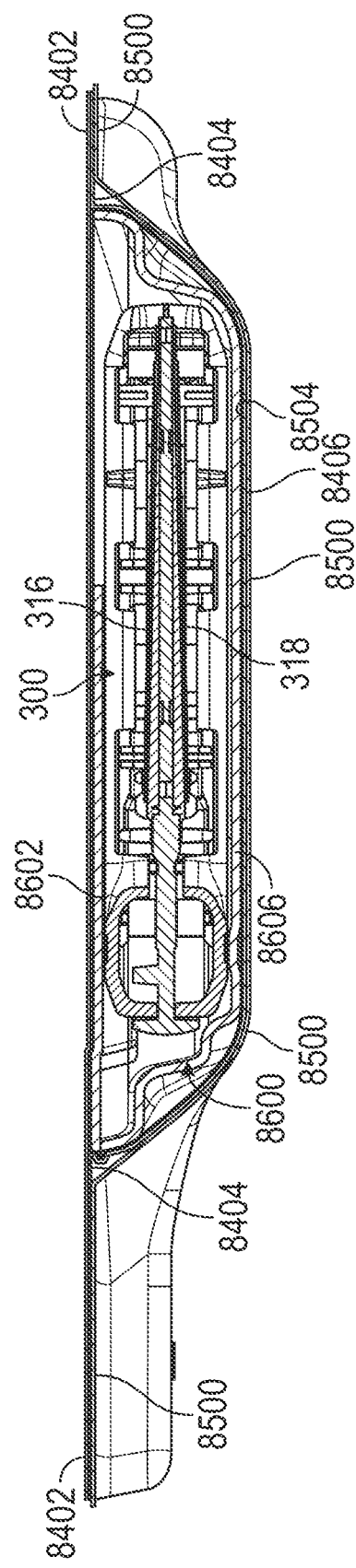

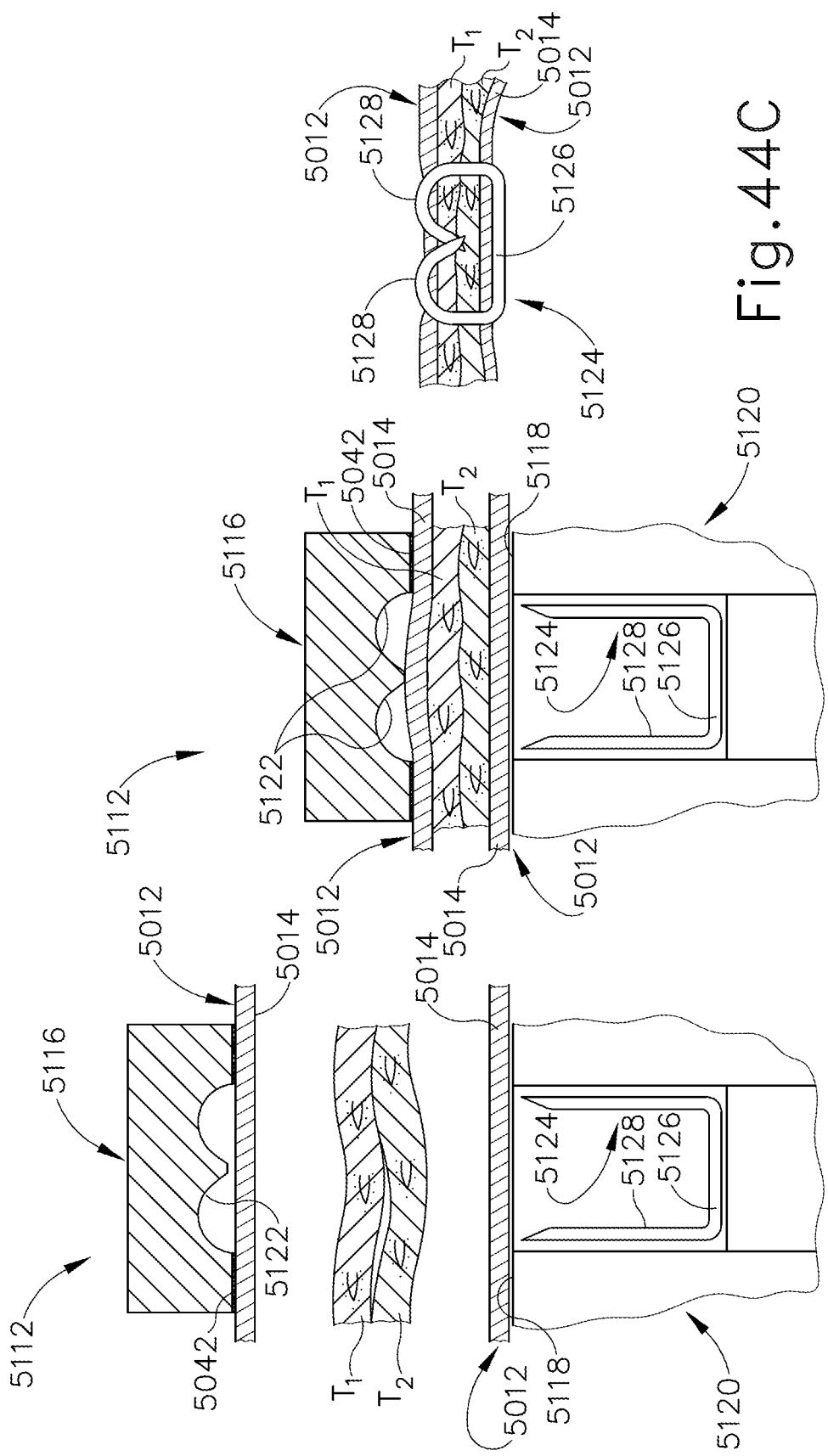

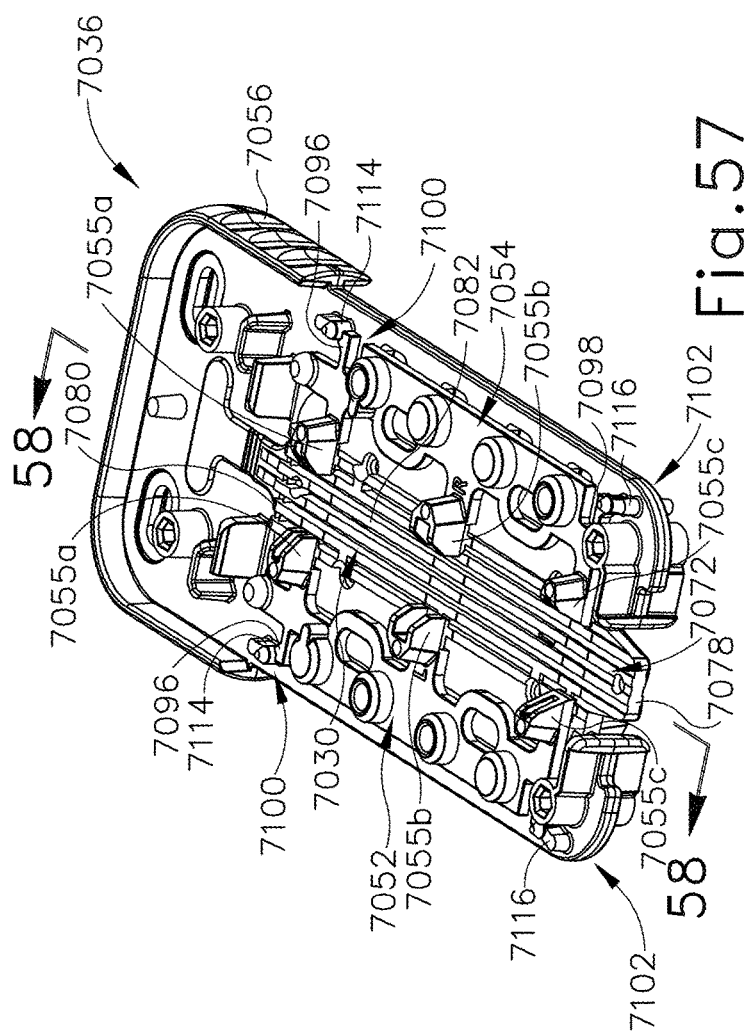
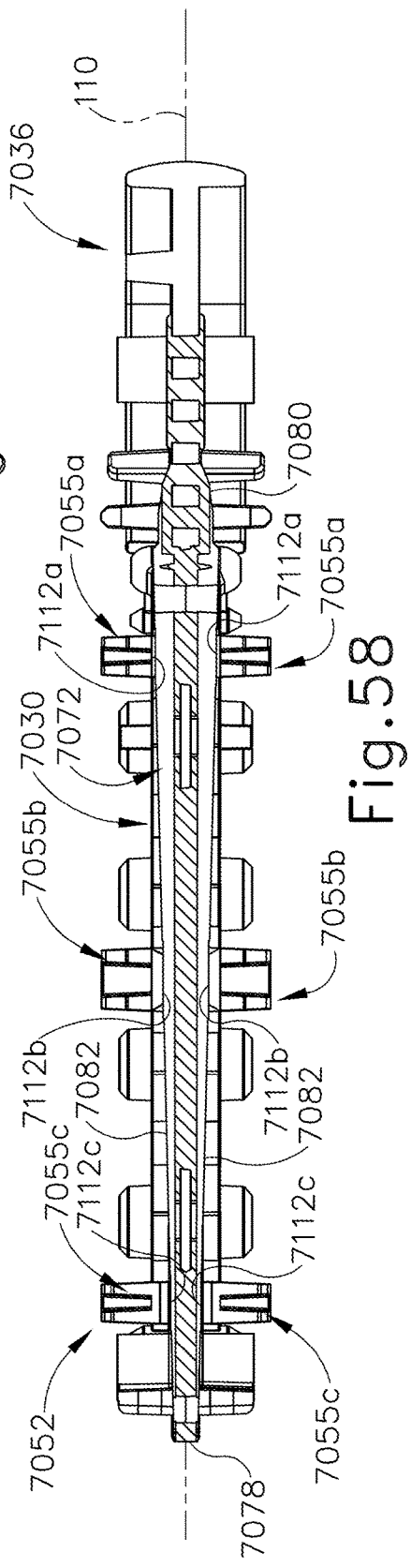
Fig.57
Fig.58

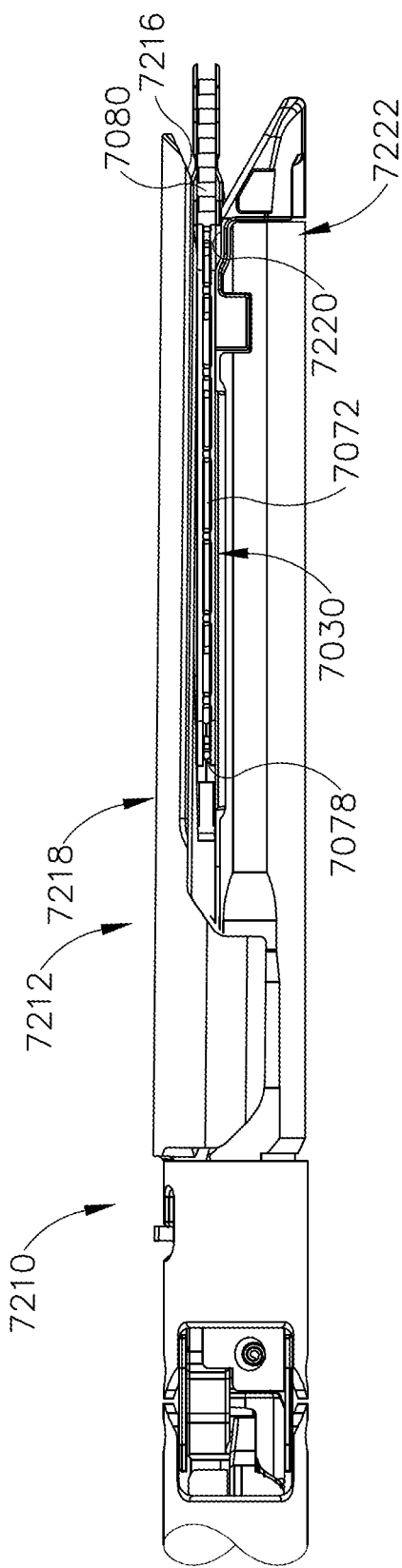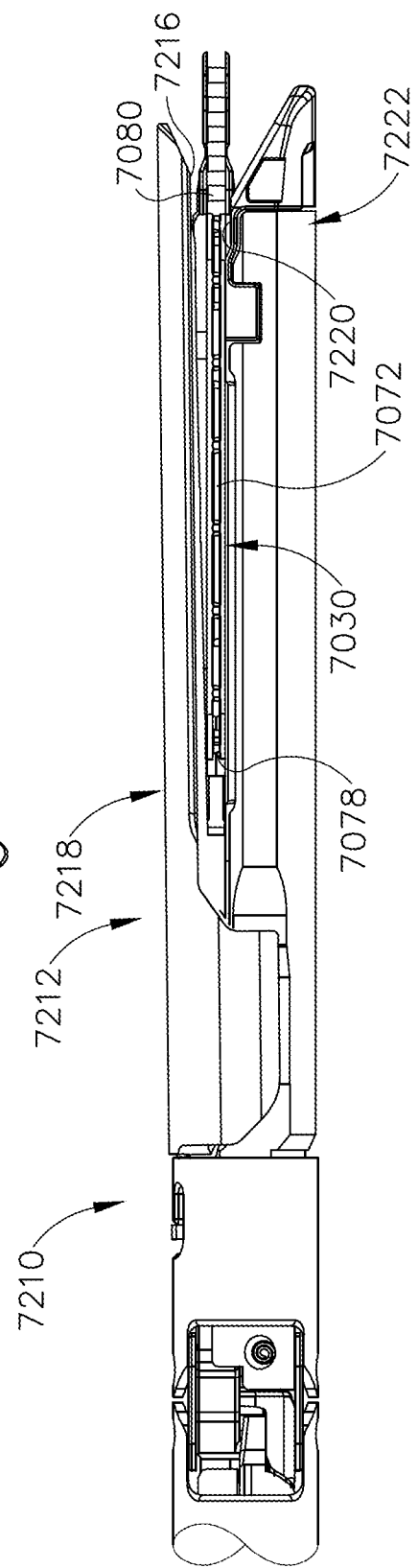

METHOD OF APPLYING BUTTRESSES TO SURGICALLY CUT AND STAPLED SITES

PRIORITY

This application is a continuation of U.S. patent application Ser. No. 18/164,665, entitled "Method of Applying Buttresses to Surgically Cut and Stapled Sites," filed Feb. 6, 2023, published as U.S. Pub. No. 2023/0210528 on Jul. 6, 2023, issued as U.S. Pat. No. 12,076,014 on Sep. 3, 2024, which is a continuation of U.S. patent application Ser. No. 17/316,920, entitled "Method of Applying Buttresses to Surgically Cut and Stapled Sites," filed May 11, 2021, issued as U.S. Pat. No. 11,602,347 on Mar. 14, 2023, which is a continuation of U.S. patent application Ser. No. 16/235,617, entitled "Method of Applying Buttresses to Surgically Cut and Stapled Sites," filed Dec. 28, 2018, and issued as U.S. Pat. No. 11,033,269 on Jun. 15, 2021, the disclosures of which are incorporated by reference herein in their entireties.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited for use through a thoracotomy are disclosed in U.S. Pat. No. 9,186,142, entitled "Surgical Instrument End Effector Articulation Drive with Pinion and Opposing Racks," issued Nov. 17, 2015; U.S. Pat. No. 9,717,497, entitled "Lockout Feature for Movable Cutting Member of Surgical Instrument," issued Aug. 1, 2017; U.S. Pat. No. 9,517,065, entitled "Integrated Tissue Positioning and Jaw Alignment Features for Surgical Stapler," issued Dec. 13, 2016; U.S. Pat. No. 9,839,421, entitled "Jaw Closure Feature for End Effector of Surgical Instrument," issued Dec. 12, 2017; U.S. Pat. No. 9,867,615, entitled "Surgical Instrument with Articulation Lock having a Detenting Binary Spring," issued Jan. 16, 2018; U.S. Pat. No. 9,622,746, entitled "Distal Tip Features for End Effector of Surgical Instrument," issued Apr. 18, 2017; U.S. Pat. No. 10,092,292, entitled "Staple Forming Features for Surgical Stapling Instrument," issued Oct. 9, 2018; U.S. Pat. No. 9,795,379, entitled "Surgical Instrument with Multi-Diameter Shaft," issued Oct. 24, 2017; and U.S. Pat. No. 9,808,248, entitled "Installation Features for Surgical Instrument End Effector Cartridge," issued Nov. 7, 2017. The disclosure of each of the above-cited U.S. Patent Publications is incorporated by reference herein.

Additional surgical stapling instruments are disclosed in U.S. Pat. No. 8,801,735, entitled "Surgical Circular Stapler with Tissue Retention Arrangements," issued Aug. 12, 2014; U.S. Pat. No. 8,141,762, entitled "Surgical Stapler Comprising a Staple Pocket," issued Mar. 27, 2012; U.S. Pat. No. 8,371,491, entitled "Surgical End Effector Having Buttress Retention Features," issued Feb. 12, 2013; U.S. Pat. No. 9,597,082, entitled "Method and Apparatus for Sealing End-to-End Anastomosis" issued Mar. 21, 2017; U.S. Pat. No. 9,398,911, entitled "Rotary Powered Surgical Instruments with Multiple Degrees of Freedom," issued Jul. 26, 2016; U.S. Pat. Pub. No. 2013/0206813, entitled "Linear Stapler," published Aug. 15, 2013, now abandoned; U.S. Pat. Pub. No. 2008/0169328, entitled "Buttress Material for Use with a Surgical Stapler," published Jul. 17, 2008, now abandoned; U.S. Pat. No. 9,848,871, entitled "Woven and Fibrous Materials for Reinforcing a Staple Line," issued Dec. 26, 2017; U.S. Pat. No. 9,936,954, entitled "Devices and Methods for Sealing Staples in Tissue" issued Apr. 10, 2018; and U.S. Pat. Pub. No. 2016/0089146, entitled "Circular Fastener Cartridges for Applying Radially Expandable Fastener Lines" published Mar. 31, 2016, issued as U.S. Pat. No. 10,426,476 on Oct. 1, 2019. The disclosure of each of the above-cited U.S. Patents, U.S. Patent Publications, and U.S. Patent Applications is incorporated by reference herein.

In some instances, it may be desirable to equip a surgical stapling instrument with a buttress material to reinforce the mechanical fastening of tissue provided by staples. Such a buttress may prevent the applied staples from pulling through tissue and may otherwise reduce a risk of tissue tearing at or near the site of applied staples.

When using a buttress material to reinforce a cut and stapled tissue site, a buttress applicator may be used to load one or more buttresses onto the end effector for subsequent deployment at the cut and stapled tissue site. To preserve the integrity of the buttresses prior to loading and deployment of buttresses at a tissue site, various packaging is used for the buttresses and/or applicators containing the buttresses.

In some instances, it may be desirable to equip a surgical stapling instrument with a buttress material to reinforce the mechanical fastening of tissue provided by staples. Such a buttress may prevent the applied staples from pulling through tissue and may otherwise reduce a risk of tissue tearing at or near the site of applied staples. Such buttress material may be applied to the surgical stapling instrument with a buttress applier cartridge. The buttress applier cartridge retains the buttress material prior to application and releases the buttress material once applied to the surgical stapling instrument. An example of such buttress applier cartridge is disclosed in U.S. Pat. Pub. No. 2017/0056016, entitled "Surgical Stapler Buttress Applicator with End Effector Actuated Release Mechanism," published Mar. 2, 2017, issued as U.S. Pat. No. 10,342,542 on Jul. 9, 2019, the disclosure of which is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 8A depicts a cross section view of the buttress assembly of FIG. 7, taken along line 8A-8A of FIG. 7;

FIG. 8B depicts a cross section view of the buttress assembly of FIG. 7, taken along line 8B-8B of FIG. 7;

FIG. 8C depicts a cross section view of the buttress assembly of FIG. 7, taken along line 8C-8C of FIG. 7;

FIG. 8D depicts a cross section view of the buttress assembly of FIG. 7, taken along line 8D-8D of FIG. 7;

FIG. 8E depicts a cross section view of the buttress assembly of FIG. 7, taken along line 8E-8E of FIG. 7;

FIG. 8F depicts a cross section view of the buttress assembly of FIG. 7, taken along line 8F-8F of FIG. 7;

FIG. 8G depicts a cross section view of the buttress assembly of FIG. 7, taken along line 8G-8G of FIG. 7;

FIG. 13 depicts a top plan view of another exemplary buttress assembly showing another exemplary asymmetric adhesive distribution;

FIG. 14 depicts a side elevation view of the end effector for a surgical stapler of FIG. 12 in an open position, showing the buttress assembly of FIG. 13 releasing from the jaws of the end effector;

FIG. 23 depicts a cross-section view of the packaging assembly of FIG. 21, taken along line 23-23 of FIG. 21;

FIG. 24 depicts a cross-section view of the packaging assembly of FIG. 22, taken along line 24-24 of FIG. 22;

FIG. 44A depicts a sectional side view of a portion of the end effector of FIG. 43B with the buttress assemblies of FIG. 34 applied to the end effector and tissue positioned between the buttress assemblies with the upper and lower jaws in the open position;

FIG. 44B depicts the sectional side view of the portion of the end effector and the buttress assemblies similar to FIG. 44A, but showing the upper and lower jaws in the closed position;

FIG. 44C depicts the sectional side view of the buttress assemblies similar to FIG. 44B, but showing the buttress assemblies secured to the tissue with a staple formed in the tissue;

FIG. 57 depicts a perspective view of the chassis and the platform of FIG. 49 with pairs of left and right actuator sleds of FIG. 53 and FIG. 55;

FIG. 58 depicts a cross-sectional view of the chassis, the platform, and the actuator sleds of FIG. 57 taken along section line 58-58 of FIG. 57;

FIG. 65 depicts the side sectional view of the end effector and the platform of the buttress applier cartridge similar to FIG. 61, but with the end effector in an exemplary over-camber orientation;

FIG. 66 depicts the side sectional view of the end effector and the platform of the buttress applier cartridge similar to FIG. 61, but with the end effector in an exemplary under-camber orientation;

FIG. 95 depicts a perspective view of the chassis and the platform of FIG. 87 and FIG. 88 with pairs of left and right actuator sleds of FIG. 91 and FIG. 93;

FIG. 96 depicts a cross-sectional view of the chassis, the platform, and the actuator sleds of FIG. 95 taken along section line 96-96 of FIG. 95;

FIG. 97 depicts a top view of the chassis, the platform, and the actuator sleds of FIG. 95 in a restraint position;

FIG. 98 depicts the top view of the chassis, the platform, and the actuator sleds similar to FIG. 97, but showing the actuator sleds being directed from the restraint position toward a release position;

FIG. 99 depicts the top view of the chassis, the platform, and the actuator sleds similar to FIG. 98, but showing the actuator sleds in the release position;

FIG. 100 depicts a top view of an exemplary end effector of a surgical instrument showing the buttress assembly applicator of FIG. 85 positioned between the upper and lower jaws of the end effector in a closed position;

FIG. 101 depicts a bottom view of the end effector of FIG. 100, showing the buttress assembly applicator of FIG. 85 positioned between the upper and lower jaws of the end effector in a closed position;

FIG. 102 depicts a top view of an exemplary end effector of a surgical instrument showing the buttress assembly applicator of FIG. 85 positioned between the upper and lower jaws of the end effector in a closed position;

FIG. 103 depicts a side elevation view of the end effector of FIG. 102, showing the buttress assembly applicator of FIG. 85 in cross-section and positioned between the upper and lower jaws of the end effector in a closed position;

FIG. 104 depicts a cross-sectional view of the buttress assembly applicator of FIG. 85 taken along line 104-104 of FIG. 85;

FIG. 105 depicts a perspective view of an exemplary alignment feature usable with the buttress assembly applicator of FIG. 85;

FIG. 106 depicts a perspective view of the alignment feature of FIG. 105 connected with the chassis of FIG. 86;

Figure 85:
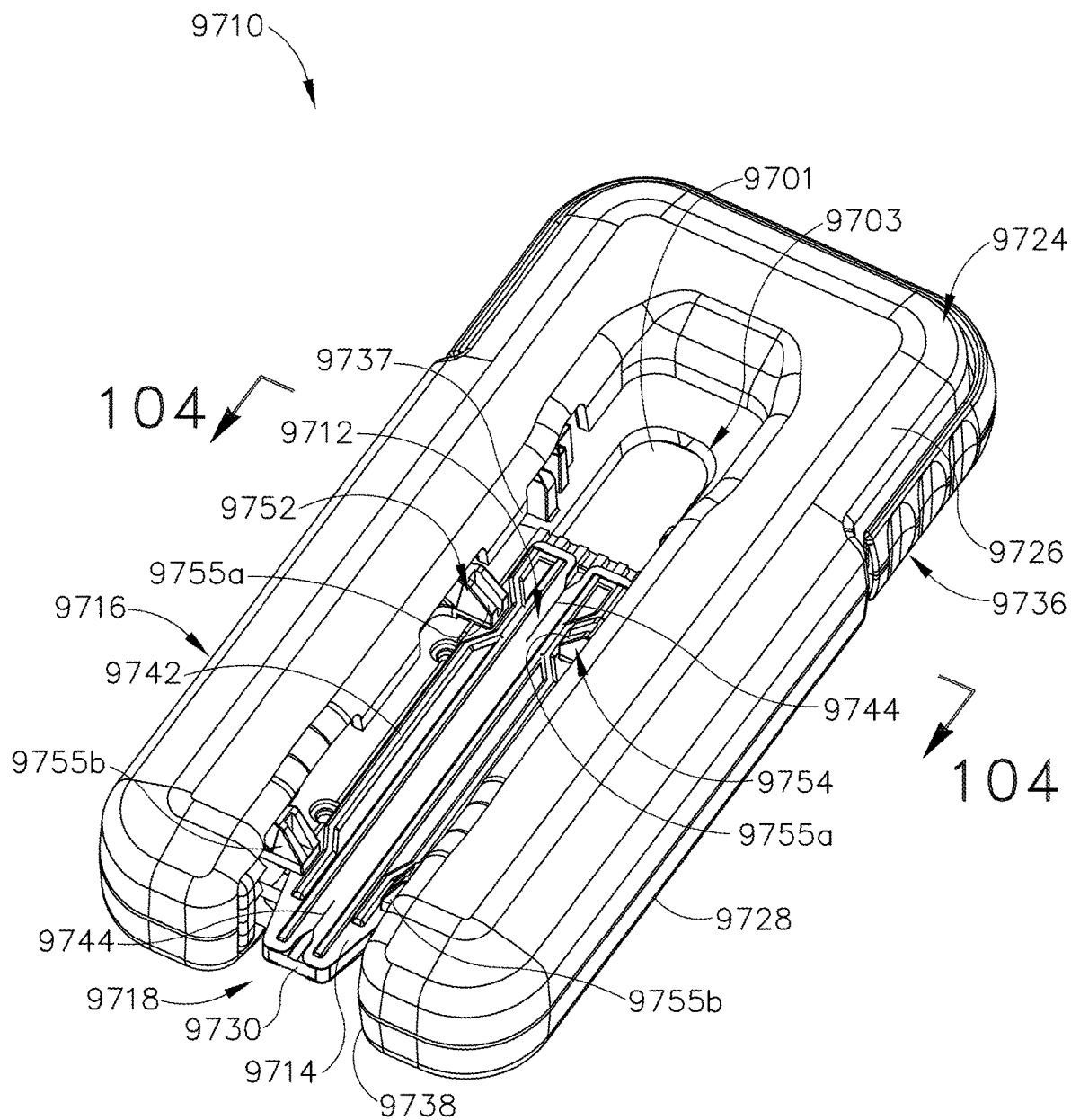
FIG. 85 depicts a perspective view of an exemplary buttress assembly applicator that includes an example of a buttress assembly applicator carrying an example of a buttress assembly for an upper jaw and an example of another buttress assembly for a lower jaw.
Figure 107:
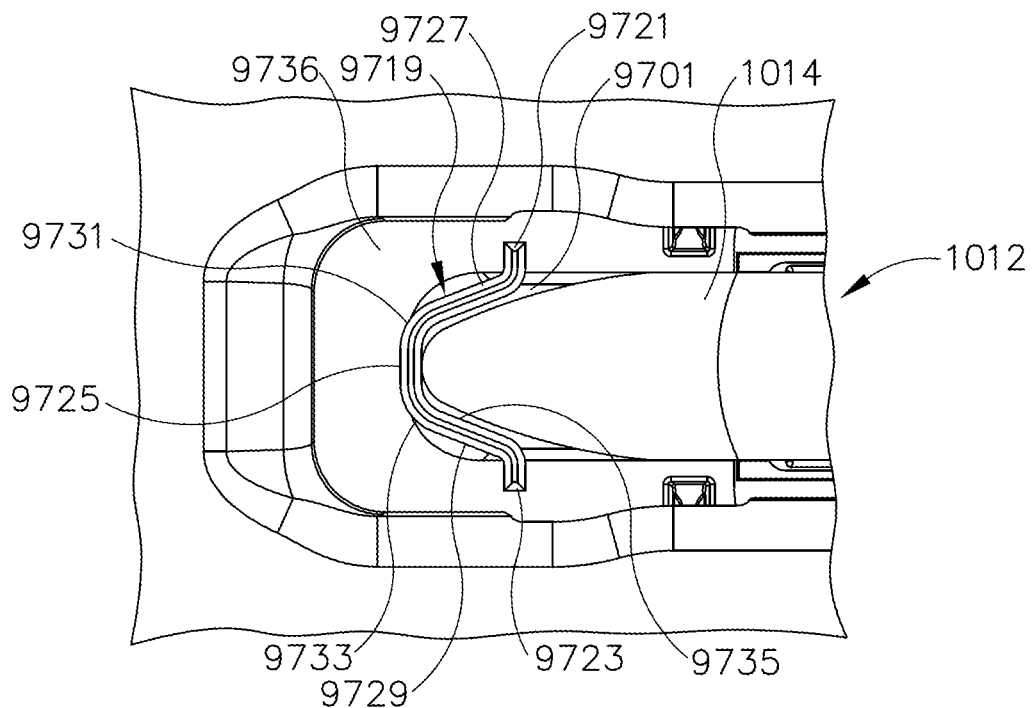
Figure 108:
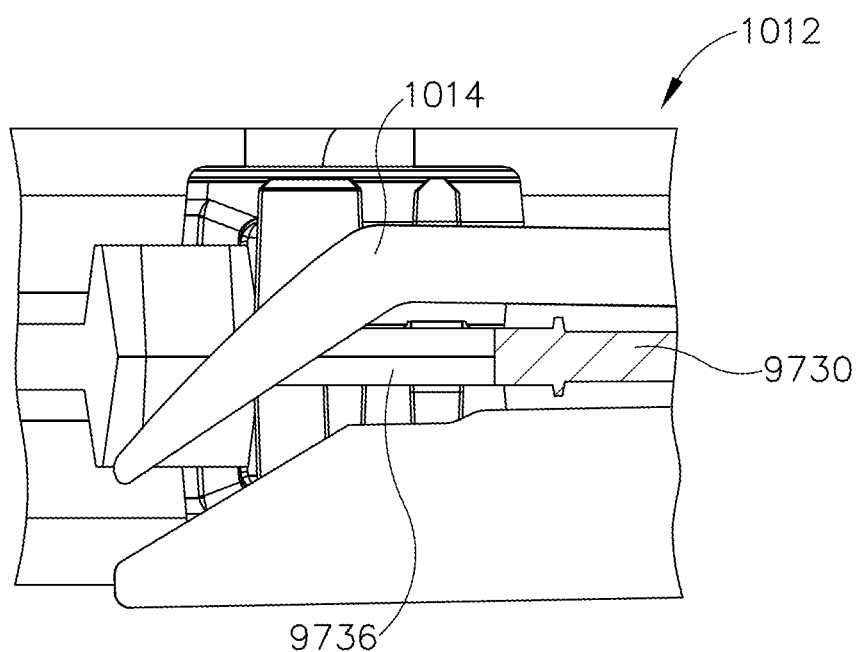
Figure 109:
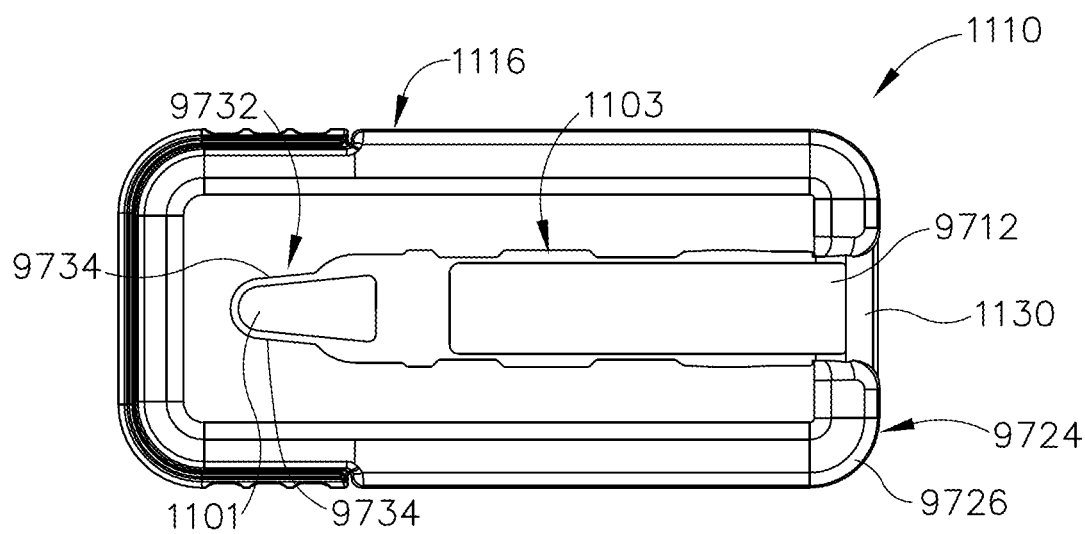
Figure 110:
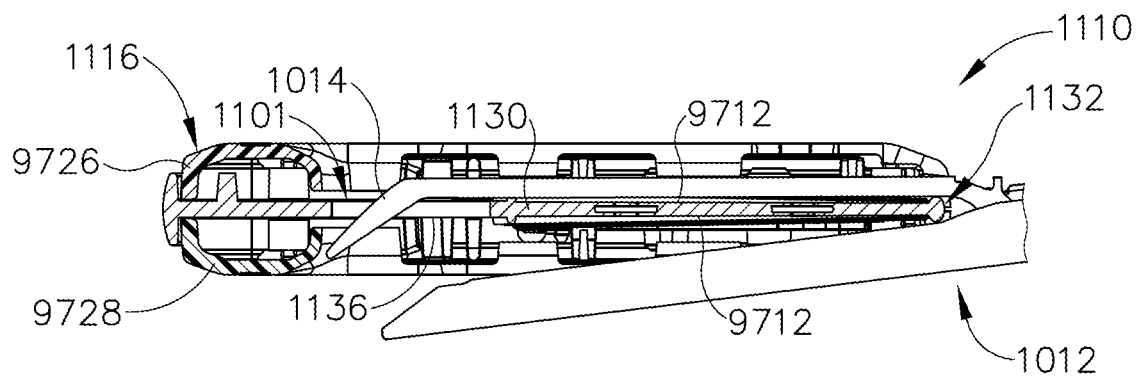
Figure 111:
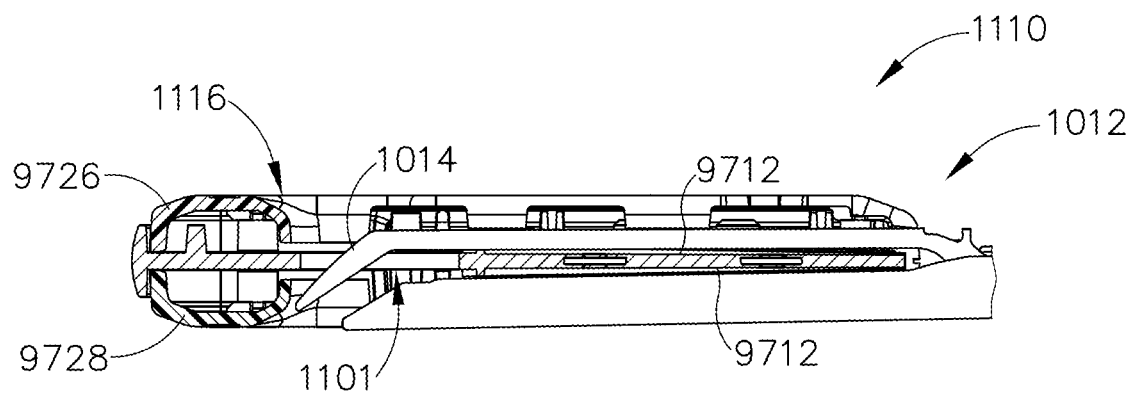
Figure 112:
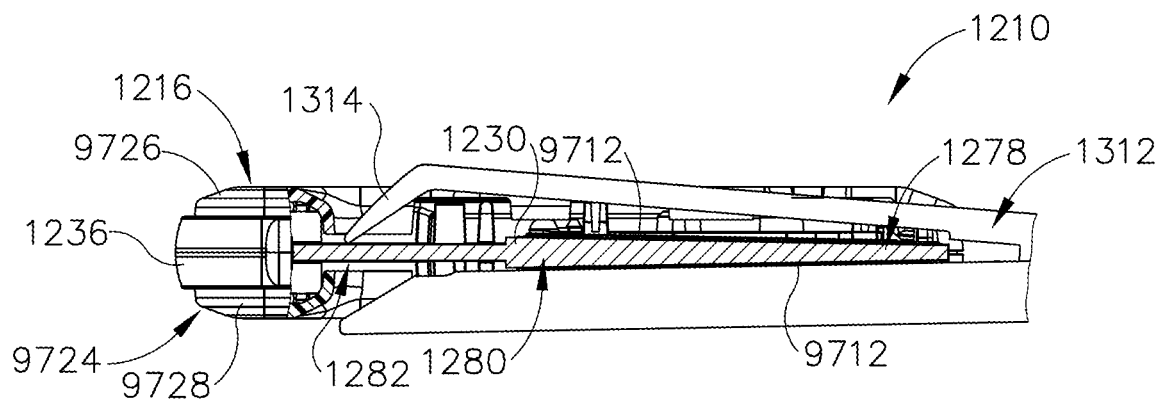
Figure 113:
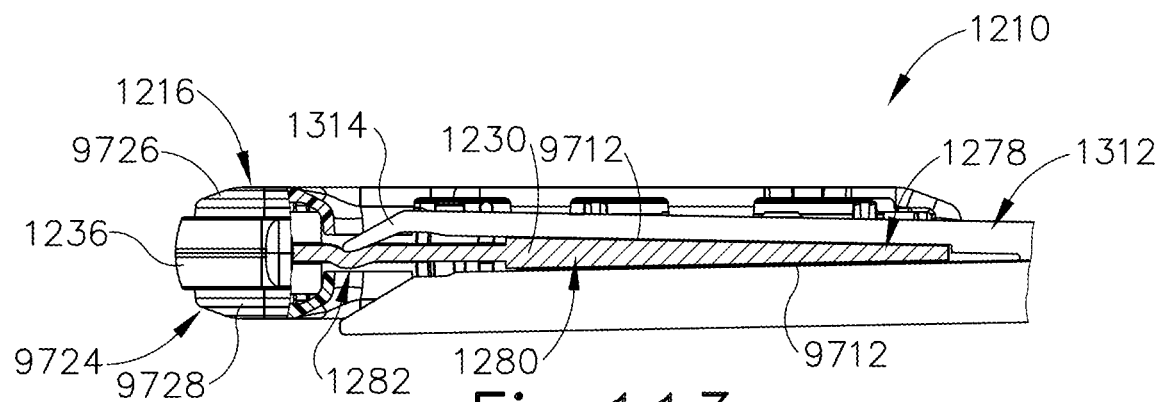
Figure 114:
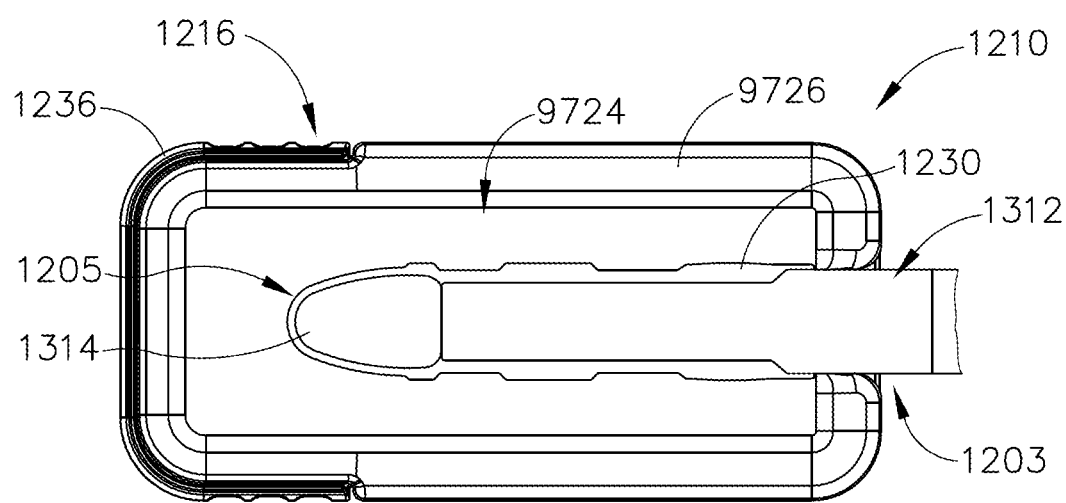
Figure 115:
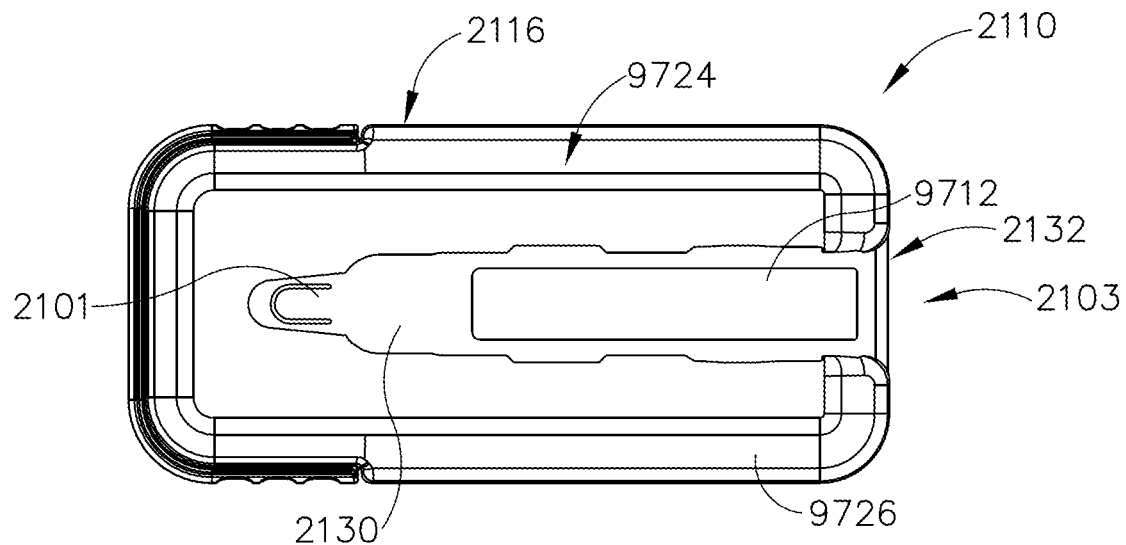
Figure 116:
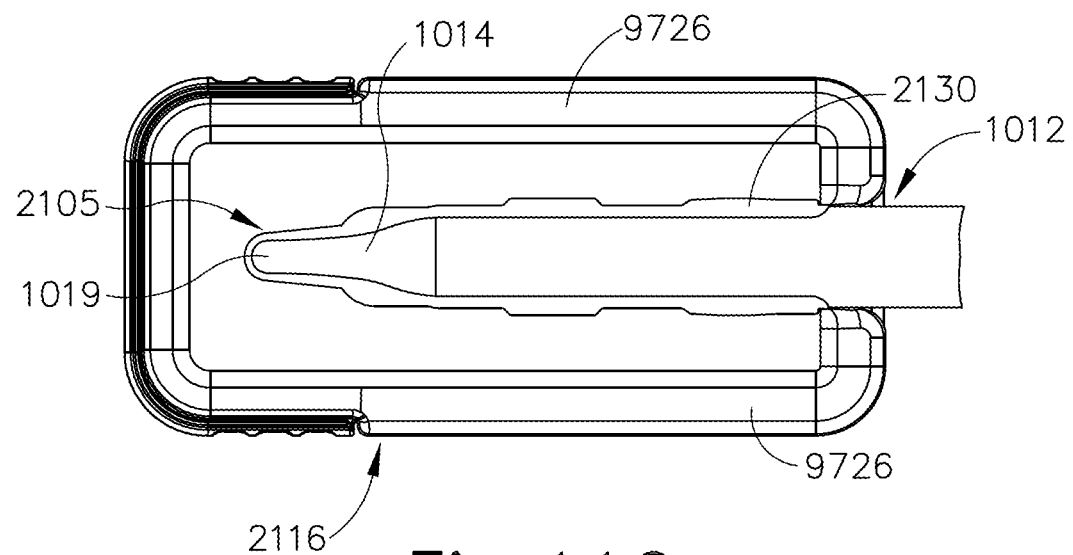
Figure 117:
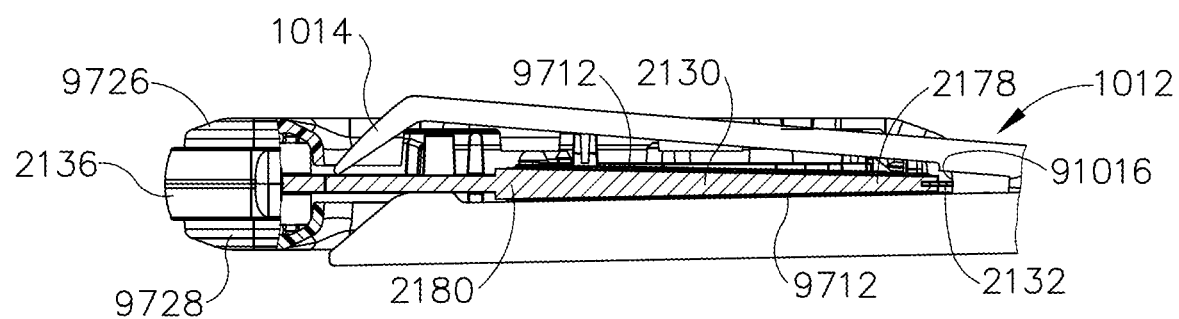
Figure 118:
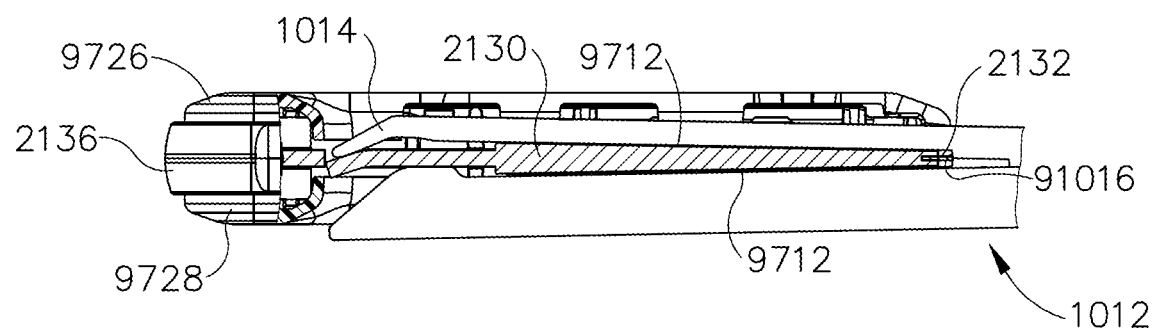
Figure 119:
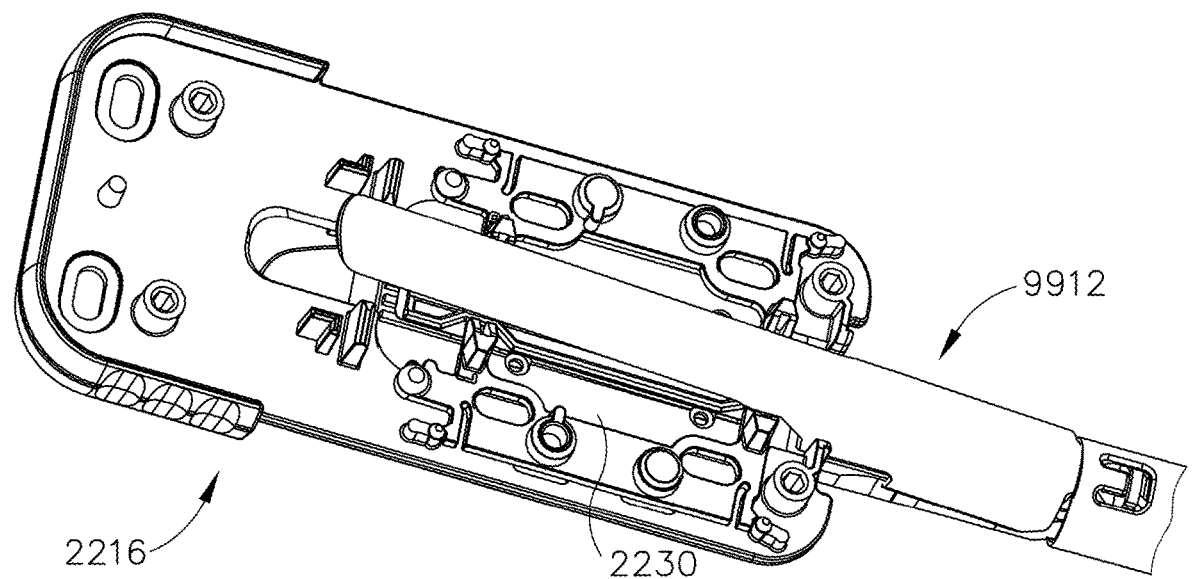
Figure 120:
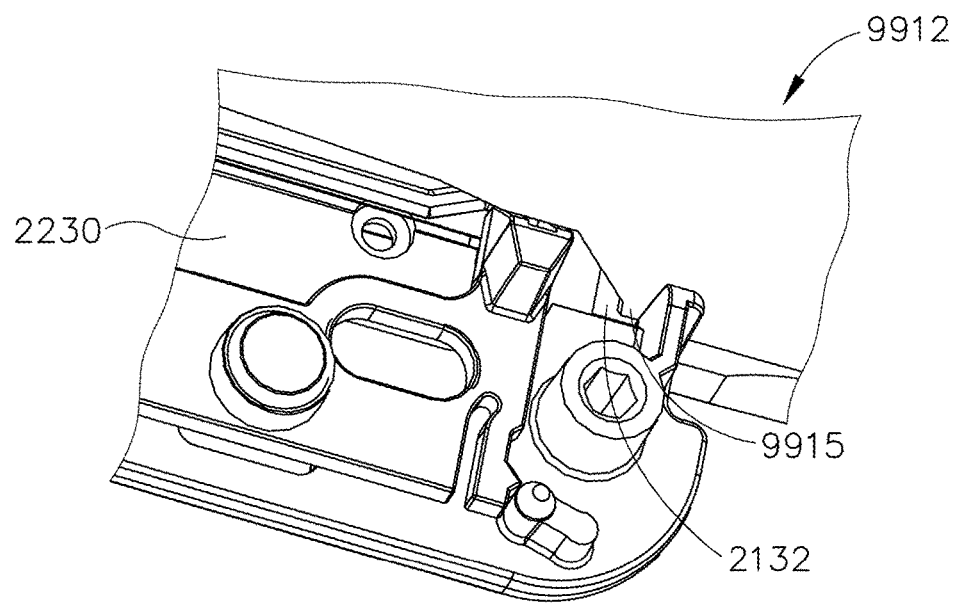
Figure 121:
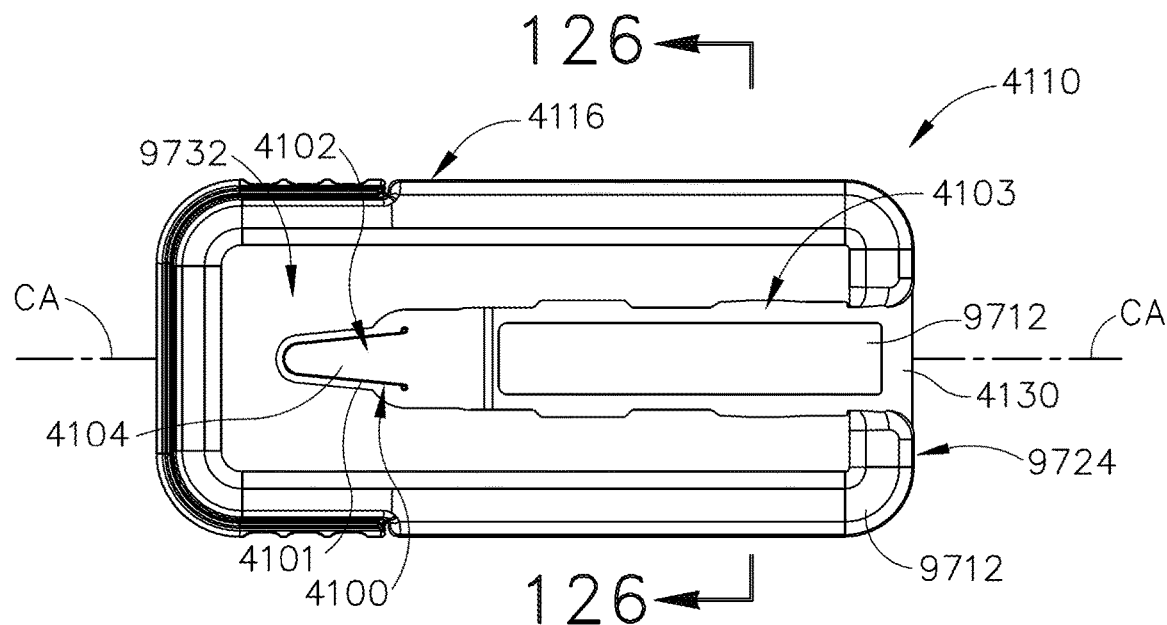
Figure 122:
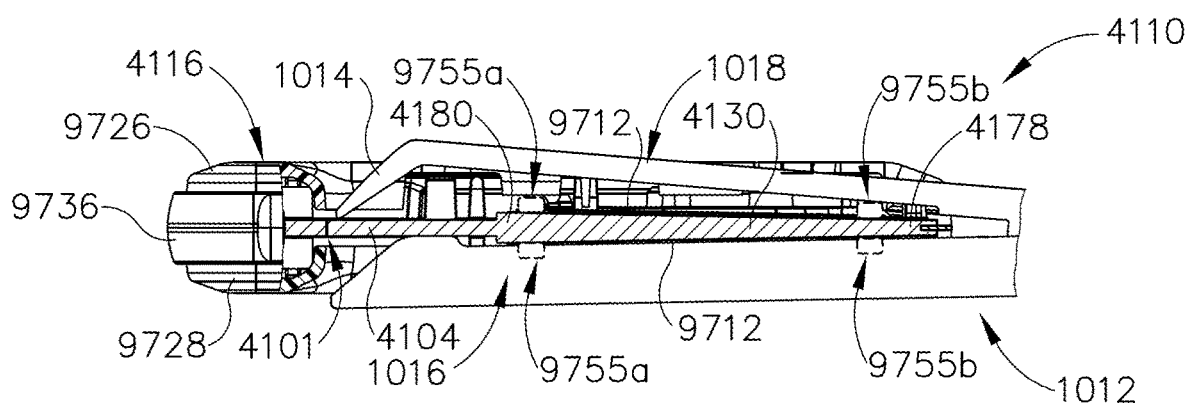
Figure 123:
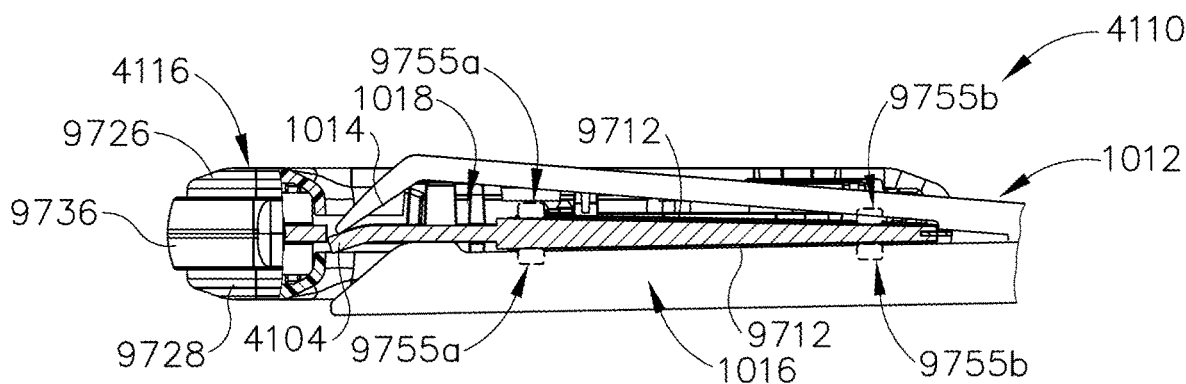
Figure 124:
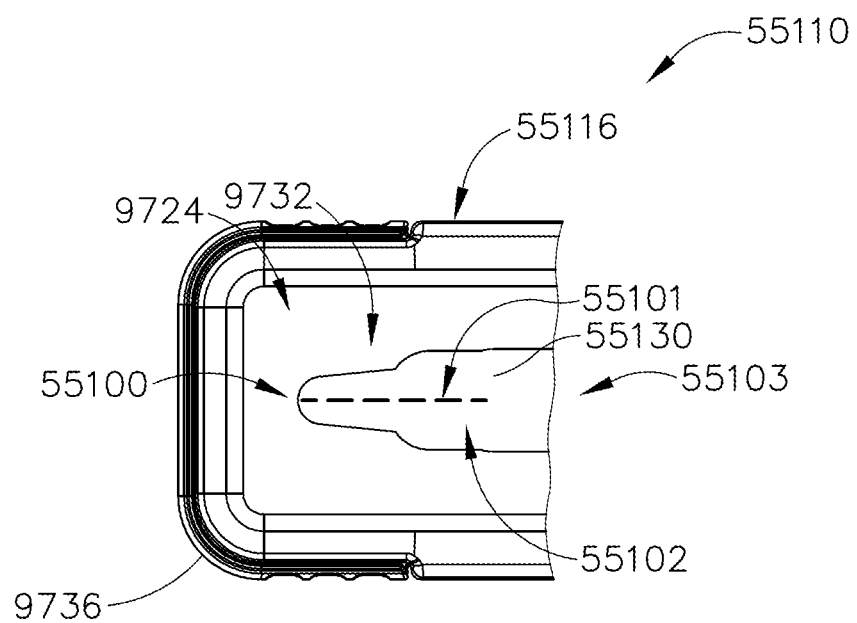
Figure 125:
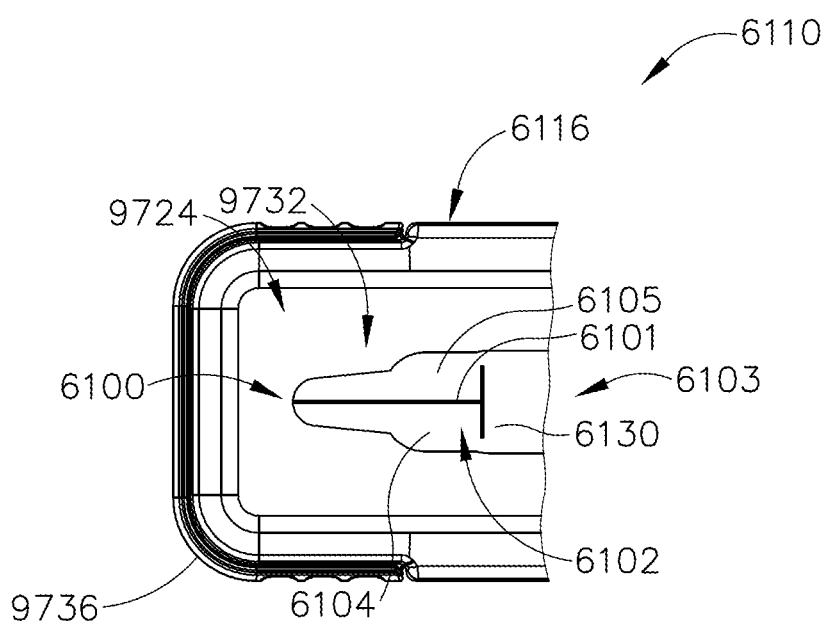
Figure 126:
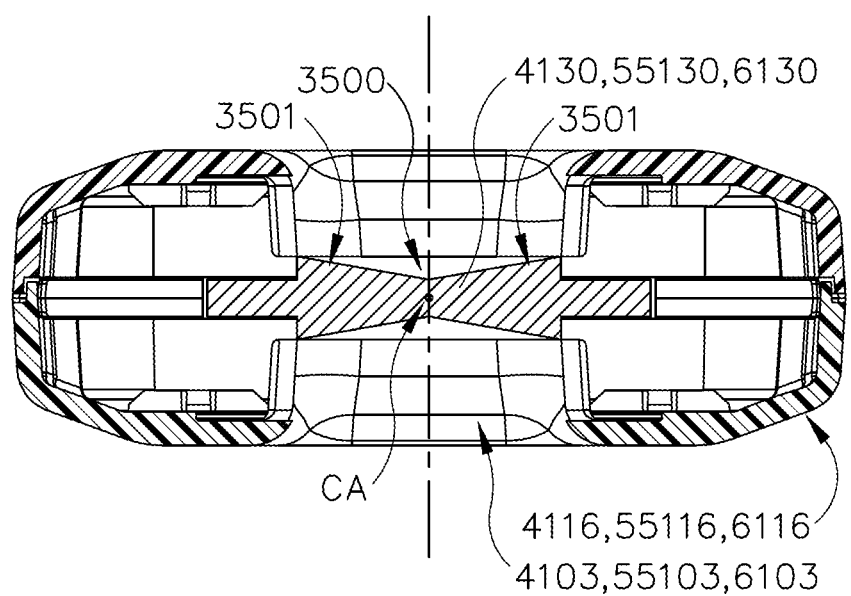

FIG. 107 depicts a perspective view of another exemplary alignment feature connected with the chassis of the buttress assembly applicator of FIG. 85, and shown with an end effector with the buttress assembly applicator positioned between the upper and lower jaws of the end effector in a closed position;

FIG. 108 depicts a cross-sectional view of the alignment feature and chassis of the buttress assembly applicator of FIG. 107, shown with the buttress assembly applicator positioned between the upper and lower jaws of the end effector of FIG. 107 in a closed position;

FIG. 109 depicts a top view of another exemplary buttress assembly applicator for use with an end effector of a surgical instrument;

FIG. 110 depicts a side elevation view of an exemplary end effector having a curved tip, showing the buttress assembly applicator of FIG. 109 in cross-section and positioned between the upper and lower jaws of the end effector in an open position;

FIG. 111 depicts a side elevation view of the end effector of FIG. 110, showing the buttress assembly applicator of FIG. 109 in cross-section and positioned between the upper and lower jaws of the end effector in a closed position;

FIG. 112 depicts a side elevation view of an exemplary end effector having a deformable curved tip, showing an exemplary buttress assembly applicator in cross-section and positioned between the upper and lower jaws of the end effector in an open position;

FIG. 113 depicts a side elevation view of the end effector of FIG. 112, showing the buttress assembly applicator of FIG. 112 in cross-section and positioned between the upper and lower jaws of the end effector in a closed position;

FIG. 114 depicts a top view of the end effector and buttress assembly applicator of FIG. 113;

FIG. 115 depicts a top view of another exemplary buttress assembly applicator carrying one or more exemplary buttress assemblies for applying to an end effector of a surgical stapler;

FIG. 116 depicts a top view of the buttress assembly applicator of FIG. 115, shown with an end effector positioned within a channel or space defined by the buttress assembly applicator prior to clamping;

FIG. 117 depicts a side elevation view of the buttress assembly applicator and end effector of FIG. 116, shown with the end effector positioned but not clamped;

FIG. 118 depicts a side elevation view of the buttress assembly applicator and end effector of FIG. 116, shown with the end effector positioned and in a clamped state;

FIG. 119 depicts a perspective view of the buttress assembly applicator of FIG. 115, shown with the housing assembly removed and with an alternate straight tip end effector positioned in an open state over the platform retaining the buttress assemblies;

FIG. 120 depicts an enlarged perspective view of a proximal portion of the combined buttress assembly applicator and end effector of FIG. 119;

FIG. 121 depicts a top view of another exemplary buttress assembly applicator for use with an end effector of a surgical instrument;

FIG. 122 depicts a side elevation view of an exemplary end effector having a curved tip, showing the buttress assembly applicator of FIG. 121 in cross-section and positioned between the upper and lower jaws of the end effector in an open position;

FIG. 123 depicts a side elevation view of the end effector of FIG. 122, showing the buttress assembly applicator of FIG. 121 in cross-section and positioned between the upper and lower jaws of the end effector in a closed position;

FIG. 124 depicts a partial top view of another exemplary buttress assembly applicator showing the platform having a distal perforated slit;

FIG. 125 depicts a partial top view of another exemplary buttress assembly applicator showing a platform having a distal T-shaped slit; and FIG. 126 depicts a cross-sectional view of the buttress assembly applicator of FIG. 121 taken along line 126-126 of FIG. 121, and shown without buttress assemblies.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It should be understood that terms such as "proximal" and "distal" are used herein with reference to a clinician gripping a surgical instrument, such as surgical and severing instrument (110) and buttress applier cartridge assembly (10) discussed below. It will be further appreciated that for convenience and clarity, spatial terms such as "upright," "upside-down," "upper," "lower," "bottom," and "top" are used herein with respect to the drawings. However, surgical instruments are used in many orientations and positions, and these terms are not intended to be limiting and absolute.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

In addition, the terms "first" and "second" are used herein to distinguish one or more portions of the surgical instrument. For example, a first assembly and a second assembly may be alternatively and respectively described as a second assembly and a first assembly. The terms "first" and "second" and other numerical designations are merely exemplary of such terminology and are not intended to unnecessarily limit the invention described herein.

I. Exemplary Buttress Loading and Application

Figure 1:
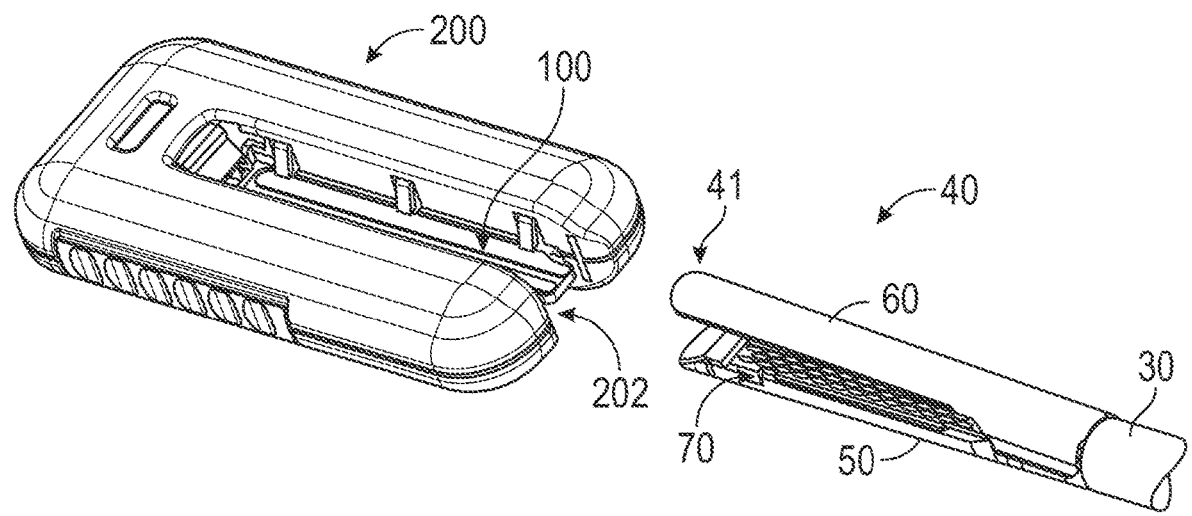
FIG. 1 depicts a perspective view of an exemplary end effector of a surgical stapler and an exemplary buttress applicator, with the end effector approaching the buttress applicator.
Figure 2:
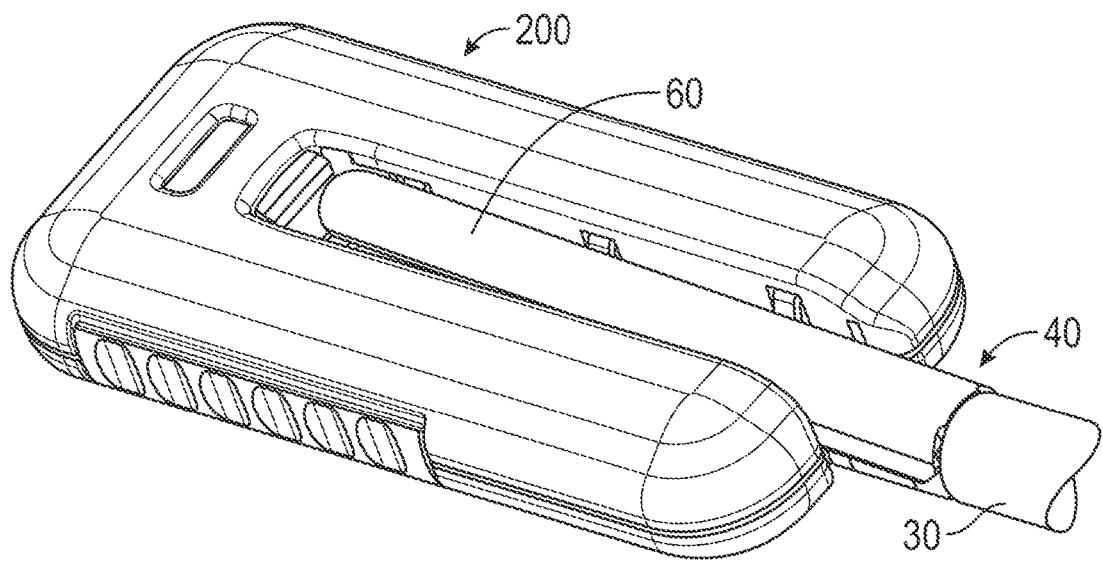
FIG. 2 depicts a perspective view of the end effector and the buttress applicator of FIG. 1, with the buttress applicator positioned in the end effector.

FIGS. 1 and 2 illustrate an exemplary end effector (40) configured to apply a buttress to a tissue site where a cutting and stapling operation is performed. End effector (40) is connected with a shaft assembly (30). End effector (40) comprises an anvil (60), a lower jaw (50), and a staple cartridge (70) received by lower jaw (50).

FIGS. 1 and 2 also illustrate an exemplary buttress applicator (200). Buttress applicator (200) is configured to selectively retain buttress assemblies (100, 110). In the present example, buttress assembly (100) is selectively retained on a top side of applicator (200) and buttress assembly (110) is selectively retained on a bottom side of applicator (200). In some other versions, applicator (200) can be configured such that only one buttress assembly (100, 110) is selectively retained by buttress applicator (200).

To use buttress applicator (200) to load end effector (40) with buttress assemblies (100, 110), the operator would first position applicator (200) and end effector (40) such that end effector (40) is aligned with an open end (202) of applicator (200) as shown in FIG. 1. The operator would then advance end effector (40) distally (and/or retract applicator (200) proximally) to position buttress assemblies (100, 110) between anvil (60) and staple cartridge (70) as shown in FIG. 2. In order to load buttress assemblies (100, 110) on end effector (40), the operator may simply close end effector (40) by pivoting anvil (60) toward staple cartridge (70). Closure of end effector (40) results in the distal ends of anvil (60) and staple cartridge (70) bearing against retaining features of buttress applicator (200) that are configured to selectively retain buttress assemblies (100, 110) with buttress applicator (200). This contact deflects such retaining features of buttress applicator (200) to thereby permit contact between a surface of anvil (60) and buttress assembly (100) on one side of buttress applicator (200), and a surface of staple cartridge (70) and buttress assembly (110) on another side of buttress applicator (200). Buttress assemblies (100, 110) comprise an adhesive on their respective surfaces such that with end effector (40) clamping on both buttress assemblies (100, 110), buttress assemblies (100, 110) are adhered respectively to an underside of anvil (60) and a deck surface of staple cartridge (70). End effector (40) may then be re-opened (i.e., pivoting anvil (60) away from staple cartridge (70)) and pulled away from buttress applicator (200). With retaining features of applicator (200) disengaged from buttress assemblies (100, 110), end effector (40) may freely pull buttress assemblies (100, 110) away from buttress applicator (200) as end effector (40) is pulled away from buttress applicator (200). With buttress assemblies (100, 110) loaded on end effector (40), end effector (40) may then be used as described further below with reference to FIGS. 3A-4.

Figures 3A, 3B, 3C:
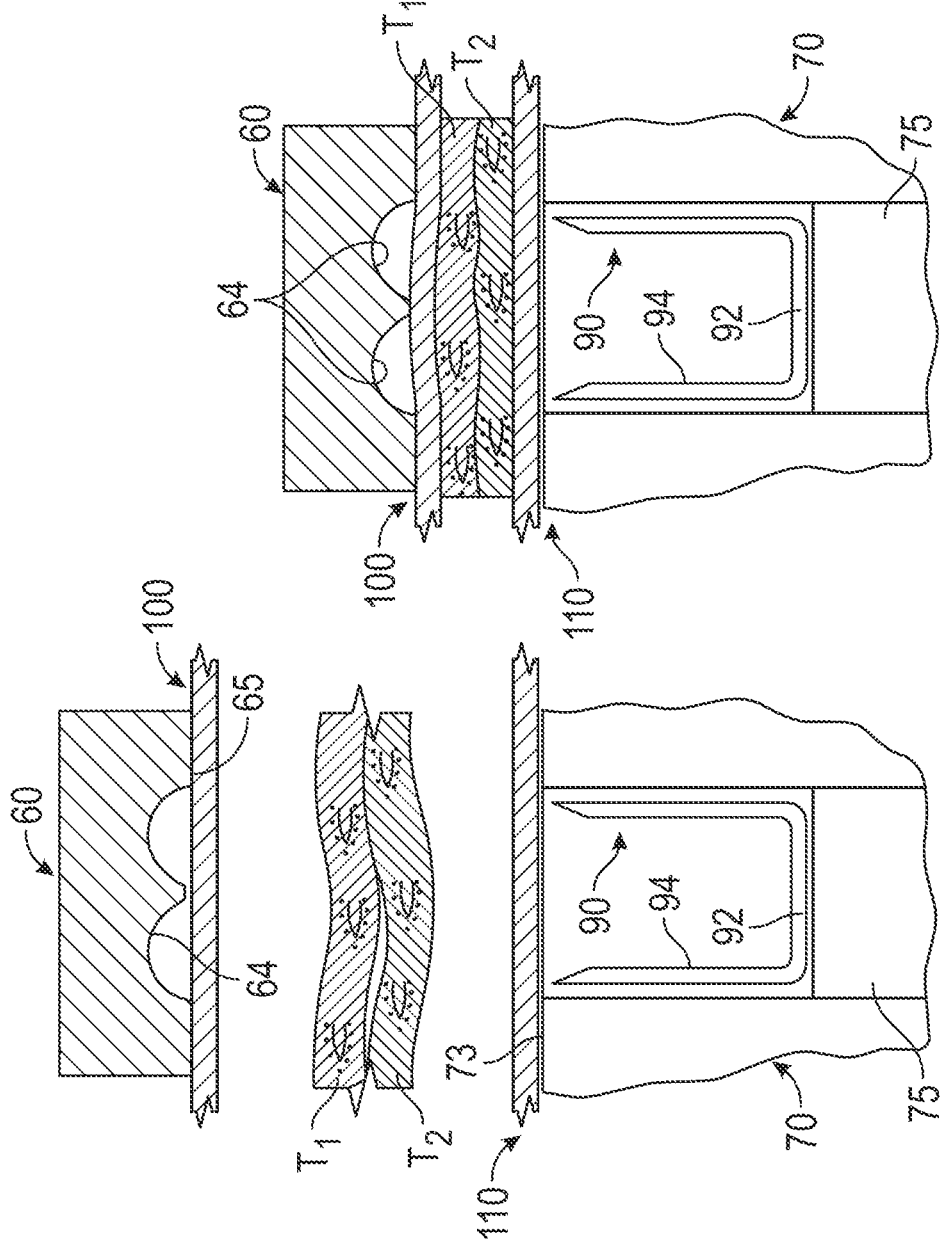
FIG. 3A depicts a cross-sectional end view of a portion of the end effector of FIG. 1 with the buttress assembly of FIG. 1 applied to the end effector, with tissue positioned between the buttresses in the end effector, and with the anvil in an open position.
FIG. 3B depicts a cross-sectional end view of the combined end effector and buttress assembly of FIG. 3A, with tissue positioned between the buttresses in the end effector, and with the anvil in a closed position.
FIG. 3C depicts a cross-sectional view of a staple and the buttress assembly of FIG. 3A having been secured to the tissue by the end effector of FIG. 1.

FIGS. 3A-3C show a sequence where an end effector (40) that has been loaded with buttress assemblies (100, 110) is actuated to drive staples (90) through two apposed layers of tissue ($T_1$, $T_2$), with buttress assemblies (100, 110) being secured to the same layers of tissue ($T_1$, $T_2$) by staples (90). In particular, FIG. 3A shows layers of tissue ($T_1$, $T_2$)

positioned between anvil (60) and staple cartridge (70), with anvil (60) in the open position. As shown, anvil (60) comprises staple forming pockets (64). Buttress assembly (100) is adhered, via adhesive, to underside (65) of anvil (60); while buttress assembly (110) is adhered, via adhesive, to deck (73) of staple cartridge (70). Layers of tissue ($T_1, T_2$) are thus interposed between buttress assemblies (100, 110). Next, end effector (40) is closed, which drives anvil (60) to the closed position as shown in FIG. 3B. At this stage, layers of tissue ($T_1, T_2$) are compressed between anvil (60) and staple cartridge (70), with buttress assemblies (100, 110) engaging opposite surfaces of tissue layers ($T_1, T_2$). End effector (40) is then actuated, whereby a staple driver (75) drives staple (90) through buttress assemblies (100, 110) and tissue layers ($T_1, T_2$). As shown in FIG. 3C, crown (92) of driven staple (90) captures and retains buttress assembly (110) against layer of tissue ($T_2$). Deformed legs (94) of staple (90) capture and retain buttress assembly (100) against layer of tissue ($T_1$).

Figure 4:
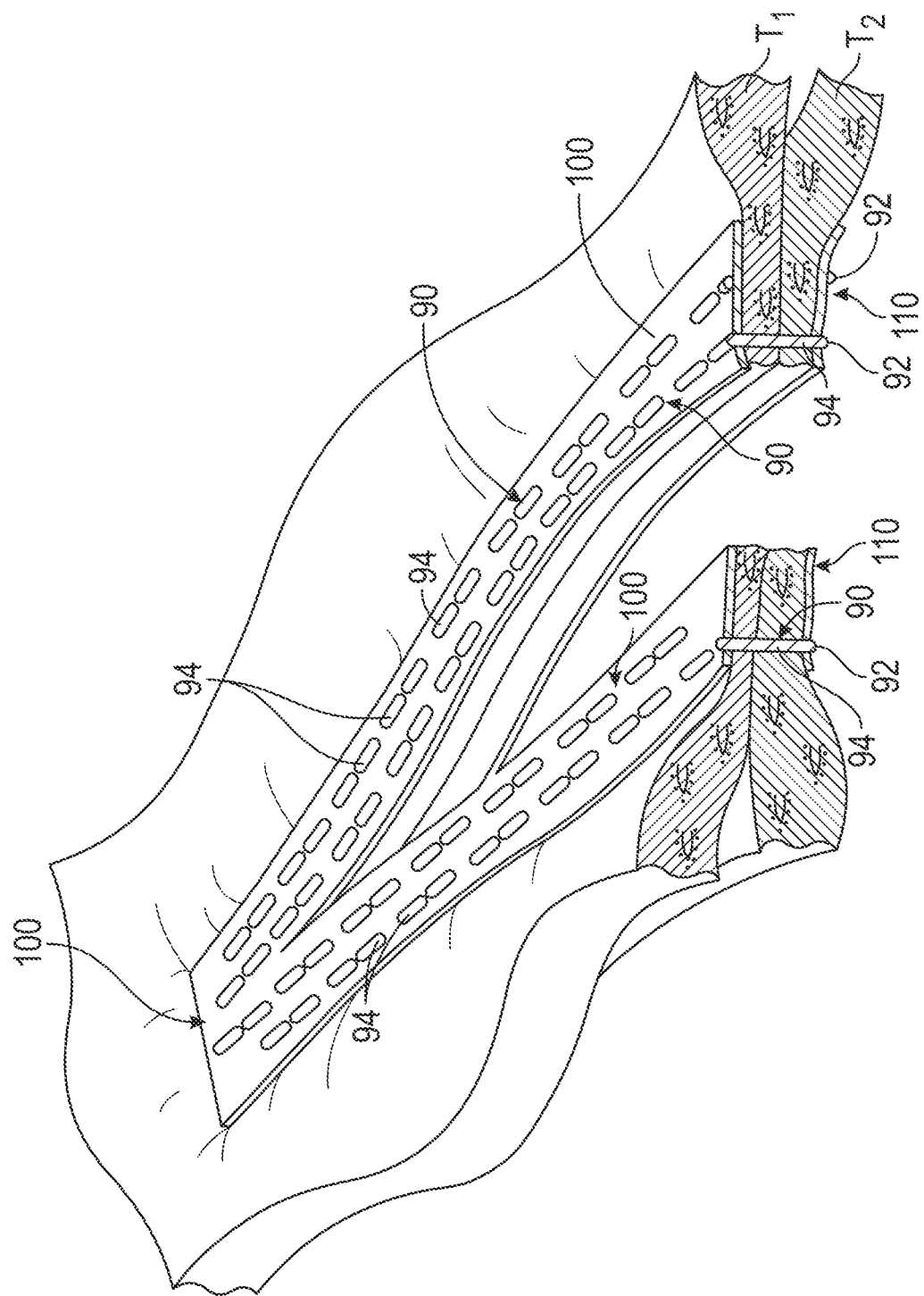
FIG. 4 depicts a perspective view of staples and the buttress assembly of FIG. 3A having been secured to the tissue by the end effector of FIG. 1.

It should be understood that a series of staples (90) will similarly capture and retain buttress assemblies (100, 110) against layers of tissue ($T_1, T_2$), thereby securing buttress assemblies (100, 110) to tissue ($T_1, T_2$) as shown in FIG. 4. As end effector (40) is pulled away from tissue (90) after deploying staples (90) and buttress assemblies (100, 110), buttress assemblies (100, 110) disengage end effector, such that buttress assemblies (100, 110) remain secured to tissue ($T_1, T_2$) with staples (90). Buttress assemblies (100, 110) thus provide structural reinforcement to the lines of staples (90). As can also be seen in FIG. 4, a knife member (not shown) passes through end effector (40) and in doing so also cuts through a centerline of buttress assemblies (100, 110), separating each buttress assembly (100, 110) into a corresponding pair of sections, such that each section remains secured to a respective severed region of tissue ($T_1, T_2$).

In the foregoing example, buttress assembly (100) is sized to span across the full width of underside (65) of anvil (60), such that a knife member (not shown) cuts through buttress assembly (100) during actuation of end effector (40). In some other examples, buttress assembly (100) is provided in two separate, laterally spaced apart portions, with one portion being disposed on underside (65) of anvil (60) on one half of anvil (60) and another portion being disposed on underside (65) of anvil (60) on the other half of anvil (60). In such versions, the knife member (not shown) does not cut through buttress assembly (100) during actuation of end effector (40).

Likewise, buttress assembly (110) may be sized to span across the full width of deck (73), such that the knife member (not shown) cuts through buttress assembly (110) during actuation of end effector (40). Alternatively, buttress assembly (110) may be provided in two separate, laterally spaced apart portions, with one portion being disposed on deck (73) on one half and another portion being disposed on deck (73) on the other half. In such versions, the knife member (not shown) does not cut through buttress assembly (110) during actuation of end effector (40).

In addition to the foregoing, it should also be understood that any of the various buttress assemblies described herein may be further constructed and operable in accordance with at least some of the teachings of U.S. Pat. Pub. No. 2016/0278774, entitled "Method of Applying a Buttress to a Surgical Stapler," published Sep. 29, 2016, issued as U.S. Pat. No. 10,349,939 on Jul. 16, 2019, the disclosure of which is incorporated by reference herein.

II. Exemplary Buttress Applicator

Figure 5:
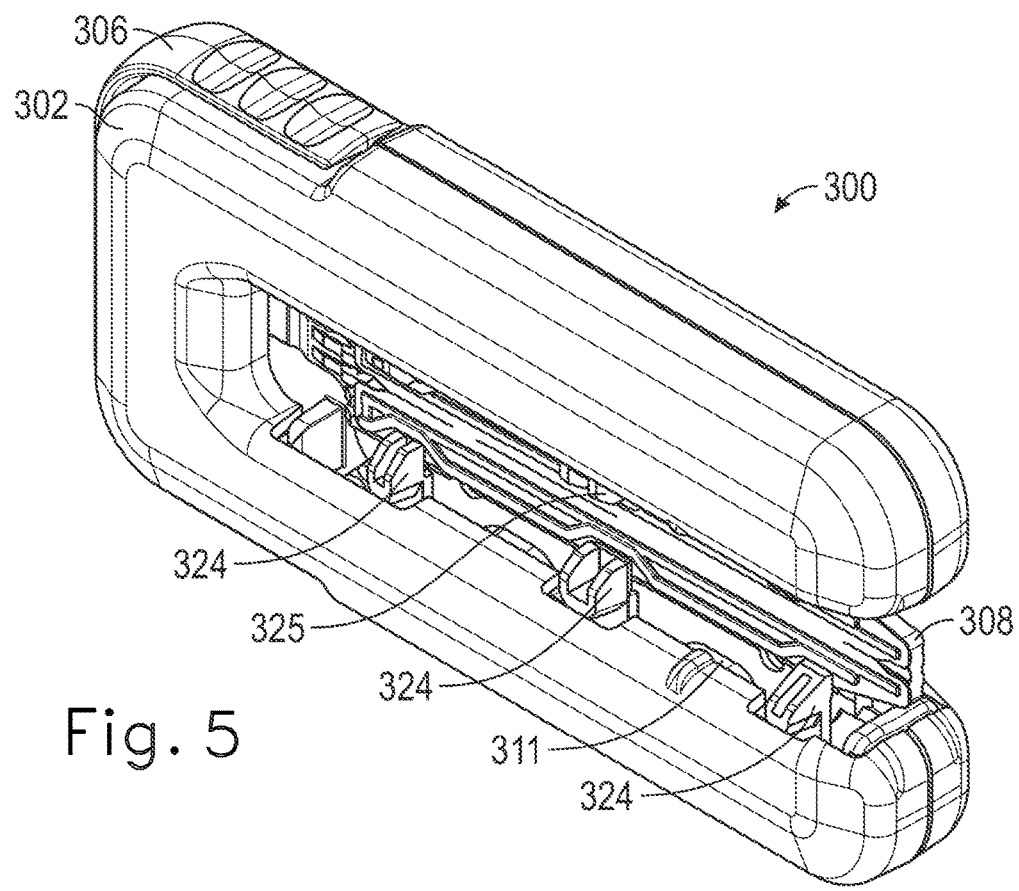
FIG. 5 depicts a perspective view of another exemplary buttress applicator usable with the end effector of FIG. 1.
Figure 6:
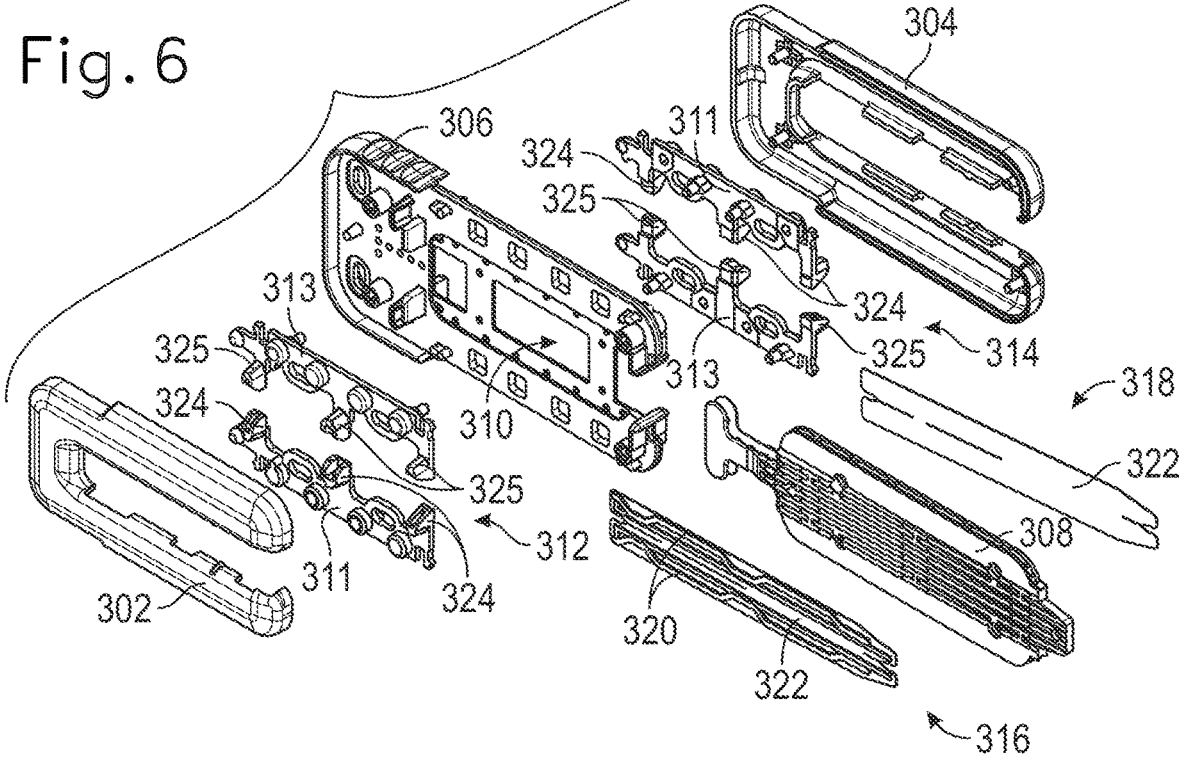
FIG. 6 depicts an exploded view of the buttress applicator of FIG. 5.

FIGS. 5 and 6 illustrate an alternate buttress applicator (300) for use with end effector (40). Buttress applicator (300) comprises a first housing portion (302) and a second housing portion (304). Each of housing portions (302, 304) connects with a frame (306). A compression pad (308) is configured to fit within a central portion (310) of frame (306). A first pair of clamp arms (312) are located on a first side of frame (306) between frame (306) and housing portion (302). A second pair of clamp arms (314) are located on a second side of frame (306) between frame (306) and housing portion (304). In the present version, clamp arms (312) comprise a left clamp arm (311) and a right clamp arm (313). Similarly, clamp arms (314) comprise a left clamp arm (311) and a right clamp arm (313). Buttress assemblies (316, 318) are located on respective sides of compression pad (308), and when buttress applicator (300) is fully assembled, pairs of clamp arms (312, 314) selectively retain buttress assemblies (316, 318) against compression pad (308). In the present example buttress assemblies (316, 318) are the same with each comprising an adhesive (320) located on a buttress (322) as will be described in greater detail below.

Buttress applicator (300) can be used with end effector (40) in the same manner as described above with respect to buttress applicator (200). For instance, buttress assemblies (316, 318) are loaded to end effector (40) in the same manner as described above where end effector (40) is moved to a closed or clamped position once anvil (60) and lower jaw (50) are positioned over central portion (310) of frame (308), e.g. as illustrated in FIG. 2. More specifically, the clamping action of end effector (40) when over buttress assemblies (316, 318) and compression pad (308) causes anvil (60) and staple cartridge (70) of lower jaw (50) to contact retention features (324) on left clamp arms (311) and retention features (325) on right clamp arms (313). This contact drives clamp arms (311, 313) laterally away from buttress assemblies (316, 318) thereby disengaging retention features (324, 325) from buttress assemblies (316, 318). With retention features (324, 325) disengaged, depending on the clamping orientation used with end effector (40), adhesive (320) of buttress assembly (316) contacts either underside (65) of anvil (60) or deck (73) of staple cartridge (70), while adhesive (320) of buttress assembly (318) contacts the other of underside (65) of anvil (60) or deck (73) of staple cartridge (70). This causes buttress assemblies (316, 318) to attach with end effector (40) and remain with end effector (40) as end effector is opened and moved away from buttress applicator (300). From this point, buttress assemblies (316, 318) may be applied to a cut and stapled tissue site as described above and illustrated with respect to FIG. 4.

III. Exemplary Buttress Assembly

Figure 7:
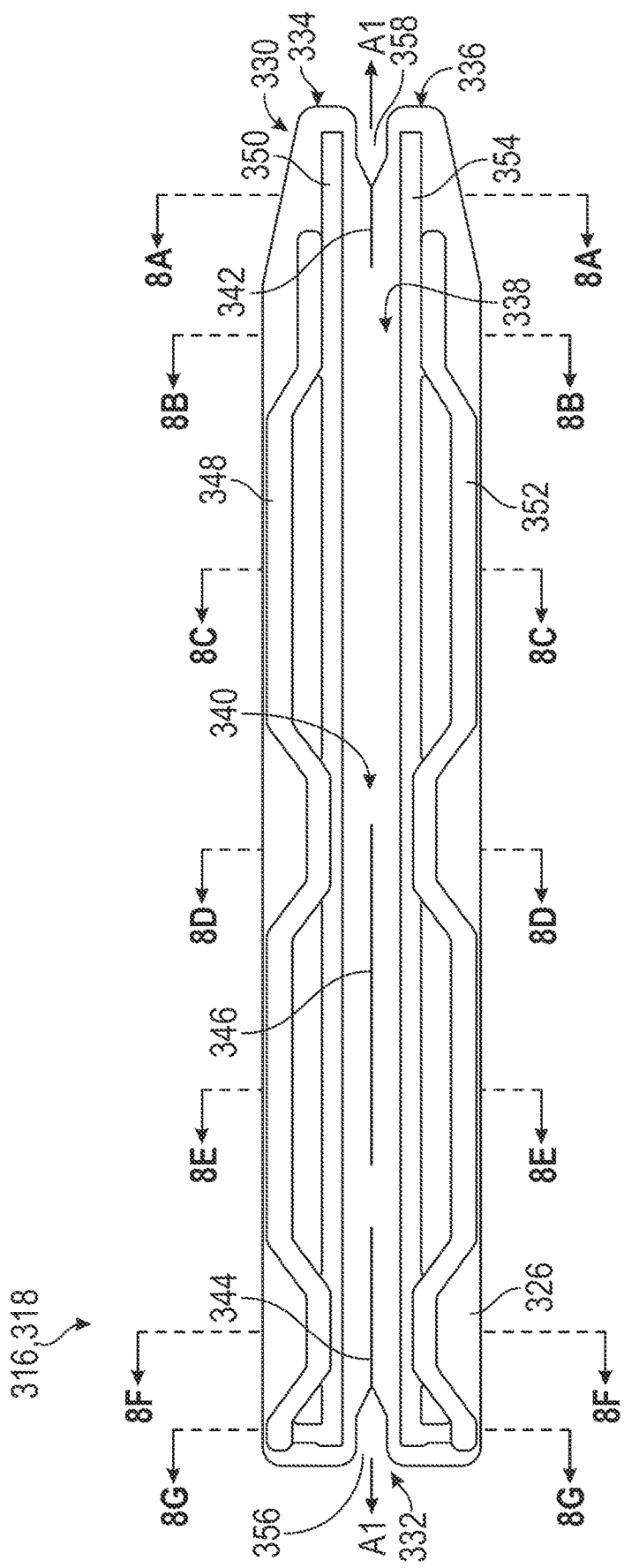
FIG. 7 depicts a top plan view of the buttress assembly of FIG. 5.

FIG. 7 illustrates buttress assembly (316), it being understood that buttress assembly (318) is identical. As mentioned, buttress assembly (316) comprises buttress (322) and adhesive (320) on one side of buttress (322). Buttress (322) comprises one or more layers of material. Where multiple layers are used the layers can be laminated together. In some examples buttress (322) comprises a mesh layer and one or more film layers laminated together. In some other examples buttress (322) comprises one or more film layers without a mesh layer. In view of the teachings herein, other various materials for one or more layers of buttress (322) will be apparent to those of ordinary skill in the art.

In the present example, buttress (322) is comprised of an absorbable material that is configured to be completed absorbed by the patient's body when used to reinforce a cut and staple site. In some examples, buttress (322) is comprised of polyglactin 910, which is 90% glycolide and 10% L-lactide. An example of polyglactin 910 is manufactured by Ethicon Inc. under the brand name Vicryl®. In view of the teachings herein, other absorbable synthetic materials for use with buttress (322) will be apparent to those of ordinary skill in the art.

A. Exemplary Adhesive Placement

Buttress (322) comprises a first surface (326) and a second surface (328) opposite to first surface (326). Buttress also includes a proximal end (330) and a distal end (332). As seen with reference to FIGS. 4 and 5, buttress assembly (316) is retained by applicator (300) such that when loading buttress assemblies (316, 318) to end effector (40), distal end (332) of buttress (322) aligns with a distal end (41) of end effector (40). With this configuration, buttress (322) defines a length extending from proximal end (330) to distal end (332). Buttress (322) further defines a longitudinal axis (A1) that extends between proximal end (330) and distal end (332). Buttress (322) includes a first edge region (334), a second edge region (336), and a center region (338) between and separating first edge region (334) and second edge region (336). Buttress (322) defines a width extending orthogonal to its length as defined above, where its width extends from first edge region (334) across center region (338) and through second edge region (336).

In the present example, adhesive (320) is applied onto first surface (326) of buttress (322). In some other versions of buttress assembly (316) adhesive (320) can be applied onto second surface (328) of buttress (322). Returning to the present example, adhesive (320) extends from proximal end (330) to distal end (332) of buttress (322). Moreover, in the present example, adhesive (320) extends continuously or in an uninterrupted manner. As shown in FIG. 7, adhesive (320) is located along first edge region (334) and second edge region (336), with center region (338) being substantially free of adhesive (320). As will be described further below, adhesive (320) is applied to buttress in a manner such that adhesive (320) comprises a height such that adhesive (320) is proud of buttress (322). The height of adhesive (320) is configured to facilitate adhesive (320) making good contact with either underside (65) of anvil (60) of end effector (40) or deck (73) of staple cartridge (70) of end effector (40) depending on the orientation of end effector (40) when loading buttress assembly (316).

The continuous nature of adhesive (320) along with the height of adhesive (320) act to seal the edges of buttress (322) to the part of end effector (40) to which buttress (322) attaches. For instance, where buttress assembly (316) is on anvil (60) side of end effector (40), the continuous adhesive (320) with its height creates a seal along the edges of buttress (322) of buttress assembly (316) where adhesive (320) contacts underside (65) of anvil (60). Similarly, where buttress assembly (318) is on staple cartridge (70) side of end effector (40), the continuous adhesive (320) with its height creates a seal along the edges of buttress (322) of buttress assembly (318) where adhesive (320) contacts deck (73) of staple cartridge (70). With this sealing attachment, in use the amount of moisture that can reach buttress assembly (316) is reduced. For instance, moisture is sealed out of the inside of buttress assembly (316), which keeps at least a portion of adhesive (320) free from moisture. By controlling moisture migration in this manner, buttress assemblies (316, 318) can have longer attachment times with end effector (40). This can give users greater lengths of time to position and manipulate end effector (40) before executing a cutting and stapling action, thereby applying buttresses (322) as reinforcing structures to the cut and stapled site.

Figure 9:
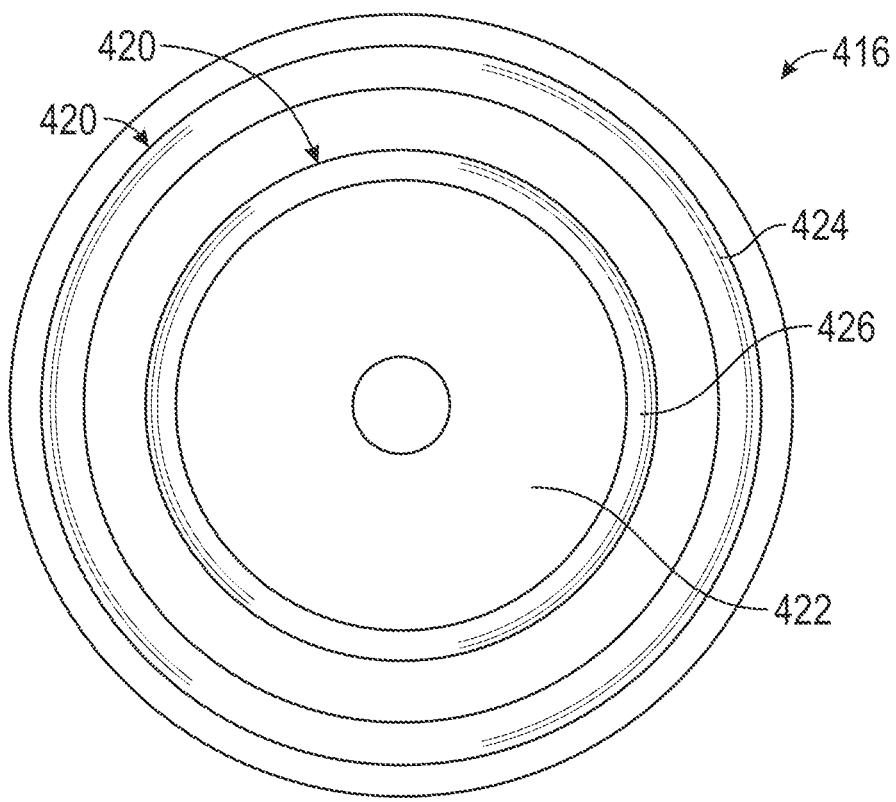
FIG. 9 depicts a top plan view of an exemplary buttress assembly configured for use with a circular surgical stapler.

Referring to FIG. 9, which shows exemplary buttress assembly (416), the sealing attachment discussed above can also apply to buttress assemblies configured for use with circular surgical staplers. For instance, buttress assembly (416) comprises a circular shape and is configured for use with a circular surgical stapler. Buttress assembly (416) comprises buttress (422) and adhesive (420). As shown, adhesive (420) is applied in a concentric circular pattern on buttress (422). In this manner, outer adhesive ring (424) creates sealing attachment with the end effector components of a circular stapler as those of ordinary skill in the art will understand in view of the teachings herein. This slows or prevents moisture from contacting a majority of buttress assembly (416), including inner adhesive ring (426), in the same or similar manner as described above with respect to buttress assemblies (316, 318).

B. Exemplary Adhesive Pattern and Distribution

Referring still to FIG. 7, and now also FIGS. 8A-8G, other details concerning buttress assemblies (316, 318) are described below relating to adhesive (320) and its pattern and amount. As shown in FIG. 7, center region (338) of buttress (322) comprises slits (340). In the illustrated version, slits (340) include a proximal slit (342), a distal slit (344), and an intermediate slit (346) between proximal and distal slits (342, 344). Slits (340) are configured to promote or facilitate cutting and separating buttress (322) into substantially equal halves during a cutting and stapling operation as discussed above. As shown in the present example, buttress assemblies (316, 318) comprise slits (342, 344) at both proximal end (330) and distal end (332) of buttress (322), where these slits (342, 344) extend all the way to the respective ends of buttress (322). This configuration helps ensure full cutting and separation of buttress (322) at its ends during a cut and staple sequence. Also in the present example, longitudinal axis (A1) passes through slits (340), and on each side of center region (338), adhesive (320) defines a pattern that is substantially symmetrical with the other side about longitudinal axis (A1).

Now considering adhesive (320) as applied to first edge region (334), adhesive (320) comprises a first bead (348) and a second bead (350). Each bead of adhesive (348, 350) extends generally from proximal end (330) of buttress (322) to distal end (332) of buttress (322). As shown in FIGS. 8A-8G, first bead of adhesive (348) partially overlaps second bead of adhesive (350) along at least a portion of a length of buttress (322). Still in other areas, first bead of adhesive (348) is spaced apart from second bead of adhesive (350) along at least a portion of a length of buttress (322). As shown best in FIG. 7, second bead of adhesive (350) extends further proximally compared to first bead of adhesive (348). Furthermore, first and second beads of adhesive (348, 350) extend distally to substantially the same extent relative to buttress (322).

Now considering adhesive (320) as applied to second edge region (336), adhesive (320) comprises a third bead (352) and a fourth bead (354). Each bead of adhesive (352, 354) extends generally from proximal end (330) of buttress (322) to distal end (332) of buttress (322). As shown in FIGS. 8A-8G, third bead of adhesive (352) partially overlaps fourth bead of adhesive (354) along at least a portion of a length of buttress (322). Still in other areas, third bead of adhesive (352) is spaced apart from fourth bead of adhesive (354) along at least a portion of a length of buttress (322). As shown best in FIG. 7, fourth bead of adhesive (354) extends further proximally compared to third bead of adhesive (352). Furthermore, third and fourth beads of adhesive (352, 354) extend distally to substantially the same extent relative to buttress (322). As mentioned above, first and second beads of adhesive (348, 350) are collectively symmetrical with third and fourth beads of adhesive (352, 354) about longitudinal axis (A1) defining a centerline of buttress (322).

Considering now adhesive (320) as applied at proximal and distal ends (330, 332) of buttress (322), in the present example, an uneven distribution of adhesive (320) is used. This uneven distribution of adhesive (320) comprises more adhesive at distal end (332) of buttress (322) than at proximal end (330) of buttress (322). In the present example, this is the case when comparing buttress (322) prior to cutting into halves or when comparing halves of cut buttress (322). This uneven distribution of adhesive (320) is created at least in part by second bead of adhesive (350) and fourth bead of adhesive (354) extending further proximally into proximal end (330) of buttress (322) compared to respective first bead of adhesive (348) and third bead of adhesive (352). And further on distal end (332) both first and second beads of adhesive (348, 350) and both third and fourth beads of adhesive (352, 354) extend to the same extent. This arraignment results in more adhesive (320) at distal end (332) compared to proximal end (330) of buttress (322). In examples like the present one where more adhesive (320) is present at distal end (332) of buttress (322), this helps buttress (322) stay attached and aligned to and with the respective parts of end effector (40) when aggressively manipulating end effector (40), i.e. when piercing through ostomies, sliding axially onto tissue, etc.

As mentioned, distal end (332) of buttress (322) aligns with distal end (41) of end effector (40). Because distal end (41) of end effector (40) is the first part of end effector (40) to contact tissue when positioning end effector (40), distal end (41) of end effector (40) can be subject to greater forces in use compared to the proximal end of end effector (40). Because of this, having stronger attachment of buttress assemblies (316, 318) at distal end (41) of end effector (40) can be beneficial to maintaining attachment and alignment of buttress assemblies (316, 318) with respective parts of end effector (40). One way to achieve such stronger attachment at distal end (332) of buttress assemblies (316, 318) is by having more adhesive placed at distal end (332) of buttress (322). More adhesive (320) can be achieved by a volume basis, a mass basis, a surface area or contact area basis, or an area density basis. In view of the teachings herein, other ways to provide for stronger attachment between buttress assemblies (316, 318) at their distal ends (332) and respective components at distal end (41) of end effector (40) will be apparent to those of ordinary skill in the art in view of the teaching herein.

In use, releasing of buttress (322) from end effector (40) is also a consideration. Buttress (322) should release from end effector (40) such that it is transferred to the tissue cut and stapled site so buttress (322) can provide structural reinforcement to the site. With the clamping action of the jaws of end effector (40), there is a large aperture or opening of distal end (41) after end effector (40) has been fired and is being opened to remove end effector (40) from a cut and stapled site. This motion of distal end (41) with the large aperture or opening enables release of buttress (322) from distal end (41) of end effector (40) even with buttress (322) initially having more adhesive (320) at its distal end (332) compared to its proximal end (330).

The described adhesive pattern and distribution above can be seen in FIGS. 8A-8G that show cross sections of adhesive (320) along the length of buttress (322). For instance, FIG. 8A is taken along proximal end (330) of buttress assembly (316). As shown in FIG. 8A, second and fourth beads of adhesive (350, 354) extend further proximally than first and third beads of adhesive (348, 352). Also evident from FIG. 8A is proximal slit (342). Furthermore, as shown in FIGS. 7 and 8A, buttress (322) comprises a taper at its proximal end (330), where a width of buttress (322) decreases as buttress (322) extends proximally.

FIG. 8B illustrates an area where first bead of adhesive (348) partially overlaps second bead of adhesive (350), and similarly an area where third bead of adhesive (352) partially overlaps fourth bead of adhesive (354). As shown in FIG. 8B as well as the other views of FIGS. 8A and 8C-8G, adhesive (320) is symmetrical about longitudinal axis (A1).

FIG. 8C illustrates how first bead of adhesive (348) is spaced apart from second bead of adhesive (350) when examining adhesive (320) further distally along the length of buttress (322). Similarly, third bead of adhesive (352) is spaced apart from fourth bead of adhesive (354). At the location shown in FIG. 8C, center region (338) lacks any slit in the present example.

FIG. 8D illustrates the adhesive pattern and distribution at an approximate middle of the length of buttress assemblies (316, 318). Here again, first bead of adhesive (348) partially overlaps second bead of adhesive (350), and similarly third bead of adhesive (352) partially overlaps fourth bead of adhesive (354). When comparing FIG. 8D with 8B, in the present example, the degree of adhesive overlap is greater at the approximate middle of the length of buttress assemblies (316, 318) as evident by the larger width of the overlap.

FIG. 8E illustrates a similar arrangement as shown in FIG. 8C. The only difference with FIG. 8E is that slit (346) splits buttress (322) into halves along the length shown in FIG. 8E, whereas center region (338) lacks any slit along the length shown in FIG. 8C.

FIG. 8F illustrates a similar arrangement as shown in FIG. 8D. The only difference with FIG. 8F is that center region (338) comprises distal slit (344) along the length shown in FIG. 8F, whereas center region (338) comprises intermediate slit (346) along the length shown in FIG. 8D.

FIG. 8G illustrates adhesive (320) at distal end (332) of buttress (322). As seen in FIGS. 7 and 8G, second bead of adhesive (350) extends away from center region (338) at distal end (332) of buttress (322). Similarly, fourth bead of adhesive (354) extends away from center region (338) at distal end (332) of buttress (322). In the present example, second bead of adhesive (350) extends away from center region (338) such that second bead of adhesive (350) connects with or contacts first bead of adhesive (348) at distal end (332) of buttress (322). Also, fourth bead of adhesive (354) extends away from center region (338) such that fourth bead of adhesive (354) connects with or contacts third bead of adhesive (352) at distal end (332) of buttress (322). As also shown in FIG. 8G, buttress (322) comprises a gap (356) at distal end (332), where gap (356) aligns with center region (338). Referring to FIG. 7, a gap (358) is also present at proximal end (330) in the present example.

C. Exemplary Adhesive Heights

Figure 10:
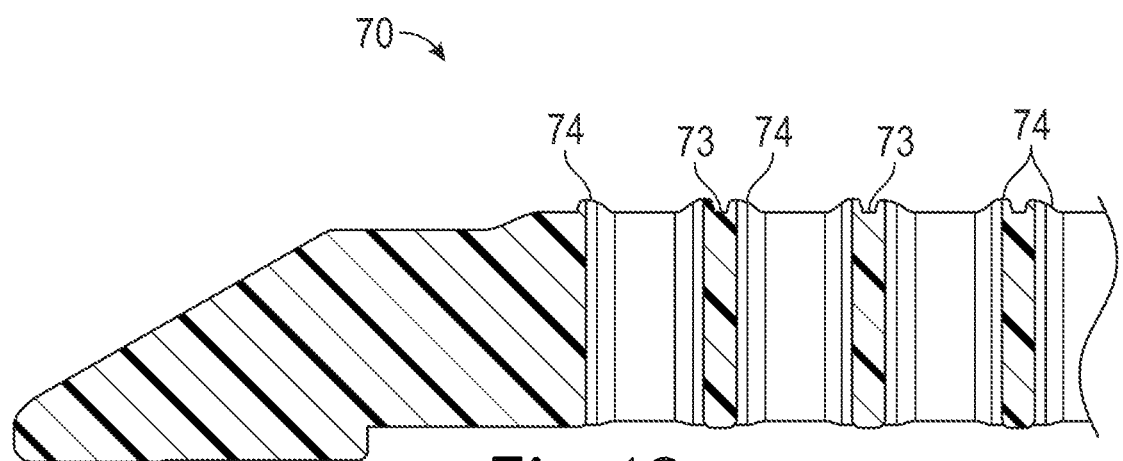
FIG. 10 depicts a cross section view of a staple cartridge of the end effector of FIG. 1.

As mentioned above adhesive height is a feature or attribute that facilitates attachment and release of buttress (322) with anvil (60) and staple cartridge (70) components of end effector (40). In this respect height of adhesive (320) is understood as the distance adhesive (320) protrudes from the surface of buttress (322) to which it is applied. In the present example, beads of adhesive (348, 350, 352, 354) have a minimum height. In one example, the minimum height is configured to approximate, match, or exceed the height of pocket extenders (74) on deck (73) of staple cartridge (70). FIG. 10 illustrates a cross section view of a version of staple cartridge (70) having pocket extenders (74). Pocket extenders (74) protrude above deck (73) of staple cartridge (70) and can assist in gripping tissue captured by end effector (40). By configuring adhesive beads (348, 350, 352, 354) with a minimum height that approximates, matches, or exceeds the distance that pocket extenders (74) protrude above deck (73), adhesive (320) can be in contact with the surface of pocket extenders (74) but also with the surface of deck (73) between pocket extenders (74). This provides for good attachment of one of buttress assemblies (316, 318) with staple cartridge (70) during the buttress loading process and increases retention of buttress (322) to this component of end effector (40) when working with and positioning end effector (40). While pocket extenders (74) are used with the version of staple cartridge (70) shown in FIG. 10, in other versions of staple cartridge (70) pocket extenders (74) are omitted such that deck (73) is flat with the exception of the openings for driving staples (90).

In one example, beads of adhesive (348, 350, 352, 354) have a height between about 0.010 inches (0.254 mm) and about 0.050 inches (1.27 mm). In another example, beads of adhesive (348, 350, 352, 354) have a height between about 0.016 inches (0.4064 mm) and about 0.030 inches (0.762 mm). In view of the teachings herein, other heights for beads of adhesive (348, 350, 352, 354) will be apparent to those of ordinary skill in the art.

In another example of a minimum adhesive height, beads of adhesive (348, 350, 352, 354) have a minimum height that is configured to approximate, match, or exceed the depth of staple forming pockets (64) of anvil (60). By way of reference, staple forming pockets (64) are illustrated in FIGS. 3A-3B. By configuring adhesive beads (348, 350, 352, 354) with a minimum height that approximates, matches, or exceeds the depth of staple forming pockets (64), adhesive (320) can be in contact with underside (65) of anvil (60) but also extend into staple forming pockets (64). This provides for good attachment of one of buttress assemblies (316, 318) with anvil (60) during the buttress loading process and increases retention of buttress (322) to this component of end effector (40) when working with and positioning end effector (40).

In some examples, like end effector (40) having anvil (60) and staple cartridge (70), the depth of staple forming pockets (64) of anvil (60) can be different from the distance that pocket extenders (74) protrude above deck (73) of staple cartridge (70). In such instances where buttress assemblies (316, 318) are identical, beads of adhesive (348, 350, 352, 354) can be configured such that the minimum height is based on the larger distance. For instance in an example where staple forming pockets (64) are shallower than pocket extenders (74)—such that staple forming pockets (64) have a depth that is less than the distance pocket extenders (74) protrude from deck (73)—beads of adhesive (348, 350, 352, 354) can be configured such that the minimum height is based on the distance pocket extenders (74) protrude above deck (73) as that is the greater distance compared with the depth of staple forming pockets (64) of anvil (60). Still in other versions, buttress assemblies (316, 318) could be configured differently in terms of adhesive heights to configure the adhesive heights specific to either the anvil side or staple cartridge side of the end effector. However, by setting the minimum adhesive height based on the greater distance, the good attachment and retention results can be obtained in a symmetric configuration that allows applicator (300) to be universal and not specific to any particular side of the end effector when loading a buttress assembly thereto.

In the present example where adhesive (320) is applied in beads, various adhesive heights can be achieved in a more efficient manner compared to applying a uniform spray of adhesive across the entire surface of buttress (322). This efficiency is realized both in terms of material usage and cost. Additionally, while the above examples show and describe adhesive height with respect to linear style buttress assemblies (316, 318), adhesive height can be controlled and configured in the same ways with circular buttresses such as buttress assembly (416) of FIG. 9.

D. Exemplary Asymmetric Adhesive Distributions

When loading buttress assemblies to an end effector and applying them to a tissue cut and stapled site, another consideration, besides good attachment and retention of the buttress assemblies with the end effector, is release of the buttress assemblies from the end effector after executing a cut and staple operation. For instance, if release is poor, buttress assemblies can adhere to the end effector instead of transferring to the tissue, or buttress assemblies can bunch or fold instead of laying flat and smooth against the tissue site. Referring now to FIGS. 11-14, buttress assemblies are shown that use asymmetric adhesive distributions to achieve both desired attachment and retention and also release of buttress assemblies.

Figure 11:
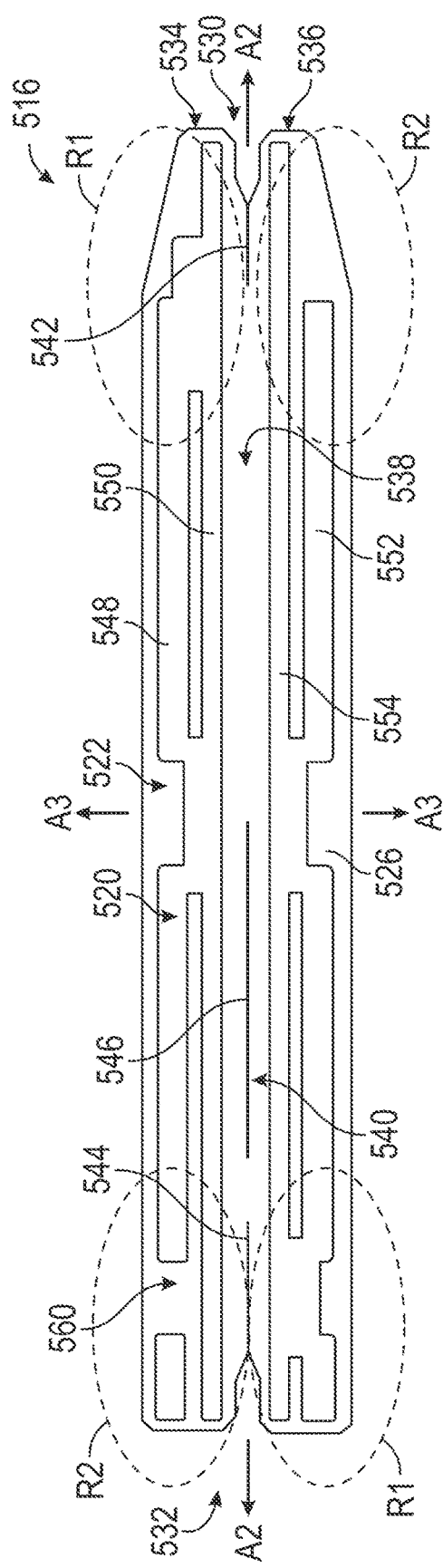
FIG. 11 depicts a top plan view of another exemplary buttress assembly showing an exemplary asymmetric adhesive distribution.

FIG. 11 illustrates a buttress assembly (516) having an asymmetric adhesive distribution. Buttress assembly (516) is configured similar to buttress assemblies (316, 318) described above, except with a different adhesive application pattern. Accordingly, two buttress assemblies (516) can be used in place of buttress assemblies (316, 318) described above. This includes being used in place of buttress assemblies (316, 318) with applicator (300) and end effector (40).

In the present example of FIG. 11, buttress assembly (516) comprises buttress (522) and adhesive (520) on one side of buttress (522). Buttress (522) comprises a first surface (526) and a second surface opposite to first surface (526). Buttress also includes a proximal end (530) and a distal end (532). As with buttress assemblies (316, 318) when buttress assembly (516) is attached with end effector (40) distal end (532) of buttress (522) aligns with a distal end (41) of end effector (40). With this configuration, buttress (522) defines a length extending from proximal end (530) to distal end (532). Buttress (522) further defines a longitudinal axis (A2) that extends between proximal end (530) and distal end (532). Buttress (522) includes a first edge region (534), a second edge region (536), and a center region (538) between and separating first edge region (534) and second edge region (536). Buttress (522) defines a width extending orthogonal to its length as defined above, where its width extends from first edge region (534) across center region (538) and through second edge region (536).

In the present example, adhesive (520) is applied onto first surface (526) of buttress (522). Adhesive (520) extends from proximal end (530) to distal end (532) of buttress (522). Moreover, in the present example, at least a portion of adhesive (520) extends continuously or in an uninterrupted manner. Adhesive (520) is located along first edge region (534) and second edge region (536), with center region (538) being substantially free of adhesive (520). As described above, adhesive (520) is applied to buttress in a manner such that adhesive (520) comprises a height such that adhesive (520) is proud of buttress (522). The height of adhesive (520) is configured to facilitate adhesive (520) making good contact with either underside (65) of anvil (60) of end effector (40) or deck (73) of staple cartridge (70) of end effector (40) depending on the orientation of end effector (40) when loading buttress assembly (516) onto end effector (40) using applicator (300).

The continuous nature of adhesive (520) along with the height of adhesive (520) act to seal the edges of buttress (522) to the part of end effector (40) to which buttress (522) attaches. With this sealing attachment, in use the amount of moisture that can reach buttress assembly (516) is reduced. By controlling moisture migration in this manner, buttress assembly (516) can have longer attachment times with end effector (40). This can give users greater lengths of time to position and manipulate end effector (40) before executing a cutting and stapling action, thereby applying buttresses (522) as reinforcing structures to the cut and stapled site.

Referring still to FIG. 11, center region (538) of buttress (522) comprises slits (540), which are structurally and functionally the same as slits (340) of buttress assemblies (316, 318). In the illustrated version, slits (540) include a proximal slit (542), a distal slit (544), and an intermediate slit (546) between proximal and distal slits (542, 544). In the present example, longitudinal axis (A2) passes through slits (540), and on each side of center region (538), adhesive (520) defines a pattern that is asymmetrical with the other side about longitudinal axis (A2). Adhesive (520) is further asymmetrical about a lateral axis (A3) that extends orthogonal relative to longitudinal axis (A2) through a midpoint of buttress assembly (516) as measured between proximal and distal ends (330, 332).

Now considering adhesive (520) as applied to first edge region (534), adhesive (520) comprises a first bead (548) and a second bead (550). Each bead of adhesive (548, 550) extends generally from proximal end (530) of buttress (522) to distal end (532) of buttress (522). First bead of adhesive (548) partially overlaps second bead of adhesive (550) along at least a portion of a length of buttress (522), specifically in the present example near proximal end (530) and near a middle area along the length of buttress (522) as shown in FIG. 11. In other areas, first bead of adhesive (548) is spaced apart from second bead of adhesive (550) along at least a portion of a length of buttress (522). Second bead of adhesive (550) extends further proximally compared to first bead of adhesive (548). Furthermore, first and second beads of adhesive (548, 550) extend distally to substantially the same extent relative to buttress (522). First bead of adhesive (548) is discontinuous near distal end (532) of buttress (522), where there is a space or gap (560) in first bead of adhesive (548). In contrast, second bead of adhesive (550) extends continuously from proximal end (530) to distal end (532) of buttress (522).

Now considering adhesive (520) as applied to second edge region (536), adhesive (520) comprises a third bead (552) and a fourth bead (554). Each bead of adhesive (552, 554) extends generally from proximal end (530) of buttress (522) to distal end (532) of buttress (522). Third bead of adhesive (552) partially overlaps fourth bead of adhesive (554) along at least a portion of a length of buttress (522), specifically in the present example near distal end (532) and near a middle area along the length of buttress (522). In other areas, third bead of adhesive (552) is spaced apart from fourth bead of adhesive (554) along at least a portion of a length of buttress (522). Fourth bead of adhesive (554) extends further proximally compared to third bead of adhesive (552). Furthermore, third and fourth beads of adhesive (552, 554) extend distally to substantially the same extent relative to buttress (522). In the present example, while third and fourth beads of adhesive (552, 554) have different shapes or patterns, both extend continuously from proximal end (530) to distal end (532) of buttress (522).

As mentioned above, first and second beads of adhesive (548, 550) are collectively asymmetrical with third and fourth beads of adhesive (552, 554) about longitudinal axis (A2) and lateral axis (A3). As also mentioned above, buttress (522) is configured to be cut into two halves about a longitudinal centerline of buttress (522). A first half of cut buttress (522) would include first edge region (534) and about half of center region (538), while a second half of cut buttress (522) would include second edge region (536) and about the other half of center region (538).

Considering now adhesive (520) as applied at proximal and distal ends (530, 532) of respective halves of buttress (522), in the present example, an uneven distribution of adhesive (520) is used. With respect to the first half of a cut buttress (522), there is more adhesive (520) at proximal end (530) of buttress (522) than at distal end (532) of buttress (522). However, with respect to the second half of a cut buttress (522), there is more adhesive (520) at distal end (532) of buttress (522) than at proximal end (530) of buttress (522). Referring to FIG. 11, these differences in adhesive (520) amounts are shown by circled regions, where first regions (R1) have more adhesive (520) than second regions (R2).

When using two buttress assemblies (516), when applied to end effector (40), each buttress assembly (516) is oriented opposite the other with first surfaces (526) containing adhesive (520) facing away from each other. In this arrangement, first edge region (534) of buttress assembly (516) attached with anvil (60) will be above and aligned with second edge region (536) of buttress assembly (516) attached with staple cartridge (70). Similarly, second edge region (536) of buttress assembly (516) attached with anvil (60) will be above and aligned with first edge region (534) of buttress assembly (516) attached with staple cartridge (70). In this arrangement, first regions (R1) having more adhesive (520) will be oriented opposite and aligned with second regions (R2) having less adhesive (520). By way of example only, at proximal end (530), buttress assembly (516) attached with anvil (60) will have first region (R1) positioned opposite and aligned with second region (R2) of the other buttress assembly (516) that is attached with staple cartridge (70). Likewise, and still at proximal end (530), buttress assembly (516) attached with anvil (60) will have second region (R2) positioned opposite and aligned with first region (R1) of the other buttress assembly (516) that is attached with staple cartridge (70). At distal end (532), buttress assembly (516) attached with anvil (60) will have second region (R2) positioned opposite and aligned with first region (R1) of the other buttress assembly (516) that is attached with staple cartridge (70). Likewise, and still at distal end (532), buttress assembly (516) attached with anvil (60) will have first region (R1) positioned opposite and aligned with second region (R2) of the other buttress assembly (516) that is attached with staple cartridge (70).

When considering buttress assembly (516) before it is cut in halves, there are two first regions (R1) in the present example for buttress assembly (516) attached on anvil (60) side of end effector (40). One such first region (R1) is within first edge region (534) at proximal end (530), and the other is within second edge region (536) at distal end (532). This is the same with respect to buttress assembly (516) attached on staple cartridge (70) side of end effector (40). These first regions (R1) with the more adhesive help buttresses (522) stay attached and aligned to and with the respective parts of end effector (40) when aggressively manipulating end effector (40), i.e. when piercing through ostomies, sliding axially onto tissue, etc. Furthermore, because buttress assemblies (516) are not yet cut, these areas of greater adhesive work to attach and retain the entire buttress assembly (516) with its respective parts of end effector (40).

Still considering buttress assembly (516) before it is cut in halves, there are two second regions (R2) in the present example for buttress assembly (516) attached on anvil (60) side of end effector (40). One such second region (R2) is within first edge region (534) at proximal end (530), and the other is within second edge region (536) at distal end (532). This is the same with respect to buttress assembly (516) attached on staple cartridge (70) side of end effector (40). These second regions (R2) with the less adhesive help buttresses (522) properly release from end effector (40) after a cut and staple operation. However, because buttress assemblies (516) are not yet cut, these areas of lower adhesive are still attached and retained on their respective parts of end effector (40) in part due to those first regions (R1) with greater adhesive (520) as discussed above.

Figure 12:
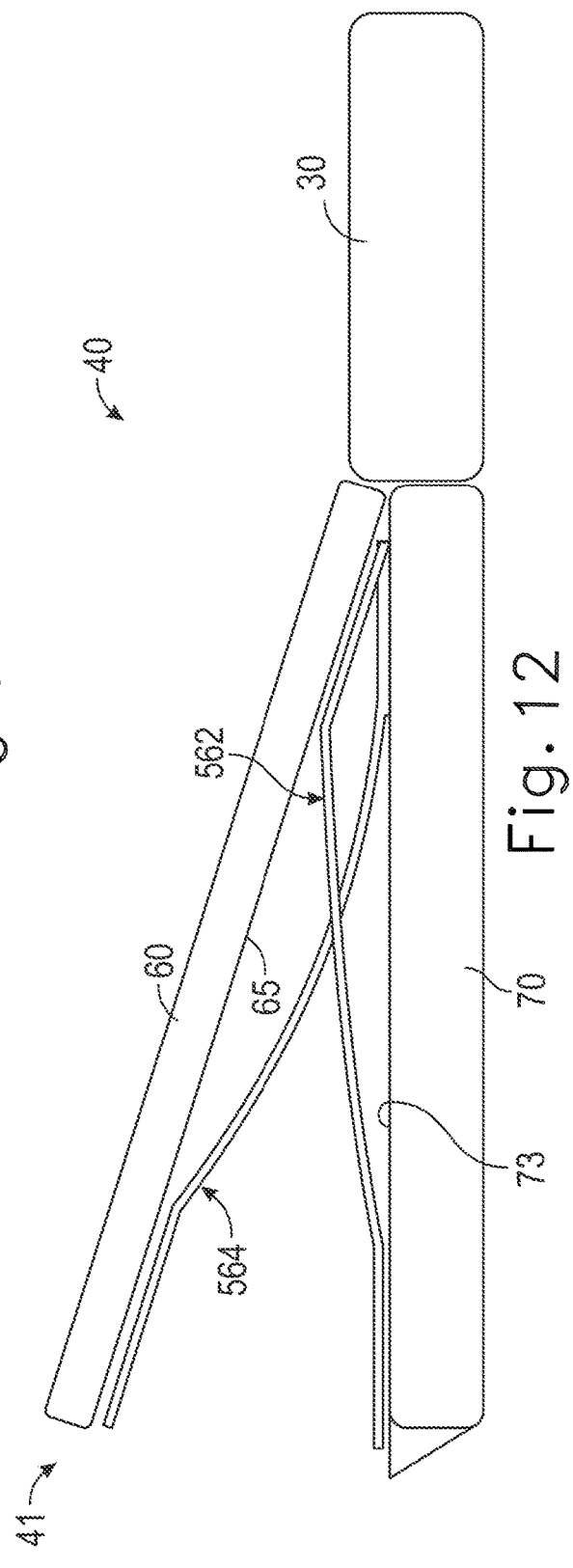
FIG. 12 depicts a side elevation view of an end effector for a surgical stapler in an open position, showing the buttress assembly of FIG. 11 releasing from the jaws of the end effector.

Referring to FIG. 12, a side view of end effector (40) is shown during an exemplary opening operation after a cut and staple action, and thus after buttress assembly (516) has been cut into halves. With the asymmetric distribution of adhesive (520) described above, when end effector (40) is opened after cutting and stapling, having first regions (R1) with more adhesive (520) opposite second regions (R2) with less adhesive (520) reduces the adhesive attachment to the respective surfaces on anvil (60) and staple cartridge (70). For instance, upon opening end effector (40) after a cutting and stapling action, second regions (R2) with less adhesive (520) detach or release from end effector (40) prior to first regions (R1) with the greater adhesive (520). As mentioned above, prior to cutting buttress assembly (516) into halves, buttress assembly (516) operates as a unit and thus the combined first areas (R1) with greater adhesive provide for attachment and retention of buttress assembly (516). However, this changes once buttress assembly (516) is cut into halves as second regions (R2) will now release from end effector (40).

For ease of illustration, FIG. 12 shows end effector (40) loaded with a single buttress assembly (516) on staple cartridge (70) side, where a cut and staple operation has occurred such that the knife of end effector (40) has cut buttress assembly (516) into halves. In FIG. 12, first half (562) and second half (564) of buttress assembly (516) are shown with their attachment and release profiles. First half (562) represents first edge region (534) and half of center region (538) as illustrated in FIG. 11. As shown, first half (562) has first region (R1) with the greater adhesive (520) located at the proximal end of staple cartridge (70). Thus when opening end effector (40) initially, first half (562) remains attached with staple cartridge (70) near the proximal end of staple cartridge (70). First half (562) has second region (R2) with less adhesive (520) located at the distal end of staple cartridge (70). Thus when opening end effector (40) initially, first half (562) releases from staple cartridge (70) near the distal end of staple cartridge (70). Second half (564) represents second edge region (536) and half of center region (538) as illustrated in FIG. 11. As shown, second half (564) has first region (R1) with the greater adhesive (520) located at the distal end of staple cartridge (70). Thus when opening end effector (40) initially, second half (564) remains attached with staple cartridge (70) near the distal end of staple cartridge (70). Second half (564) has second region (R2) with less adhesive (520) located at the proximal end of staple cartridge (70). Thus when opening end effector (40) initially, second half (564) releases from staple cartridge (70) near the proximal end of staple cartridge (70). This pattern of attachment and release post cutting and stapling would also be evident on anvil (60) side of end effector (40) for buttress assembly (516) loaded onto anvil (60).

Other than the disparity in adhesive (520) described above, another factor that contributes to the release of buttress assembly (516) from end effector (40) is the large aperture or large motion of distal end (41) of end effector (40) when being opened after a cut and staple action. This large range of motion for distal end (41) of end effector (40) also works with the fact that after the cut and staple action two opposing halves of two buttress assemblies (516) are now stapled together with tissue therebetween. Accordingly, these factors provide for release of buttress assemblies (516) even at first regions (R1) that have greater adhesive that was adhering buttress assemblies (516) to respective parts of end effector (40).

Referring now to FIGS. 13 and 14, FIG. 13 illustrates a buttress assembly (616) having another exemplary asymmetric adhesive distribution. Buttress assembly (616) is configured similar to buttress assemblies (316, 318) described above, except with a different adhesive application pattern. Accordingly, two buttress assemblies (616) can be used in place of buttress assemblies (316, 318) described above. This includes being used in place of buttress assemblies (316, 318) with applicator (300) and end effector (40).

In the present example of FIG. 13, buttress assembly (616) comprises buttress (622) and adhesive (620) on one side of buttress (622). Buttress (622) comprises a first surface (626) and a second surface opposite to first surface (626). Buttress also includes a proximal end (630) and a distal end (632). As with buttress assemblies (316, 318) when buttress assembly (616) is attached with end effector (40) distal end (632) of buttress (622) aligns with a distal end (41) of end effector (40). With this configuration, buttress (622) defines a length extending from proximal end (630) to distal end (632). Buttress (622) further defines a longitudinal axis (A4) that extends between proximal end (630) and distal end (632). Buttress (622) includes a first edge region (634), a second edge region (636), and a center region (638) between and separating first edge region (634) and second edge region (636). Buttress (622) defines a width extending orthogonal to its length as defined above, where its width extends from first edge region (634) across center region (638) and through second edge region (636).

In the present example, adhesive (620) is applied onto first surface (626) of buttress (622). Adhesive (620) extends from proximal end (630) to distal end (632) of buttress (622). Moreover, in the present example, at least a portion of adhesive (620) extends continuously or in an uninterrupted manner. Adhesive (620) is located along first edge region (634) and second edge region (636), with center region (638) being substantially free of adhesive (620). As described above, adhesive (620) is applied to buttress in a manner such that adhesive (620) comprises a height such that adhesive (620) is proud of buttress (622). The height of adhesive (620) is configured to facilitate adhesive (620) making good contact with either underside (65) of anvil (60) of end effector (40) or deck (73) of staple cartridge (70) of end effector (40) depending on the orientation of end effector (40) when loading buttress assembly (616) onto end effector (40) using applicator (300).

The continuous nature of adhesive (620) along with the height of adhesive (620) act to seal the edges of buttress (622) to the part of end effector (40) to which buttress (622) attaches. With this sealing attachment, in use the amount of moisture that can reach buttress assembly (616) is reduced. By controlling moisture migration in this manner, buttress assembly (616) can have longer attachment times with end effector (40). This can give users greater lengths of time to position and manipulate end effector (40) before executing a cutting and stapling action, thereby applying buttresses (622) as reinforcing structures to the cut and stapled site.

Referring still to FIG. 13, center region (638) of buttress (622) comprises slits (640), which are structurally and functionally the same as slits (340) of buttress assemblies (316, 318). In the illustrated version, slits (640) include a proximal slit (642), a distal slit (644), and an intermediate slit (646) between proximal and distal slits (642, 644). In the present example, longitudinal axis (A4) passes through slits (640), and on each side of center region (638), adhesive (620) defines a pattern that is asymmetrical with the other side about longitudinal axis (A4). Adhesive (620) is further asymmetrical about a lateral axis (A5) that extends orthogonal relative to longitudinal axis (A4) through a midpoint of buttress assembly (616) as measured between proximal and distal ends (630, 632).

Now considering adhesive (620) as applied to first edge region (634), adhesive (620) comprises a first bead (648) and a second bead (650). Each bead of adhesive (648, 650) extends generally from proximal end (630) of buttress (622) to distal end (632) of buttress (622). First bead of adhesive (648) partially overlaps second bead of adhesive (650) along at least a portion of a length of buttress (622), specifically in the present example near proximal end (630), near a middle area along the length of buttress (622), and near distal end (632) as shown in FIG. 13. In other areas, first bead of adhesive (648) is spaced apart from second bead of adhesive (650) along at least a portion of a length of buttress (622). Second bead of adhesive (650) extends further proximally compared to first bead of adhesive (648). Furthermore, first and second beads of adhesive (648, 650) extend distally to substantially the same extent relative to buttress (622). In the present example, while first and second beads of adhesive (648, 650) have different shapes or patterns, both extend continuously from proximal end (630) to distal end (632) of buttress (622).

Now considering adhesive (620) as applied to second edge region (636), adhesive (620) comprises a third bead (652) and a fourth bead (654). Each bead of adhesive (652, 654) extends generally from proximal end (630) of buttress (622) to distal end (632) of buttress (622). Third bead of adhesive (652) partially overlaps fourth bead of adhesive (654) along at least a portion of a length of buttress (622), specifically in the present example near distal end (632) and near proximal end (630). In other areas, third bead of adhesive (652) is spaced apart from fourth bead of adhesive (654) along at least a portion of a length of buttress (622). Fourth bead of adhesive (654) extends further proximally compared to third bead of adhesive (652). Furthermore, third and fourth beads of adhesive (652, 654) extend distally to substantially the same extent relative to buttress (622). Third bead of adhesive (652) is discontinuous near a middle section of buttress (622), where there is a space or gap (660) in third bead of adhesive (652). In contrast, fourth bead of adhesive (654) extends continuously from proximal end (630) to distal end (632) of buttress (622).

As mentioned above, first and second beads of adhesive (648, 650) are collectively asymmetrical with third and fourth beads of adhesive (652, 654) about longitudinal axis (A4) and lateral axis (A5). As also mentioned above, buttress (622) is configured to be cut into two halves about a longitudinal centerline of buttress (622). A first half of cut buttress (622) would include first edge region (634) and about half of center region (638), while a second half of cut buttress (622) would include second edge region (636) and about the other half of center region (638).

Considering now adhesive (620) as applied at proximal and distal ends (630, 632) of respective halves of buttress (622), in the present example, an uneven distribution of adhesive (620) is used. With respect to the first half of a cut buttress (622), there is more adhesive (620) at a middle region of buttress (622) than at proximal and distal ends (630, 632) of buttress (622). However, with respect to the second half of a cut buttress (622), there is more adhesive (620) at proximal and distal ends (630, 632) of buttress (522) than at the middle region of buttress (622). Referring to FIG. 13, these differences in adhesive (620) amounts are shown by circled regions, where first regions (R1) have more adhesive (620) than second regions (R2).

When using two buttress assemblies (616), when applied to end effector (40), each buttress assembly (616) is oriented opposite the other with first surfaces (626) containing adhesive (620) facing away from each other. In this arrangement, first edge region (634) of buttress assembly (616) attached with anvil (60) will be above and aligned with second edge region (636) of buttress assembly (616) attached with staple cartridge (70). Similarly, second edge region (636) of buttress assembly (616) attached with anvil (60) will be above and aligned with first edge region (634) of buttress assembly (616) attached with staple cartridge (70). In this arrangement, first regions (R1) having more adhesive (620) will be oriented opposite and aligned with second regions (R2) having less adhesive (620). By way of example only, at proximal end (630), buttress assembly (616) attached with anvil (60) will have first region (R1) positioned opposite and aligned with second region (R2) of the other buttress assembly (616) that is attached with staple cartridge (70). Likewise, and still at proximal end (630), buttress assembly (616) attached with anvil (60) will have second region (R2) positioned opposite and aligned with first region (R1) of the other buttress assembly (616) that is attached with staple cartridge (70). At distal end (632), buttress assembly (616) attached with anvil (60) will have second region (R2) positioned opposite and aligned with first region (R1) of the other buttress assembly (616) that is attached with staple cartridge (70). Likewise, and still at distal end (632), buttress assembly (616) attached with anvil (60) will have first region (R1) positioned opposite and aligned with second region (R2) of the other buttress assembly (616) that is attached with staple cartridge (70). Near the middle region, buttress assembly (616) attached with anvil (60) will have first region (R1) positioned opposite and aligned with second region (R2) of the other buttress assembly (616) that is attached with staple cartridge (70). Likewise, and still at the middle region, buttress assembly (616) attached with anvil (60) will have second region (R2) positioned opposite and aligned with first region (R1) of the other buttress assembly (616) that is attached with staple cartridge (70).

When considering buttress assembly (616) before it is cut in halves, there are three first regions (R1) in the present example for buttress assembly (616) attached on anvil (60) side of end effector (40). One such first region (R1) is within first edge region (634) at the middle region of buttress (622), another first region (R1) is within second edge region (636) at distal end (632), and another first region (R1) is also within second edge region (636) at proximal end (630). This is the same with respect to buttress assembly (616) attached on staple cartridge (70) side of end effector (40). These first regions (R1) with the more adhesive help buttresses (622)

stay attached and aligned to and with the respective parts of end effector (40) when aggressively manipulating end effector (40), i.e. when piercing through ostomies, sliding axially onto tissue, etc. Furthermore, because buttress assemblies (616) are not yet cut, these areas of greater adhesive work to attach and retain the entire buttress assembly (616) with its respective parts of end effector (40).

Still considering buttress assembly (616) before it is cut in halves, there are three second regions (R2) in the present example for buttress assembly (616) attached on anvil (60) side of end effector (40). One such second region (R2) is within first edge region (634) at proximal end (630), another is within first edge region (634) at distal end (632), another is within second edge region (636) at the middle region of buttress (622). This is the same with respect to buttress assembly (616) attached on staple cartridge (70) side of end effector (40). These second regions (R2) with the less adhesive help buttresses (622) properly release from end effector (40) after a cut and staple operation. However, because buttress assemblies (616) are not yet cut, these areas of lower adhesive are still attached and retained on their respective parts of end effector (40) in part due to those first regions (R1) with greater adhesive (620) as discussed above.

Referring to FIG. 14, a side view of end effector (40) is shown during an exemplary opening operation after a cut and staple action, and thus after buttress assembly (616) has been cut into halves. With the asymmetric distribution of adhesive (620) described above, when end effector (40) is opened after cutting and stapling, having first regions (R1) with more adhesive (620) opposite second regions (R2) with less adhesive (620) reduces the adhesive attachment to the respective surfaces on anvil (60) and staple cartridge (70). For instance, upon opening end effector (40) after a cutting and stapling action, second regions (R2) with less adhesive (620) detach or release from end effector (40) prior to first regions (R1) with the greater adhesive (620). As mentioned above, prior to cutting buttress assembly (616) into halves, buttress assembly (616) operates as a unit and thus the combined first areas (R1) with greater adhesive provide for attachment and retention of buttress assembly (616). However, this changes once buttress assembly (616) is cut into halves as second regions (R2) will now release from end effector (40).

For ease of illustration, FIG. 14 shows end effector (40) loaded with a single buttress assembly (616) on staple cartridge (70) side, where a cut and staple operation has occurred such that the knife of end effector (40) has cut buttress assembly (616) into halves. In FIG. 14, first half (662) and second half (664) of buttress assembly (616) are shown with their attachment and release profiles. First half (662) represents first edge region (634) and half of center region (638) as illustrated in FIG. 13. As shown, first half (662) has first region (R1) with the greater adhesive (620) located at a middle region of staple cartridge (70). Thus when opening end effector (40) initially, first half (662) remains attached with staple cartridge (70) near the middle region of staple cartridge (70). First half (662) has second region (R2) with less adhesive (620) located at the proximal and distal ends of staple cartridge (70). Thus when opening end effector (40) initially, first half (662) releases from staple cartridge (70) near the proximal and distal ends of staple cartridge (70).

Second half (664) represents second edge region (636) and half of center region (638) as illustrated in FIG. 13. As shown, second half (664) has first region (R1) with the greater adhesive (620) located at the proximal and distal ends of staple cartridge (70). Thus when opening end effector (40) initially, second half (664) remains attached with staple cartridge (70) near the proximal and distal ends of staple cartridge (70). Second half (664) has second region (R2) with less adhesive (620) located at the middle region of staple cartridge (70). Thus when opening end effector (40) initially, second half (664) releases from staple cartridge (70) near the middle region of staple cartridge (70). This pattern of attachment and release post cutting and stapling would also be evident on anvil (60) side of end effector (40) for buttress assembly (616) loaded onto anvil (60).

Other than the disparity in adhesive (620) described above, another factor that contributes to the release of buttress assembly (616) from end effector (40) is the large aperture or large motion of distal end (41) of end effector (40) when being opened after a cut and staple action. This large range of motion for distal end (41) of end effector (40) also works with the fact that after the cut and staple action two opposing halves of two buttress assemblies (616) are now stapled together with tissue therebetween. Accordingly, these factors provide for release of buttress assemblies (616) even at first regions (R1) that have greater adhesive that was adhering buttress assemblies (616) to respective parts of end effector (40).

As shown and described in the examples above, using an asymmetric distribution of adhesive (520, 620) on buttress assemblies (516, 616) allows for a reduction in the release force, or force required to release buttress assemblies (516, 616) from end effector (40) after buttress assemblies (516, 616) are cut into halves. This allows for buttress assemblies (516, 616) to be configured with a controlled release where certain portions of buttress assemblies (516, 616) are configured to release earlier or sooner than other portions. Furthermore, strategically locating regions of asymmetric adhesive distribution provides for adequate attachment and retention of the uncut buttress assemblies (516, 616). While multiple adhesive distributions have been shown and described herein, other adhesive distributions can be used to achieve desired attachment, retention, and release properties for buttress assemblies described herein. In view of the teachings herein, such other patterns of adhesive distribution for buttress assemblies described herein will be apparent to those of ordinary skill in the art.

IV. Exemplary Buttress Construction and Arrangement

Figure 15:
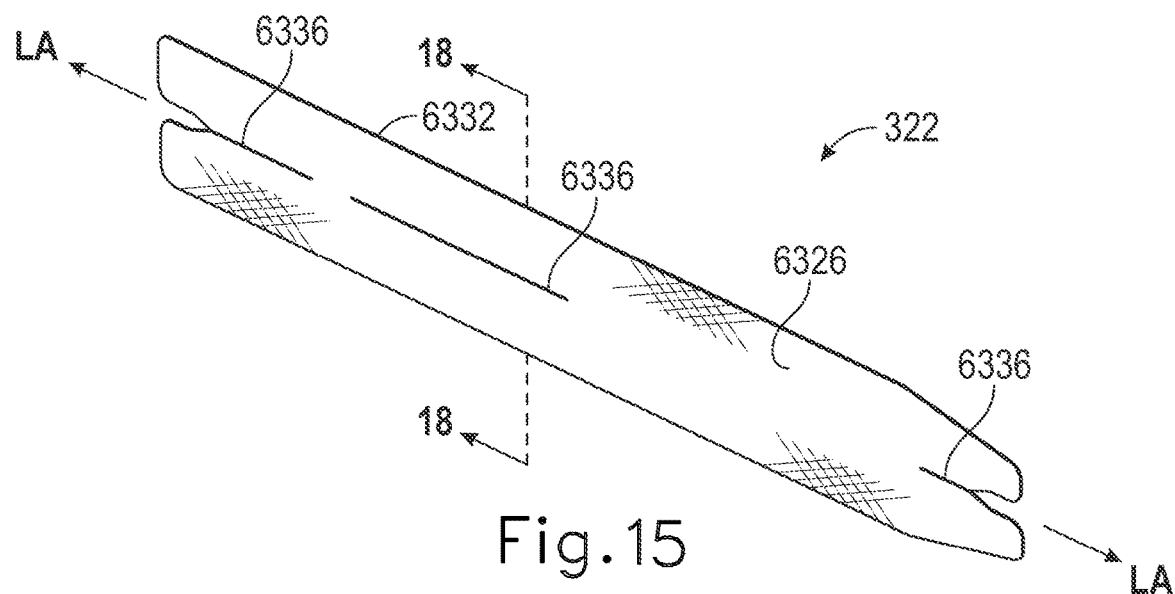
FIG. 15 depicts a perspective view of an exemplary buttress of the buttress assembly of the buttress applicator of FIG. 5, showing a mesh layer.
Figure 16:
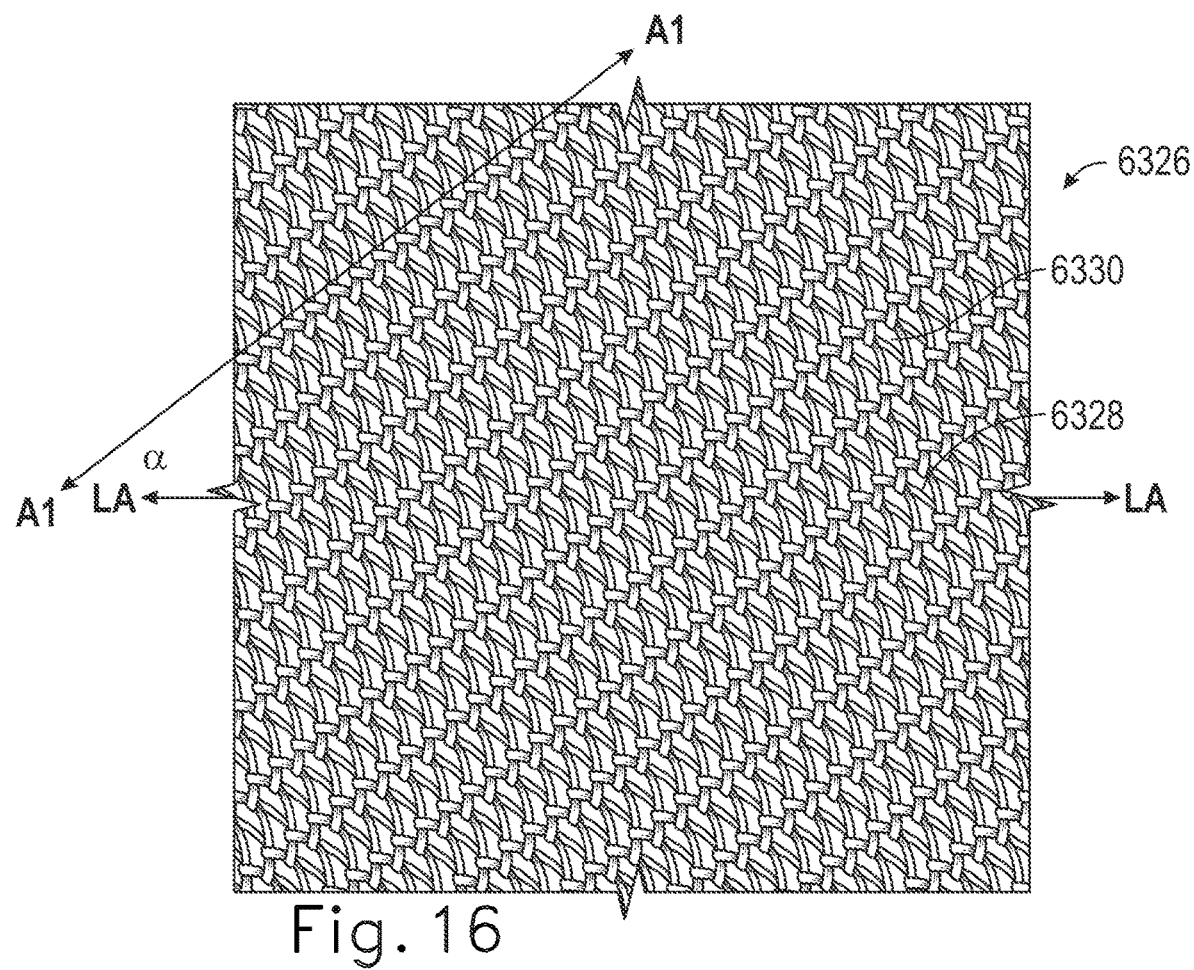
FIG. 16 depicts an enlarged view of the mesh layer of the buttress of FIG. 15.

FIGS. 15 and 16 illustrate buttress (322) of buttress assemblies (316, 318). Buttress (322) comprises a multilayer material that is laminated together. In the present example, buttress (322) comprises a mesh layer (6326) and two film layers (6332, 6334). Mesh layer (6326) comprises a knitted synthetic absorbable material. In some examples, mesh layer (6326) is knit using yarns (6328) comprised of polyglactin 910, which is 90% glycolide and 10% L-lactide. An example of polyglactin 910 is manufactured by Ethicon Inc. under the brand name Vicryl®. In view of the teachings herein, other absorbable synthetic materials for use with mesh layer (6326) will be apparent to those of ordinary skill in the art.

FIG. 16 illustrates an enlarged portion of mesh layer (6326), showing an exemplary knit pattern produced by the arrangement of yarns (6328). In the present example, each yarn (6328) comprises a bundle or structure having 28 individual filaments. However, in other versions each yarn (6328) can comprise a single filament or a multifilament bundle with greater or fewer than 28 individual filaments. An example of the multifilament structures of mesh layer (6326) can be seen in FIG. 18, where the uncut yarns in cross section illustrate multiple filaments (6329) that make up the multifilament structure of yarns (6328).

As best seen in FIG. 16, mesh layer (6326) comprises a plurality of openings (6330) defined by the knit yarns (6328). With its openings (6330) mesh layer (6326) comprises a porosity. Depending on the number and/or size of openings (6330) the porosity of mesh layer (6326) can be changed with various mesh layers (6326). Furthermore, the knit pattern as well as the yarn size can influence openings (6330) and the resultant porosity. In the present example, plurality of openings (6330) are configured in size and/or number such that they promote tissue ingrowth when one side of mesh layer (6326) of buttress (322) is placed adjacent or in contact with tissue at a stapled site. In this manner, buttress (322) comprises one or more tissue ingrowth features, which are configured to promote tissue ingrowth with buttress (322). Such tissue ingrowth can provide strength to the cut and stapled site and promote healing of the tissue. In view of the teachings herein, various ways to modify mesh layer (6328) to achieve a desired porosity, and/or size of openings (6330), and/or number of openings (6330), will be apparent to those of ordinary skill in the art in view of the teachings herein.

Figure 18:
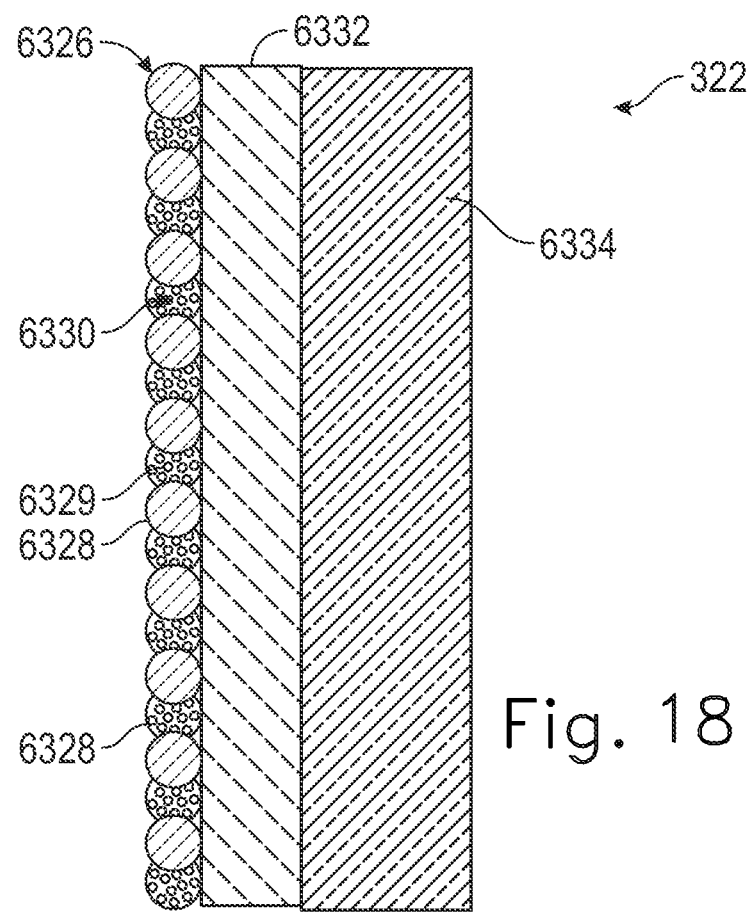
FIG. 18 depicts a cross section view of the buttress of FIG. 15 taken along line 18-18 as shown in FIG. 15.

Referring now to FIG. 18, as mentioned above, buttress (322) also comprises a film layer (6332). Film layer (6332) is configured as an adhesive layer. In the present example, film layer (6332) is located on one side of mesh layer (6326), and is configured to adhesively attach mesh layer (6326) with film layer (6334). Film layer (6332), in the present example, comprises a polydioxanone (PDO) film; however, in other versions other types of film may be used and will be apparent to those of ordinary skill in the art in view of the teachings herein. Furthermore, film layer (6332) is about 8 micrometers in thickness in the present example; however, in other versions the thickness of film layer (6332) may be greater or less than 8 micrometers. In some versions, the polydioxanone film can be included in the construct as a thin film either on its own at the time of lamination or coextruded onto film layer (6334) prior to lamination to the mesh layer (6326).

Figure 17:
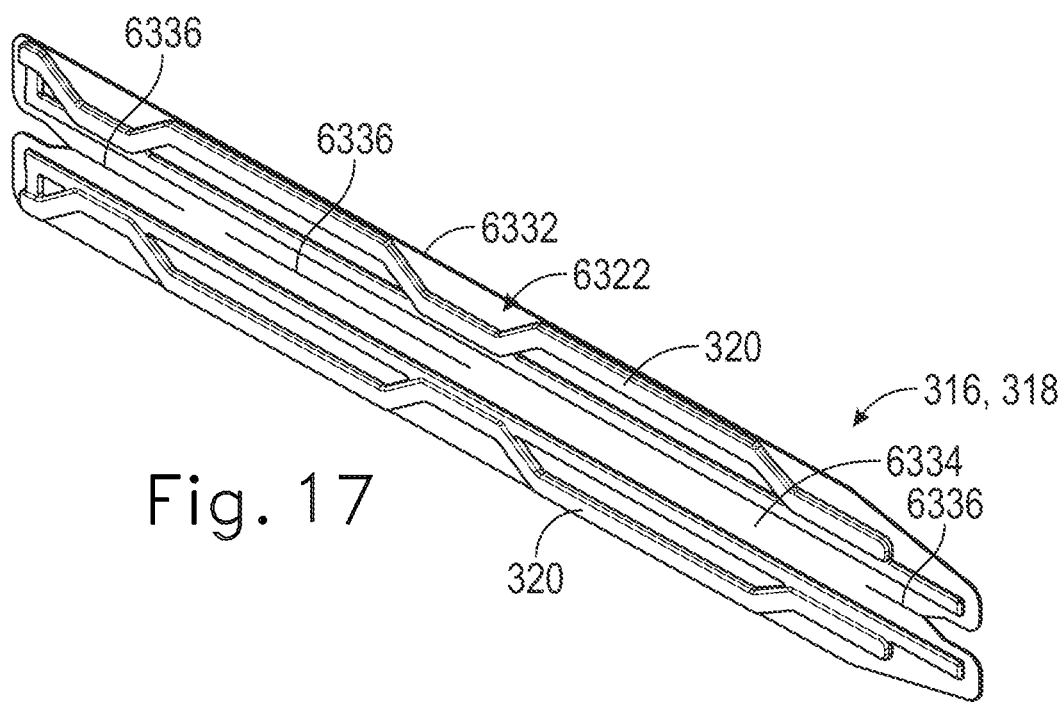
FIG. 17 depicts a perspective view of an exemplary buttress assembly of the buttress applicator of FIG. 5, showing a film layer with adhesive thereon.

Referring still to FIG. 18, and also FIG. 17, film layer (6332) is also in contact with film layer (6334). Film layer (6334) contacts film layer (6332) on the side opposite to where film layer (6332) contacts mesh layer (6326). In the present example, film layer (6334) is configured as an adhesion barrier to prevent tissue adhesions from forming at or near the surgically stapled site. Film layer (6334), in the present example, is constructed of poliglecaprone 25. An example poliglecaprone 25 is manufactured by Ethicon Inc. under the brand name Moncryl®. In other versions, other types of film may be used and will be apparent to those of ordinary skill in the art in view of the teachings herein. In the present example, film layer (6334) is about 10 micrometers in thickness; however, in other versions the thickness of film layer (6334) may be greater or less than 10 micrometers.

Film layer (6334) is also substantially continuous in the present example, and is configured to receive adhesive (320) as described above and as shown best in FIG. 17. With this configuration, film layer (6334) is on the side of buttress (322) that releasably attaches with end effector (40) when buttress assemblies (316, 318) are loaded to end effector (40) as described above. Furthermore, with this configuration, after actuating end effector (40) in a stapling action, film layer (6334) is positioned facing away form the stapled tissue site, whereas openings (6330) of mesh layer (6326) are positioned facing the stapled tissue site as mentioned above to promote tissue ingrowth. While film layer (6334) is illustrated as substantially continuous, with the exception of slits (6336) described further below, in some other versions film layer (6334) can include openings therein, for example as disclosed in U.S. Pat. No. 8,579,990, entitled "Tissue Repair Devices of Rapid Therapeutic Absorbency," issued Nov. 12, 2013, and incorporated by reference herein.

When constructing buttress (322), mesh layer (6326) and film layers (6332, 6334) are laminated together to form the multi-layer material comprising buttress (322). In one version, the lamination occurs under elevated pressure and temperature. Buttress (322) is subjected to these conditions for a predetermined time to achieve acceptable lamination of the layers.

In the present example, buttress (322) is mechanically cut from a larger piece or fabric of multi-layer material having the same construction as described above for buttress (322). This mechanical cutting can be done at lower temperatures compared to other cutting applications, which allows for buttresses (322) to be cut from larger fabrics while avoiding charred or burnt edges that can occur with heated cutting techniques.

Also in the present example, buttresses (322) are mechanically cut out from the larger fabric such that the knit pattern is cut along a 45 degree angle relative to a longitudinal axis (LA) of buttress (322). Referring to FIGS. 15 and 16, the knit pattern of mesh layer (6326) is illustrated having been cut out at about 45 degrees relative to longitudinal axis (LA). For instance, axis (A1) illustrates the direction of the knit pattern of mesh layer (6326). Furthermore, the intersection of axis (A1) and longitudinal axis (LA) of buttress (322) forms an angle (α), which is approximately 45 degrees in the present example. By using this configuration for the cut out angle, unraveling of the mesh layer (6326) of cut out buttress (322) can be avoided. In view of the teachings herein, other cut out angles and ways to prevent unraveling of a cut mesh layer (6326) will be apparent to those of ordinary skill in the art.

Referring again to FIGS. 15 and 17, buttress (322) also comprises multiple slits (6336) that extend longitudinally along buttress (322). Slits (6336) extend all the way through mesh layer (6326), through film layer (6332), and through film layer (6334). Furthermore, slits (6336) are positioned to generally divide buttress (6332) into two equal sections. Referring to FIG. 4, when buttress assemblies (316, 318) are used with end effector (40) in a cutting and stapling procedure, the knife (not shown) of the stapler will travel longitudinally down end effector (40) to cut clamped tissue and at the same time cut buttresses (322) of buttress assemblies (316, 318) along slits (6336). This creates the cut and stapled site as illustrated in FIG. 4. Slits (6336) act as precuts in buttress (6332) such that during a cutting and stapling action, buttress (6332) offers less resistance to being cut, which promotes buttress (6332) remaining properly placed relative to the surgically cut and stapled site, instead of buttress (6332) being pushed longitudinally by the cutting knife and bunching. While the present example uses slits (6336) to precut and promote ease of cutting buttress (322), in view of the teachings herein, other techniques and precut geometries can be used and will be apparent to those of ordinary skill in the art.

V. Exemplary Packaging Assembly for Buttress Applicator

As mentioned above, it can be beneficial to apply a buttress to a cut and stapled surgical site as a reinforcement.

In doing so, the buttress must be loaded onto an end effector of a surgical stapler, and then applied at the site releasing from the end effector in the process. In use the buttress can be configured to be bioabsorbable so over time it is completely absorbed by the body of the patient. To achieve the desired loading and release properties of the buttress, as well as desired reinforcement properties when in use, the buttress material itself, as well as materials applied to the buttress such as adhesive, can be susceptible to degradation when exposed prematurely to environmental factors such as moisture, etc. Using a packaging assembly as shown and described herein can preserve the integrity of the buttress prior to its use and application.

A. Exemplary Outer Tray and Foil Assembly

Figure 19:
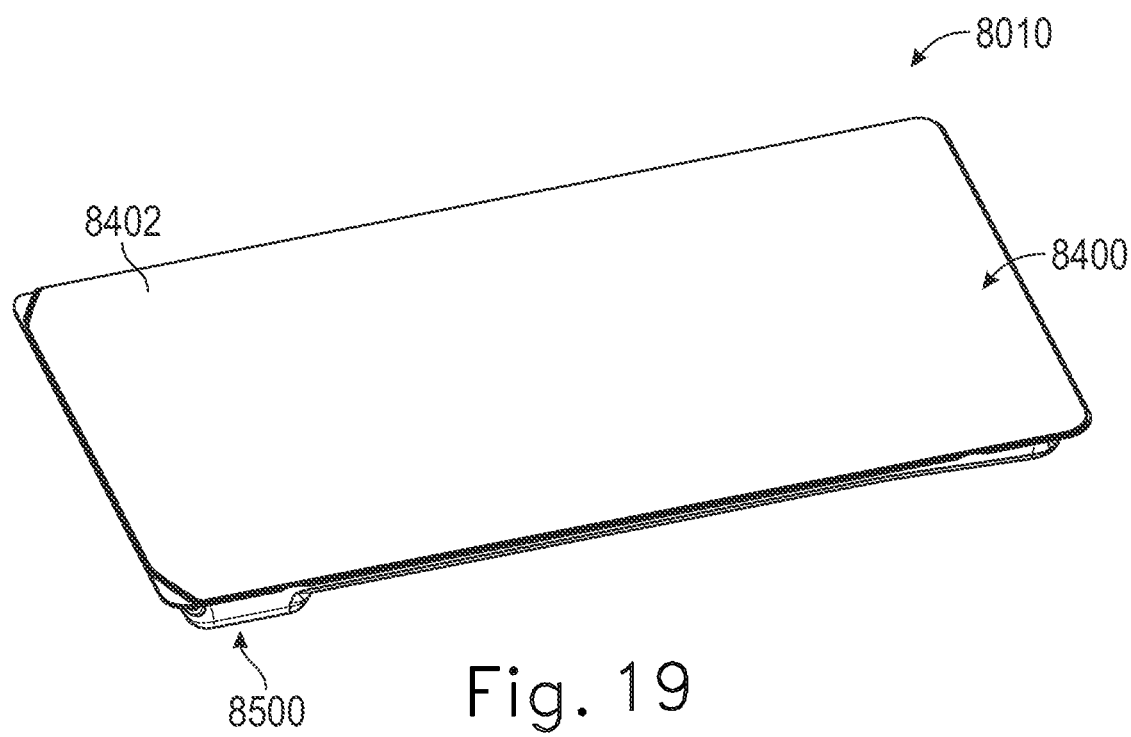
FIG. 19 depicts a top perspective view of an exemplary packaging assembly for an applicator having a buttress assembly for use with a surgical stapler.
Figure 26:
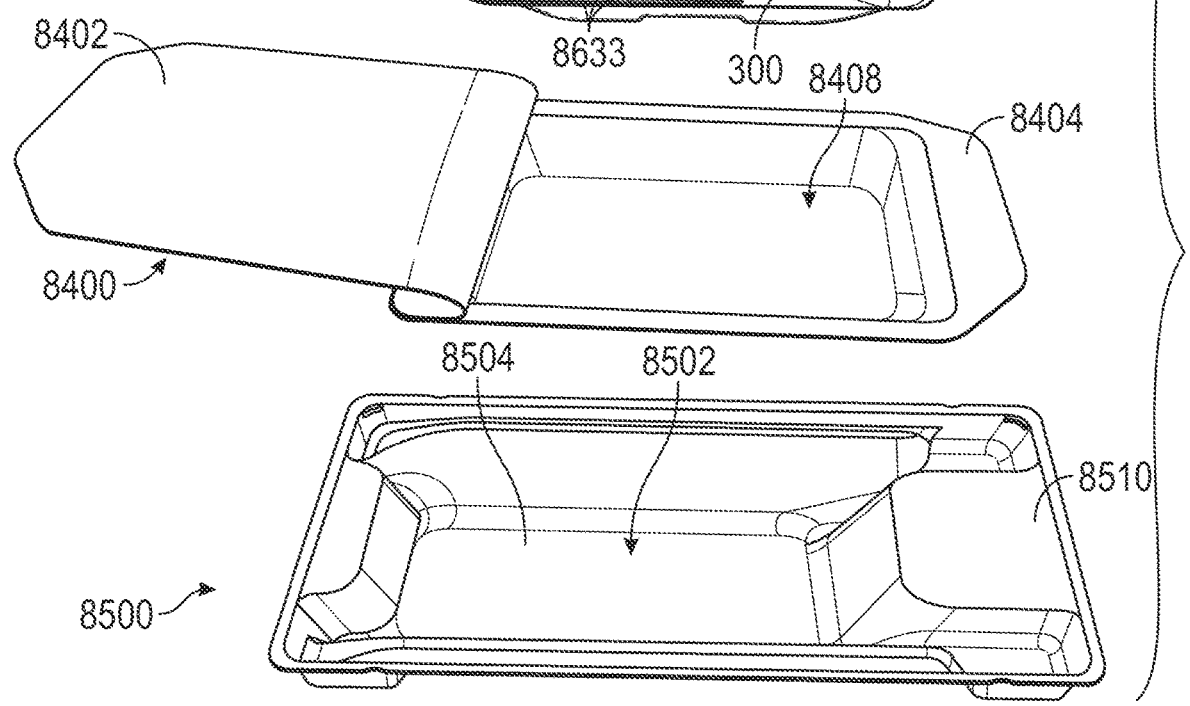
FIG. 26 depicts a partial exploded view of the packaging assembly of FIG. 19, shown with the outer tray, foil assembly, and inner tray with applicator separate one another, and with the flap of the inner tray in a closed position.

FIGS. 19-24 illustrate an exemplary packaging assembly (8010) for a buttress applicator of a surgical stapler. Packaging assembly comprises a foil assembly or foil pouch (8400) and an outer tray (8500). Foil pouch (8400) comprises a top layer (8402) as shown in FIG. 19, and a bottom layer (8404) as shown in FIGS. 23-24. Outer tray (8500) is positioned such that foil pouch (8400) sits within outer tray (8500). In this respect, outer tray (8500) comprises a cavity or space (8502), as shown in FIG. 26, configured to received foil pouch (8400). At least a portion of outer tray (8500) has a shape that matches or closely matches a shape of an underside (8406) of foil pouch (8400) as best seen in FIGS. 23 and 24. In this manner in the present example, a surface (8504) of cavity (8502) is immediately adjacent to underside (8406) of foil pouch (8400). With this configuration, outer tray (8500) is configured to protect bottom layer (8404) of foil pouch (8400) from damage by fitting closely against bottom layer (8404).

Figure 20:
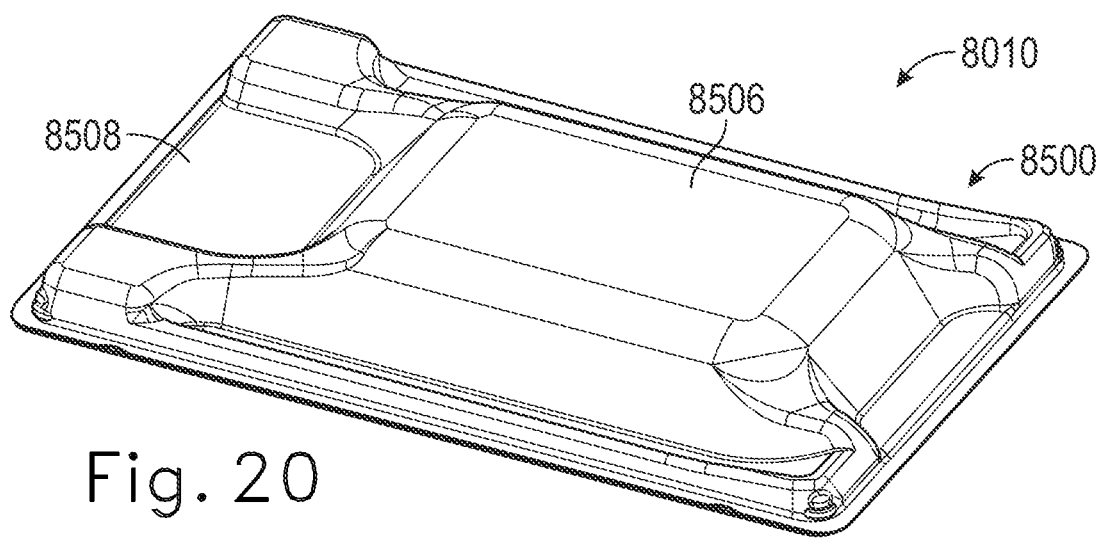
FIG. 20 depicts a bottom perspective view of the packaging assembly of FIG. 19.
Figure 21:
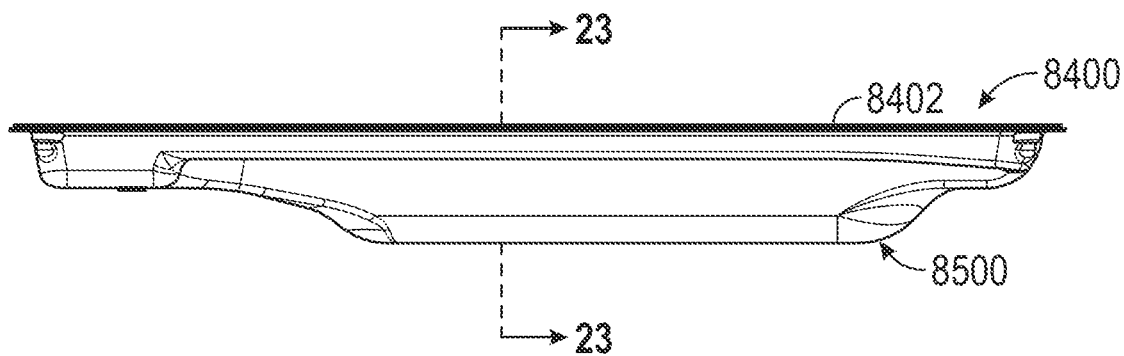
FIG. 21 depicts a side view of the packaging assembly of FIG. 19, taken along the long side of the packaging assembly.
Figure 22:
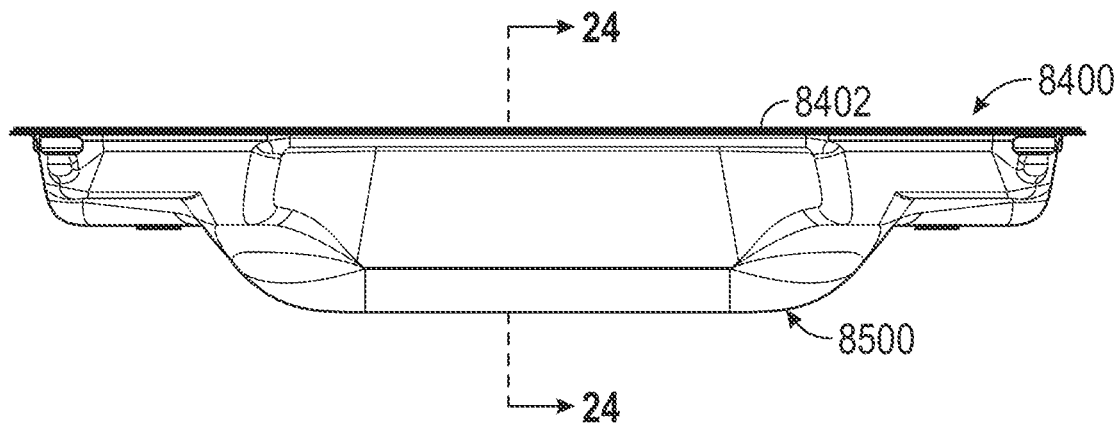
FIG. 22 depicts a side view of the packaging assembly of FIG. 19, taken along the short side of the packaging assembly.

Referring to FIG. 20, outer tray (8500) is configured for stacking with outer tray (8500) comprising a smooth flat underside (8506). The smooth and flat nature of underside (8506) allows for stacking multiple packaging assemblies (8010) on top of one another, without underside surface (8506) damaging top layer (8402) of an adjacent foil pouch (8400). The size and shape of underside (8506) is configured such that a flap (8602) of an inner tray (8600)—as shown in FIGS. 23 and 24—of one packaging assembly (8010) can provide structural support to bear the weight of another packaging assembly (8010) stacked thereupon. In this manner, top layer (8402) of foil pouch (8400) is not required in all cases to bear the weight or load of whatever packaging assemblies (8010) are stacked above, which preserves the integrity of foil pouch (8400) by preventing creasing or puncture of top layers (8402) of stacked packaging assemblies (8010).

Still referring to FIG. 20, outer tray (8500) also comprises recess (8508) on a bottom side. Recess (8508) is configured as an area that can be easily accessed and grasped by a user to pick up a select packaging assembly (8010) either separately or from a group of stacked packaging assemblies (8010). With this configuration, opposite recess (8508) on a top side of outer tray (8500) is a flat surface (8510) as shown in FIG. 26, which is configured as a complementary area that can be easily accessed and grasped by a user to pick up a select packaging assembly (8010) either separately or from a group of stacked packaging assemblies (8010). In this manner, outer tray (8500) is configured with an accessible area for a user to grasp, hold, or pick up packaging assembly (8010) easily and safely without risk of contacting buttress and/or buttress applicator.

B. Exemplary Foil Assembly and Inner Tray

Figure 25:
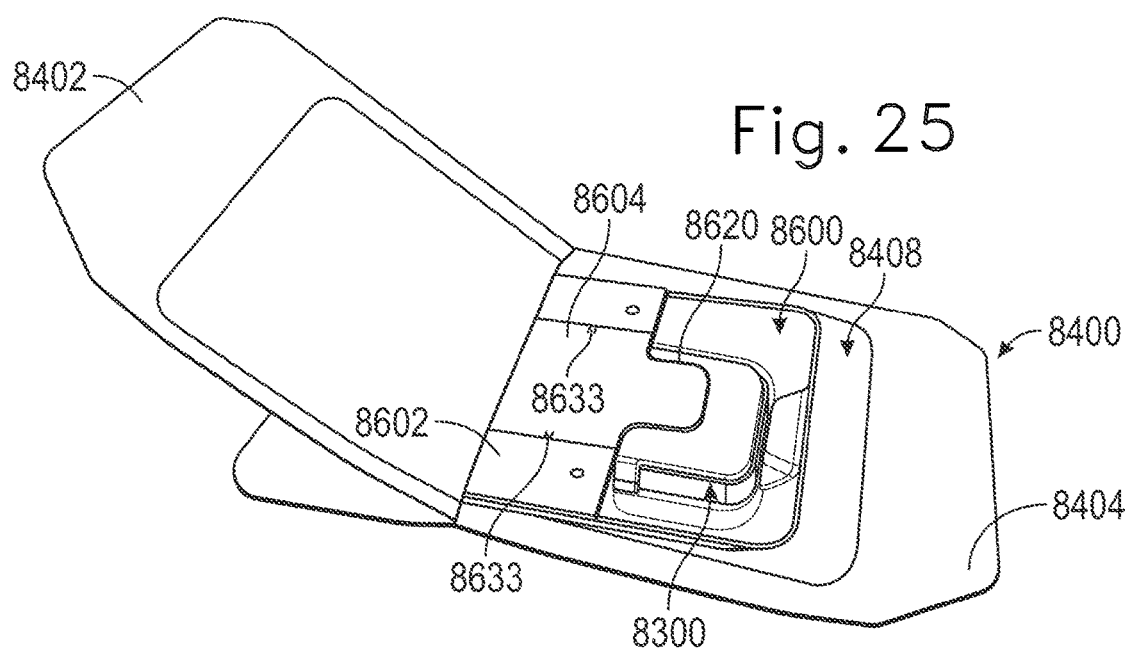
FIG. 25 depicts a top perspective view of the packaging assembly of FIG. 19, shown without the outer tray and with the foil assembly partially opened.

FIG. 25 illustrates a portion of packaging assembly (8010), where outer tray (8500) has been set aside. Furthermore, foil pouch (8400) is shown as partially opened, with top layer (8402) peeled back and away from bottom layer (8404). As shown, foil pouch (8400) comprises an interior (8408) between top and bottom layers (8402, 8404). Furthermore, interior (8408) is configured to receive, retain, or hold inner tray (8600), which receives, retains, or holds a buttress applicator (300). Prior to top layer (8402) and bottom layer (8404) being separated, top layer (8402) and bottom layer (8404) are connectable to seal inner tray (8600) with buttress applicator (300) within foil pouch (8400). In the present example, top and bottom layers (8402, 8404) seal together to form a hermetic seal. In this way, the seal is airtight such that moisture outside foil pouch (8400) cannot enter and thereby damage or degrade the buttress assemblies (316, 318) of buttress applicator (300). As noted and shown, the hermetic seal between top layer (8402) and bottom layer (8404) is selective and not permanent such that a user can separate top and bottom layers (8402, 8404) to retrieve buttress applicator (300). In some examples, foil pouch (8400) is sealed under dry nitrogen to provide interior (8408) with an extremely low moisture and oxygen environment.

With foil pouch (8400) sealed and surrounding inner tray (8600), top layer (8402) of foil pouch (8400) and bottom layer (8404) of foil pouch (8400) are configured to closely follow the contour of inner tray (8600). This close fit, which can be seen in the cross-section views of FIGS. 23 and 24, promotes protection of foil pouch (8400) from damage when and if being contacted, as inner tray (8600) provides support to top and bottom layers (8402, 8404) of foil pouch (8600) from the inside of foil pouch (8400) outward. By way of example only, if too much space is provided between foil pouch (8400) and inner tray (8600) when inner tray (8600) is sealed within foil pouch (8400), then top and/or bottom layers (8402, 8404) of foil pouch (8400) are more susceptible to damage in the form of creases, cuts, and/or punctures.

With the configuration described above, packaging assembly (8010) is configured with two trays: inner tray (8600) and outer tray (8500). Moreover, inner tray (8600) and outer tray (8500) are separable from one another. In the present example, foil pouch (8400) separates inner tray (8600) from outer tray (8500), and more specifically, bottom layer (8404) of foil pouch (8400) separates inner tray (8600) from outer tray (8500). Foil pouch (8400) is configured as an impermeable material such that water and air cannot pass through layers (8402, 8404) of foil pouch (8400). Thus, in one version packaging assembly (8010) comprises outer tray (8500) and inner tray (8600) configured to selectively retain buttress applicator (300), where there is an impermeable material positionable between outer tray (8500) and inner tray (8600). Furthermore, the impermeable material surrounds buttress applicator (300) retained by inner tray (8600) forming a hermetic seal around inner tray (8600) and buttress applicator (300). Further yet, with the above-described configuration, outer tray (8500) is configured to protect the impermeable material from damage. While the present example shows packaging assembly (8010) with two trays (8600, 8500) separable by impermeable bottom foil layer (8404), in other versions, packaging assembly (8010) can be configured with greater or fewer trays and separable by other materials as will be appreciated by those of ordinary skill in the art in view of the teachings herein.

While examples of packaging assembly (8010) herein describe pouch (8400) as foil pouch (8400), it should be understood that pouch (8400) is not limited to being constructed of foil. In other examples, pouch (8400) is constructed of other suitable materials that can provide a hermetic seal. Such other suitable materials can include impermeable films such as films made of various plastics. In view of the teachings herein, other materials for use in constructing pouch (8400) of packaging assembly (8010) will be apparent to those of ordinary skill in the art.

C. Exemplary Inner Tray and Buttress Applicator

Figure 27:
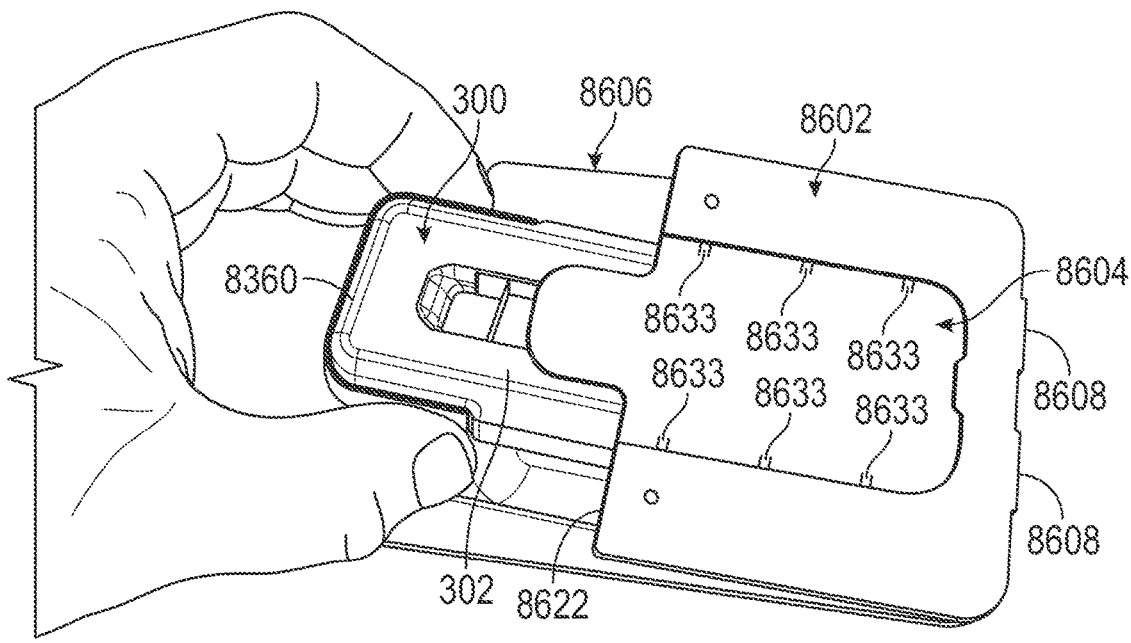
FIG. 27 depicts a top perspective view of the inner tray and applicator of FIG. 25, with the applicator partially lifted from the inner tray and the flap of the inner tray partially lifted.
Figure 28:
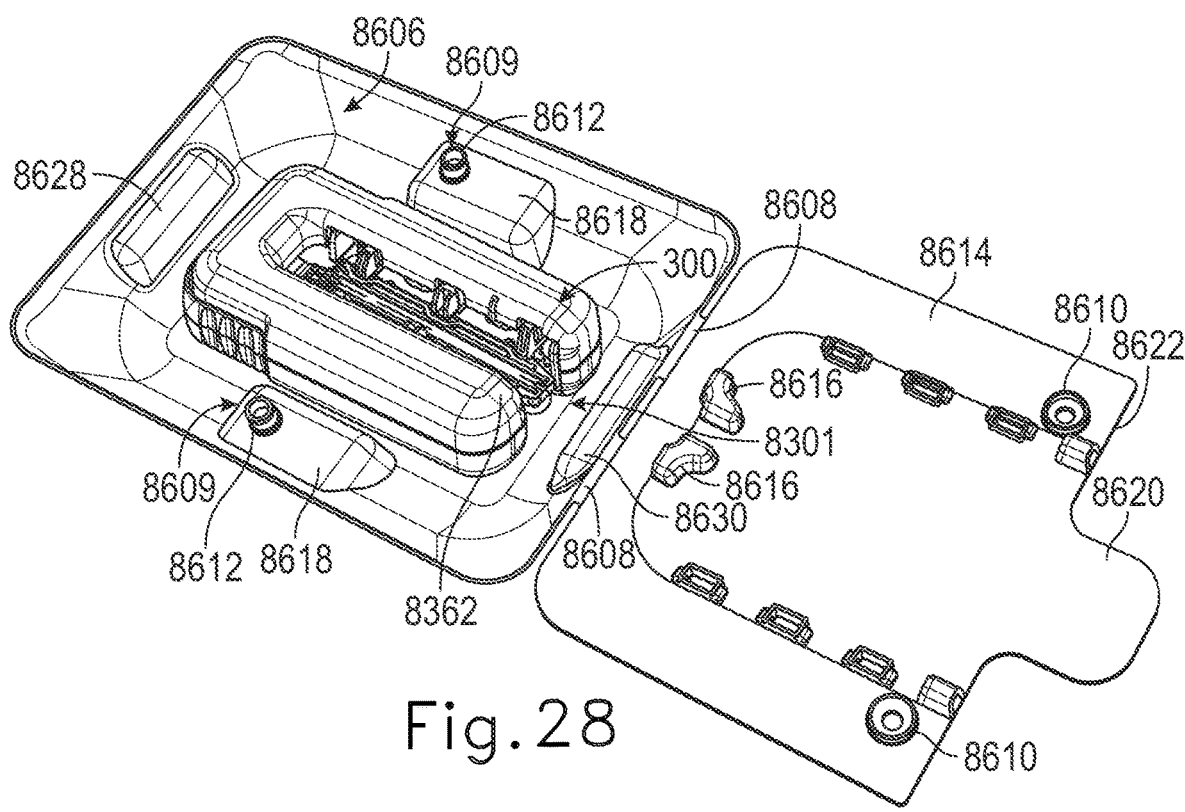
FIG. 28 depicts a top perspective view of the inner tray and applicator of FIG. 25, shown with the flap of the inner tray in an open position.
Figure 29:
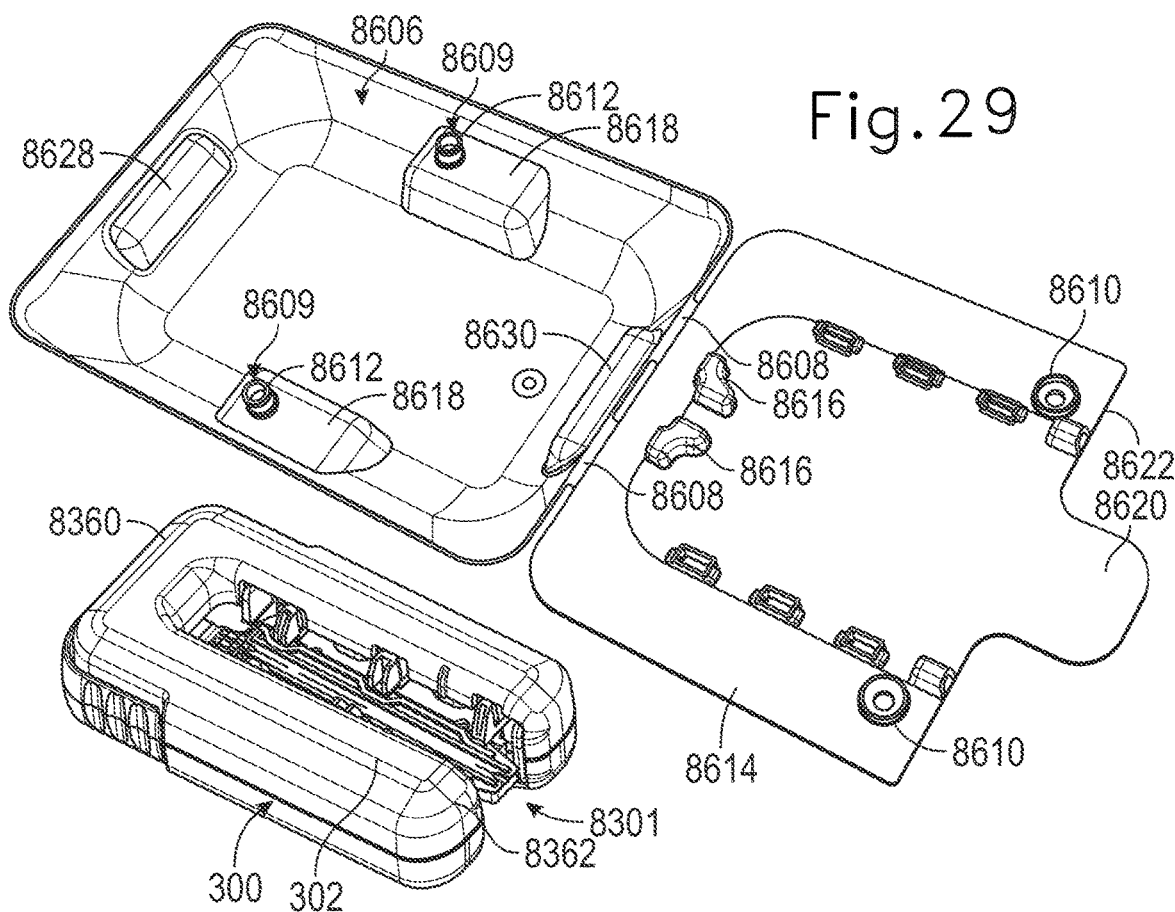
FIG. 29 depicts a top perspective view of the inner tray and applicator of FIG. 25, shown with the applicator removed from the inner tray.

FIGS. 27-29 illustrate inner tray (8600), including buttress applicator (300). In some instances buttress applicator (300) is referred to herein as merely applicator (300). It should be understood that these terms are used and understood herein to be interchangeable. As illustrated, inner tray (8600) comprises a base (8606), flap (8602), and a living hinge (8608) connecting flap (8602) with base (8606). Base (8606) of inner tray (8600) is configured to selectively retain applicator (300). Flap (8602) is rotatable from a closed position as seen in FIGS. 25-27, to an open position as seen in FIGS. 28 and 29. In the closed position, flap (8602) at least partially covers applicator (300) when applicator (300) is retained within base (8606). In the open position, flap (8602) reveals applicator (300) such that it may be removed from inner tray (8600).

Figure 31:
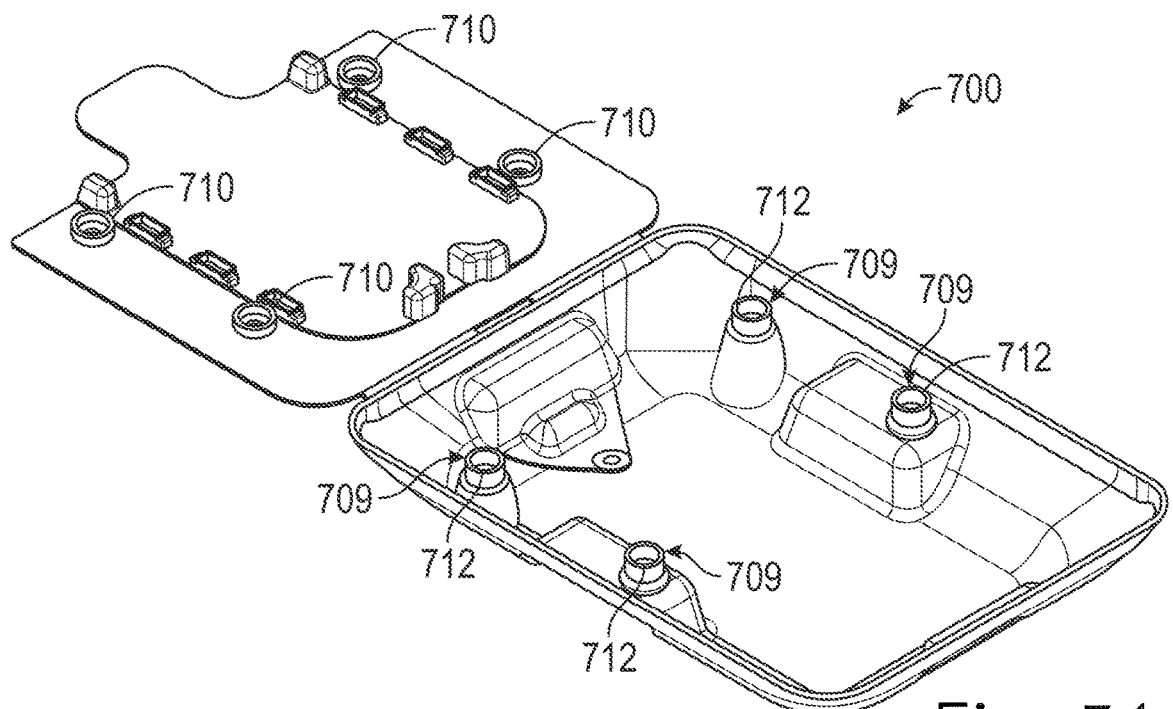
FIG. 31 depicts a top perspective view of another exemplary inner tray configured for use with the packaging assembly of FIG. 19.
Figure 32:
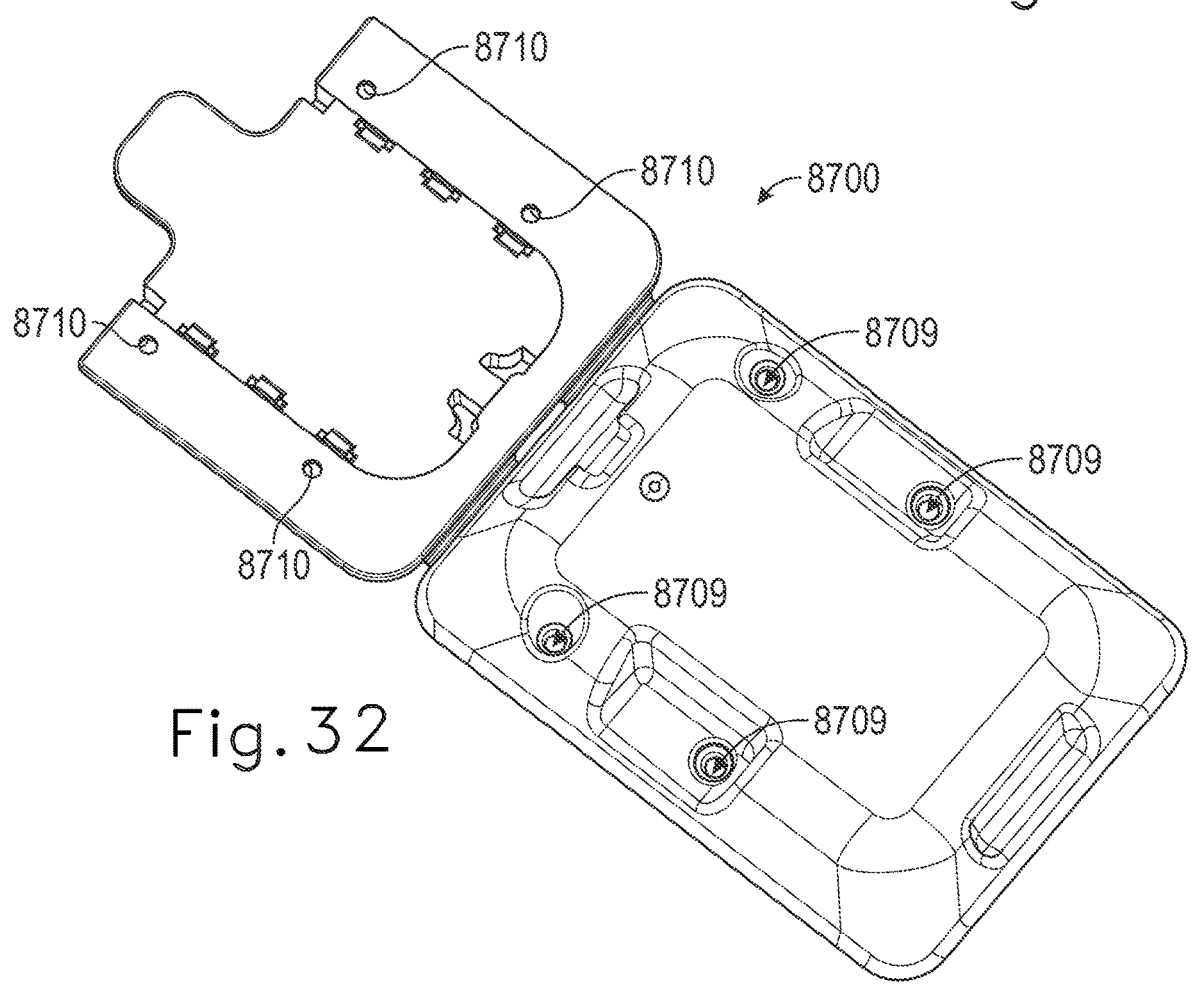
FIG. 32 depicts a bottom perspective view of the inner tray of FIG. 31.

Inner tray (8600) includes fastening features (8609) that are configured to selectively engage so that flap (8602) connects with base (8606) as mentioned above. In the present example, one fastening feature (8609) comprises fastening members (8610, 8612), with one fastening member (8610) located on an underside (8614) of flap (8602), and the other fastening member (8612) located on a ridge (8618) within base (8606). Fastening members (8610) engage with fastening members (8612) when flap (8602) is in the closed position. While the illustrated version of FIGS. 27-29 shows a pair of fastening features (8609), in other versions greater or fewer fastening features (8609)—and their associated fastening members (8610, 8612)—may be used to achieve selective closure of flap (8602) with body (8606). By way of example only, and not limitation, FIGS. 31 and 32 illustrate another exemplary inner tray (8700). Inner tray (8700) is the same as inner tray (8600) with the exception that inner tray (8700) comprises two pair, or four total, fastening features (8709), each with fastening members (8710) that are configured to selectively engage with fastening members (8712).

Returning to FIGS. 27 and 28, in some versions, inner tray (8600) is configured such that applicator (300) only sits within base (8606) and with flap (8602) closable when applicator (300) is oriented or positioned in a certain manner. For instance, as shown in FIG. 27, inner tray (8600) presents a distal end (8360) of applicator (300) for a user to grasp. Proximal end (8362) of applicator (300) is covered by flap (8602) when flap (8602) is closed. Flap (8602) is configured with guide features (8616) along its underside (8614), where guide features (8616) are configured to locate within a space created by an open end (8301) of applicator (300). Because applicator (300) is a closed structure along its distal end (8360), if applicator (300) is positioned within base (8606) with its proximal end (8362) presenting towards a user for grasping-opposite of what is shown in FIG. 27 then guide features (8616) will interfere with the closed distal end (8360) of applicator (300) such that flap (8602) cannot close fully with fastening members (8610) engaging fastening members (8612).

In this configuration, a poka-yoke relationship or configuration exists among inner tray (8600) and applicator (300) to ensure applicator (300) is oriented with its distal end (8360) visible and its proximal end (8362) covered by flap (8602) when flap (8602) is closed. This orientation of applicator (300) relative to inner tray (8600) provides that flap (8602) shields buttress assemblies (316, 318) of applicator (300) so that buttress assemblies (316, 318) are inaccessible. In this manner, flap (8602) protects buttress assemblies (316, 318) from contact when applicator (300) is positioned within inner tray (8600) with flap (8602) closed. Additionally, base (8606) of inner tray (8600) further includes ridges (8618) and stops (8628, 8630) as shown in FIGS. 28 and 29 that help minimize applicator (300) shifting or moving when seated within base (8606) of tray (8600). For instance, ridges (8618) help minimize lateral movement of applicator (300), while stops (8628, 8630) help minimize longitudinal movement of applicator (300).

Referring to FIG. 27, inner tray (8600) and applicator (300) are configured in the present example such that flap (8602) can be disengaged from base (8606) by lifting distal end (8360) of applicator (300). In this way, housing portion (302) of applicator (300) pushes on underside (8614) of flap (8602) to release the engagement between fastening members (8610, 8612). This opening technique helps prevent or shield buttress assemblies (316, 318) from contact. Still other ways to open flap (8602) exist. For example, flap (8602) comprises peninsula portion (8620). Portion (8620) may be grasped by a user and lifted to open flap (8602) for removal of applicator (300). Peninsula portion (8620) further allows for a center region of applicator (300) having buttress assemblies (316, 318) to be covered when flap (8602) is closed, while exposing distal end (8360) of applicator (300) for visualization or grasping by a user. Still further, flap (8602) presents a leading edge (8622), which can be contacted by a user and lifted to move flap (8602) from its closed position to its open position. In view of the teachings herein, other ways to facilitate opening flap (8602) to remove applicator (300) from inner tray (8600) while protecting buttress assemblies (316, 318) from contact and other environmental exposure will be apparent to those of ordinary skill in the art.

D. Exemplary Inner Tray and Desiccant Material

Figure 30:
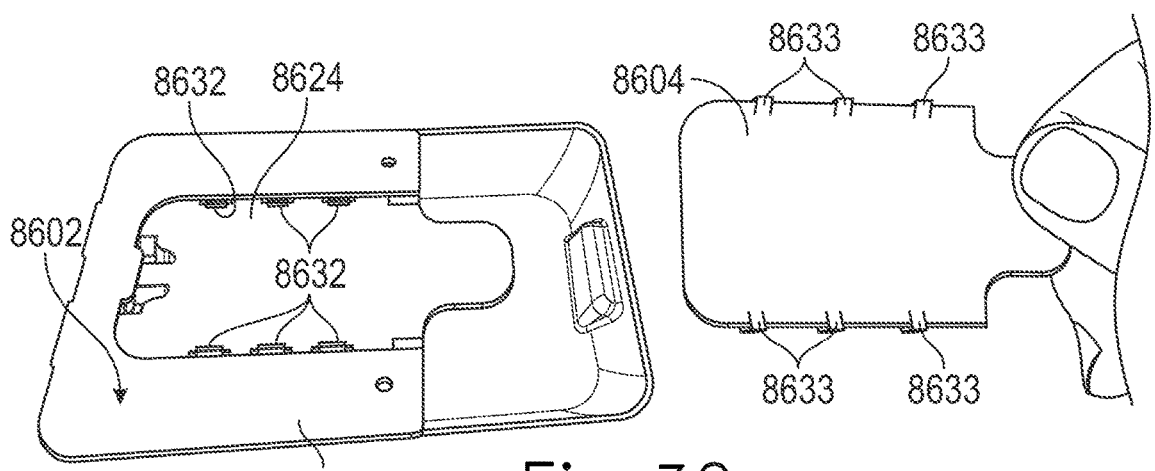
FIG. 30 depicts a top perspective view of the inner tray of FIG. 25, shown with the desiccant material removed from the inner tray.

As shown in FIGS. 27 and 30, inner tray (8600) is configured to selectively retain a desiccant material (8604). Desiccant material (8604) is configured to preferentially absorb any moisture within interior (8408) of foil pouch (8400). In this way, desiccant material (8604) may be an overdried material that is combined with inner tray (8600) and then sealed within foil pouch (8400). Any moisture that exists within foil pouch (8400) will be first absorbed by the overdried desiccant material (8604) before being absorbed by buttress assemblies (316, 318) of buttress applicator (300). In the present example, desiccant material (8604) comprises a piece of paperboard, but in other versions desiccant material (8604) can be made of other materials such as cotton, silica, and other materials that will be apparent to those of ordinary skill in the art in view of the teachings herein.

Referring to FIG. 30, inner tray (8600) comprises an area (8624) on an outer surface (8626) of flap (8602) that is configured to selectively retain desiccant material (8604). In this configuration, inner tray (8600) selective retains desiccant material (8604) in a way where desiccant material (8604) does not contact applicator (300). In one example, area (8624) of flap (8602) comprises tabs. In the present example, inner tray (8600) comprises a molded plastic and accordingly area (8624) and tabs are molded features of inner tray (8600). Desiccant material (8604) and tabs are configured such that desiccant material (8604) can be slid along area (8624) with tabs sliding above desiccant material (8604) to selectively retain desiccant material (8604) adjacent to area (8624) of flap (8602). Similarly, desiccant material (8604) can be removed from inner tray (8600) by sliding desiccant material (8604) distally away from area (8624) such that tabs no longer impinge on and retain desiccant material (8604) with inner tray (8600). Referring to FIG. 30, in another example, area (8624) of flap (8602) comprises openings (8632). In the present example, inner tray (8600) comprises a molded plastic and accordingly area (8624) and openings (8632) are molded features of inner tray (8600). Furthermore, desiccant material (8604) comprises tabs (8633), which are engagement features that can be inserted into and received by openings (8632) such that desiccant material (8604) can be selectively attached with area (8624). In the present example, tabs (8633) are resiliently biased outward from a longitudinal centerline of desiccant material (8604). When inserted within openings (8632) tabs (8633) deflect inward and the resilient bias of tabs (8633) provide a selective interference fitting between tabs (8633) and openings (8632) to selectively retain desiccant material (8604) with area (8624) of flap (8602). Desiccant material (8604) can be removed from inner tray (8600) by pulling desiccant material (8604) upward away from area (8624) of flap (8602) to overcome the interference fitting such that tabs (8633) disengage from openings (8632). In view of the teachings herein, other ways to attach and remove desiccant material (8604) with inner tray (8600) will be apparent to those of ordinary skill in the art.

VI. Exemplary Method of Packaging a Buttress Applicator

Figure 33:
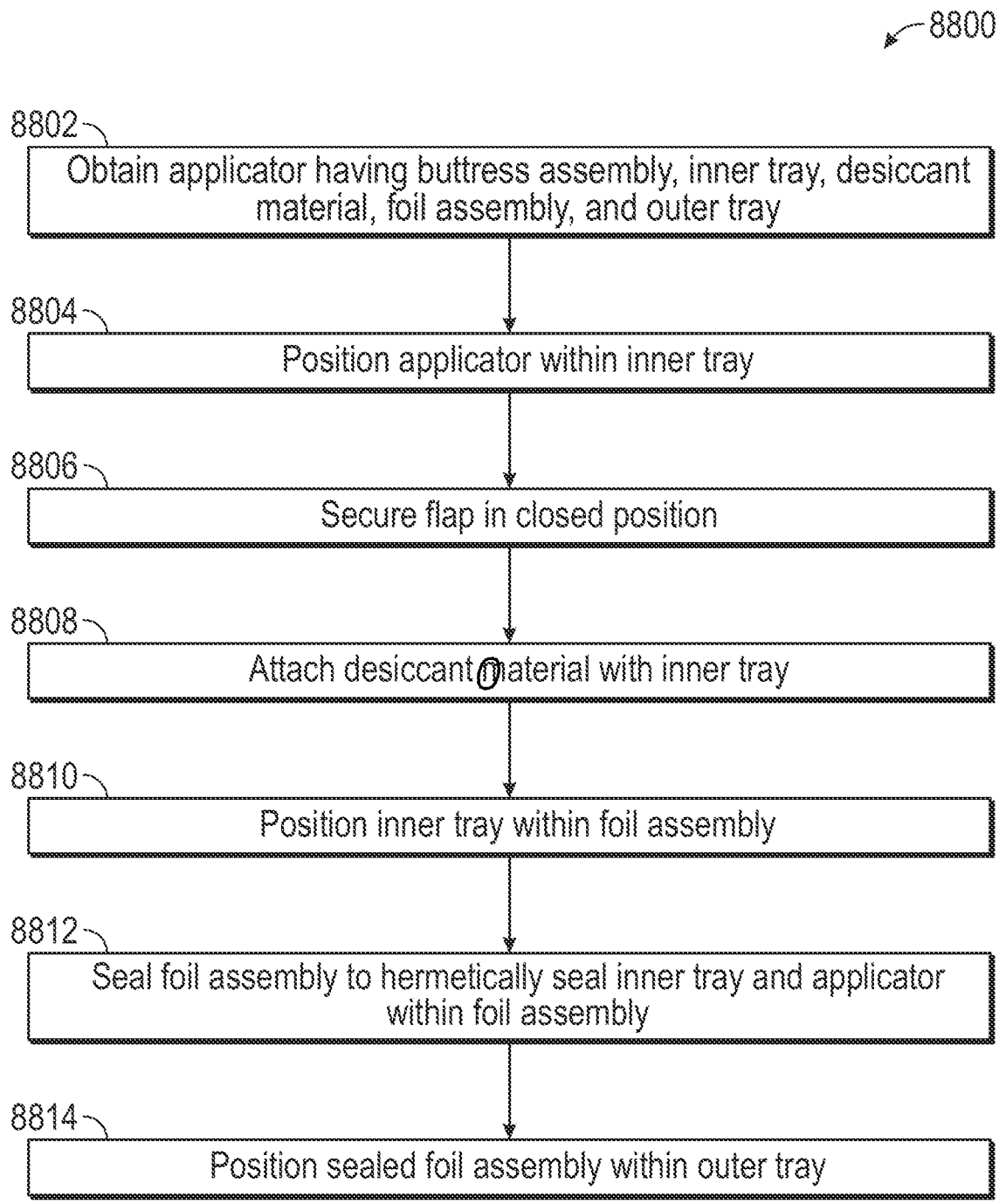
FIG. 33 depicts a schematic view of an exemplary method for packaging an applicator having a buttress assembly for use with a surgical stapler.

FIG. 33 schematically illustrates an exemplary method for packaging a buttress applicator (8800) such as buttress applicators (200, 300) described above. At step (8802), applicator (300) with buttress assemblies (316, 318) is obtained, along with inner tray (8600), desiccant material (8604), foil assembly (8400), and outer tray (8500). At step (8804), applicator (300) is positioned within inner tray (8600). In some instances this includes positioning applicator (300) is a specific orientation relative to base (8606) of inner tray (8600) so that applicator (300) sits flat within base (8606) of inner tray (8600) and allows flap (8602) to properly and fully close. At step (8806), flap (8602) is secured in the closed position by engaging fastening features (8609). At step (8808), desiccant material (8604) is attached with area (8624) of inner tray (8600) and selectively secured by tabs (8632). At step (8810), inner tray (8600) is positioned within foil assembly (8400). In particular, inner tray (8600) may be placed between top and bottom layers (8402, 8404) of foil assembly (8400). At step (8812), foil assembly (8400) is sealed to hermetically seal inner tray (8600) and applicator (300) within foil assembly (8400). At step (8814) sealed foil assembly (8400) containing inner tray (8600) with applicator (300) is positioned within outer tray (8500), where outer tray (8500) is configured to protect foil assembly (8400) from damage.

While the above steps describe one exemplary packaging method, other methods may be used, or modifications to method (8800) may be made as will be apparent to those of ordinary skill in the art in view of the teachings herein. For instance, the order of the steps of method (8800) as shown and described above are not required in all versions. For instance, where practical or convenient or desired, certain steps can be completed before others such that the above shown and described steps should not be considered limited to their presented sequential order. Still other modifications may involve adding or omitting certain steps.

VII. Exemplary Buttress Assembly for a Buttress Applier Cartridge

Figure 34:
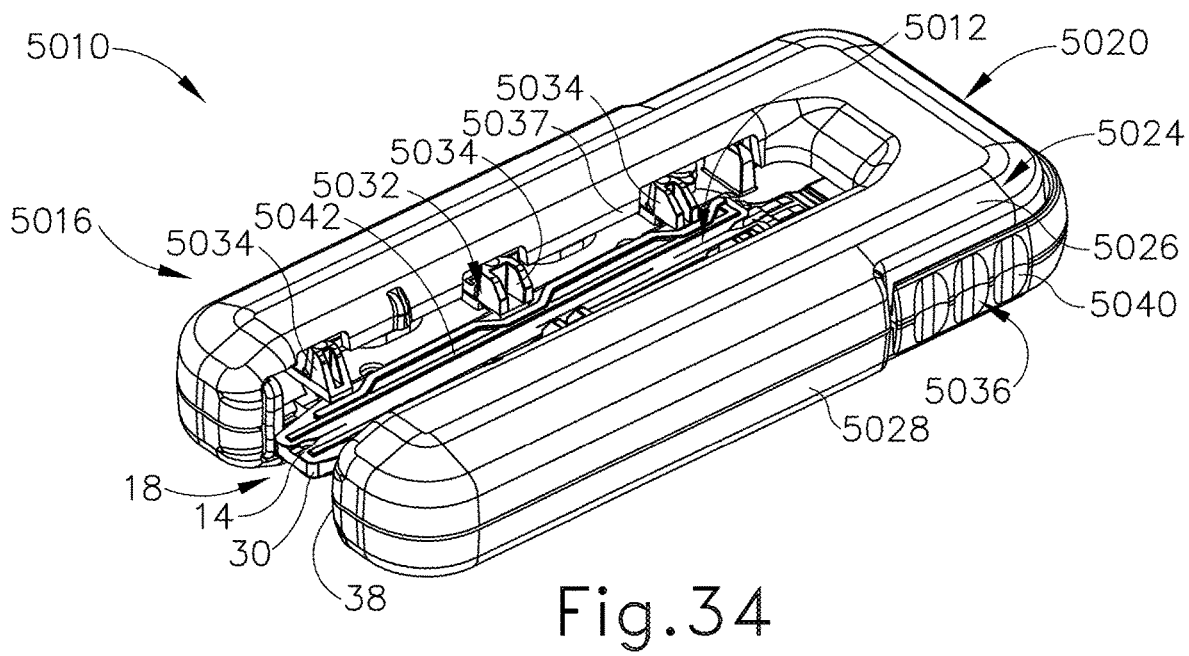
FIG. 34 depicts a perspective view of an exemplary buttress applier cartridge assembly that includes an example of a buttress applier cartridge carrying an example of a buttress assembly for an upper jaw and an example of another buttress assembly for a lower jaw.

In some instances, it may be desirable to use an exemplary buttress applier cartridge assembly (5010) as shown in FIG. 34 to equip a surgical instrument with a buttress assembly (5012) for forming staples in tissue with a buttress (5014). Such buttress (5014) inhibits the formed staples from pulling through the tissue to thereby reduce a risk of tissue tearing at or near the site of formed staples. In addition to or as an alternative to providing structural support and integrity to a line of staples, buttress (5014) may provide various other kinds of effects such as spacing or gap-filling, administration of therapeutic agents, and/or other effects. Prior to use with the surgical instrument, one or more buttresses (5014) is releasably retained on a buttress applier cartridge (5016), which is configured to deposit buttress assembly (5010) onto surgical instrument for use as discussed below in more detail in an exemplary surgical instrument (5018) (see FIG. 43A).

Additional features may be combined as applicable with the following example of buttress applier cartridge assembly (5010). Such features are described in U.S. patent application Ser. No. 16/235,473, entitled "Adhesive Distribution on Buttress for Surgical Stapler," filed on Dec. 28, 2018, published as U.S. Pub. No. 2020/0205820 on Jul. 2, 2020, issued as U.S. Pat. No. 11,166,724 on Nov. 9, 2021; U.S. patent application Ser. No. 16/235,503, entitled "Surgical Stapler Buttress with Tissue In-Growth Promotion," filed on Dec. 28, 2018, published as U.S. Pub. No. 2020/0205822 on Jul. 2, 2020, now abandoned; U.S. patent application Ser. No. 16/235,522, entitled "Applicator for Surgical Stapler Buttress," filed on Dec. 28, 2018, published as U.S. Pub. No. 2020/0205823 on Jul. 2, 2020, issued as U.S. Pat. No. 11,116,505 on Sep. 14, 2021; U.S. patent application Ser. No. 16/235,541, entitled "Packaging for Surgical Stapler Buttress," filed on—Dec. 28, 2018, published as U.S. Pub. No. 2020/0205824 on Jul. 2, 2020, issued as U.S. Pat. No. 11,432,817 on Sep. 6, 2022; U.S. patent application Ser. No. 16/235,630, entitled "Curved Tip Surgical Stapler Buttress Assembly Applicator with Opening Feature for Curved Tip Alignment," filed on Dec. 28, 2018, published as U.S. Pub. No. 2020/0205826 on Jul. 2, 2020, issued as U.S. Pat. No. 11,272,935 on Mar. 15, 2022; U.S. patent application Ser. No. 16/235,670, entitled "Curved Tip Surgical Stapler Buttress Assembly Applicator with Proximal Alignment Features," filed on Dec. 28, 2018, issued as U.S. Pat. No. 10,905,424 on Feb. 2, 2021; and U.S. patent application Ser. No. 16/235,681, entitled "Curved Tip Surgical Stapler Buttress Assembly Applicator with Compression Layer Pocket Feature," filed on Dec. 28, 2018, published as U.S. Pub. No. 2020/0205807 on Jul. 2, 2020, issued as U.S. Pat. No. 11,103,243 on Aug. 31, 2021, the disclosures of which are hereby incorporated by reference.

A. Exemplary Buttress Applier Cartridge

Figure 35:
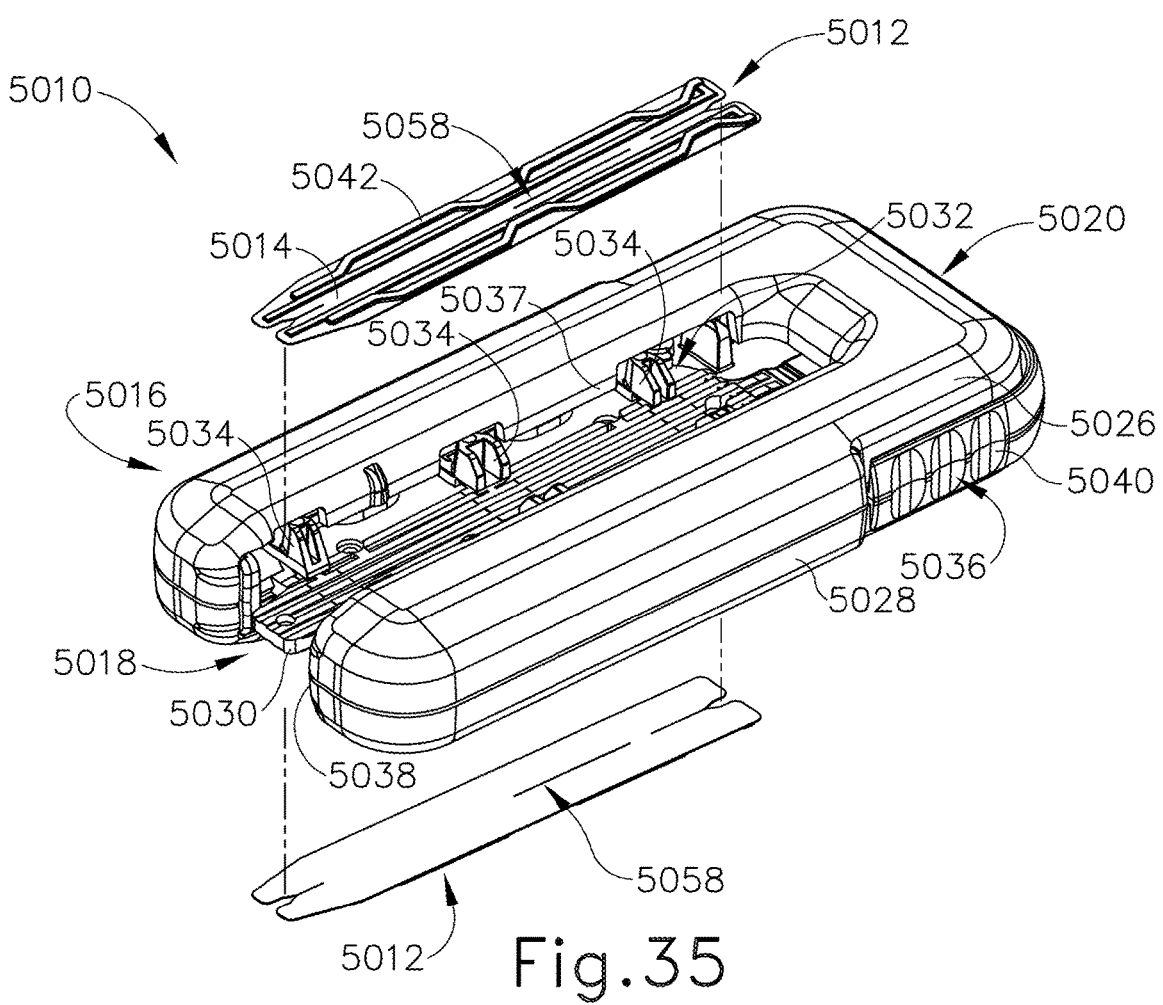
FIG. 35 depicts a partially exploded perspective view of the buttress applier cartridge assembly of FIG. 34 showing the buttress assemblies removed from the buttress applier cartridge.
Figure 43A:
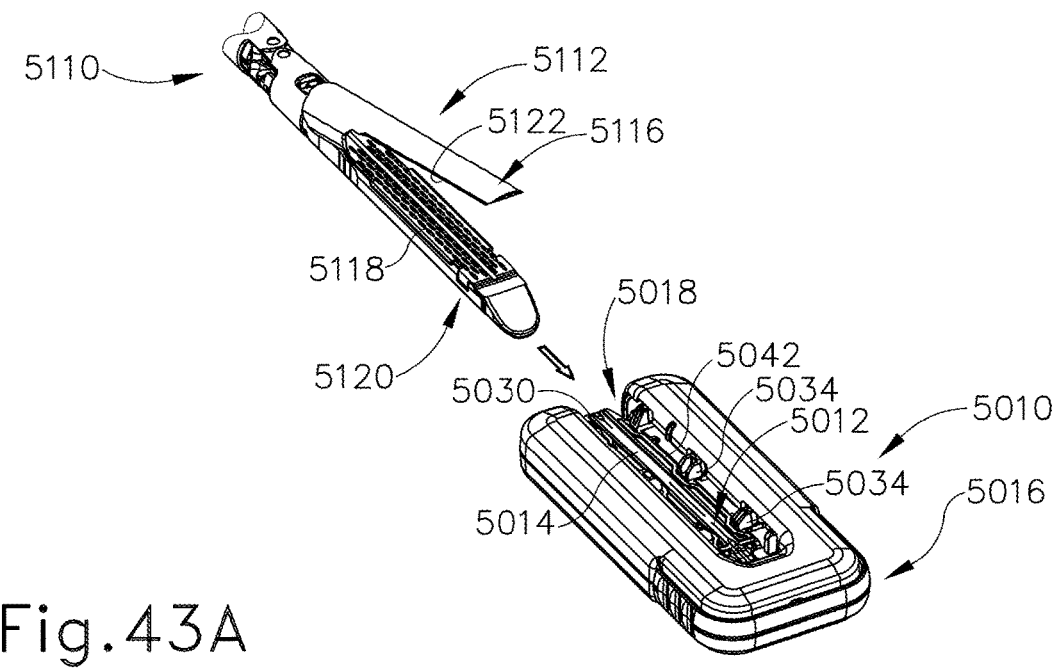
FIG. 43A depicts a perspective view of an end effector of an exemplary surgical instrument showing the buttress applier cartridge assembly of FIG. 34 approaching the end effector with the upper and lower jaws in an open position.

FIGS. 34-35 show buttress applier cartridge assembly (5010) including a pair of buttress assemblies (5012) releasably retained on buttress applier cartridge (5016), which supports and protects buttress assemblies (5012) prior to use and further aids with loading buttress assemblies (5012) on surgical instrument (5110) (see FIG. 43A). Buttress applier cartridge (5016) of the present example includes an open end (5018) and a closed end (5020). Open end (5018) is configured to receive end effector (5112) (see FIG. 43A) as described below in greater detail. Buttress applier cartridge (5016) further includes a housing assembly (5024) having an upper housing (5026) and a lower housing (5028), which each generally define a "U" shape to present open end (5018). Various components are interposed between upper and lower housings (5026, 5028). In particular, these components include a platform (5030), a pair of actuator sleds (5032) having arms (5034), and a chassis (5036).

Platform (5030) of the present example supports upper buttress assembly (5012) on one side of platform (5030) and lower buttress assembly (5012) on the other side of platform (5030). Platform (5030) is exposed in recesses that are formed between the prongs of the "U" configuration of upper and lower housings (5026, 5028). Thus, upper housing (5026) has an upper gap (5037) extending to the open end (5018) along an upper surface of platform (5030), and lower housing (5028) similarly has a lower gap (5038) extending to the open end (5018) along the lower surface of platform (5030). The location of platform (5030) and buttress assemblies (5012) in such recesses may prevent inadvertent contact between buttress assemblies (5012) and other devices in the operating room. In other words, upper and lower housings (5026, 5028) may provide some degree of physical shielding of buttress assemblies (5012).

In the present example, the outer edges of platform (5030) are captured between upper and lower housings (5026, 5028) and include retention features (not shown) that further engage upper and lower housings (5026, 5028) to prevent platform (5030) from sliding relative to upper and lower housings (5026, 5028). In some versions, platform (5030) is formed of a material that provides a high coefficient of friction, thereby reducing any tendency that buttress assemblies (5012) might otherwise have to slide along corresponding surfaces of platform (5030). For instance, platform (5030) may comprise an elastomeric material and/or a foam material. In some instances, platform (5030) is formed of a compressible foam material that is configured to maintain a compressed configuration after being compressed by end effector (5112) (see FIG. 43A). By way of example only, platform (5030) may comprise Santoprene, closed-cell polyurethane foam, any other compressible material, and/or a material that may be made compressible via geometry (e.g., a rubber material with deformable standing features). Various suitable materials and structural configurations that may be used to form platform (5030) will be apparent to those of ordinary skill in the art in view of the teachings herein.

Chassis (5036) is configured to cooperate with upper and lower housings (5026, 5028) to provide a mechanical ground for moving components of buttress applier cartridge (5016) and provide structural support for components of buttress applier cartridge (5016). Chassis (5030) further includes integral gripping features (5040) that are exposed on opposite sides of housing assembly (5024). Gripping features (5040) have a surface geometry configured to promote an operator's grip of buttress applier cartridge (5016) during use of buttress applier cartridge (5016). Various suitable configurations that may be used for gripping features (5040) will be apparent to those of ordinary skill in the art in view of the teachings herein. Similarly, various surface treatments (e.g., elastomeric material, etc.) that may be applied to gripping features (5040) will be apparent to those of ordinary skill in the art in view of the teachings herein.

Actuator sleds (5032) are slidably positioned on opposite faces of chassis (5030). Arms (5034) of actuator sleds (5032) extend laterally inward to selectively and releasably secure buttress assemblies (5012) to platform (5030). In particular, FIG. 34 show arms (5034) positioned such that buttress assemblies (5012) are interposed between the free ends of arms (5034) and platform (5030). Arms (5034) are movable laterally outwardly such that arms (5034) disengage buttress assemblies (5012) as shown in FIG. 35, thereby enabling buttress assemblies (5012) to be removed from platform (5030). In the present example, arms (5034) are configured to bear against buttress assemblies (5012), thereby pinching buttress assemblies (5012) against platform (5030). Other suitable ways in which arms (5034) may engage buttress assemblies (5012) will be apparent to those of ordinary skill in the art in view of the teachings herein.

B. Exemplary Buttress Assembly

Figure 36:
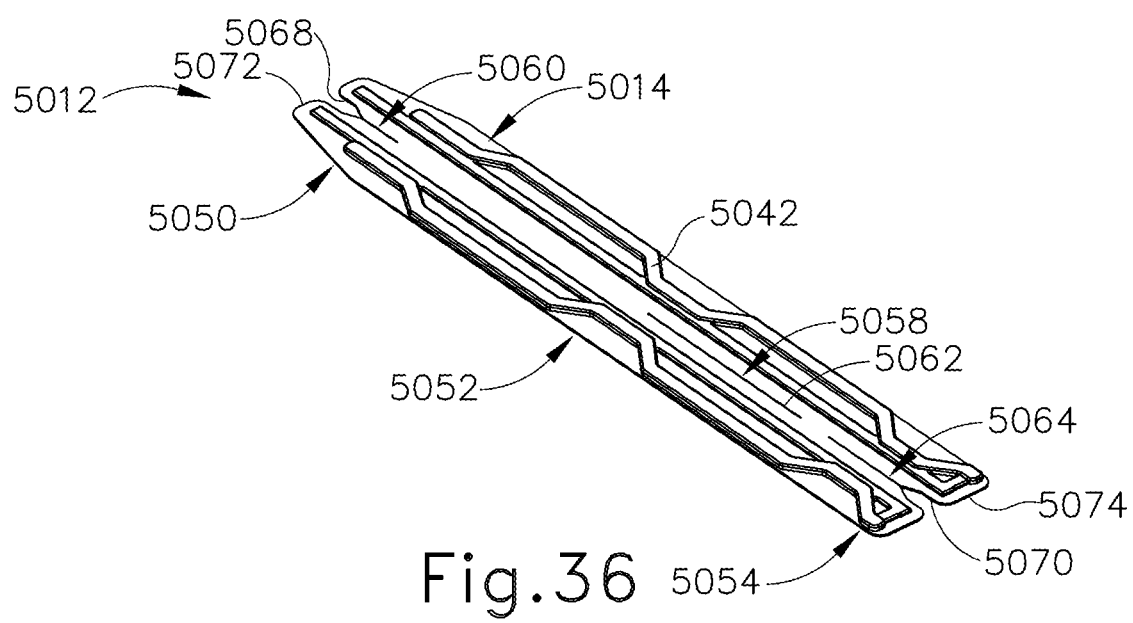
FIG. 36 depicts a perspective view of the buttress assembly of FIG. 34.
Figure 37:
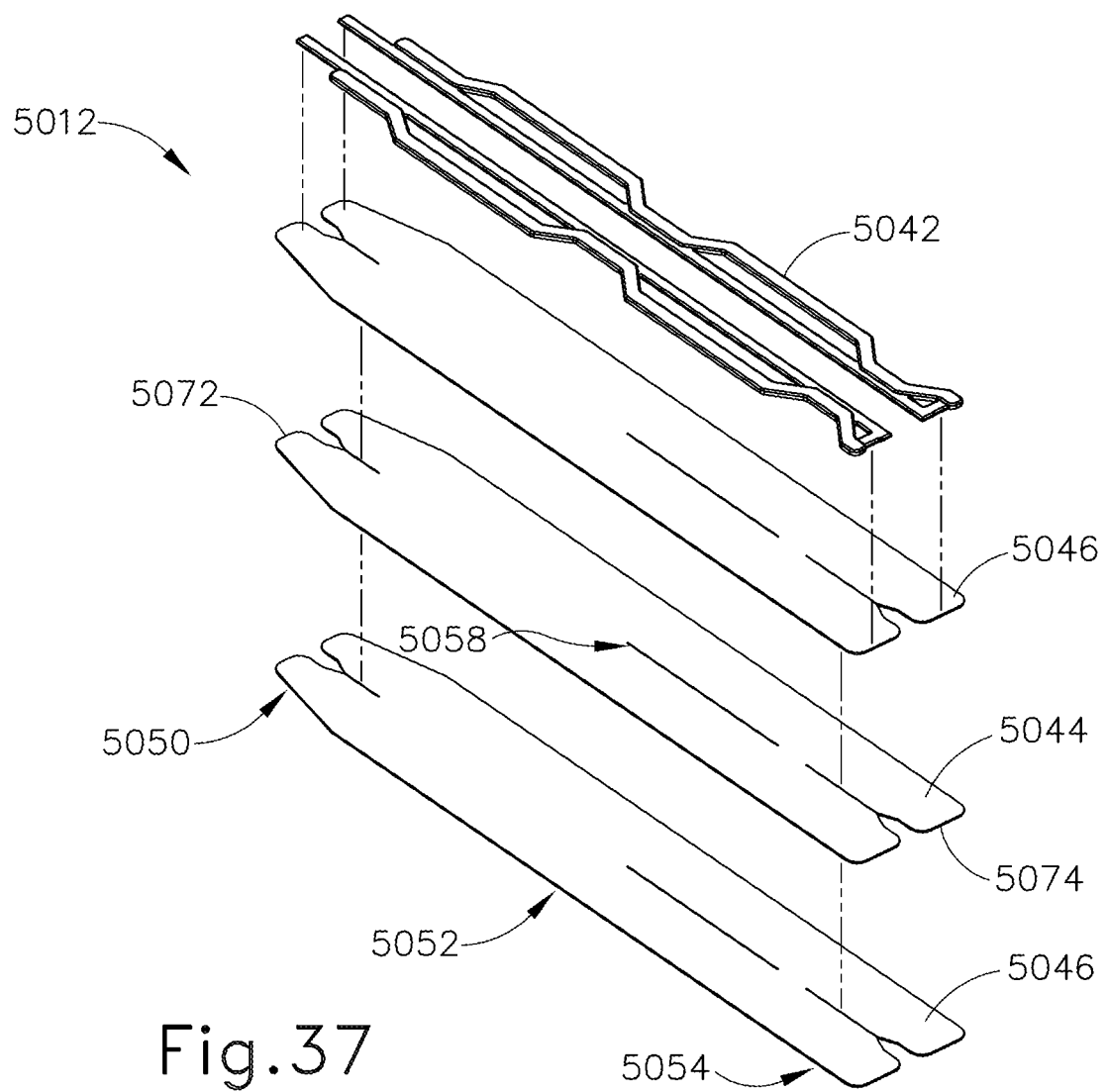
FIG. 37 depicts an exploded perspective view of the buttress assembly of FIG. 36.

FIG. 35 shows upper and lower buttress assemblies (5012) removed from buttress applier cartridge (5016), whereas FIG. 36 and FIG. 37 show upper buttress assembly (5012) in more detail. Notably, in the present example, upper and lower buttress assemblies (5012) are structurally identical, but for the relative positions of upper and lower buttress assemblies (5012) retained on buttress applier cartridge (5016). Buttress applier cartridge assembly (5010) may thus be used in more than one orientation with surgical instrument (5110) (see FIG. 43A). It will be appreciated that the following description of upper buttress assembly (5012) similarly applies to lower buttress assembly (5012) but for the respective orientations.

With respect to FIG. 36 and FIG. 37, upper buttress assembly (5012) includes a buttress (5014) and an upper adhesive layer (5042). Buttress (5014) of the present example more particularly has a three-layer, polymer construction including a core layer (5044) sandwiched between two outer layers (5046) to be collectively strong yet flexible to support a line of staples. In the present example, core layer (5044) is a polyglactin 910 material, which is manufactured and sold by Ethicon, Inc. of Somerville, New Jersey as VICRYL, whereas each outer layer is a polydioxanone (PDO) film material. More particularly, the polyglactin 910 material of core layer (5044) in one example has a transverse thickness of 206 micrometers, while the polydioxanone (PDO) film material of each outer layer (5046) has a transverse thickness of 8 micrometers. In another example, the polydioxanone (PDO) film material of each outer layer (5046) has a transverse thickness of 9.5 micrometers. Buttress (5014) of the present example is formed by laminating core layer (5044) between outer layers (5046) under a predetermined pressure, a predetermined temperature, and a predetermined time. Once laminated in one example, the polyglactin 910 material of core layer (5044) has a transverse thickness of 161.5 micrometers. Such materials of layers (5044, 5046) in one example are composed of fibers arranged to extend in a direction 45 degrees from a longitudinally extending direction along each buttress assembly (5012) to control lateral material stretch. Buttress (5014) is further mechanically cut to size thereby inhibiting abrasive edges, such as burrs and/or delamination, that could damage sensitive tissues. It will be appreciated that alternative methods of cutting buttresses (5014), such as a laser cutting or hot knife cutting, may be similarly used.

By way of further example only, each buttress (5014) may comprise one or more portions of the following: NEOVEIL absorbable PGA felt by Gunze Limited, of Kyoto, Japan; SEAMGUARD polyglycolic acid: trimethylene carbonate (PGA:TMC) reinforcement material by W.L. Gore & Associates, Inc., of Flagstaff, Arizona; PERI-STRIPS DRY with VERITAS Collagen Matrix (PSDV) reinforcement material, by Baxter Healthcare Corporation of Deerfield, Illinois; BIODESIGN biologic graft material by Cook Medical, Bloomington, Indiana; and/or SURGICEL NU-KNIT hemostat material by Ethicon, Inc. of Somerville, New Jersey. Still other suitable materials that may be used to form each buttress (5014) will be apparent to those of ordinary skill in the art in view of the teachings herein.

In addition or in the alternative, each buttress (5014) may comprise a material including, for example, a hemostatic agent such as fibrin to assist in coagulating blood and reduce bleeding at the severed and/or stapled surgical site along tissue. As another merely illustrative example, each buttress (5014) may comprise other adjuncts or hemostatic agents such as thrombin may be used such that each buttress (5014) may assist to coagulate blood and reduce the amount of bleeding at the surgical site. Other adjuncts or reagents that may be incorporated into each buttress (5014) may further include but are not limited to medical fluid or matrix components. Merely illustrative examples of materials that may be used to form each buttress (5014), as well as materials that may be otherwise incorporated into each buttress (5014), are disclosed in U.S. patent application Ser. No. 14/667,842, entitled "Method of Applying a Buttress to a Surgical Stapler," filed Mar. 25, 2015, issued as U.S. Pat. No. 10,349,939 on Jul. 16, 2019, the disclosure of which is incorporated by reference herein. Alternatively, any other suitable materials may be used.

By way of further example only, each buttress (5014) may be constructed in accordance with at least some of the teachings of U.S. Patent Pub. No. 2012/0241493, entitled "Tissue Thickness Compensator Comprising Controlled Release and Expansion," published Sep. 27, 2012, issued as U.S. Pat. No. 10,123,798 on Nov. 13, 2018, the disclosure of which is incorporated by reference herein; U.S. Patent Pub. No. 2013/0068816, entitled "Surgical Instrument and Buttress Material," published Mar. 21, 2013, now abandoned, the disclosure of which is incorporated by reference herein; U.S. Pat. No. 9,999,408, entitled "Surgical Instrument with Fluid Fillable Buttress," issued Jun. 19, 2018, the disclosure of which is incorporated by reference herein; U.S. Pat. No. 8,814,025, entitled "Fibrin Pad Matrix with Suspended Heat Activated Beads of Adhesive," issued Aug. 26, 2014, the disclosure of which is incorporated by reference herein; U.S. Pat. No. 8,899,464, entitled "Attachment of Surgical Staple Buttress to Cartridge," issued Dec. 2, 2014, the disclosure of which is incorporated by reference herein; U.S. Pat. No. 9,492,170, entitled "Device for Applying Adjunct in Endoscopic Procedure," issued Nov. 15, 2016, the disclosure of which is incorporated by reference herein; U.S. Pat. No. 8,998,060, entitled "Resistive Heated Surgical Staple Cartridge with Phase Change Sealant," issued Apr. 7, 2015, the disclosure of which is incorporated by reference herein; U.S. Pat. No. 9,393,018, entitled "Surgical Staple Assembly with Hemostatic Feature," issued Jul. 19, 2016, the disclosure of which is incorporated by reference herein; U.S. Pat. No. 9,101,359, entitled "Surgical Staple Cartridge with Self-Dispensing Staple Buttress," issued Aug. 11, 2015, the disclosure of which is incorporated by reference herein; U.S. Pat. No. 9,198,644, entitled "Anvil Cartridge for Surgical Fastening Device," issued Dec. 1, 2015, the disclosure of which is incorporated by reference herein; U.S. Patent Pub. No. 2013/0075447, entitled "Adjunct Therapy for Applying Hemostatic Agent," published Mar. 28, 2013, now abandoned, the disclosure of which is incorporated by reference herein; U.S. Pat. No. 9,211,120, entitled "Tissue Thickness Compensator Comprising a Plurality of Medicaments," issued Dec. 15, 2015, the disclosure of which is incorporated by reference herein; U.S. Patent Pub. No. 2015/0351758, entitled "Adjunct Materials and Methods of Using Same in Surgical Methods for Tissue Sealing," published Dec. 10, 2015, issued as U.S. Pat. No. 10,172,611 on Jan. 8, 2019, the disclosure of which is incorporated by reference herein; U.S. Patent Pub. No. 2017/0049444, entitled "Implantable Layers for a Surgical Instrument," published Feb. 23, 2017, issued as U.S. Pat. No. 10,835,249 on Nov. 17, 2020, the disclosure of which is incorporated by reference herein; U.S. Patent Pub. No. 2017/0055986, entitled "Drug Eluting Adjuncts and Methods of Using Drug Eluting Adjuncts," published Mar. 2, 2017, issued as U.S. Pat. No. 10,569,071 on Feb. 25, 2020, the disclosure of which is incorporated by reference herein; U.S. Patent Pub. No. 2017/0086837, entitled "Compressible Adjunct with Crossing Spacer Fibers," published Mar. 30, 2017, issued as U.S. Pat. No. 10,433,846 on Oct. 8, 2019, the disclosure of which is incorporated by reference herein; and/or U.S. Patent Pub. No. 2017/0086842, entitled "Method for Applying an Implantable Layer to a Fastener Cartridge," published Mar. 30, 2017, issued as U.S. Pat. No. 11,690,623 on Jul. 4, 2023, the disclosure of which is incorporated by reference herein.

Furthermore, buttress (5014) is configured to be cut by a knife (5114) (see FIG. 45A) from a proximal portion (5050) of buttress (5014), along an intermediate portion (5052) of buttress (5014), and further through a distal portion (5054) of buttress (5014) such that inward edges are adjacent to cut tissue as discussed below in more detail. Buttress (5014) further includes a longitudinally extending pre-cut slit (5058) configured to receive knife (5114) (see FIG. 45A) and aid in separating lateral portions of buttress (5014) as inward edges form therealong. Pre-cut slit (5058) thus also reduces wear on knife (5114) (see FIG. 45A) during use.

Pre-cut slit (5058) of the present example has three distinct portions longitudinally separated by core and outer layers (5044, 5046). With respect to FIG. 38 and FIG. 39, a proximal portion of pre-cut slit (5058) includes a proximal end slit (5060) in proximal end portion (5050) of buttress (5014) extending entirely through buttress (5014) in a transverse direction. An intermediate portion of pre-cut slit (5058) includes an intermediate slit (5062) in intermediate portion (5052) of buttress (5014) extending entirely through buttress (5014) in the transverse direction. Furthermore, a distal portion of pre-cut slit (5058) includes a distal end slit (5064) extending entirely through buttress (5014) in the transverse direction. In the present example, proximal end slit (5060), intermediate slit (5062), and distal end slit (5064) are longitudinally aligned along a central longitudinal axis that laterally bifurcates lateral halves of buttress (5014). Intermediate slit (5062) is spaced apart from each of proximal and distal end slits (5060, 5064) such that the portions of buttress (5014) between slits (5060, 5062, 5064) remain uncut. Such uncut portions that may also be referred to as "bridge" portions are sized large enough to remain intact during assembly, storage, and application with tissue, but small enough to substantially reduce resistance while cutting buttress (5014). However, it will be appreciated that some further perforation may be formed along the central longitudinal axis in alternative examples to further aid severability between lateral halves of buttress (5014).

Proximal end slit (5060) and distal end slit (5064) portions of pre-cut slit (5058) further include a proximal end opening (5068) and a distal end opening (5070), respectively. Proximal end opening (5068) of proximal end slit (5060) widens symmetrically about the central longitudinal axis to a proximal end (5072) of buttress (5014), whereas distal end opening (5070) of distal end slit (5064) widens symmetrically about the central longitudinal axis to a distal end (5074) of buttress (5014). Such widened proximal and distal end openings (5068, 5070) are configured to respectively aid knife's (5114) introduction and departure from buttress (5014) while cutting as discussed below in greater detail.

Figure 40:
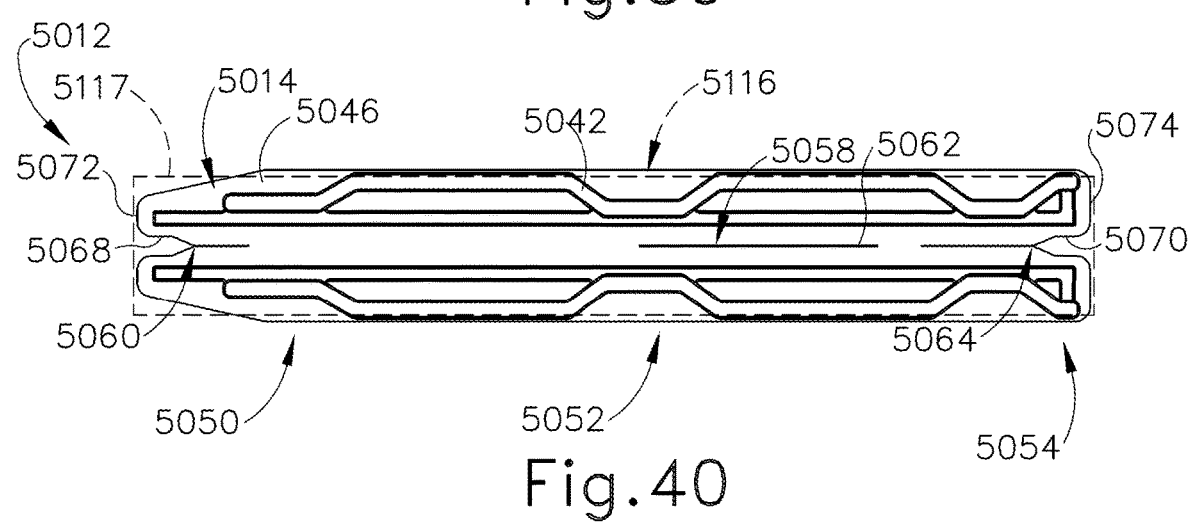
FIG. 40 depicts a top view of the buttress assembly of FIG. 34 for the upper jaw showing an outer profile of the upper jaw thereon.

With respect to FIG. 40, upper adhesive layer (5042) is provided on outer layer (5046) of buttress (5014) in order to adhere buttress (5014) within effector (5112) (see FIG. 43A) of surgical instrument (5110) (see FIG. 43A). Adherence of the buttress (5014) can occur through a variety of mechanisms including but not limited to a pressure sensitive adhesive. In some versions, each adhesive layer (5042) includes a pressure sensitive adhesive material. Examples of various suitable materials that may be used to form adhesive layers (5042) are disclosed in U.S. Patent Pub. No. 2016/0278774, entitled "Method of Applying a Buttress to a Surgical Stapler," published Sep. 29, 2016, issued as U.S. Pat. No. 10,349,939 on Jul. 16, 2019, the disclosure of which is incorporated by reference herein. Alternatively, any other suitable materials may be used. As shown in the present example, adhesive layer (5042) is applied to form a continuous outer seal to enhance longevity once applied to end effector (5112) (see FIG. 43A).

It should be understood that the term "adhesive," as used herein, may include (but is not limited to) tacky materials and also materials that are pliable or wax-like and adhere to a complex geometry via deformation and conformance. Some suitable adhesives may provide such pliability to adhere to a complex geometry via deformation and conformance without necessarily providing a high initial tack. In some instances, adhesives with lower tackiness may be removed more cleanly from surfaces. Various suitable materials that may be used to form adhesive layers (5042) will be apparent to those of ordinary skill in the art in view of the teachings herein.

Figure 38:
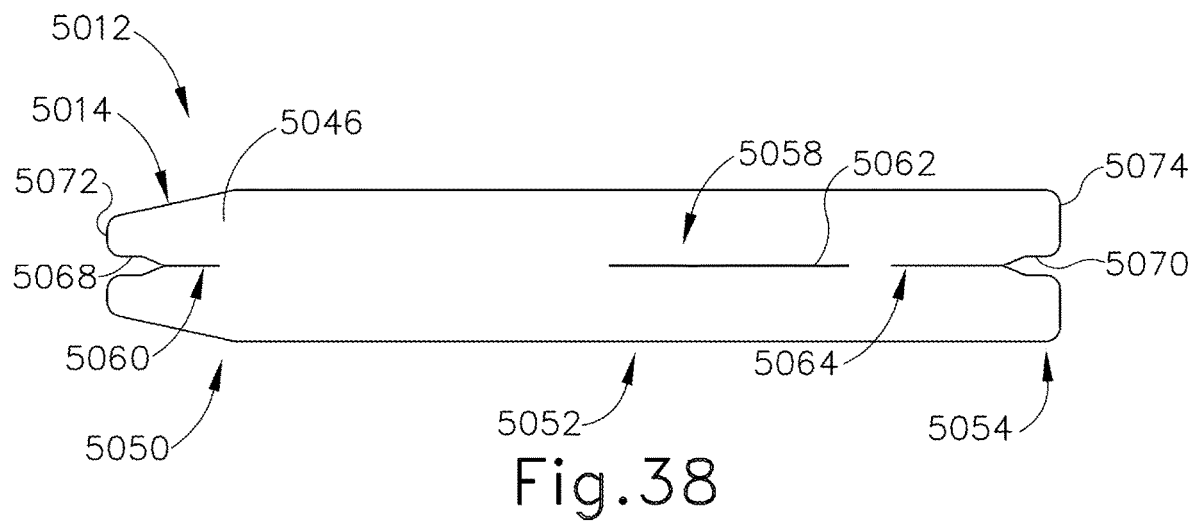
FIG. 38 depicts a bottom view of the buttress assembly of FIG. 34 for the upper jaw.
Figure 39:
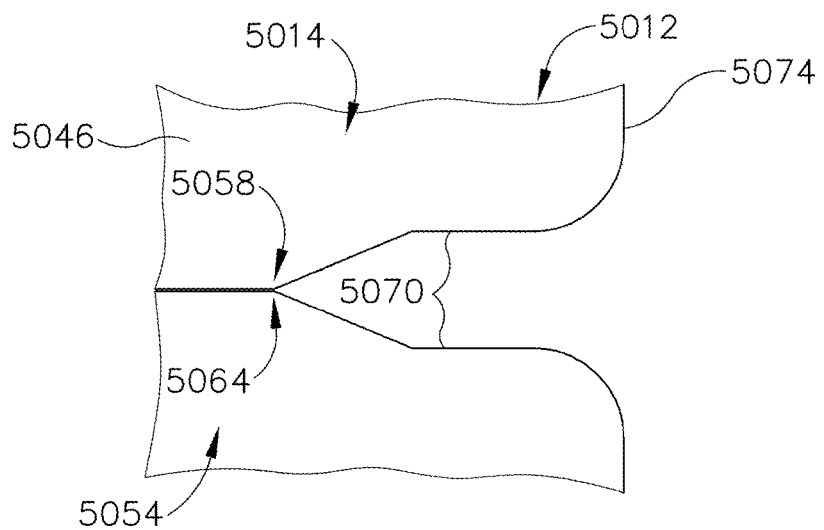
FIG. 39 depicts an enlarged bottom view of a distal end portion of the buttress assembly of FIG. 34 showing a pre-formed slit.
Figure 41:
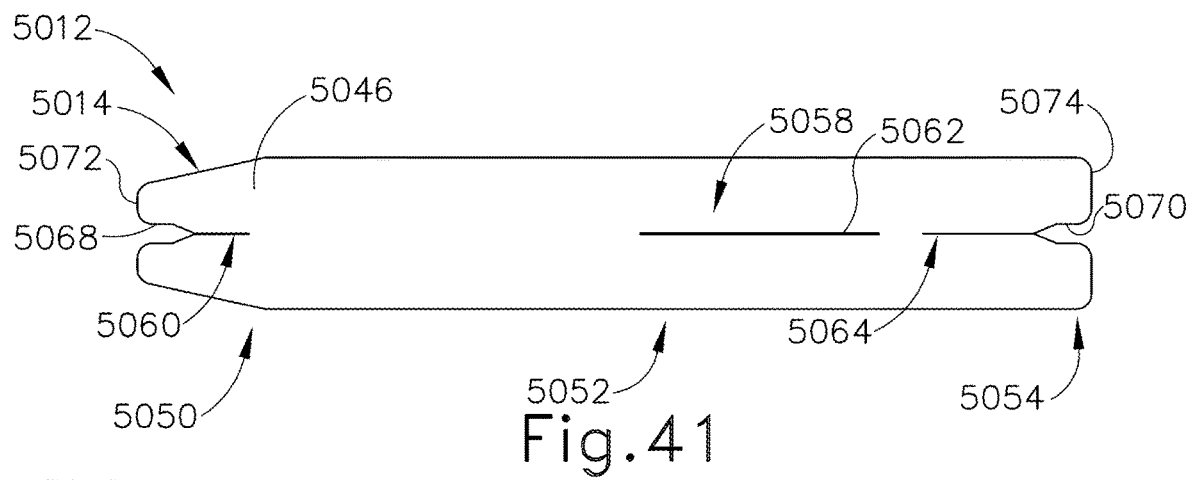
FIG. 41 depicts a top view of the buttress assembly of FIG. 34 for the lower jaw.
Figure 42:
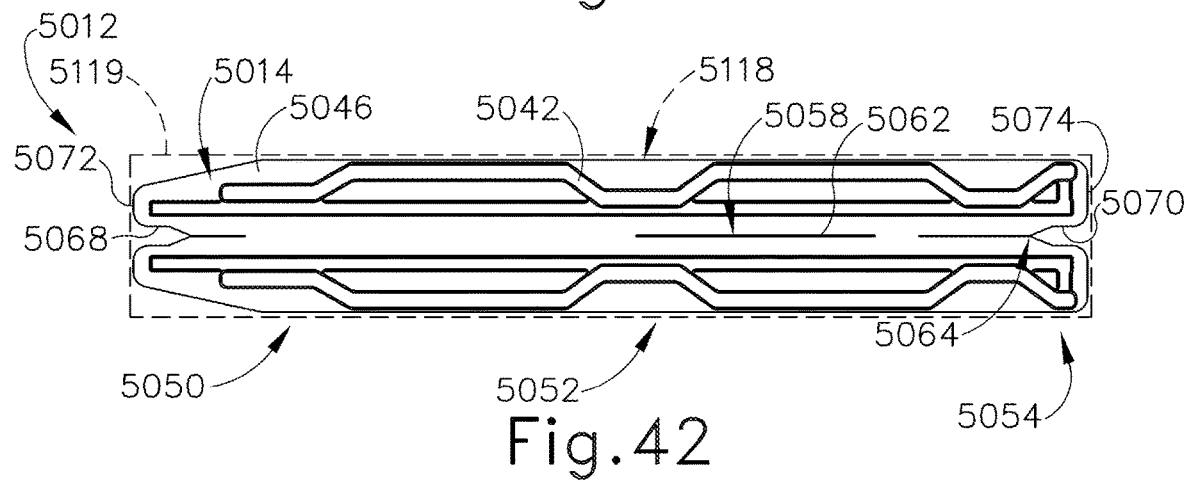
FIG. 42 depicts a bottom view of the buttress assembly of FIG. 34 for the lower jaw showing an outer profile of the lower jaw thereon.

As generally discussed above and with respect to FIGS. 38-42, upper and lower buttress assemblies (5012) are structurally identical. In this respect, FIG. 38 shows a lower surface of upper buttress assembly (5012) from a lower transverse direction, whereas FIG. 41 shows an upper surface of lower buttress assembly (5012) from an upper transverse direction. These lower and upper surfaces of the present example have the same lateral width and longitudinal lengths. Similarly, FIG. 40 shows an upper surface of upper buttress assembly (5012) from an upper transverse direction, whereas FIG. 42 shows an lower surface of lower buttress assembly (5012) from a lower transverse direction. In each instance in the present example, these lower and upper surfaces have the same lateral width and longitudinal lengths. In addition, adhesive layers (5042) of each respective buttress assembly (5012) are formed as adhesive bead layers (5042) in a predetermined adhesive pattern. The adhesive pattern for each of the upper and lower buttress assemblies (5012) shown respectively in FIG. 40 and FIG. 42 is again identical, having the same lateral width and longitudinal lengths. The lateral width and longitudinal length of the adhesive pattern collectively define an outer adhesive profile sized to accommodate both an anvil (5116) and a deck (5118) of a staple cartridge (5120). In other words, the outer adhesive profile of adhesive layer (5042) as well as buttress (5014) are interchangeable with anvil (5116) and deck (5118) such that buttress applier cartridge assembly (5010) may be used in an upright orientation or flipped about the central longitudinal axis in an upside-down orientation while loading end buttress assemblies (5012) for use.

To this end, FIG. 40 shows an outer anvil profile (5117) overlaid onto upper buttress assembly (5012), and FIG. 42 shows an outer deck profile (5119) overlaid onto lower buttress assembly (5012) to illustrate the interface between the adhesive pattern of adhesive layer (5042) with an underside (5122) of anvil (5116) and deck (5118). The adhesive pattern of the present example is symmetric about the central longitudinal axis such that upper adhesive layer (5042) mirrors lower adhesive layer (5042) in lateral and longitudinal alignment when arranged offset from each other on platform (5030) (see FIG. 34). More particularly, each adhesive layer (5042) of the present example has a lateral width generally equivalent to the lateral width of outer deck profile (5119), but larger than the lateral width of outer anvil profile (5117). Adhesive layer (5042) thereby fits within outer deck profile (5119) of FIG. 42 with a greater surface area contact to deck (5118) to increase adhesive force therebetween. However, adhesive layer (5042) is laterally wider than outer anvil profile (5117) of FIG. 40 and extends laterally beyond outer anvil profile (5117) with less surface area contact to underside (5122) of anvil to decrease adhesive force therebetween. More particularly, each adhesive layer (5042) of the present example has a lateral width of approximately 0.41 inches. In contrast, deck (5118) is wider than underside (5122) of anvil (5116) with deck (5118) having a lateral width of approximately 0.41 inches, and underside (5122) of anvil (5116) having a lateral width of approximately 0.37 inches.

While the above referenced interchangeability between anvil (5116) and deck (5118) simplifies loading buttress assemblies (5012) and reduces the likelihood of improper loading, the reduced surface area contact between underside (5122) of anvil (5116) and adhesive layer (5042) eases removal of buttress assembly (5012) from anvil (5116). In one example, underside (5122) of anvil (5116) is a relatively smooth material that adheres to buttress (5014) via adhesive layer (5042) with a relatively higher adhesive force than the relatively lower adhesive force of buttress assembly (5012) to deck (5118). Decreasing the surface area contact between adhesive layer (5042) and underside (5122) of anvil (5116) relative to the surface area contact with deck (5118) may thus result in more equalized and/or predictable removal forces of buttress assemblies (5012) from anvil (5116) and deck (5118).

C. Exemplary Adhesion of Buttress to Surgical Stapler and Cutting of Buttress Assembly with Tissue As noted above and discussed below in greater detail with respect to FIG. 43A, upper and lower buttress assemblies (5012) include upper and lower adhesive layers (5042) (or other form of adhesive material) to adhere respective buttresses (5014) to an underside (5122) of anvil (5116) and deck (5118) of staple cartridge (5120). Such adhesive may provide proper positioning of buttress (5014) before and during actuation of end effector (5112); then allow buttress (5014) to separate from end effector (5112) after end effector (5112) has been actuated, without causing damage to buttress (5014) that is substantial enough to compromise the proper subsequent functioning of buttress (5014).

Figure 43B:
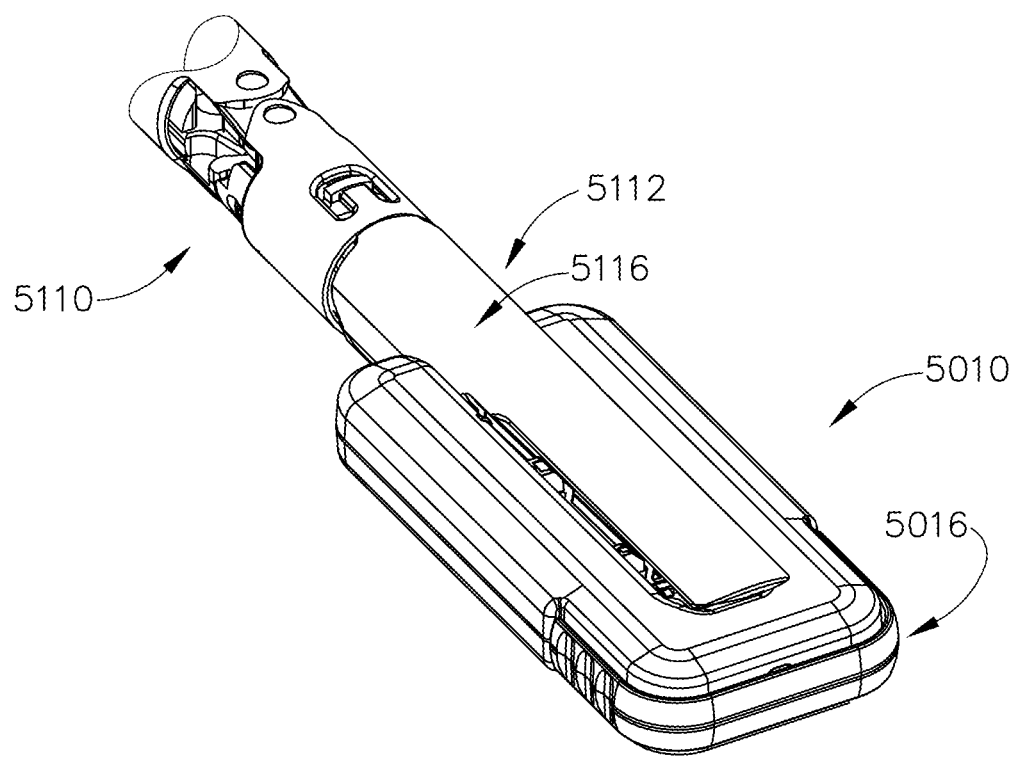
FIG. 43B depicts the perspective view of the end effector similar to FIG. 43B, but showing the buttress applier cartridge assembly of FIG. 34 positioned between the upper and lower jaws in a closed position.
Figure 43C:
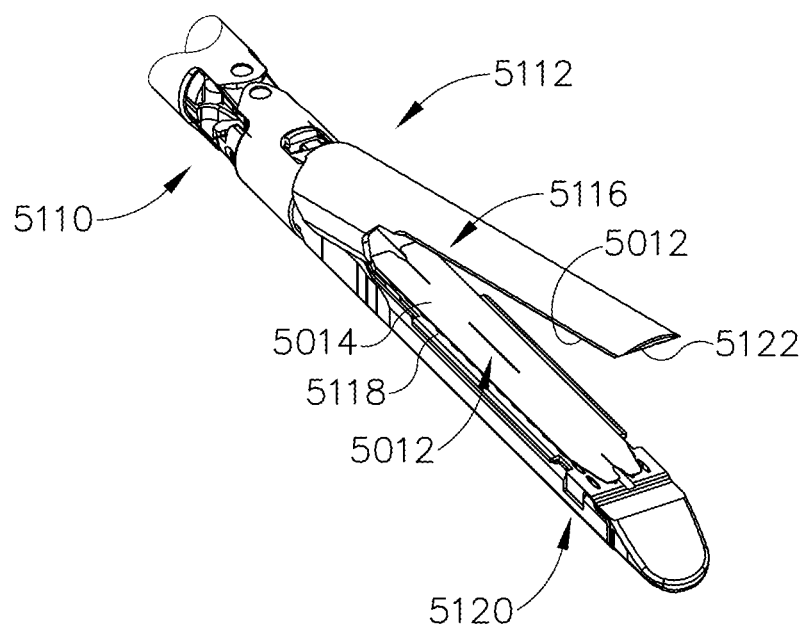
FIG. 43C depicts the perspective view of the end effector similar to FIG. 43B, but showing the buttress assemblies respectively secured to the upper and lower jaws in the open position.

To use buttress applier cartridge (5016) to load end effector (5112), the operator would first position buttress applier cartridge (5016) and end effector (5112) such that end effector (5112) is aligned with open end (5018) of buttress applier cartridge (5016) as shown in FIG. 43A. The operator would then advance end effector (5040) distally (and/or retract buttress applier cartridge (5016) proximally) to position platform (5030) and buttress assemblies (5012) between anvil (5116) and staple cartridge (5120). In order to load buttress assemblies (5012) on end effector (5112), the operator simply closes end effector (5112) by pivoting anvil (5116) toward staple cartridge (5120) to reach the state shown in FIG. 43B. As shown, closure of end effector (5040) results in anvil (5060) and staple cartridge (5120) bearing against actuator sleds (5032), thereby urging arms (5034) to unlock buttress assemblies (5012) from buttress applier cartridge (5016). Adhesive layers (5042) of upper and lower buttress assemblies (5012) are sufficiently compressed against anvil (5116) and deck (5118) as shown in FIG. 43C to retain upper and lower buttress assemblies (5012) to end effector (5112) for stapling tissue.

To this end, FIGS. 44A-44C show a sequence where end effector (5112) loaded with buttress assemblies (5012) is actuated to drive a plurality of staples (5124) through two apposed layers of tissue ($T_1$, $T_2$), with buttress assemblies (5012) being secured to the same layers of tissue ($T_1$, $T_2$) by staples (5124). In particular, FIG. 44A shows layers of tissue ($T_1$, $T_2$) positioned between anvil (5116) and staple cartridge (5120), with anvil (5116) in the open position. Upper buttress assembly (5012) is adhered to the underside (5122) of anvil (5116) via adhesive layer (5042); while lower buttress assembly (5012) is adhered to deck (5118) of staple cartridge (5120) via adhesive layer (5042). Layers of tissue ($T_1$, $T_2$) are thus interposed between upper and lower buttress assemblies (5012). Next, a trigger (not shown) is pivoted to drive anvil (5116) to the closed position as shown in FIG. 44B. At this stage, layers of tissue ($T_1$, $T_2$) are compressed between anvil (5116) and staple cartridge (5120), with upper and lower buttress assemblies (5012) engaging opposite surfaces of tissue layers ($T_1$, $T_2$). End effector (5112) is then actuated as described above, driving staple (5124) through upper and lower buttress assemblies (5012) and layers of tissue ($T_1$, $T_2$). As shown in FIG. 44C, a crown (5126) of driven staple (5124) captures and retains lower buttress assembly (5012) against layer of tissue ($T_2$). Deformed legs (5128) of staple (5124) capture and retain upper buttress assembly (5012) against layer of tissue ($T_1$).

It should be understood that a series of staples (5124) will similarly capture and retain upper and lower buttress assemblies (5012) against layers of tissue ($T_1$, $T_2$), thereby securing upper and lower buttress assemblies (5012) to tissue ($T_1$, $T_2$). As can also be seen in FIGS. 45A-45D, knife (5114) also cuts through a centerline of buttress assemblies (5012), separating each buttress assembly (5012) into a corresponding pair of sections, such that each section remains secured to a respective severed region of tissue ($T_1$, $T_2$). For example, with tissue ($T_1$, $T_2$) stapled as shown in FIG. 44C, knife (5114) is driven distally from a proximal position severing tissue ($T_1$, $T_2$) and upper and lower buttress assemblies (5012).

Figure 45A:
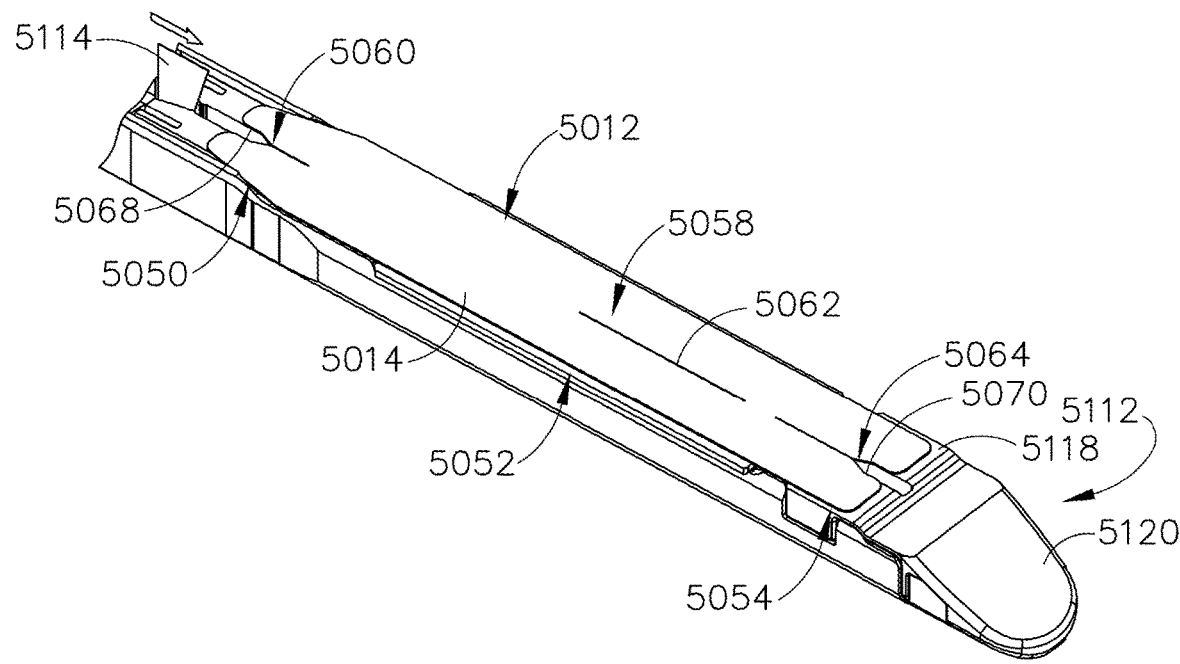
FIG. 45A depicts a perspective view of the buttress assembly of FIG. 43C secured to the lower jaw of FIG. 43C and a knife of the end effector being driven distally therethrough.
Figure 45B:
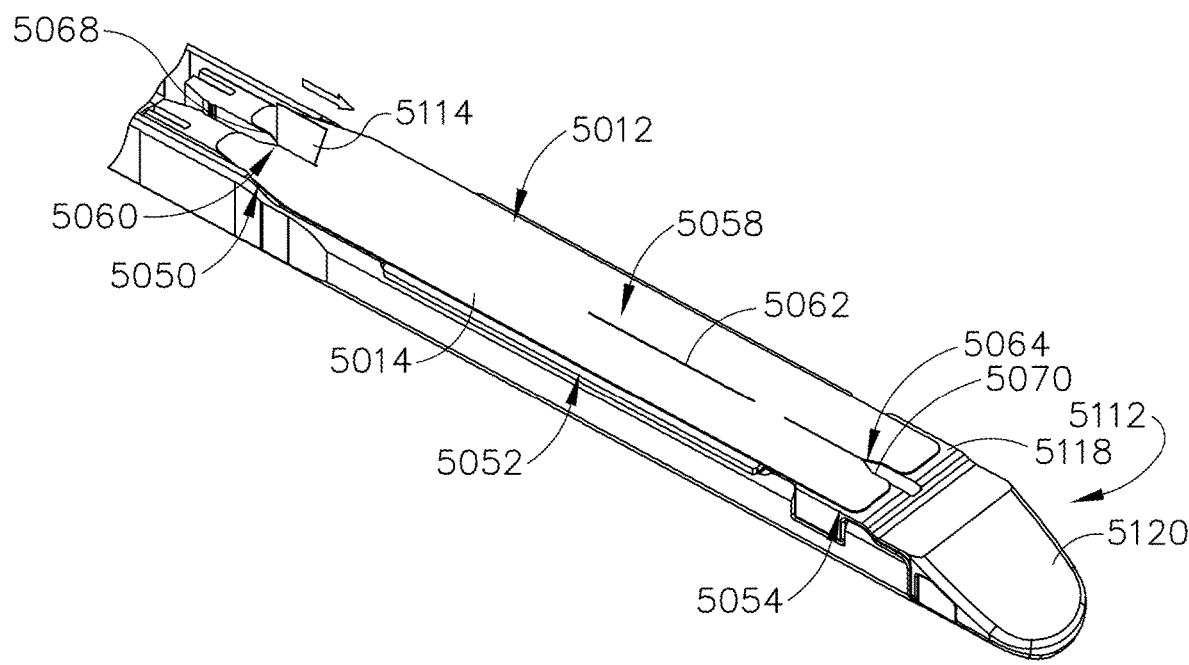
FIG. 45B depicts the perspective view of the buttress assembly and the lower jaw similar to FIG. 45A, but showing the knife cutting a proximal portion of the buttress assembly while being driven distally therethrough.

FIGS. 45A-45D illustrate knife severing buttress assemblies (5012) and tissue ($T_1$, $T_2$) as shown in FIG. 44C, but with tissue ($T_1$, $T_2$), upper buttress assembly (5012), and anvil (5116) hidden for additional clarity. As shown in FIGS. 45A-45B, knife (5114) is introduced into proximal end opening (5068) and further through the remainder of proximal end slit (5060). Proximal end slit (5060) thereby inhibits buttress (5014) from gathering onto knife (5114) with staggered, uneven cutting in the event that tissue ($T_1$, $T_2$) is not compressed against proximal portion (5050) of buttress (5014).

Figure 45C:
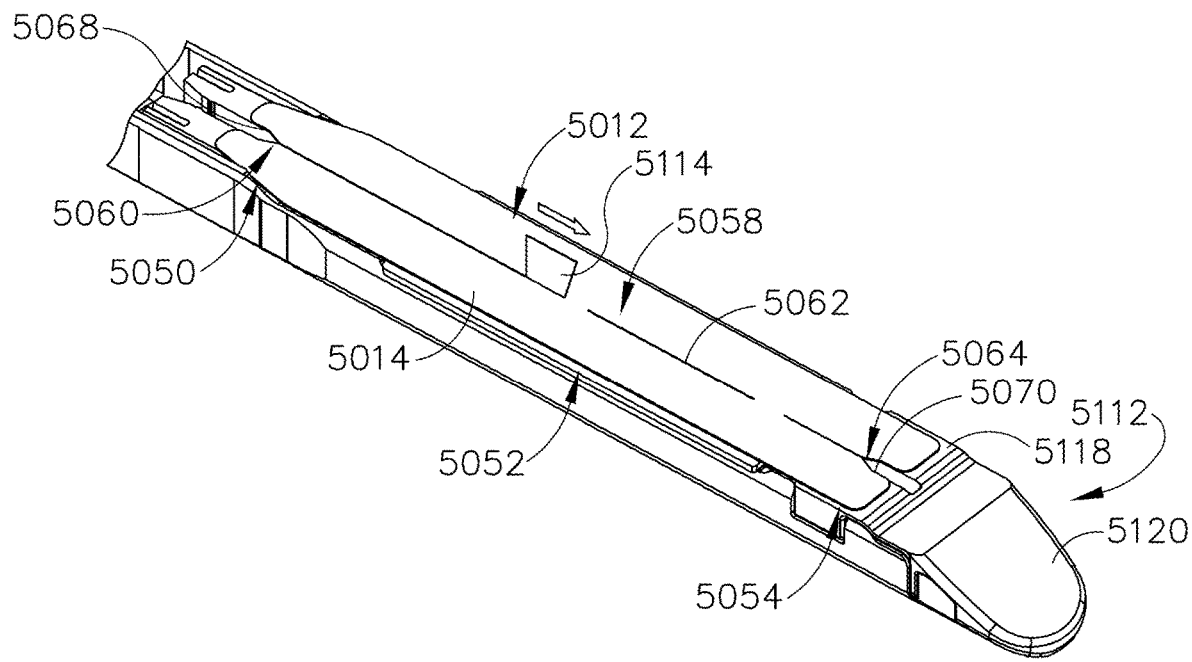
FIG. 45C depicts the perspective view of the buttress assembly and the lower jaw similar to FIG. 45B, but showing the knife cutting an intermediate portion of the buttress assembly while being driven distally therethrough.
Figure 45D:
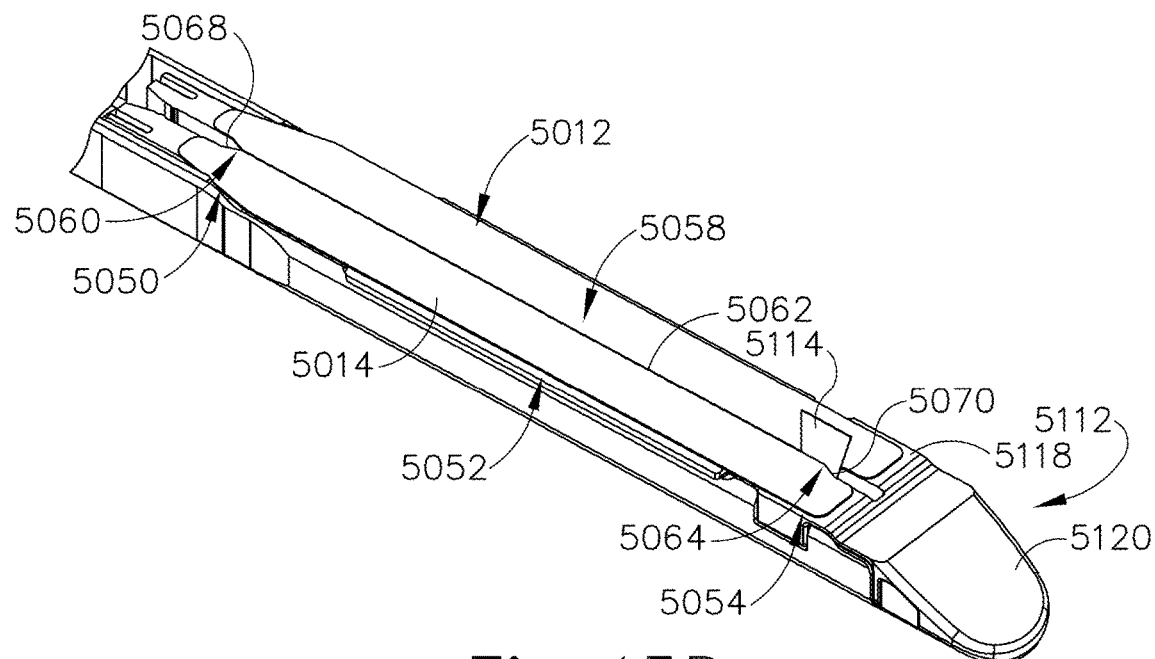
FIG. 45D depicts the perspective view of the buttress assembly and the lower jaw similar to FIG. 45C, but showing the knife cutting a distal portion of the buttress assembly while being driven distally therethrough.

With respect to FIG. 45C, knife (5114) distally translates from proximal end slit (5060) of pre-cut slit (5058) severing proximal and intermediate portions (5050, 5052) of buttress (5014) until received within intermediate slit (5062) of pre-cut slit (5058). Intermediate slit (5062) reduces the likelihood of inadvertently tearing intermediate and/or distal portions (5052, 5054) of buttress (5014) in the event that tissue ($T_1$, $T_2$) is only compressed against the proximal portion (5050) and not present against the intermediate and distal portions (5052, 5054) of buttress (5014). As knife (5114) cuts from intermediate portion (5052) of buttress (5014) through distal portion (5054) of buttress (5014), FIG. 45D shown knife (5114) departing through distal end opening (5070) to the distal position having severed buttress assembly (5012) into a pair of lateral halves. Distal end slit (5064) is sized to accommodate manufacturing tolerances associated with the particular position of knife's (5114) distal position to ensure that buttress assembly (5012) is fully severed into two lateral halves upon completion without requiring the operator to manually rip or cut a remaining distal portion of buttress (5014).

Figure 46:
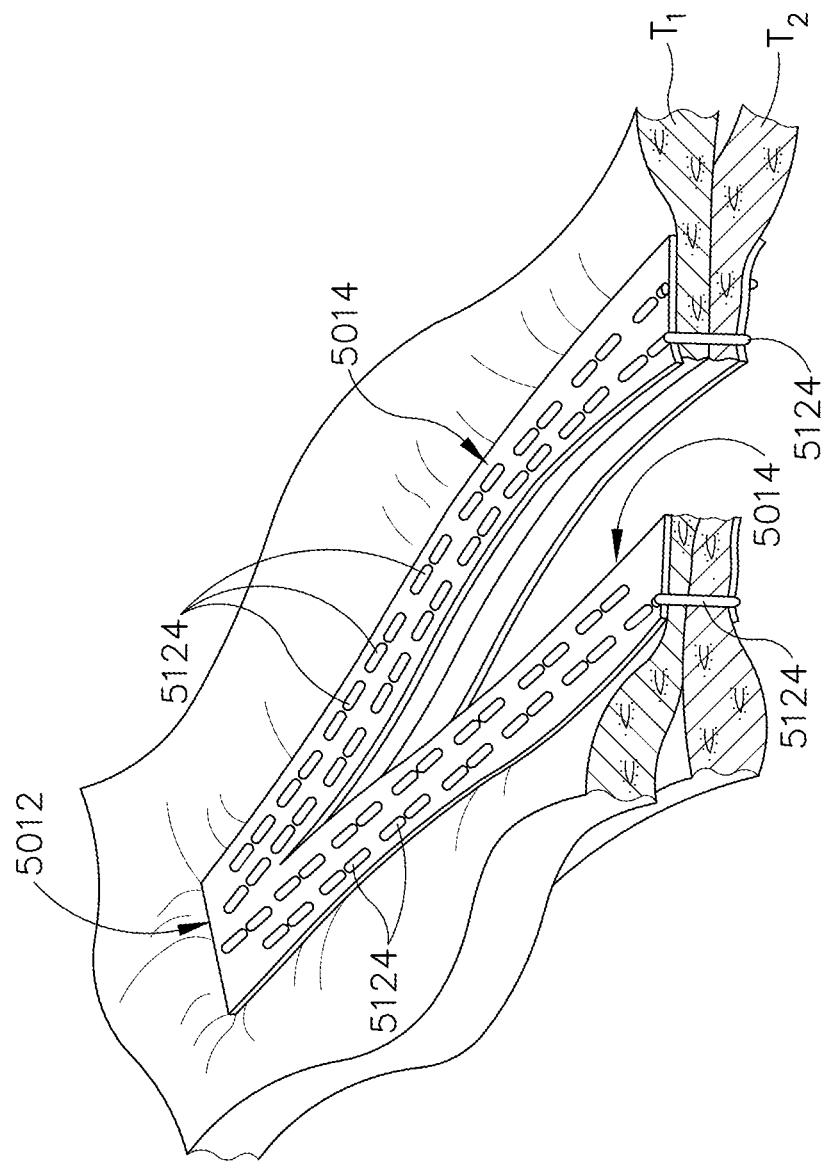
FIG. 46 depicts a perspective view of staples and the buttress assembly of FIG. 45D having been secured to the tissue by the end effector as shown in FIG. 44C and cut as shown in FIG. 45D.

With respect to FIG. 46, as end effector (5112) (see FIG. 45D) is pulled away from tissue ($T_1$, $T_2$) after deploying staples (5124) and upper and lower buttress assemblies (5012), upper and lower buttress assemblies (5012) disengage end effector (5112), such that upper and lower buttress assemblies (5012) remain secured to tissue ($T_1$, $T_2$) with staples (5124). Buttressed tissue ($T_1$, $T_2$) thus provides structural reinforcement to the lines of staples (5124). In addition to the foregoing, it should also be understood that any of the various buttress assemblies described herein may be further constructed and operable in accordance with at least some of the teachings of U.S. Patent Pub. No. 2016/0278774, entitled "Method of Applying a Buttress to a Surgical Stapler," published Sep. 29, 2016, issued as U.S. Pat. No. 10,349,939 on Jul. 16, 2019, the disclosure of which is incorporated by reference herein.

VIII. Exemplary Buttress Applier Cartridge for Use with Buttress Assembly

Figure 47:
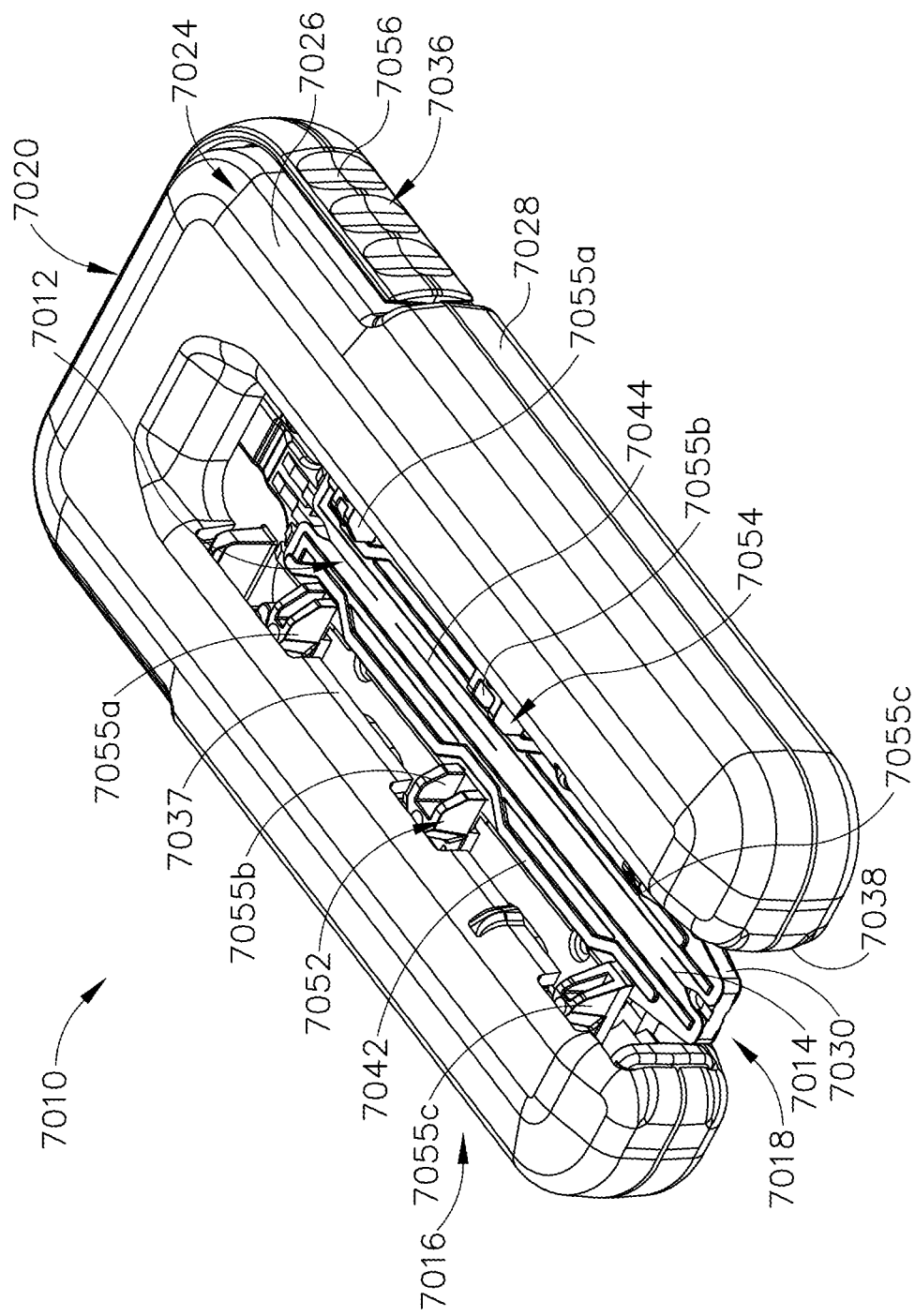
FIG. 47 depicts a perspective view of an exemplary buttress applier cartridge assembly that includes an example of a buttress applier cartridge carrying an example of a buttress assembly for an upper jaw and an example of another buttress assembly for a lower jaw.

In some instances, it may be desirable to use an exemplary buttress applier cartridge assembly (7010) as shown in FIG. 47 to equip a surgical instrument with a buttress assembly (7012) for forming staples in tissue with a buttress (7014). Such buttress (7014) inhibits the formed staples from pulling through the tissue to thereby reduce a risk of tissue tearing at or near the site of formed staples. In addition to or as an alternative to providing structural support and integrity to a line of staples, buttress (7014) may provide various other kinds of effects such as spacing or gap-filling, administration of therapeutic agents, and/or other effects. Prior to use with the surgical instrument, one or more buttresses (7014) is releasably retained on a buttress applier cartridge (7016), which is configured to deposit buttress assembly (7010) onto surgical instrument for use as discussed below in more detail in an exemplary surgical instrument (7018) (see FIG. 56A).

FIG. 47 shows buttress applier cartridge assembly (7010) including a pair of buttress assemblies (7012) releasably retained on buttress applier cartridge (7016), which supports and protects buttress assemblies (7012) prior to use and further aids with loading buttress assemblies (7012) on surgical instrument (7210) (see FIG. 56A). Buttress applier cartridge (7016) of the present example includes an open end (7018) and a closed end (7020). Open end (7018) is configured to receive end effector (7212) (see FIG. 56A) as described below in greater detail. Buttress applier cartridge (7016) further includes a housing assembly (7024) having an upper housing (7026) and a lower housing (7028), which each generally define a "U" shape to present open end (7018). Various components are interposed between upper and lower housings (7026, 7028). In particular, these components include a platform (7030) supporting a chassis (7036).

Platform (7030) of the present example supports upper buttress assembly (7012) on one side of platform (7030) and lower buttress assembly (7012) on the other side of platform (7030). Platform (7030) is exposed in recesses that are formed between the prongs of the "U" configuration of upper and lower housings (7026, 7028). Thus, upper housing (7026) has an upper gap (7037) extending to the open end (7018) along an upper surface of platform (7030), and lower housing (7028) similarly has a lower gap (7038) extending to the open end (7018) along the lower surface of platform (7030). The location of platform (7030) and buttress assemblies (7012) in such recesses may prevent inadvertent contact between buttress assemblies (7012) and other devices in the operating room. In other words, upper and lower housings (7026, 7028) may provide some degree of physical shielding of buttress assemblies (7012) while buttress assemblies are retained on platform (7030).

Additional features may be combined as applicable with the following example of buttress applier cartridge assembly (7010). Such features are described in U.S. patent application Ser. No. 16/235,473, entitled "Adhesive Distribution on Buttress for Surgical Stapler," filed on Dec. 28, 2018, published as U.S. Pub. No. 2020/0205820 on Jul. 2, 2020, issued as U.S. Pat. No. 11,166,724 on Nov. 9, 2021; U.S. patent application Ser. No. 16/235,503, entitled "Surgical Stapler Buttress with Tissue In-Growth Promotion," filed on Dec. 28, 2018, published as U.S. Pub. No. 2020/0205822 on Jul. 2, 2020, now abandoned; U.S. patent application Ser. No. 16/235,488, entitled "Configuration of Buttress for Surgical Stapler," filed on Dec. 28, 2020, published as U.S. Pub. No. 2020/0205821 on Jul. 2, 2020, issued as U.S. Pat. No. 11,166,725 on Nov. 9, 2021; U.S. patent application Ser. No. 16/235,541, entitled "Packaging for Surgical Stapler Buttress," filed on Dec. 28, 2018, published as U.S. Pub. No. 2020/0205824 on Jul. 2, 2020, issued as U.S. Pat. No. 11,432,817 on Sep. 6, 2022; U.S. patent application Ser. No. 16/235,630, entitled "Curved Tip Surgical Stapler Buttress Assembly Applicator with Opening Feature for Curved Tip Alignment," filed on Dec. 28, 2018, published as U.S. Pub. No. 2020/0205826 on Jul. 2, 2020, issued as U.S. Pat. No. 11,272,935 on Mar. 15, 2022; U.S. patent application Ser. No. 16/235,670, entitled "Curved Tip Surgical Stapler Buttress Assembly Applicator with Proximal Alignment Features," filed on Dec. 28, 2018, issued as U.S. Pat. No. 10,905,424 on Feb. 2, 2021; and U.S. patent application Ser. No. 16/235,681, entitled "Curved Tip Surgical Stapler Buttress Assembly Applicator with Compression Layer Pocket Feature," filed on Dec. 28, 2018, published as U.S. Pub. No. 2020/0205807 on Jul. 2, 2020, issued as U.S. Pat. No. 11,103,246 on Aug. 31, 2021, the disclosures of which are hereby incorporated by reference.

A. Exemplary Buttress Assembly

With respect to FIG. 47, upper and lower buttress assemblies (7012) are structurally identical, but for the relative positions of upper and lower buttress assemblies (7012) retained on buttress applier cartridge (7016). Buttress applier cartridge assembly (7010) may thus be used in more than one orientation with surgical instrument (7210) (see FIG. 60A). It will be appreciated that the following description of upper buttress assembly (7012) similarly applies to lower buttress assembly (7012) but for the respective orientations.

Upper buttress assembly (7012) includes buttress (7014) and an upper adhesive layer (7042). Buttress (7014) of the present example more particularly has a three-layer, polymer construction including a core layer sandwiched between two outer layers to be collectively strong yet flexible to support a line of staples. In the present example, core layer is a polyglactin 910 material, which is manufactured and sold by Ethicon, Inc. of Somerville, New Jersey as VICRYL, whereas each outer layer is a polydioxanone (PDO) film material. Buttress (7014) of the present example is formed by laminating core layer between outer layers under a predetermined pressure, a predetermined temperature, and a predetermine time. Buttress (7014) is further mechanically cut to size thereby inhibiting abrasive edges, such as burrs and/or delamination, that could damage sensitive tissues. It will be appreciated that alternative methods of cutting buttresses (7014), such as a laser cutting or hot knife cutting, may be similarly used.

By way of further example only, each buttress (7014) may comprise one or more of the following: NEOVEIL absorbable PGA felt by Gunze Limited, of Kyoto, Japan; SEAMGUARD polyglycolic acid: trimethylene carbonate (PGA: TMC) reinforcement material by W.L. Gore & Associates, Inc., of Flagstaff, Arizona; PERI-STRIPS DRY with VERITAS Collagen Matrix (PSDV) reinforcement material, by Baxter Healthcare Corporation of Deerfield, Illinois; BIO-DESIGN biologic graft material by Cook Medical, Bloomington, Indiana; and/or SURGICEL NU-KNIT hemostat material by Ethicon, Inc. of Somerville, New Jersey. Still other suitable materials that may be used to form each buttress (7014) will be apparent to those of ordinary skill in the art in view of the teachings herein.

In addition or in the alternative, each buttress (7014) may comprise a material including, for example, a hemostatic agent such as fibrin to assist in coagulating blood and reduce bleeding at the severed and/or stapled surgical site along tissue. As another merely illustrative example, each buttress (7014) may comprise other adjuncts or hemostatic agents such as thrombin may be used such that each buttress (7014) may assist to coagulate blood and reduce the amount of bleeding at the surgical site. Other adjuncts or reagents that may be incorporated into each buttress (7014) may further include but are not limited to medical fluid or matrix components. Merely illustrative examples of materials that may be used to form each buttress (7014), as well as materials that may be otherwise incorporated into each buttress (7014), are disclosed in U.S. patent application Ser. No. 14/667,842, entitled "Method of Applying a Buttress to a Surgical Stapler," filed Mar. 25, 2015, issued as U.S. Pat. No. 10,349,939 on Jul. 16, 2019, the disclosure of which is incorporated by reference herein. Alternatively, any other suitable materials may be used.

By way of further example only, each buttress (7014) may be constructed in accordance with at least some of the teachings of U.S. Pat. Pub. No. 2012/0241493, entitled "Tissue Thickness Compensator Comprising Controlled Release and Expansion," published Sep. 27, 2012, issued as U.S. Pat. No. 10,123,789 on Nov. 13, 2018, the disclosure of which is incorporated by reference herein; U.S. Pat. Pub. No. 2013/0068816, entitled "Surgical Instrument and Buttress Material," published Mar. 21, 2013, now abandoned, the disclosure of which is incorporated by reference herein; U.S. Pat. No. 9,999,408, entitled "Surgical Instrument with Fluid Fillable Buttress," issued Jun. 19, 2018, the disclosure of which is incorporated by reference herein; U.S. Pat. No. 8,814,025, entitled "Fibrin Pad Matrix with Suspended Heat Activated Beads of Adhesive," issued Aug. 26, 2014, the disclosure of which is incorporated by reference herein; U.S. Pat. No. 8,899,464, entitled "Attachment of Surgical Staple Buttress to Cartridge," issued Dec. 2, 2014, the disclosure of which is incorporated by reference herein; U.S. Pat. No. 9,492,170, entitled "Device for Applying Adjunct in Endoscopic Procedure," issued Nov. 15, 2016, the disclosure of which is incorporated by reference herein; U.S. Pat. No. 8,998,060, entitled "Resistive Heated Surgical Staple Cartridge with Phase Change Sealant," issued Apr. 7, 2015, the disclosure of which is incorporated by reference herein; U.S. Pat. No. 9,393,018, entitled "Surgical Staple Assembly with Hemostatic Feature," issued Jul. 19, 2016, the disclosure of which is incorporated by reference herein; U.S. Pat. No. 9,101,359, entitled "Surgical Staple Cartridge with Self-Dispensing Staple Buttress," issued Aug. 11, 2015, the disclosure of which is incorporated by reference herein; U.S. Pat. No. 9,198,644, entitled "Anvil Cartridge for Surgical Fastening Device," issued Dec. 1, 2015, the disclosure of which is incorporated by reference herein; U.S. Pat. Pub. No. 2013/0075447, entitled "Adjunct Therapy for Applying Hemostatic Agent," published Mar. 28, 2013, now abandoned, the disclosure of which is incorporated by reference herein; U.S. Pat. No. 9,211,120, entitled "Tissue Thickness Compensator Comprising a Plurality of Medicaments," issued Dec. 15, 2015, the disclosure of which is incorporated by reference herein; U.S. Pat. Pub. No. 2015/0351758, entitled "Adjunct Materials and Methods of Using Same in Surgical Methods for Tissue Sealing," published Dec. 10, 2015, issued as U.S. Pat. No. 10,172,611 on Jan. 8, 2019, the disclosure of which is incorporated by reference herein; U.S. Pat. Pub. No. 2017/0049444, entitled "Implantable Layers for a Surgical Instrument," published Feb. 23, 2017, issued as U.S. Pat. No. 10,835,249 on Nov. 17, 2020, the disclosure of which is incorporated by reference herein; U.S. Pat. Pub. No. 2017/0055986, entitled "Drug Eluting Adjuncts and Methods of Using Drug Eluting Adjuncts," published Mar. 2, 2017, issued as U.S. Pat. No. 10,569,071 on Feb. 25, 2020, the disclosure of which is incorporated by reference herein; U.S. Pat. Pub. No. 2017/0086837, entitled "Compressible Adjunct with Crossing Spacer Fibers," published Mar. 30, 2017, issued as U.S. Pat. No. 10,433,846 on Oct. 8, 2019, the disclosure of which is incorporated by reference herein; and/or U.S. Pat. Pub. No. 2017/0086842, entitled "Method for Applying an Implantable Layer to a Fastener Cartridge," published Mar. 30, 2017, issued as U.S. Pat. No. 11,690,623 on Jul. 4, 2023, the disclosure of which is incorporated by reference herein.

Furthermore, buttress (7014) is configured to be cut by a knife (not shown) from a proximal portion of buttress (7014), along an intermediate portion of buttress (7014), and further through a distal portion of buttress (7014) such that inward edges are adjacent to cut tissue as discussed below in more detail. Buttress (7014) further includes a longitudinally extending pre-cut slit (7044) configured to receive knife (not shown) and aid in separating lateral portions of buttress (7014) as inward edges form therealong.

Figure 60A:
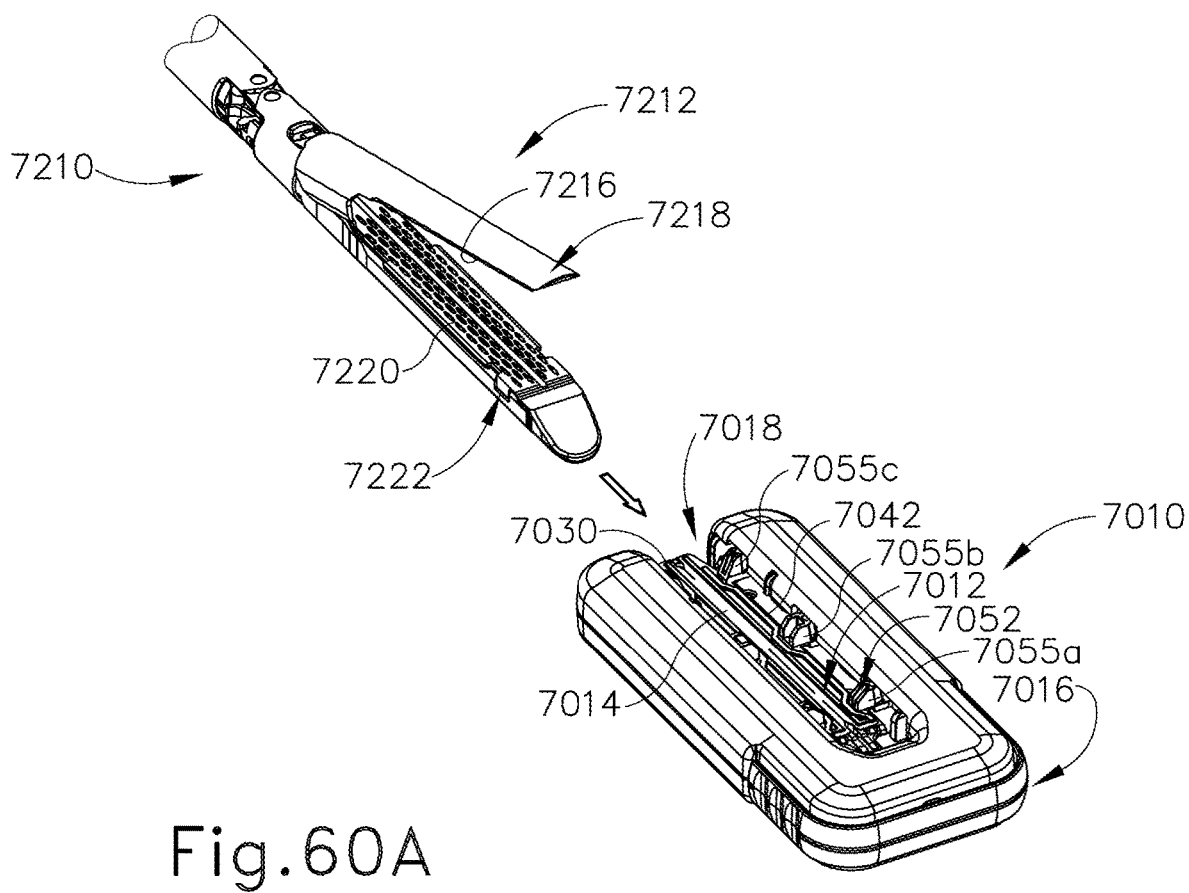
FIG. 60A depicts a perspective view of an end effector of an exemplary surgical instrument showing the buttress applier cartridge assembly of FIG. 47 approaching the end effector with the upper and lower jaws in an open position.

Upper adhesive layer (7042) is provided on outer layer of buttress (7014) in order to adhere buttress (7014) within effector (7212) (see FIG. 60A) of surgical instrument (7210) (see FIG. 60A). Adherence of the buttress (7014) can occur through a variety of mechanisms including but not limited to a pressure sensitive adhesive. In the case of pressure sensitive adhesion, adhesion occurs upon the application of at least a predetermined minimum force. In some versions, each adhesive layer (7042) includes a pressure sensitive adhesive material. Examples of various suitable materials that may be used to form adhesive layers (7042) are disclosed in U.S. Pat. Pub. No. 2016/0278774, entitled "Method of Applying a Buttress to a Surgical Stapler," published Sep. 29, 2016, issued as U.S. Pat. No. 10,349,939 on Jul. 16, 2019, the disclosure of which is incorporated by reference herein. Alternatively, any other suitable materials may be used. As shown in the present example, adhesive layer (7042) is applied to form a continuous outer seal to enhance longevity once applied to end effector (7212) (see FIG. 60A).

It should be understood that the term "adhesive," as used herein, may include (but is not limited to) tacky materials and also materials that are pliable or wax-like and adhere to a complex geometry via deformation and conformance. Some suitable adhesives may provide such pliability to adhere to a complex geometry via deformation and conformance without necessarily providing a high initial tack. In some instances, adhesives with lower tackiness may be removed more cleanly from surfaces. Various suitable materials that may be used to form adhesive layers (7042) will be apparent to those of ordinary skill in the art in view of the teachings herein.

B. Exemplary Buttress Applier Cartridge

Figure 48:
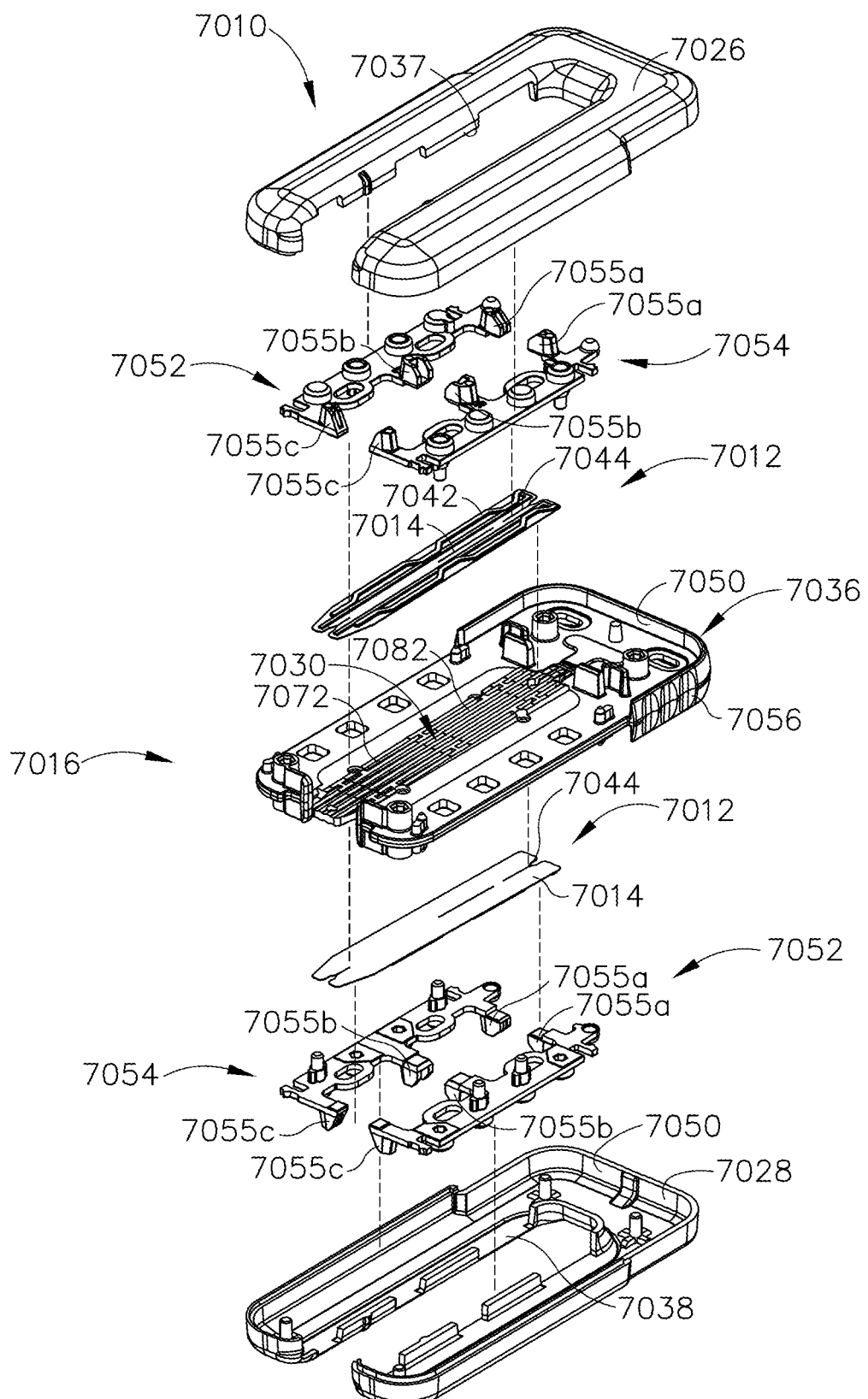
FIG. 48 depicts an exploded perspective view of the buttress applier cartridge assembly of FIG. 47 including a chassis and a platform in addition to a pair of buttress assemblies.

As shown in FIG. 48, buttress applier cartridge (7016) includes chassis (7036) supporting platform (7030) as well as upper and lower housings (7026, 7028) of housing assembly (7024) configured to connect together to define an interior space (7050). An upper left actuator sled (7052) and an upper right actuator sled (7054) are movably connected to an upper face chassis (7036) within interior space (7050), while a lower left actuator sled (7052) and a lower right actuator sled (7054) are movably connected to a lower face of chassis (7036) within interior space (7050). Upper right and left actuator sleds (7052, 7054) retain upper buttress assembly (7012) on platform (7030) in a restraint position, but are configured to move from the restraint position to a release position for depositing the upper buttress assembly (7012) on end effector (7212) (see FIG. 60A). Similarly, lower right and left actuator sleds (7052, 7054) retain lower buttress assembly (7012) on platform (7030) in the restraint position, but are configured to move from the restraint position to the release position for depositing the lower buttress assembly (7012) on end effector (7212) (see FIG. 60A). In the present example, left actuator sled (7052) is distinct from right actuator sled (7054) for reasons discussed below in greater detail. Also, upper and lower right actuator sleds (7052) are structurally identical to each other, and upper and lower left actuator sleds (7054) are structurally identical to each other. Thus, upper and lower actuator sleds (7052, 7054) are interchangeable in this respect and any discussion contained herein directed to a pair of upper actuator sleds (7052, 7054) is similarly applicable to a pair of lower actuator sleds (7052, 7054).

Each actuator sled (7052, 7054) includes a plurality of arms (7055*a*, 7055*b*, 7055*c*) extending laterally inward to selectively and releasably secure buttress assemblies (7012) to platform (7030). In particular, FIG. 48 show arms (7055*a*, 7055*b*, 7055*c*) positioned such that buttress assemblies (7012) are interposed between the free ends of arms (7034) and platform (7030). Arms (7055*a*, 7055*b*, 7055*c*) are movable laterally outwardly such that arms (7055*a*, 7055*b*, 7055*c*) disengage buttress assemblies (7012) as shown in FIG. 48, thereby enabling buttress assemblies (7012) to be removed from platform (7030). In the present example, arms (7055*a*, 7055*b*, 7055*c*) are configured to bear against buttress assemblies (7012) in the restraint position, thereby pinching buttress assemblies (7012) against platform (7030). Other suitable ways in which arms (7055*a*, 7055*b*, 7055*c*) may engage buttress assemblies (7012) will be apparent to those of ordinary skill in the art in view of the teachings herein.

Chassis (7036) is configured to cooperate with upper and lower housings (7026, 7028) to provide a mechanical ground for moving components of buttress applier cartridge (7016) and provide structural support for components of buttress applier cartridge (7016). Chassis (7036) further includes integral gripping features (7056) that are exposed on opposite sides of housing assembly (7024). Gripping features (7056) have a surface geometry configured to promote an operator's grip of buttress applier cartridge (7016) during use of buttress applier cartridge (7016). Various suitable configurations that may be used for gripping features (7056) will be apparent to those of ordinary skill in the art in view of the teachings herein. Similarly, various surface treatments (e.g., elastomeric material, etc.) that may be applied to gripping features (7056) will be apparent to those of ordinary skill in the art in view of the teachings herein.

Figure 49:
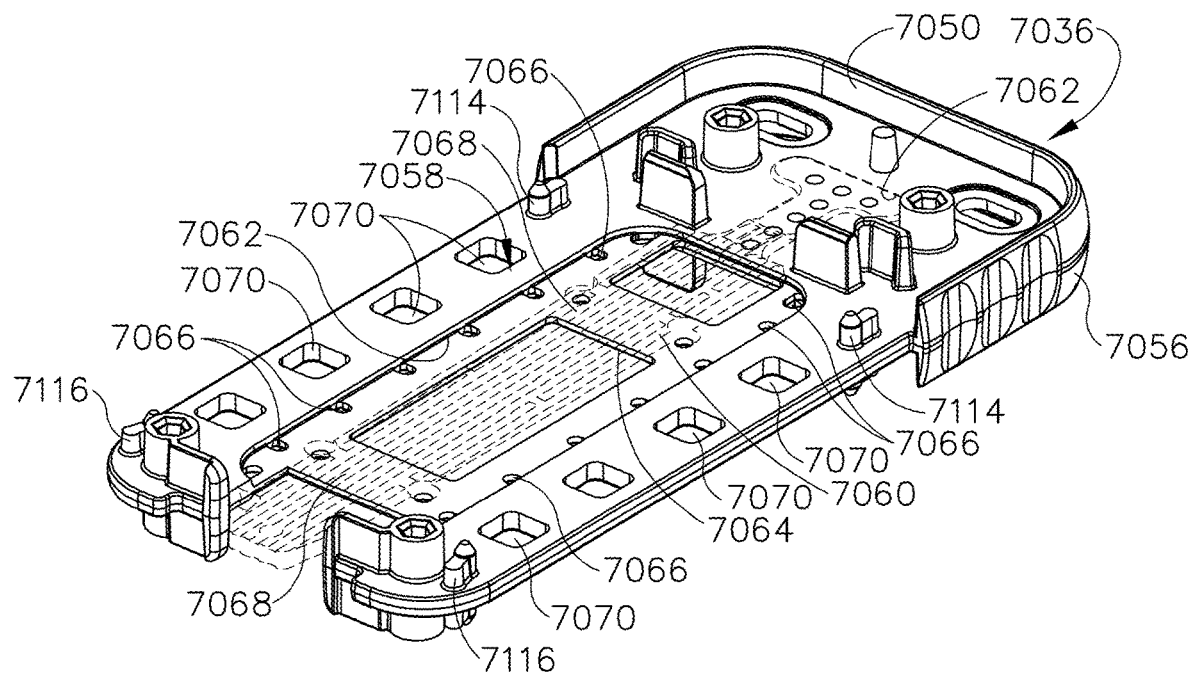
FIG. 49 depicts a perspective view of the chassis with the platform of FIG. 48.

With respect to FIG. 49, platform (7030) is connected to and supported by chassis (7036) to secure platform (7030) relative to upper and lower housing (7026, 7028) (see FIG. 48). In the present example, platform (7030) is unitarily formed and molded to a rigid web portion (7058) including a frame (7060) and defining a plurality of holes (7062, 7064, 7066) configured provide material overlap for mold securement. Holes (7062, 7064, 7066) more particularly include an upper and a lower peripheral recess (7062) to the centrally located frame (7060). A central slot (7064) extends through frame (7060) as well as a plurality of through holes (7066) spaced laterally about central slot (7064). Frame (7060) also extends laterally across central slot (7064) at bridge portions (7068) to provide additional structural rigidity to chassis (7036) while providing platform (7030) with sufficient clearance for resilient deformation as discussed below in greater detail. Thereby, recess (7062), central slot (7064), and through holes (7066) receive a resilient, elastomeric material to form and secure the material as platform (7030) to chassis (7036). While the present platform (7030) is molded to chassis (7036), it will be appreciated that platform (7030) may be alternatively secured to chassis (7036), and the invention is not intended to be limited to the particular rigid web portion (7058) and molding as discussed herein. Various suitable materials and structural configurations that may be used to form platform (7030) will be apparent to those of ordinary skill in the art in view of the teachings herein.

Chassis (7036) further includes a plurality of sled clearance holes (7070) arranged in a pair of rows on opposing lateral sides of chassis (7036). Left and right actuator sleds (7052, 7054) (see FIGS. 53-56) connect together on opposing sides of chassis (7036) through such sled clearance holes (7070) to slide inwardly together in connected pairs. Additional details regarding connection and actuation of left and right actuator sleds (7052, 7054) (see FIGS. 53-56) will be discussed below in greater detail. However, it will be appreciated that any such hole through chassis (7036) to provide for fastening clearance of left and right actuator sleds (7052, 7054) (see FIGS. 53-56) may be used, and the invention is not intended to be unnecessarily limited to sled clearance holes (7070) as discussed herein.

i. Exemplary Varying Stiffness Platform for Supporting Buttress Assemblies

FIGS. 49-52 show one example of platform (7030) in additional detail as including a pad (7072) having a peripheral securement (7074) laterally extending therefrom and an anchor securement (7076) distally extending therefrom. Collectively, peripheral and anchor securements (7074, 7076) are positioned in recesses (7062) and extend into through holes (7066) to secure pad (7072) to chassis (7036). In some versions, platform (7030) is formed of a material that provides a high coefficient of friction, thereby reducing any tendency that buttress assemblies (7012) might otherwise have to slide along corresponding surfaces of platform (7030). For instance, platform (7030) may comprise a resilient, elastomeric material, such as silicone, to be molded to be formed as both securements (7074, 7076) and pad (7072). One example silicone material is a 30 Durometer, Shore A silicone. To this end, pad (7072) is formed with varying stiffness along its longitudinal length to simultaneously provide sufficient reactionary forces of at least the predetermined minimum force for adhesion while accommodating a parallel-camber orientation, an over-camber orientation, and an under-camber orientation of end effector (7212) (see FIG. 60A) as discussed below in greater detail. As used herein, the term "parallel-camber orientation" refers to an upper jaw and a lower jaw of an end effector being functionally parallel to each other. The term "over-camber orientation" refers to an upper jaw of an end effector being over rotated relative a lower jaw of an end effector. The term "under-camber orientation" refers to an upper jaw being under rotated relative to a lower jaw of an end effector. Exemplary upper and lower jaws will be described in this context below in greater detail.

Figure 50:
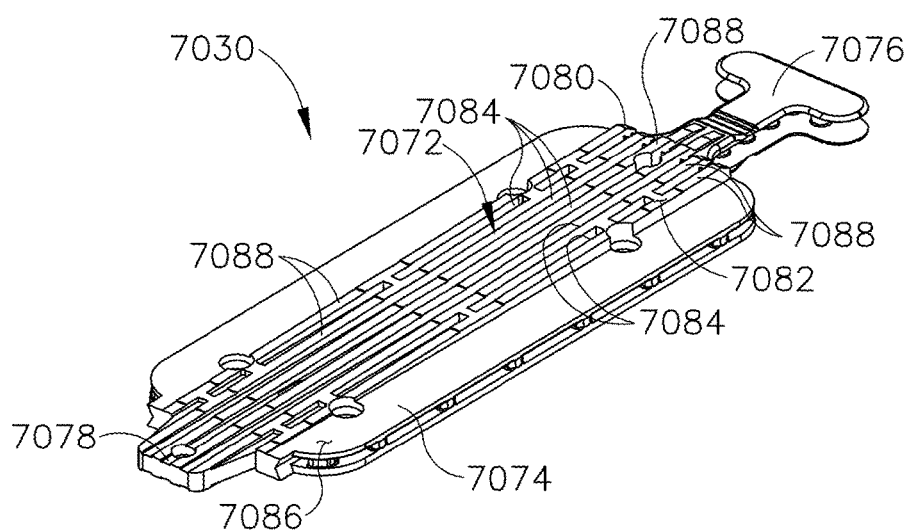
FIG. 50 depicts a front perspective view of the platform of FIG. 48.
Figure 51:
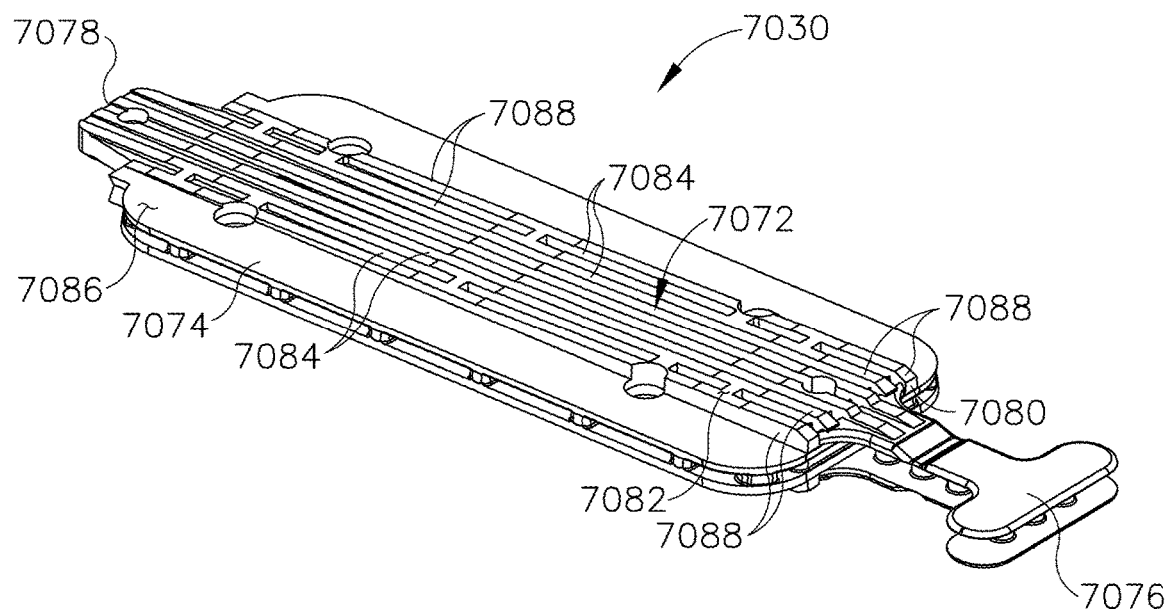
FIG. 51 depicts a rear perspective view of the platform of FIG. 48.

With respect to FIGS. 50-51, a resilient proximal end (7078) pad (7072) has a proximal end stiffness and a proximal transverse depth, whereas a resilient distal end (7080) of pad (7072) has a distal end stiffness and a distal transverse depth. In the present example, proximal end stiffness is generally greater than the distal end stiffness such that initial compression of distal end (7080) requires less compressive force than compression of proximal end (7078). Of course, further compression of distal end (7080) relative to proximal end (7078) may result in distal end stiffness increasing to or even exceeding proximal end stiffness so long as the lesser stiffness of distal end (7080) is included therein for accommodating the over-cambered orientation of end effector (7212) (see FIG. 60A).

In addition, distal transverse depth is greater than proximal transverse depth. Thereby, the greater distal transverse depth effectively props up buttress assembly (7012) (see FIG. 47) for improved engagement with end effector (7212) (see FIG. 56A) in the under-camber orientation, but the decreased distal end stiffness allows for greater compression to accommodate end effector (7212) (see FIG. 56A) in the over-camber orientation. Pad (7072) of the present example is wedge-shaped having opposing ramp surfaces (7082) continuously tapering together from the distal end (7080) to the proximal end (7078) for accommodating parallel-camber, over-camber, and under-camber orientations along the entire longitudinal length of pad (7072). In some examples, depths and stiffnesses along pad (7072) are configured to receive a full range of over-camber to under-camber orientations based on determined manufacturing tolerances of end effector (7011) (see FIG. 56A).

Figure 52:
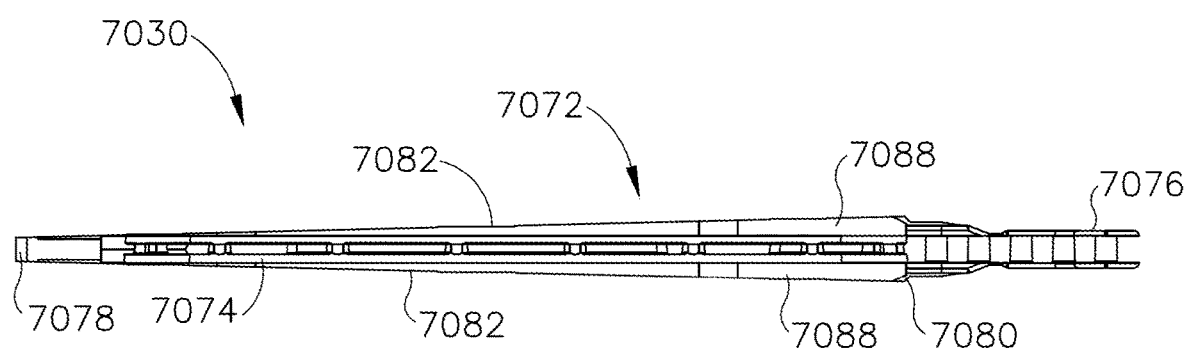
FIG. 52 depicts an elevational side view of the platform of FIG. 48.

Pad (7072) shown in FIGS. 50-52 is unitarily formed of a resilient material having a consistent stiffness throughout. Such longitudinally varying stiffness discussed above is thus generated by forming a plurality of reliefs, such as channels (7084), in at least the distal end (7080) to reduce the distal end stiffness relative to the proximal end stiffness. In the present example, channels (7084), such as five channels (7084) are equally spaced laterally apart from each other and longitudinally extend from distal end (7080) to proximal end (7078). Channels (7084) further transversely extend to a base surface (7086) common to securements (7074, 7077) and proximal end (7078) to define varying channel depths in the longitudinal direction along pad (7072). More particularly, upper channels (7084) extend transversely downward from upper ramp surface (7082) to upper base surface (7086), whereas lower channels (7084) extend transversely upward from lower ramp surface (7082) to lower base surface (7086). In turn, a plurality of ribs (7088) are defined between channels (7084) and similarly extend from ramp surfaces (7082) to base surfaces (7086) to support buttress assemblies (7012) (see FIG. 47) and have varying stiffness from the proximal end (7078) to the distal end (7080) on each opposing side of pad (7072).

ii. Exemplary Restraint Features for Retention of Buttress Assemblies on Varying Stiffness Platform FIGS. 48 and 53-56 show restraint features, such as left and right actuator sleds (7052, 7054) discussed briefly above for releasably securing buttress assemblies (7012) to platform (7030) in the restraint position. Each of left and right actuator sleds (7052, 7054) has arms (7055a, 7055b, 7055c) configured to accommodate varying transverse depths along the longitudinal length of pad (7072). More particularly, arms (7055a, 7055b, 7055c) include a distal arm (7055a), an intermediate arm (7055b), and a proximal arm (7055c) spaced longitudinally apart from each other and extending laterally inward toward platform (7030). Each distal arm (7055a), intermediate arm (7055b), and proximal arm (7055c) of left or right actuator sled (7052, 7054) transversely extends toward platform (7030) such that each of distal arm (7055a), intermediate arm (7055b), and proximal arm (7055c) is offset from the other arms (7055a, 7055b, 7055c) in the transverse direction. Thereby, distal arm (7055a), intermediate arm (7055b), and proximal arm (7055c) are transversely spaced from the ramp surface (7082) to trace the contour of the ramp surface (7082).

Figure 53:
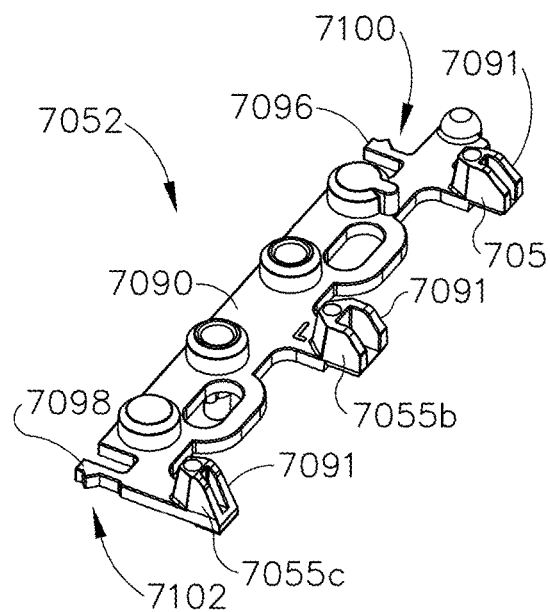
FIG. 53 depicts a top perspective view of a left actuator sled of the buttress applier cartridge assembly of FIG. 48.
Figure 54:
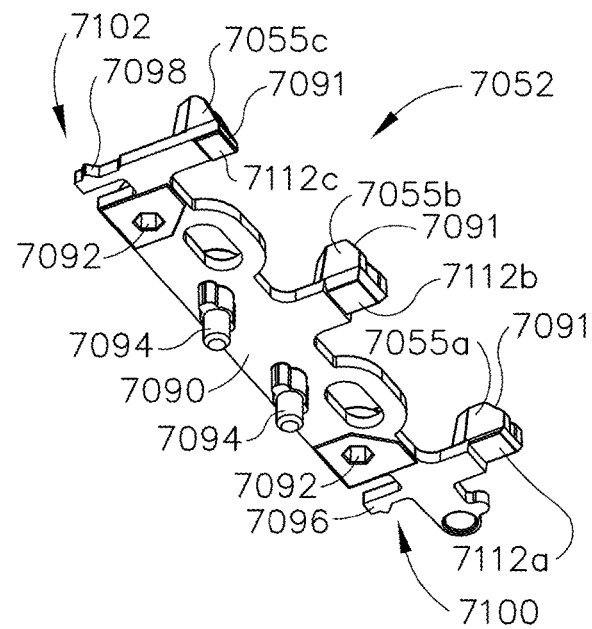
FIG. 54 depicts a bottom perspective view of the left actuator sled of FIG. 53.

With respect to FIGS. 53-54, upper left actuator sled (7052) has a longitudinally extending upper left sled body (7090) with distal, intermediate, and proximal arms (7055a, 7055b, 7055c) laterally extending inward toward the right. Each arm (7055a, 7055b, 7055c) of left actuator sled (7052) has a cam surface (7091) configured to receive end effector (7212) (see FIG. 60A) thereagainst to urge left actuator sled (7052) toward the release position. In addition, a pair of outer dowel holes (7092) open downward and are respectively positioned on distal and proximal end portions of upper left sled body (7090). A pair of inner dowels (7094) extend downward from left sled body (7090) between outer dowel holes (7092) and in longitudinal alignment with outer dowel holes (7092). In order to arrest movement of upper left actuator sled (7052) in the restraint and release positions, a distal cantilever catch (7096) laterally extends to the left from the distal portion of upper left sled body (7090), and a proximal cantilever catch (7096) laterally extends to the left from the proximal portion of upper left sled body (7090). Distal and proximal cantilever catches (7096, 7098) are respectively portions of distal and proximal detent couplings (7100, 7102) discussed below in greater detail.

Figure 55:
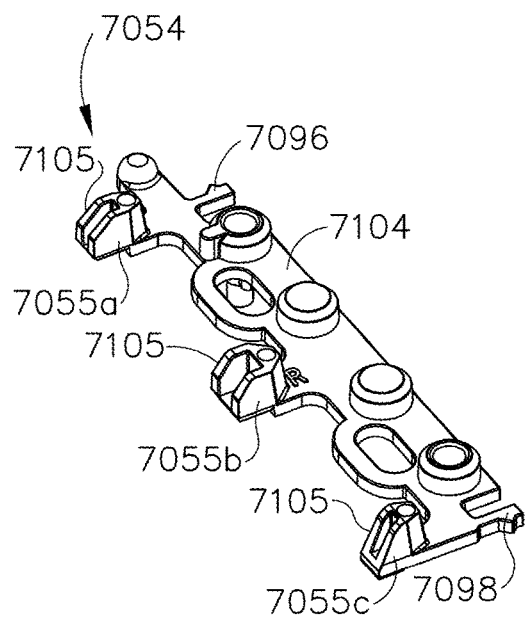
FIG. 55 depicts a top perspective view of a right actuator sled of the buttress applier cartridge assembly of FIG. 48.
Figure 56:
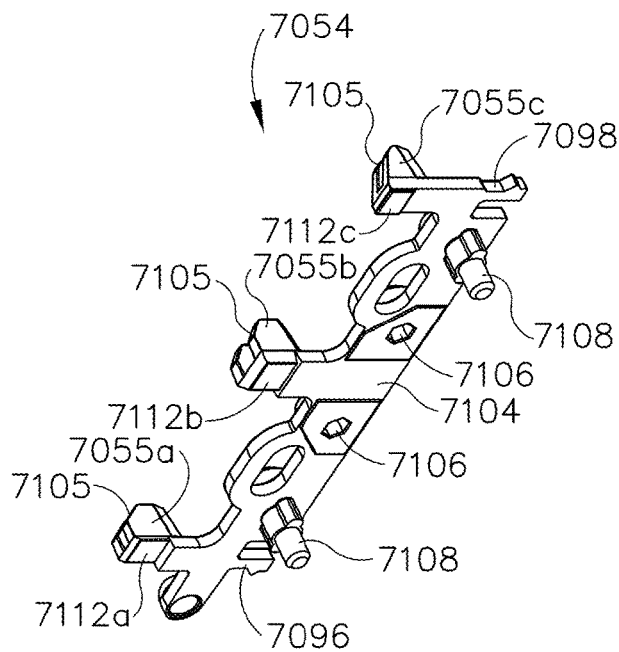
FIG. 56 depicts a bottom perspective view of the right actuator sled of FIG. 55.

With respect to FIGS. 55-56, upper right actuator sled (7054) has a longitudinally extending upper right sled body (7104) with distal, intermediate, and proximal arms (7055a, 7055b, 7055c) laterally extending inward toward the left. Each arm (7055a, 7055b, 7055c) of right actuator sled (7054) has a cam surface (7105) configured to receive end effector (7212) (see FIG. 60A) thereagainst to urge left actuator sled (7052) toward the release position. In addition, a pair of inner dowel holes (7106) open downward and are positioned on upper right sled body (7104). A pair of outer dowels (7108) extend downward from right sled body (7104) and are respectively positioned on distal and proximal end portion of upper right sled body (7104) in longitudinal alignment with inner dowel holes (7106). In order to arrest movement of upper right actuator sled (7054) in the restraint and release positions, another distal cantilever catch (7096) laterally extends to the right from the distal portion of upper right sled body (7104), and another proximal cantilever catch (7096) laterally extends to the right from the proximal portion of upper right sled body (7104). Again, distal and proximal cantilever catches (7096, 7098) are respectively portions of distal and proximal detent couplings (7100, 7102) discussed below in greater detail.

FIG. 48 and FIGS. 57-58 show upper right and left actuator sleds (7052, 7054) as discussed above in detail as well as lower right and left actuator sleds (7052, 7054). As briefly discussed above, the description of upper right and left actuator sleds (7052, 7054) similarly applies to lower right and left actuator sleds (7052, 7054) with like features having like numbers, but with reversed transverse directions (e.g. lower, upward, etc.). To this end, upper left actuator sled (7052) and lower right actuator sled (7054) connect together as outer dowels (7108) snap into outer dowel holes (7092) and inner dowels (7094) snap into inner dowel holes (7106) with chassis (7036) positioned therebetween. Upper right actuator sled (7054) and lower left actuator sled (7052) similarly connect together as outer dowels (7108) snap into outer dowel holes (7092) and inner dowels (7094) snap into inner dowel holes (7106) with chassis (7036) positioned therebetween. Each of inner and outer dowels (7094, 7108) extend through sled clearance holes (7070) to slidably connect left and right actuator sleds (7052, 7054) to chassis (7036).

FIG. 58 shows one example of a pair of distal arms (7055a), a pair of intermediate arms (7055b), and a pair of proximal arms (7055c) respectively having platform (7030) positioned therebetween and tracing opposing ramp surfaces (7082). A central plane (7110) is shown in FIG. 58 bisecting upper and lower portions of buttress applier cartridge (7016) through a central core of platform (7030). Distal arm (7055a) has a distal retention surface (7112a) transversely offset from central plane (7110) a relatively greater distance, intermediate arm (7055b) has an intermediate retention surface (7112b) transversely offset from central plane (7110) a relatively intermediate distance, and proximal arm (7055c) has a proximal retention surface (7112c) transversely offset from central plane (7110) a relatively lesser distance. Thereby, greater, intermediate, and lesser distances of distal, intermediate, and proximal retention surfaces (7112a, 7112b, 7112c) trace ramp surfaces (7082) tapering from distal end (7080) of pad (7072) to proximal end (7078) of pad (7072). Thus, distal, intermediate, and proximal retention surfaces (7112a, 7112b, 7112c) are offset in the transverse direction from each other and from central plane (7110). In the present example, each of distal arm (7055a), intermediate arm (7055b), and proximal arm (7055c) are transversely spaced from the ramp surface (7082) an equal transverse dimension such that arms (7055a, 7055b, 7055c) equally trace ramp surfaces (7082) tapering from distal end (7080) of pad (7072) to proximal end (7078) of pad (7072).

Figure 59A:
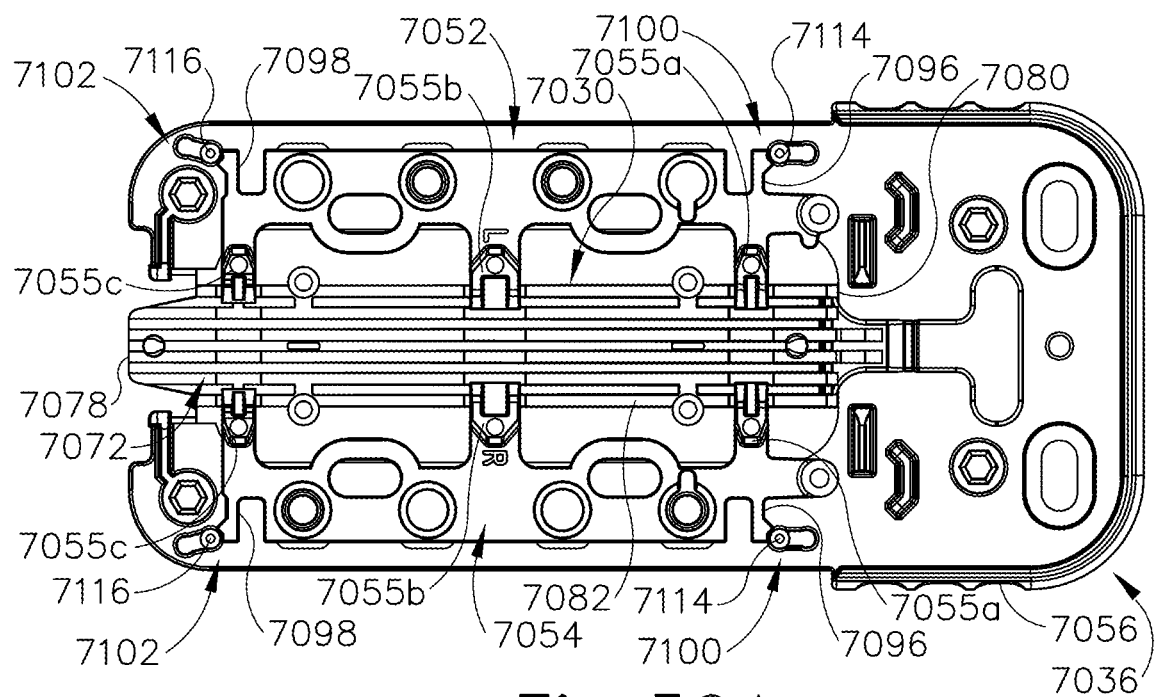
FIG. 59A depicts a top view of the chassis, the platform, and the actuator sleds of FIG. 57 in a restraint position.
Figure 59B:
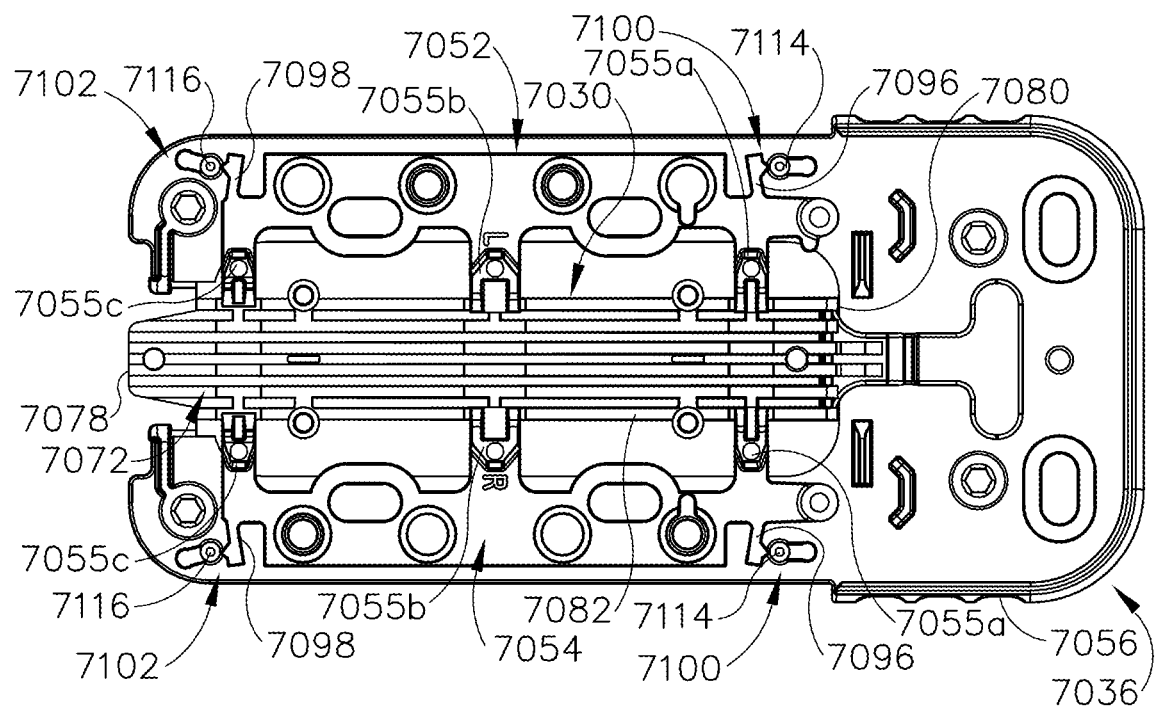
FIG. 59B depicts the top view of the chassis, the platform, and the actuator sleds similar to FIG. 59A, but showing the actuator sleds being directed from the restraint position toward a release position.
Figure 59C:
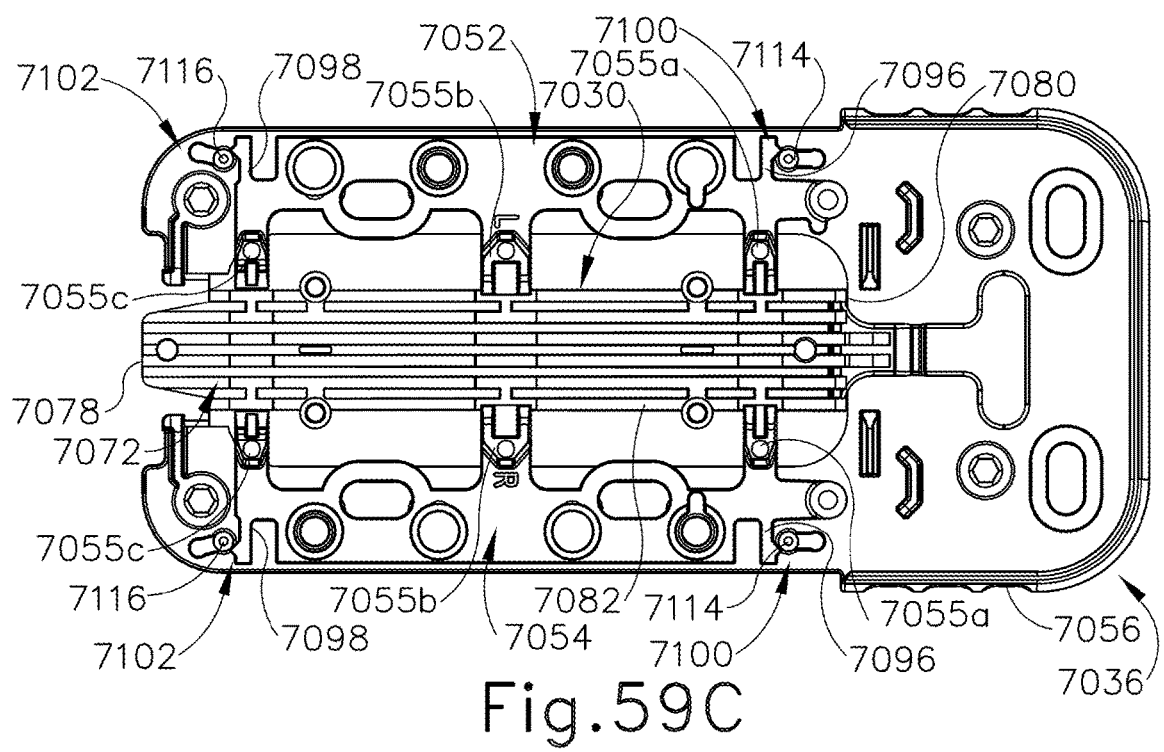
FIG. 59C depicts the top view of the chassis, the platform, and the actuator sleds similar to FIG. 59B, but showing the actuator sleds in the release position.

As shown in FIGS. 59A-59C, left and right actuator sleds (7052, 7054) are respectively urged outward from the restraint position to the release position away from platform to disengage arms (7055a, 7055b, 7055c) from buttress assemblies (7012) (see FIG. 47) on platform (7030) as discussed herein. More particularly, distal and proximal detent couplings (7100, 7102) releasably connected left and right actuator sleds (7052, 7054) to chassis (7036) to arrest movement of left and right actuator sleds (7052, 7054) in the restraint position and the release position. Distal and proximal detent couplings (7100, 7102) include distal and proximal cantilever catches (7096, 7098) extending from each of left and right actuator sleds (7052, 7054) as discussed briefly above. In addition, distal and proximal detent couplings (7100, 7102) respectively further include distal and proximal ground cams (7114, 7116) extending from chassis (7036) in respective engagement with distal and proximal cantilever catches (7096, 7098).

In the restraint position shown in FIG. 59A, each distal cantilever catch (7096) is respectively engaged with each distal ground cam (7114), and each proximal cantilever catch (7098) is respectively engaged with each proximal ground cam (7116) to urge left and right actuator sleds (7052, 7054) inward toward the restraint position. Directing left and right actuator sleds (7052, 7054) outward from the restraint position toward the release position as shown in FIG. 59B resiliently deflects distal and proximal cantilever catches (7096, 7098) as distal and proximal cantilever catches (7096, 7098) follow distal and proximal ground cams (7114, 7116). As distal and proximal cantilever catches (7096, 7098) pass around distal and proximal ground cams (7114, 7116), distal and proximal cantilever catches (7096, 7098) reach a tipping point where distal and proximal cantilever catches (7096, 7098) urge left and right actuator sleds (7052, 7054) to the release position shown in FIG. 59C. In the release position, each distal cantilever catch (7096) is respectively engaged with each distal ground cam (7114), and each proximal cantilever catch (7098) is respectively engaged with each proximal ground cam (7116) to urge left and right actuator sleds (7052, 7054) outward toward the release position. Thereby, distal and proximal detent couplings (7100, 7102) effectively hold left and right actuator sleds (7052, 7054) in the release position to inhibit arms (7055a, 7055b, 7055c) from inadvertently returning inward and catching buttress assembly (7012) (see FIG. 62) upon removal of end effector (7212) (see FIG. 62) as discussed below in greater detail.

C. Exemplary Adhesion of Buttress to Surgical Stapler and Cutting of Buttress Assembly with Tissue As noted above and discussed below in greater detail with respect to FIG. 60A, upper and lower buttress assemblies (7012) include upper and lower adhesive layers (7042) (or other form of adhesive material) to adhere respective buttresses (7014) to an underside (7216) of anvil (7218) and deck (7220) of staple cartridge (7222). Such adhesive may provide proper positioning of buttress (7014) before and during actuation of end effector (7212); then allow buttress (7014) to separate from end effector (7212) after end effector (7212) has been actuated, without causing damage to buttress (7014) that is substantial enough to compromise the proper subsequent functioning of buttress (7014).

Figure 60B:
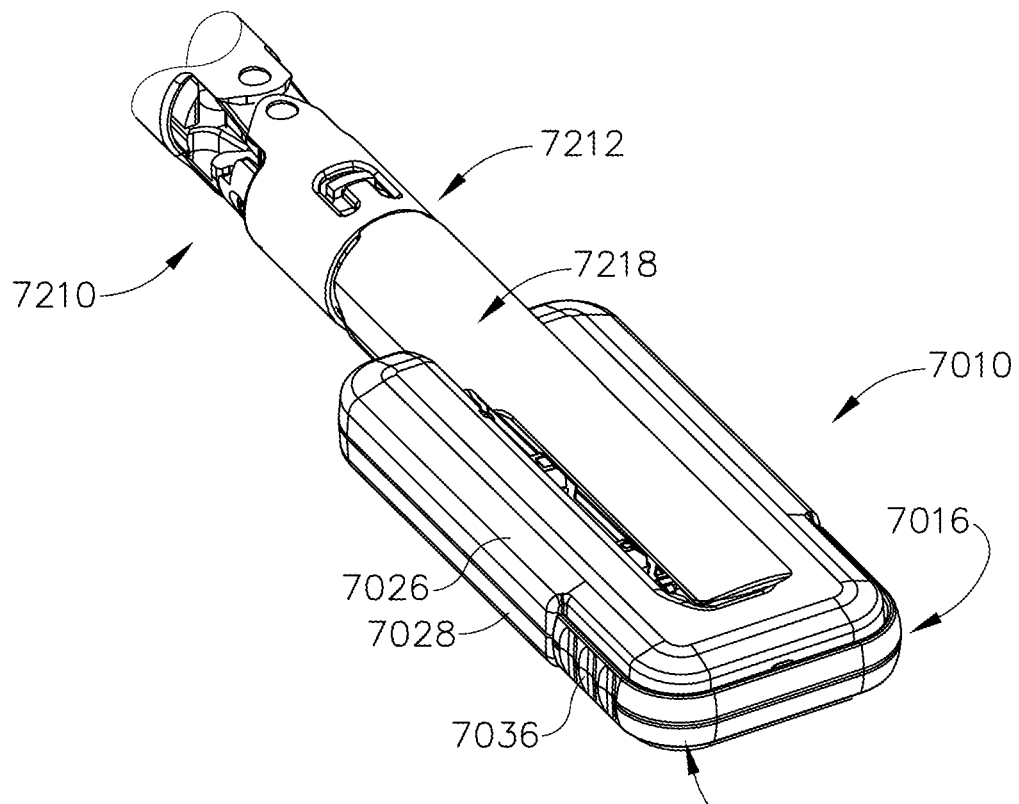
FIG. 60B depicts the perspective view of the end effector similar to FIG. 60A, but showing the buttress applier cartridge assembly of FIG. 47 positioned between the upper and lower jaws in a closed position.

To use buttress applier cartridge (7016) to load end effector (7212), the operator would first position buttress applier cartridge (7016) and end effector (7212) such that end effector (7212) is aligned with open end (7018) of buttress applier cartridge (7016) as shown in FIG. 60A. The operator would then advance end effector (7212) distally (and/or retract buttress applier cartridge (7016) proximally) to position platform (7030) and buttress assemblies (7012) between anvil (7218) and staple cartridge (7222). In order to load buttress assemblies (7012) on end effector (7212), the operator simply closes end effector (7212) by pivoting anvil (7218) toward staple cartridge (7222) to reach the state shown in FIG. 60B.

Figure 61:
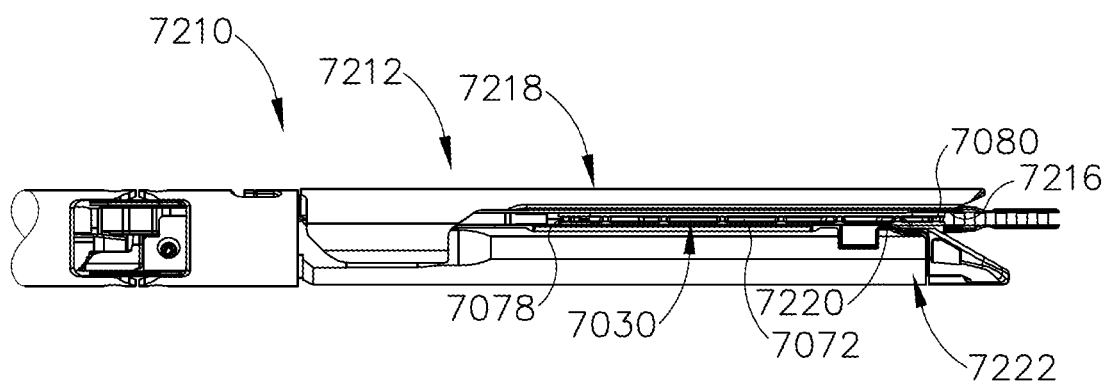
FIG. 61 depicts a side sectional view of the end effector and the platform of the buttress applier cartridge of FIG. 60B in an exemplary parallel-camber orientation, but with various features hidden for greater clarity.
Figure 62:
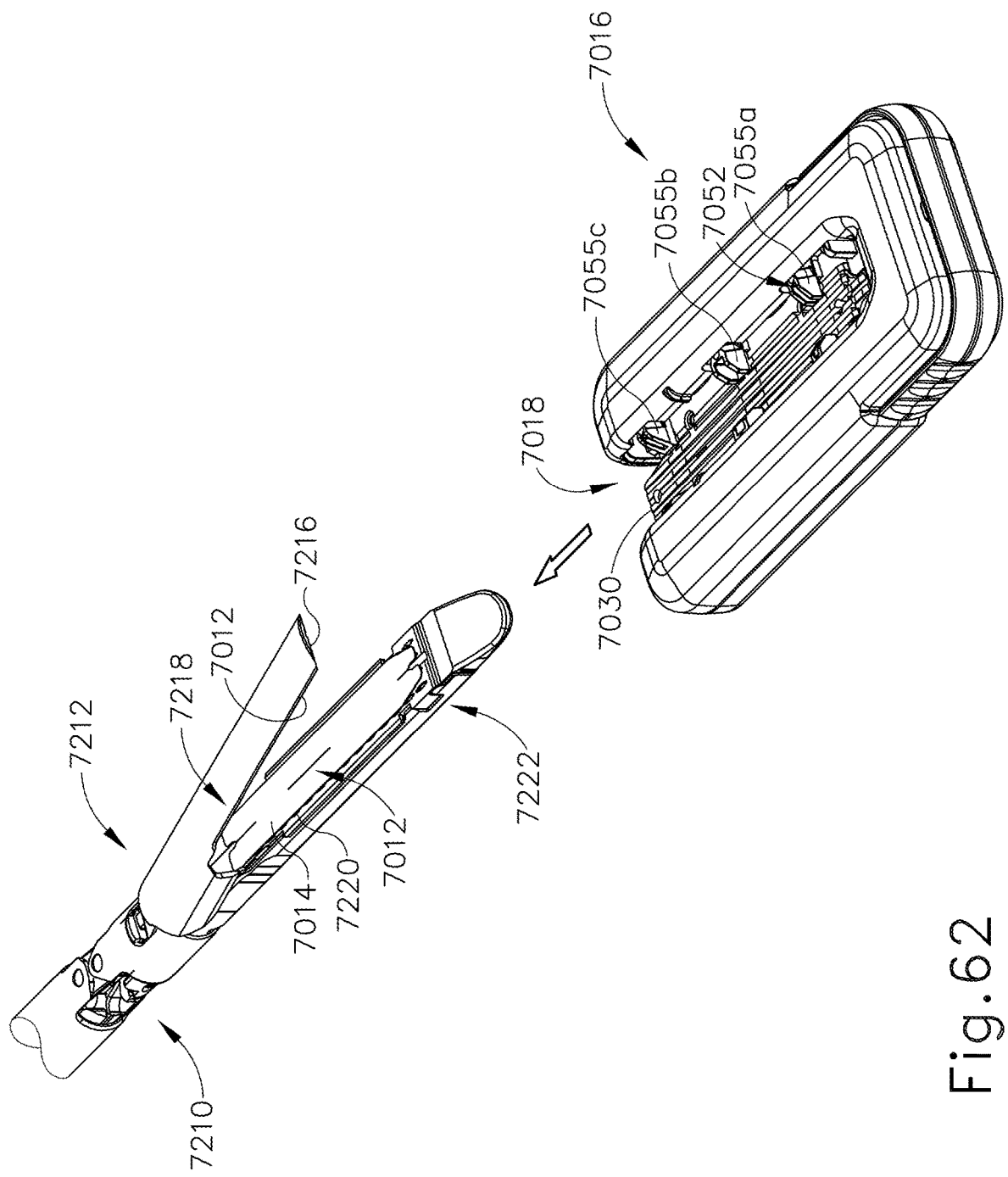
FIG. 62 depicts a perspective view of the end effector similar to FIG. 60B, but showing the buttress assemblies respectively secured to the upper and lower jaws in the open position and the buttress applier cartridge removed therefrom.

As shown, closure of end effector (7212) to the parallel-camber orientation results in anvil (7218) and staple cartridge (7222) bearing against actuator sleds (7032), thereby urging arms (7034) to unlock buttress assemblies (7012) from buttress applier cartridge (7016). Adhesive layers (7042) of upper and lower buttress assemblies (7012) are sufficiently compressed against anvil (7218) and deck (7220) to retain upper and lower buttress assemblies (7012) to end effector (7212) for stapling tissue. Pad (7072) accommodates the parallel-camber orientation shown in FIG. 61 by providing reaction forces of at least the predetermined minimum force for adhesion along the longitudinal length of buttress assemblies (7012). Upon depositing buttress assemblies (7012) onto anvil (7218) and staple cartridge (7222), the operator removes buttress applier cartridge (7016) from end effector (7212) as shown in FIG. 62.

Figure 63:
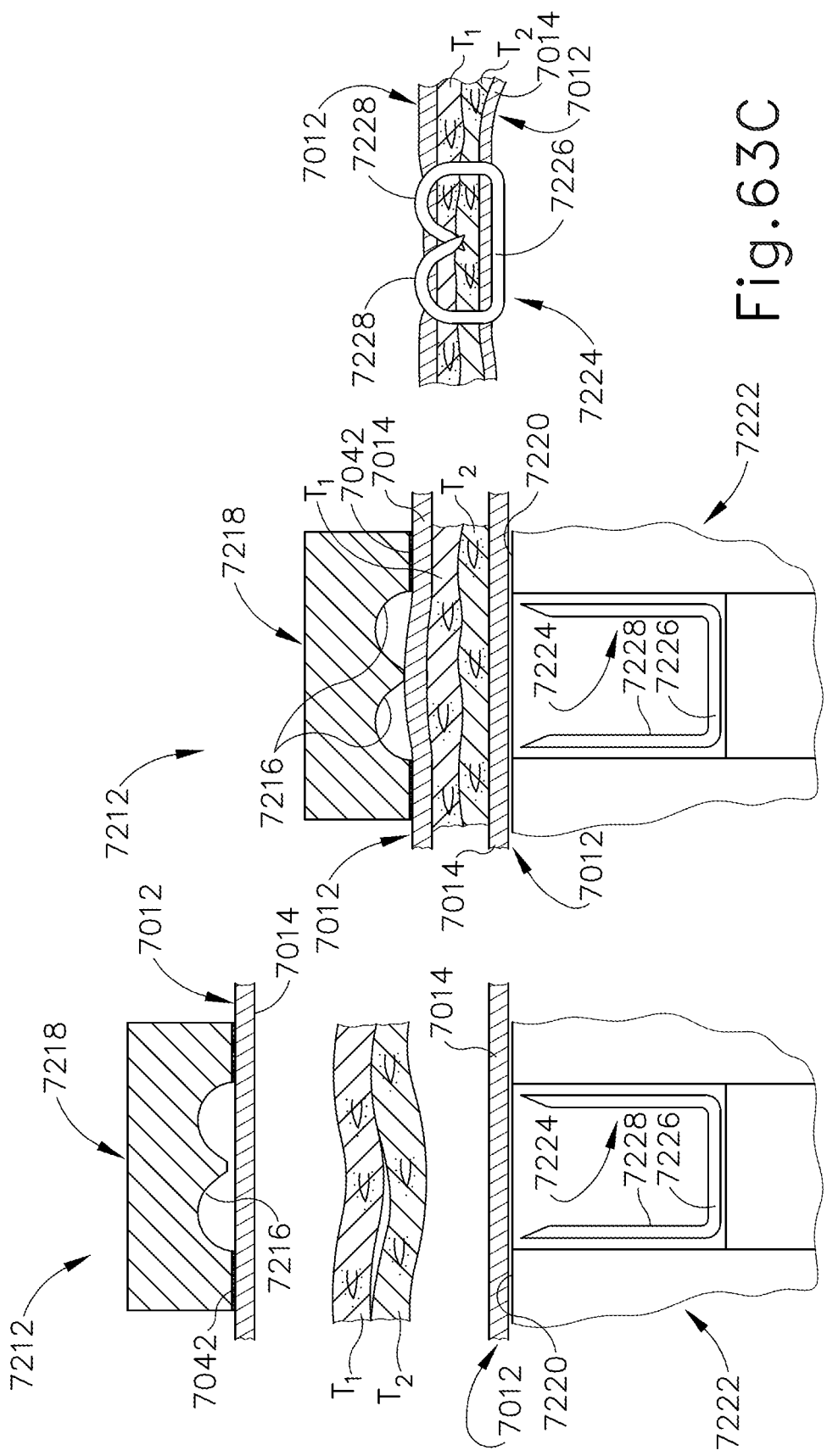
FIG. 63A depicts a sectional side view of a portion of the end effector of FIG. 60B with the buttress assemblies of FIG. 47 applied to the end effector and tissue positioned between the buttress assemblies with the upper and lower jaws in the open position.
FIG. 63B depicts the sectional side view of the portion of the end effector and the buttress assemblies similar to FIG. 63A, but showing the upper and lower jaws in the closed position.
FIG. 63C depicts the sectional side view of the buttress assemblies similar to FIG. 63B, but showing the buttress assemblies secured to the tissue with a staple formed in the tissue.

To this end, FIGS. 63A-63C show a sequence where end effector (7212) loaded with buttress assemblies (7012) is actuated to drive a plurality of staples (7224) through two apposed layers of tissue ($T_1$, $T_2$) with buttress assemblies (7012) being secured to the same layers of tissue ($T_1$, $T_2$) by staples (7224). In particular, FIG. 63A shows layers of tissue ($T_1$, $T_2$) positioned between anvil (7218) and staple cartridge (7222), with anvil (7218) in the open position. Upper buttress assembly (7012) is adhered to the underside (7216) of anvil (7218) via adhesive layer (7042); while lower buttress assembly (7012) is adhered to deck (7220) of staple cartridge (7222) via adhesive layer (7042). Layers of tissue ($T_1$, $T_2$) are thus interposed between upper and lower buttress assemblies (7012). Next, a trigger (not shown) is pivoted to drive anvil (7218) to the closed position as shown in FIG. 63B. At this stage, layers of tissue ($T_1$, $T_2$) are compressed between anvil (7218) and staple cartridge (7222), with upper and lower buttress assemblies (7012) engaging opposite surfaces of tissue layers ($T_1$, $T_2$). End effector (7212) is then actuated as described above, driving staple (7224) through upper and lower buttress assemblies (7012) and layers of tissue ($T_1$, $T_2$). As shown in FIG. 63C, a crown (7226) of driven staple (7224) captures and retains lower buttress assembly (7012) against layer of tissue ($T_2$). Deformed legs (7228) of staple (7224) capture and retain upper buttress assembly (7012) against layer of tissue ($T_1$).

It should be understood that a series of staples (7224) will similarly capture and retain upper and lower buttress assemblies (7012) against layers of tissue ($T_1$, $T_2$), thereby securing upper and lower buttress assemblies (7012) to tissue ($T_1$, $T_2$). In one example, knife (not shown) cuts through a centerline of buttress assemblies (7012), separating buttress assemblies (7012) into a corresponding pair of sections, such that each section remains secured to a respective severed region of tissue ($T_1$, $T_2$) as shown in FIG. 64.

Figure 64:
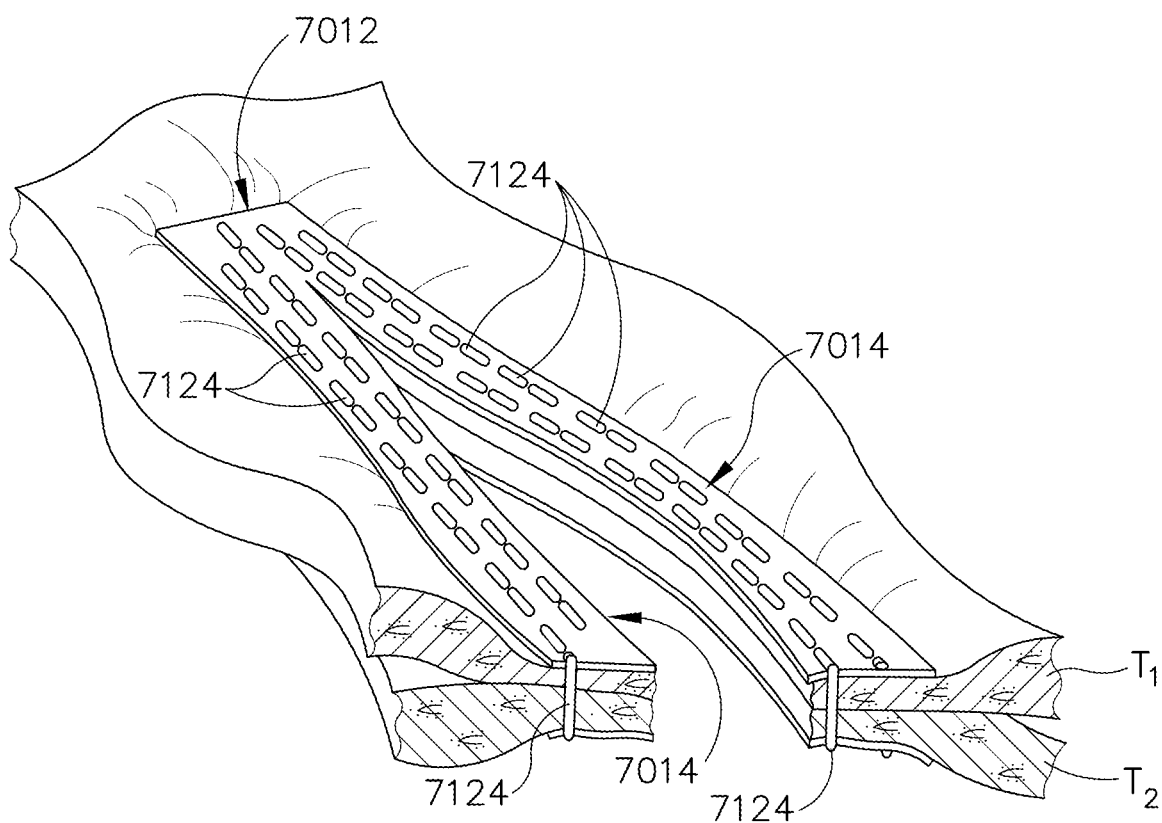
FIG. 64 depicts a perspective view of staples and the buttress assembly of FIG. 63C having been secured to the tissue by the end effector and cut by a knife.

With respect to FIG. 64, as end effector (7212) (see FIG. 62) is pulled away from tissue ($T_1$, $T_2$) after deploying staples (7224) and upper and lower buttress assemblies (7012), upper and lower buttress assemblies (7012) disengage end effector (7212), such that upper and lower buttress assemblies (7012) remain secured to tissue ($T_1$, $T_2$) with staples (7224). Buttressed tissue ($T_1$, $T_2$) thus provides structural reinforcement to the lines of staples (7224). In addition to the foregoing, it should also be understood that any of the various buttress assemblies described herein may be further constructed and operable in accordance with at least some of the teachings of U.S. Pat. Pub. No. 2016/0278774, entitled "Method of Applying a Buttress to a Surgical Stapler," published Sep. 29, 2016, issued as U.S. Pat. No. 10,349,939 on Jul. 16, 2019, the disclosure of which is incorporated by reference herein.

FIGS. 65-66 show pad (7072) accommodating alternative camber orientations of end effector (7212), such as the over-camber orientation and the under-camber orientation. With respect to FIG. 65, closure of end effector (7212) to the over-camber orientation results in anvil (7218) and staple cartridge (7222) unlocking buttress assemblies (7012) from buttress applier cartridge (7016) as discussed above. Adhesive layers (7042) of upper and lower buttress assemblies (7012) are sufficiently compressed against anvil (7218) and deck (7220) to retain upper and lower buttress assemblies (7012) to end effector (7212) for stapling tissue. Pad (7072) accommodates the over-camber orientation by providing reaction forces of at least the predetermined minimum force for adhesion along the longitudinal length of buttress assemblies (7012).

Similarly, FIG. 66 shows closure of end effector (7212) to the under-camber orientation resulting in anvil (7218) and staple cartridge (7222) unlocking buttress assemblies (7012) from buttress applier cartridge (7016) as discussed above. Adhesive layers (7042) of upper and lower buttress assemblies (7012) are sufficiently compressed against anvil (7218) and deck (7220) to retain upper and lower buttress assemblies (7012) to end effector (7212) for stapling tissue. Pad (7072) accommodates the under-camber orientation by providing reaction forces of at least the predetermined minimum force for adhesion along the longitudinal length of buttress assemblies (7012).

IX. Exemplary Surgical Stapler

Figure 67:
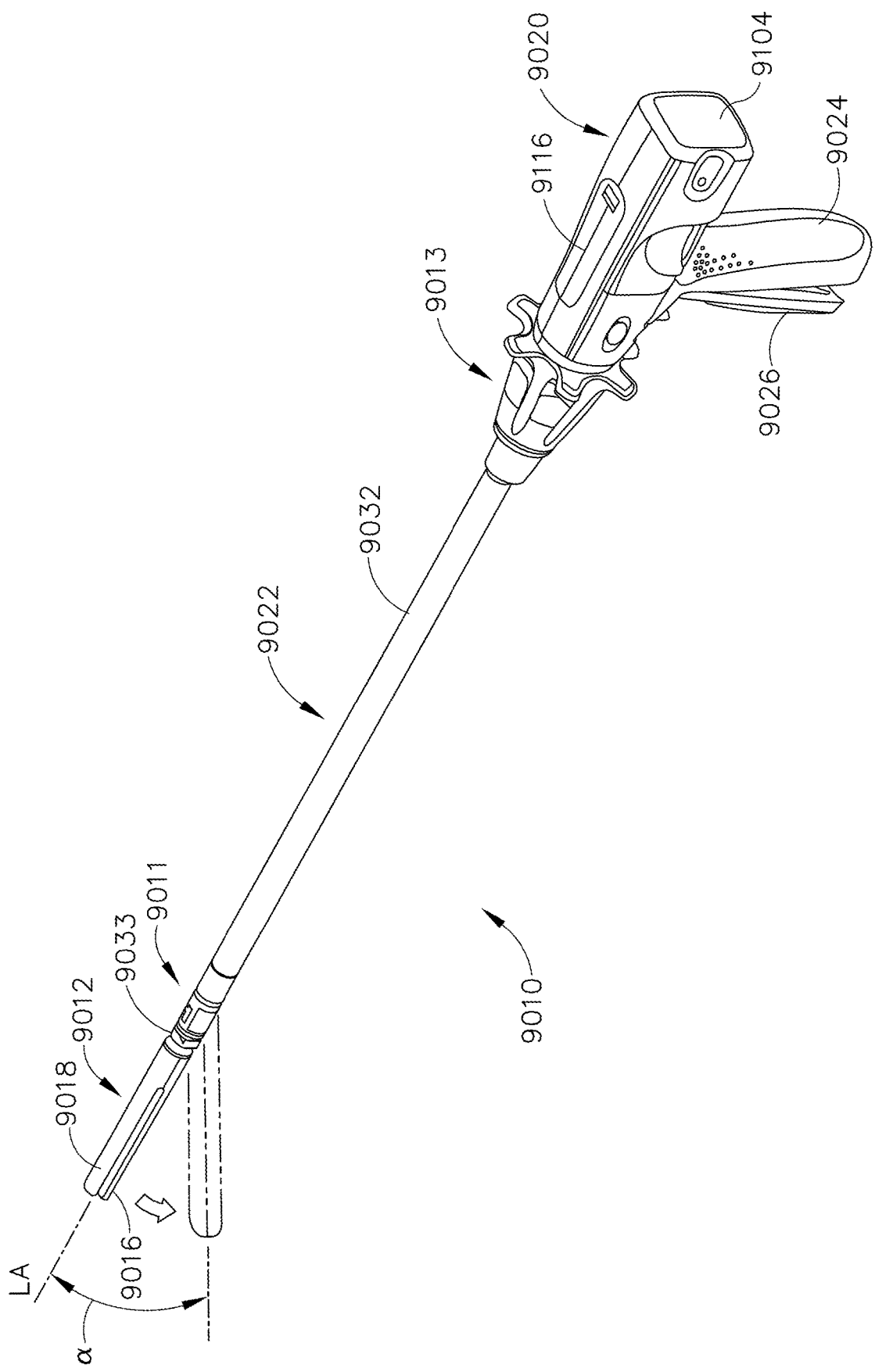
FIG. 67 depicts a perspective view of an exemplary articulating surgical stapling instrument.

FIGS. 67-73 depict an exemplary surgical stapling and severing instrument (9010) that is sized for insertion, in a nonarticulated state as depicted in FIG. 67, through a trocar cannula to a surgical site in a patient for performing a surgical procedure. By way of example only, such a trocar may be inserted in a patient's abdomen, between two of the patient's ribs, or elsewhere. In some settings, instrument (9010) is used without a trocar. For instance, instrument (9010) may be inserted directly through a thoracotomy or other type of incision. Instrument (9010) of the present example includes a handle portion (9020) connected to a shaft (9022). Shaft (9022) distally terminates in an articulation joint (9011), which is further coupled with an end effector (9012). It should be understood that terms such as "proximal" and "distal" are used herein with reference to a clinician gripping handle portion (9020) of instrument (9010). Thus, end effector (9012) is distal with respect to the more proximal handle portion (9020). It will be further appreciated that for convenience and clarity, spatial terms such as "vertical," "horizontal," "upper," and "lower" are used herein with respect to the drawings. However, surgical instruments are used in many orientations and positions, and these terms are not intended to be limiting and absolute.

In some versions, shaft (9022) is constructed in accordance with at least some of the teachings of U.S. Pat. No. 9,795,379, entitled "Surgical Instrument with Multi-Diameter Shaft," issued Oct. 24, 2017, the disclosure of which is incorporated by reference herein. Other suitable configurations for shaft (9022) will be apparent to those of ordinary skill in the art in view of the teachings herein.

Once articulation joint (9011) and end effector (9012) are inserted through the cannula passageway of a trocar, articulation joint (9011) may be remotely articulated, as depicted in phantom in FIG. 67, by an articulation control (9013), such that end effector (9012) may be deflected from the longitudinal axis (LA) of shaft (9022) at a desired angle (a). End effector (9012) may thereby reach behind an organ or approach tissue from a desired angle or for other reasons. In some versions, articulation joint (9011) enables deflection of end effector (9012) along a single plane. In some other versions, articulation joint (9011) enables deflection of end effector along more than one plane. Articulation joint (9011) and articulation control (9013) may be configured in accordance with the teachings of any of the numerous references that are cited herein. Alternatively, articulation joint (9011) and/or articulation control (9013) may have any other suitable configuration. By way of example only, articulation control (9013) may instead be configured as a knob that rotates about an axis that is perpendicular to the longitudinal axis (LA) of shaft (9022).

In some versions, articulation joint (9011) and/or articulation control (9013) are/is constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein. Articulation joint (9011) may also be constructed and operable in accordance with at least some of the teachings of U.S. Pat. No. 9,795,379, entitled "Surgical Instrument with Multi-Diameter Shaft," issued Oct. 24, 2017, the disclosure of which is incorporated by reference herein. Other suitable forms that articulation joint (9011) and articulation control (9013) may take will be apparent to those of ordinary skill in the art in view of the teachings herein.

End effector (9012) of the present example includes a lower jaw (9016) and a pivotable anvil (9018). In the present example, anvil (9018) can also be considered an upper jaw. Furthermore, in some versions like the present example, the upper jaw or anvil (9018) pivots with respect to a stationary lower jaw (9016); however, in some other versions the upper jaw or anvil (9018) is stationary while the lower jaw (9016) pivots. In some versions, lower jaw (9016) is constructed in accordance with at least some of the teachings of U.S. Pat. No. 9,808,248, entitled "Installation Features for Surgical Instrument End Effector Cartridge," issued Nov. 7, 2017, the disclosure of which is incorporated by reference herein. Anvil (9018) may be constructed in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pat. No. 9,839,421, entitled "Jaw Closure Feature for End Effector of Surgical Instrument," issued Dec. 12, 2017, the disclosure of which is incorporated by reference herein; and/or at least some of the teachings of U.S. Pat. No. 10,092,292, entitled "Staple Forming Features for Surgical Stapling Instrument," issued Oct. 9, 2018, the disclosure of which is incorporated by reference herein. Other suitable forms that lower jaw (9016) and anvil (9018) may take will be apparent to those of ordinary skill in the art in view of the teachings herein.

Handle portion (9020) includes a pistol grip (9024) and a closure trigger (9026). Closure trigger (9026) is pivotable toward pistol grip (9024) to cause clamping, or closing, of the anvil (9018) toward lower jaw (9016) of end effector (9012). Such closing of anvil (9018) is provided through a closure tube (9032) and a closure ring (9033), which both longitudinally translate relative to handle portion (9020) in response to pivoting of closure trigger (9026) relative to pistol grip (9024). Closure tube (9032) extends along the length of shaft (9022); and closure ring (9033) is positioned distal to articulation joint (9011). Articulation joint (9011) is operable to communicate/transmit longitudinal movement from closure tube (9032) to closure ring (9033).

Handle portion (9020) also includes a firing trigger (9028). An elongate member (not shown) longitudinally extends through shaft (9022) and communicates a longitudinal firing motion from handle portion (9020) to a firing beam (9014) in response to actuation of firing trigger (9028). This distal translation of firing beam (9014) causes the stapling and severing of clamped tissue in end effector (9012), as will be described in greater detail below. Thereafter, triggers (9026, 9028) may be released to release the tissue from end effector (9012).

FIGS. 69-72 depict end effector (9012) employing an E-beam form of firing beam (9014) to perform a number of functions. It should be understood that an E-beam form is just a merely illustrative example. Firing beam (9014) may take any other suitable form, including but not limited to non-E-beam forms. As best seen in FIGS. 70A-70B, firing beam (9014) includes a transversely oriented upper pin (9038), a firing beam cap (9044), a transversely oriented middle pin (9046), and a distally presented cutting edge (9048). Upper pin (9038) is positioned and translatable within a longitudinal anvil slot (9042) of anvil (9018). Firing beam cap (9044) slidably engages a lower surface of lower jaw (9016) by having firing beam (9014) extend through lower jaw slot (9045) (shown in FIG. 70B) that is formed through lower jaw (9016). Middle pin (9046) slidingly engages a top surface of lower jaw (9016), cooperating with firing beam cap (9044). Thereby, firing beam (9014) affirmatively spaces end effector (9012) during firing.

Some non-E-beam forms of firing beam (9014) may lack upper pin (9038), middle pin (9046) and/or firing beam cap (9044). Some such versions of instrument (9010) may simply rely on closure ring (9033) or some other feature to pivot anvil (9018) to a closed position and hold anvil (9018) in the closed position while firing beam (9014) advances to the distal position. By way of example only, firing beam (9014) and/or associated lockout features may be constructed and operable in accordance with at least some of the teachings of U.S. Pat. No. 9,717,497, entitled "Lockout Feature for Movable Cutting Member of Surgical Instrument," issued Aug. 1, 2017, the disclosure of which is incorporated by reference herein. Other suitable forms that firing beam (9014) may take will be apparent to those of ordinary skill in the art in view of the teachings herein.

Figure 69:
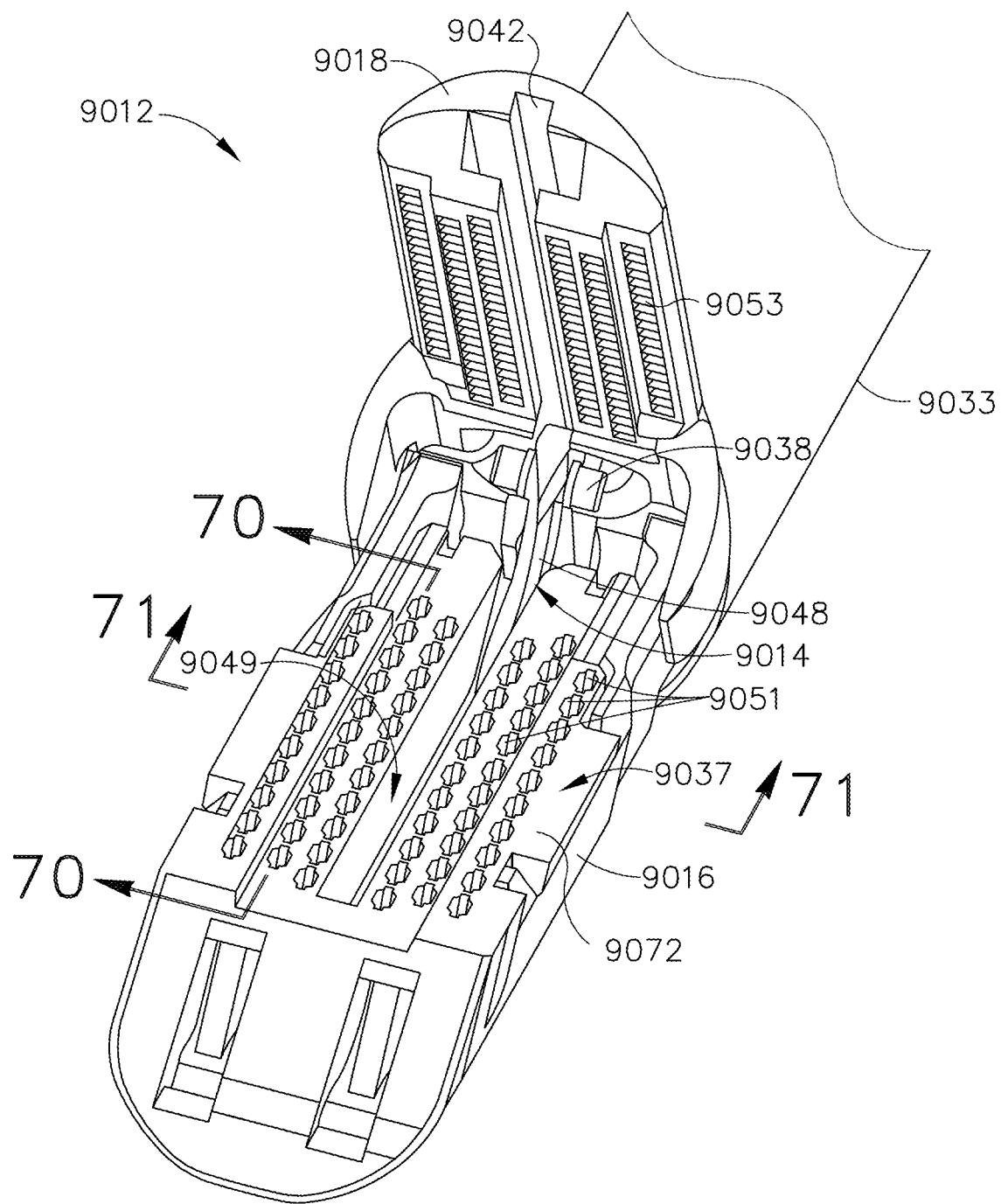
FIG. 69 depicts a perspective view of an opened end effector of the instrument of FIG. 67.
Figure 70A:
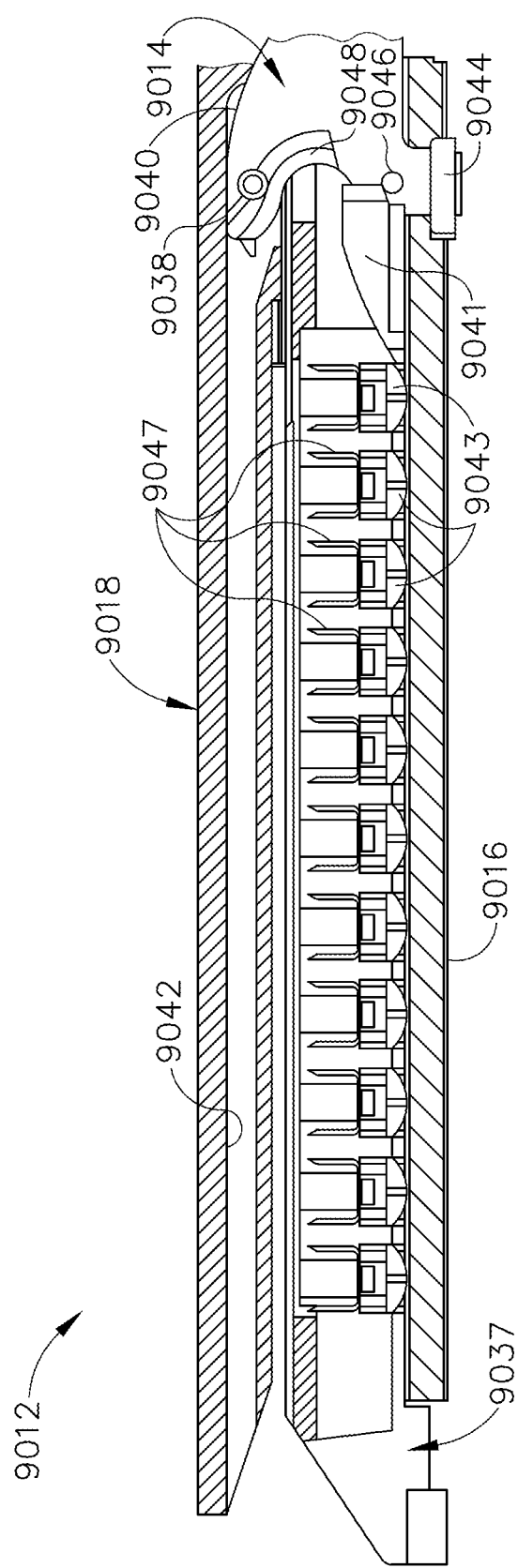
FIG. 70A depicts a side cross-sectional view of the end effector of FIG. 69, taken along line 70-70 of FIG. 69, with the firing beam in a proximal position.
Figure 70B:
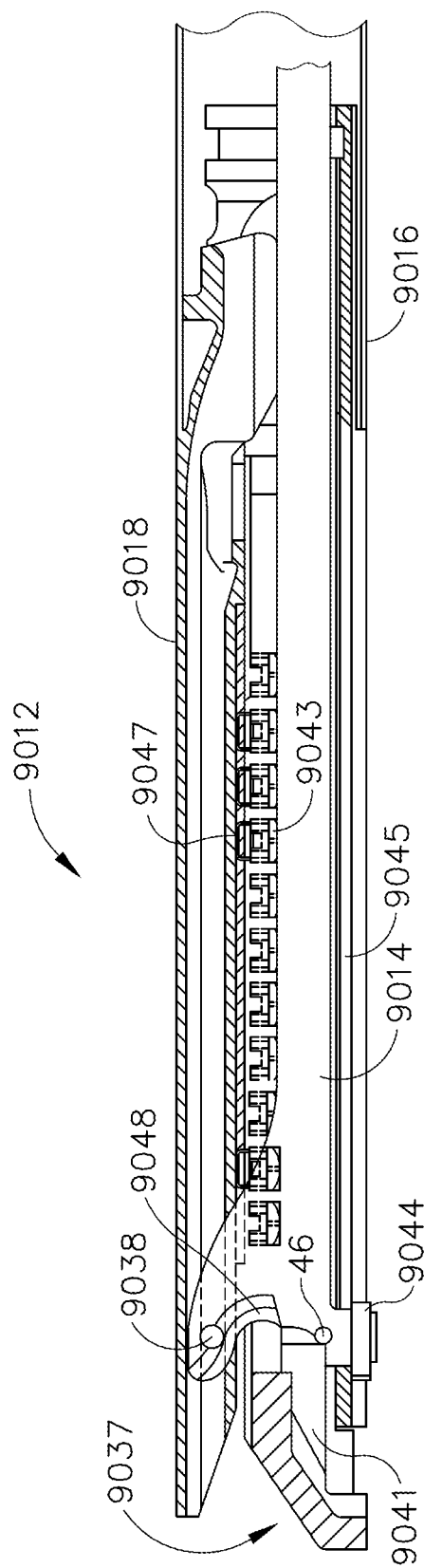
FIG. 70B depicts a side cross-sectional view of the end effector of FIG. 69, taken along line 70-70 of FIG. 69, with the firing beam in a distal position.
Figure 71:
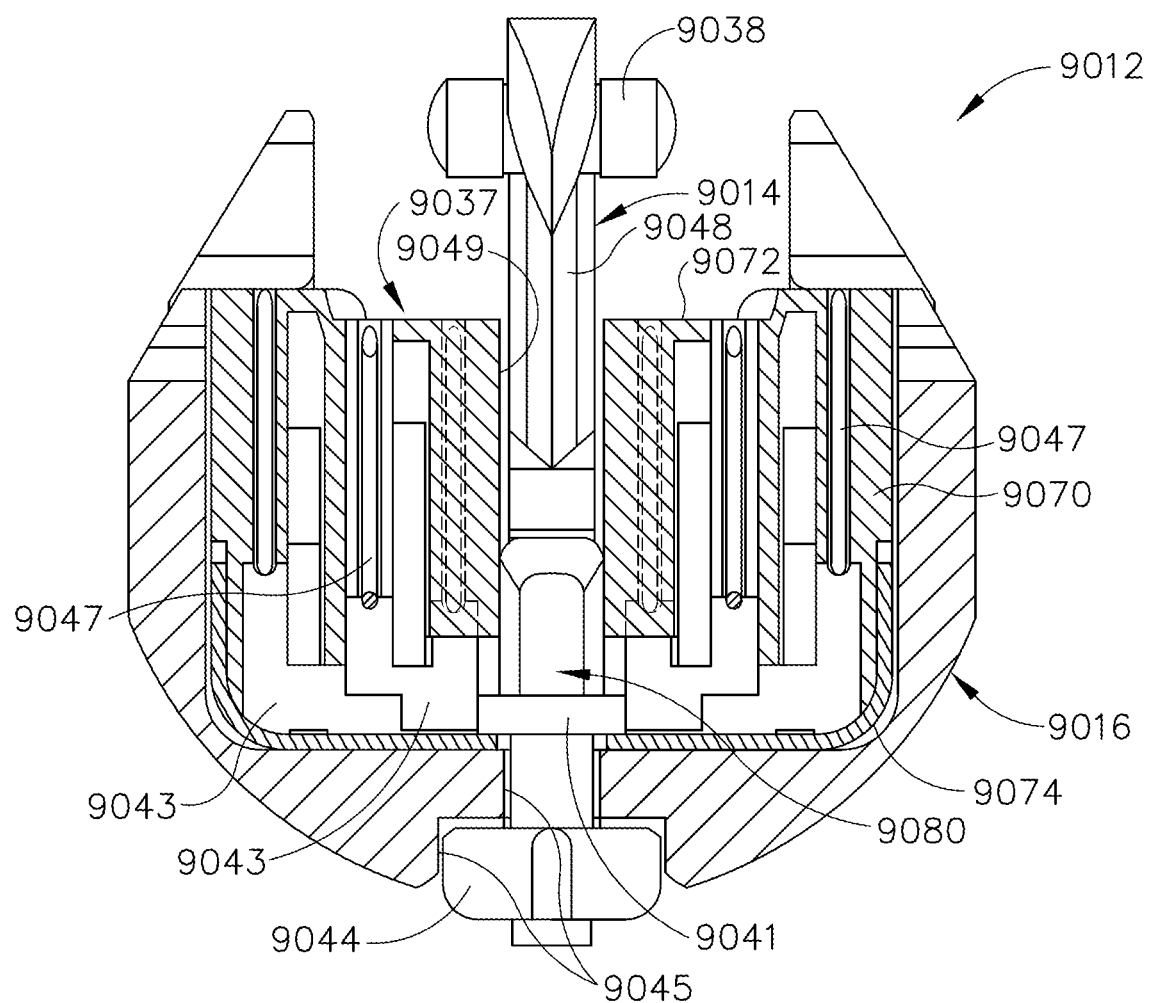
FIG. 71 depicts an end cross-sectional view of the end effector of FIG. 69, taken along line 71-71 of FIG. 69.
Figure 72:
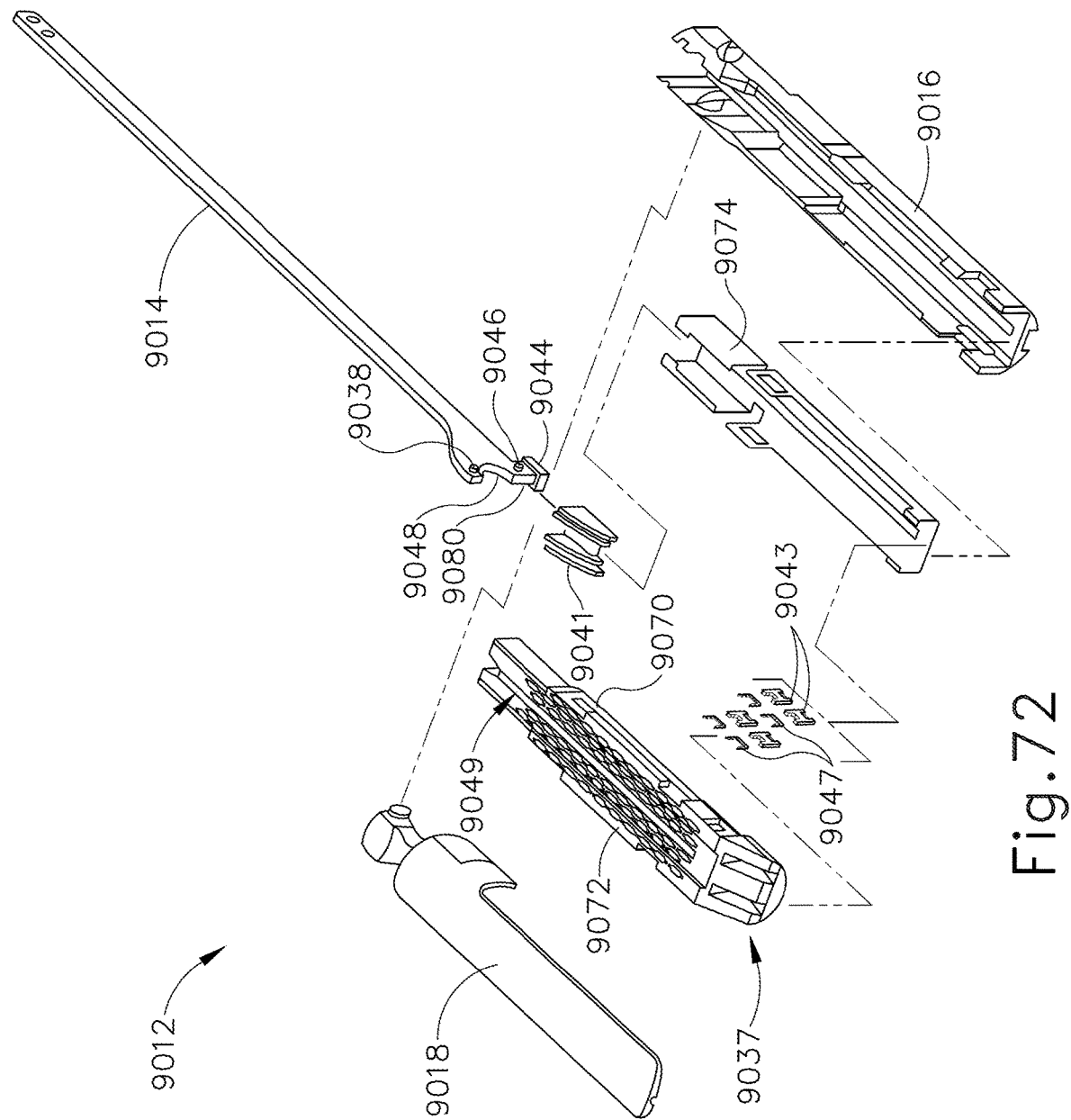
FIG. 72 depicts an exploded perspective view of the end effector of FIG. 69.

FIG. 69 shows firing beam (9014) of the present example proximally positioned and anvil (9018) pivoted to an open position, allowing an unspent staple cartridge (9037) to be removably installed into a channel of lower jaw (9016). As best seen in FIGS. 71-72, staple cartridge (9037) of this example includes a cartridge body (9070), which presents an upper deck (9072) and is coupled with a lower cartridge tray (9074). As best seen in FIG. 69, a vertical slot (9049) is formed through part of staple cartridge (9037). As also best seen in FIG. 69, three rows of staple apertures (9051) are formed through upper deck (9072) on one side of vertical slot (9049), with another set of three rows of staple apertures (9051) being formed through upper deck (9072) on the other side of vertical slot (9049). Of course, any other suitable number of staple rows (e.g., two rows, four rows, any other number) may be provided. Referring back to FIGS. 70A-72, a wedge sled (9041) and a plurality of staple drivers (9043) are captured between cartridge body (9070) and tray (9074), with wedge sled (9041) being located proximal to staple drivers (9043). Wedge sled (9041) is movable longitudinally within staple cartridge (9037); while staple drivers (9043) are movable vertically within staple cartridge (9037). Staples (9047) are also positioned within cartridge body (9070), above corresponding staple drivers (9043). In particular, each staple (9047) is driven vertically within cartridge body (9070) by a staple driver (9043) to drive staple (9047) out through an associated staple aperture (9051). As best seen in FIGS. 70A-70B and 6, wedge sled (9041) presents inclined cam surfaces that urge staple drivers (9043) upwardly as wedge sled (9041) is driven distally through staple cartridge (9037).

In some versions, staple cartridge (9037) is constructed and operable in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein. In addition or in the alternative, staple cartridge (9037) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein. Other suitable forms that staple cartridge (9037) may take will be apparent to those of ordinary skill in the art in view of the teachings herein.

With end effector (9012) closed as depicted in FIGS. 70A-70B by distally advancing closure tube (9032) and closure ring (9033), firing beam (9014) is then advanced in engagement with anvil (9018) by having upper pin (9038) enter longitudinal anvil slot (9042). A pusher block (9080) (shown in FIG. 71) is located at the distal end of firing beam (9014) and is configured to engage wedge sled (9041) such that wedge sled (9041) is pushed distally by pusher block (9080) as firing beam (9014) is advanced distally through staple cartridge (9037) when firing trigger (9028) is actuated. During such firing, cutting edge (9048) of firing beam (9014) enters vertical slot (9049) of staple cartridge (9037), severing tissue clamped between staple cartridge (9037) and anvil (9018). As shown in FIGS. 70A-70B, middle pin (9046) and pusher block (9080) together actuate staple cartridge (9037) by entering into vertical slot (9049) within staple cartridge (9037), driving wedge sled (9041) into upward camming contact with staple drivers (9043) that in turn drive staples (9047) out through staple apertures (9051) and into forming contact with staple forming pockets (9053) (shown in FIG. 69) on the inner surface of anvil (9018). FIG. 70B depicts firing beam (9014) fully distally translated after completing severing and stapling of tissue. It should be understood that staple forming pockets (9053) are intentionally omitted from the view in FIGS. 70A-70B; but staple forming pockets (9053) are shown in FIG. 69. It should also be understood that anvil (9018) is intentionally omitted from the view in FIG. 71.

Figure 73:
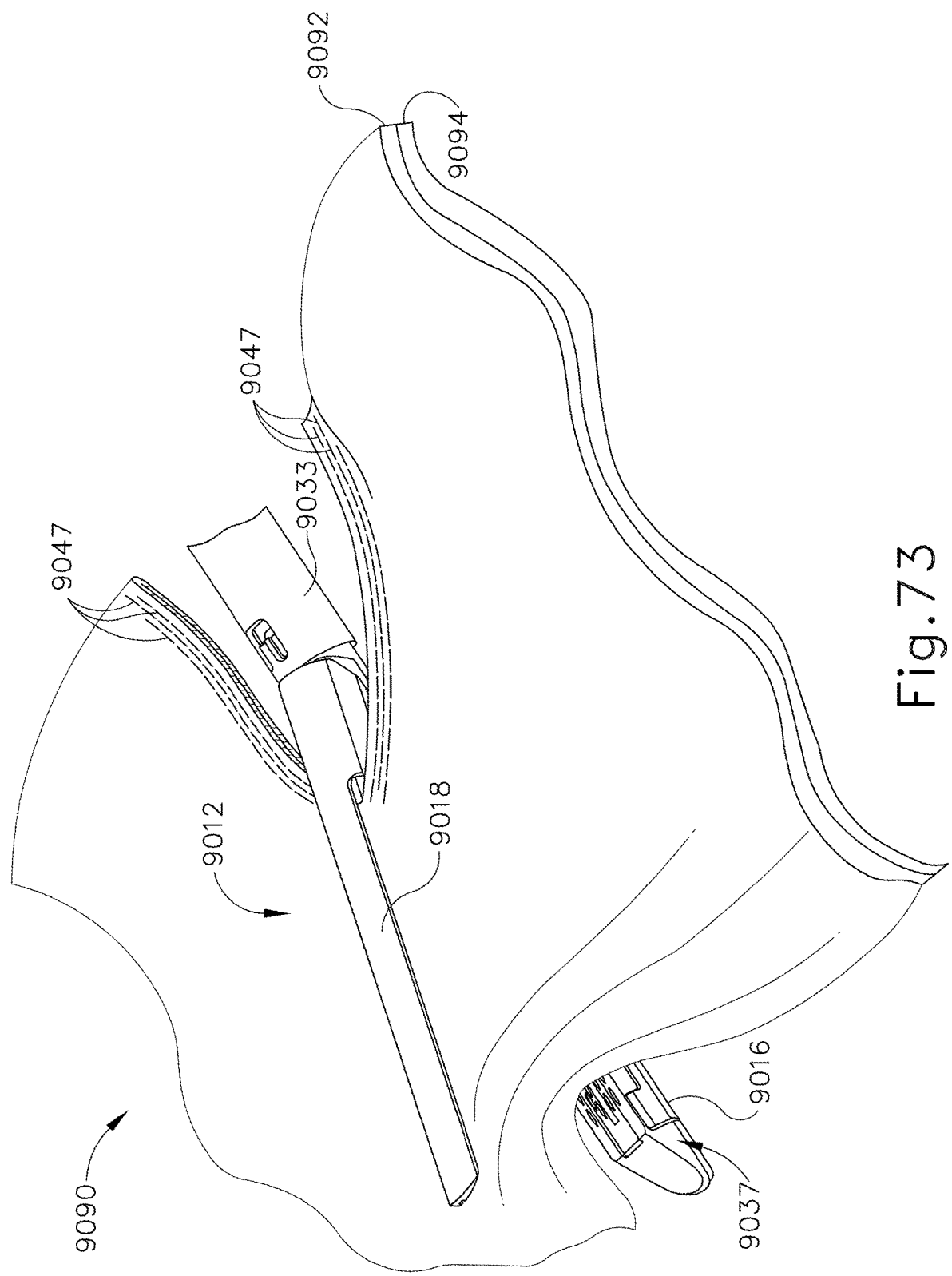
FIG. 73 depicts a perspective view of the end effector of FIG. 69, positioned at tissue and having been actuated once in the tissue.

FIG. 73 shows end effector (9012) having been actuated through a single stroke through tissue (9090). As shown, cutting edge (9048) (obscured in FIG. 73) has cut through tissue (9090), while staple drivers (9043) have driven three alternating rows of staples (9047) through the tissue (9090) on each side of the cut line produced by cutting edge (9048). Staples (9047) are all oriented substantially parallel to the cut line in this example, though it should be understood that staples (9047) may be positioned at any suitable orientations. In the present example, end effector (9012) is withdrawn from the trocar after the first stroke is complete, spent staple cartridge (9037) is replaced with a new staple cartridge, and end effector (9012) is then again inserted through the trocar to reach the stapling site for further cutting and stapling. This process may be repeated until the desired number of cuts and staples (9047) have been provided. Anvil (9018) may need to be closed to facilitate insertion and withdrawal through the trocar; and anvil (9018) may need to be opened to facilitate replacement of staple cartridge (9037).

It should be understood that cutting edge (9048) may sever tissue substantially contemporaneously with staples (9047) being driven through tissue during each actuation stroke. In the present example, cutting edge (9048) just slightly lags behind driving of staples (9047), such that a staple (9047) is driven through the tissue just before cutting edge (9048) passes through the same region of tissue, though it should be understood that this order may be reversed or that cutting edge (9048) may be directly synchronized with adjacent staples. While FIG. 73 shows end effector (9012) being actuated in two layers (9092, 9094) of tissue (9090), it should be understood that end effector (9012) may be actuated through a single layer of tissue (9090) or more than two layers (9092, 9094) of tissue. It should also be understood that the formation and positioning of staples (9047) adjacent to the cut line produced by cutting edge (9048) may substantially seal the tissue at the cut line, thereby reducing or preventing bleeding and/or leaking of other bodily fluids at the cut line. Furthermore, while FIG. 73 shows end effector (9012) being actuated in two substantially flat, apposed planar layers (9092, 9094) of tissue, it should be understood that end effector (9012) may also be actuated across a tubular structure such as a blood vessel, a section of the gastrointestinal tract, etc. FIG. 73 should therefore not be viewed as demonstrating any limitation on the contemplated uses for end effector (9012). Various suitable settings and procedures in which instrument (9010) may be used will be apparent to those of ordinary skill in the art in view of the teachings herein.

In one version, instrument (9010) provides motorized control of firing beam (9014). Exemplary components that may be used to provide motorized control of firing beam (9014) are shown and described in U.S. Pat. No. 9,622,746, entitled "Distal Tip Features for End Effector of Surgical Instrument," issued Apr. 18, 2017, the disclosure of which is incorporated by reference herein. In addition to or in lieu of the foregoing, at least part of the motorized control may be configured in accordance with at least some of the teachings of U.S. Pat. No. 8,210,411, entitled "Motor-Driven Surgical Instrument," issued Jul. 3, 2012, the disclosure of which is incorporated by reference herein. In addition to or in lieu of the foregoing, the features operable to drive firing beam (9014) may be configured in accordance with at least some of the teachings of U.S. Pat. No. 8,453,914, the disclosure of which is incorporated by reference herein; and/or in accordance with at least some of the teachings of U.S. Pat. No. 8,453,914, the disclosure of which is also incorporated by reference herein. Other suitable components, features, and configurations for providing motorization of firing beam (9014) will be apparent to those of ordinary skill in the art in view of the teachings herein. It should also be understood that some other versions may provide manual driving of firing beam (9014), such that a motor may be omitted. By way of example only, firing beam (9014) may be actuated in accordance with at least some of the teachings of any other patent/publication reference cited herein.

Instrument (9010) may also include a lockout switch and lockout indicator as shown and described in U.S. Pat. No. 9,622,746, entitled "Distal Tip Features for End Effector of Surgical Instrument," issued Apr. 18, 2017, the disclosure of which is incorporated by reference herein. Additionally, a lockout switch and/or lockout indication and associated components/functionality may be configured in accordance with at least some of the teachings of U.S. Pat. No. 7,644,848, entitled "Electronic Lockouts and Surgical Instrument Including Same," issued Jan. 12, 2010, the disclosure of which is incorporated by reference herein.

Instrument (9010) also include a manual return switch (9116) configured to act as a "bailout" feature, enabling the operator to quickly begin retracting firing beam (9014) proximally during a firing stroke. In other words, manual return switch (9116) may be manually actuated when firing beam (9014) has only been partially advanced distally. Manual return switch (9116) may provide further functionality in accordance with at least some of the teachings of U.S. Pat. No. 9,622,746, entitled "Distal Tip Features for End Effector of Surgical Instrument," issued Apr. 18, 2017, the disclosure of which is incorporated by reference herein.

In describing the operation of instrument (9010), use of the term "pivot" (and similar terms with "pivot" as a base) should not be read as necessarily requiring pivotal movement about a fixed axis. In some versions, anvil (9018) pivots about an axis that is defined by a pin (or similar feature) that slides along an elongate slot or channel as anvil (9018) moves toward lower jaw (9016). In such versions, the pivot axis translates along the path defined by the slot or channel while anvil (9018) simultaneously pivots about that axis. In addition or in the alternative, the pivot axis may slide along the slot/channel first, with anvil (9018) then pivoting about the pivot axis after the pivot axis has slid a certain distance along the slot/channel. It should be understood that such sliding/translating pivotal movement is encompassed within terms such as "pivot," "pivots," "pivotal," "pivotable," "pivoting," and the like. Of course, some versions may provide pivotal movement of anvil (9018) about an axis that remains fixed and does not translate within a slot or channel, etc.

It should be understood that instrument (9010) may be configured and operable in accordance with any of the teachings of U.S. Pat. Nos. 4,805,823; 5,415,334; 5,465,895; 5,597,107; 5,632,432; 5,673,840; 5,704,534; 5,814,055; 6,978,921; 7,000,818; 7,143,923; 7,303,108; 7,367,485; 7,380,695; 7,380,696; 7,404,508; 7,434,715; 7,721,930; 8,408,439; and/or U.S. Pat. No. 8,453,914. As noted above, the disclosures of each of those patents and publications are incorporated by reference herein. Additional exemplary modifications that may be provided for instrument (9010) will be described in greater detail below. Various suitable ways in which the below teachings may be incorporated into instrument (9010) will be apparent to those of ordinary skill in the art. Similarly, various suitable ways in which the below teachings may be combined with various teachings of the patents/publications cited herein will be apparent to those of ordinary skill in the art. It should also be understood that the below teachings are not limited to instrument (9010) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

X. Exemplary End Effector with Visualization, Lead-In, and Gathering Feature

In some instances, it may be desirable to provide the user with better visualization of end effector (9012). In particular, as end effector (9012) is inserted into a surgical site, the user may rotate shaft (9022) of instrument (9010) during the procedure. As a result, end effector (9012) also rotates. As end effector (9012) rotates, it may be desirable for the user to have visual access to the surgical site. For instance, the user may wish to see the interface or contact between tissue (9090) and end effector (9012). Since end effector (9012) may be rotated about the longitudinal axis (LA) relative to handle portion (9020), the user may view the surgical site such that lower jaw (9016) of end effector is visible rather than anvil (9018). Alternatively, end effector (9012) could be rotated such that when the user views end effector (9012), anvil (9018) is visible by the user. It may be desirable to provide visibility of the surgical site for the user beyond what is possible in instrument (9010) of FIG. 67. For instance, in the case of some surgical procedures where fluid carrying vessels are transected and stapled, it may be desirable to have visual confirmation that anvil (9018) and lower jaw (9016) completely cover the vessel to be cut, such that the vessel may be fully cut and stapled in one single actuation. In other words, the user may wish to avoid cutting and stapling only a portion of a vessel. Thus, some means of visual monitoring and/or feedback may be desirable so that the user will know that end effector (9012) has been positioned properly within the surgical site for anvil (9018) and lower jaw (9016) to fully clamp the vessel. One potential way of monitoring the surgical site may include improving visualization of the area adjacent to the distal tip of lower jaw (9016) and anvil (9018). Furthermore, not only visualization of the distal end of end effector (9012) may be desirable, but also it may be desirable to construct end effector (9012) such that the distal end of anvil (9018) is configured to urge tissue (e.g., a large vessel) proximally into the space between anvil (9018) and lower jaw (9016) as anvil (9018) closes toward lower jaw (9016).

Figure 74:
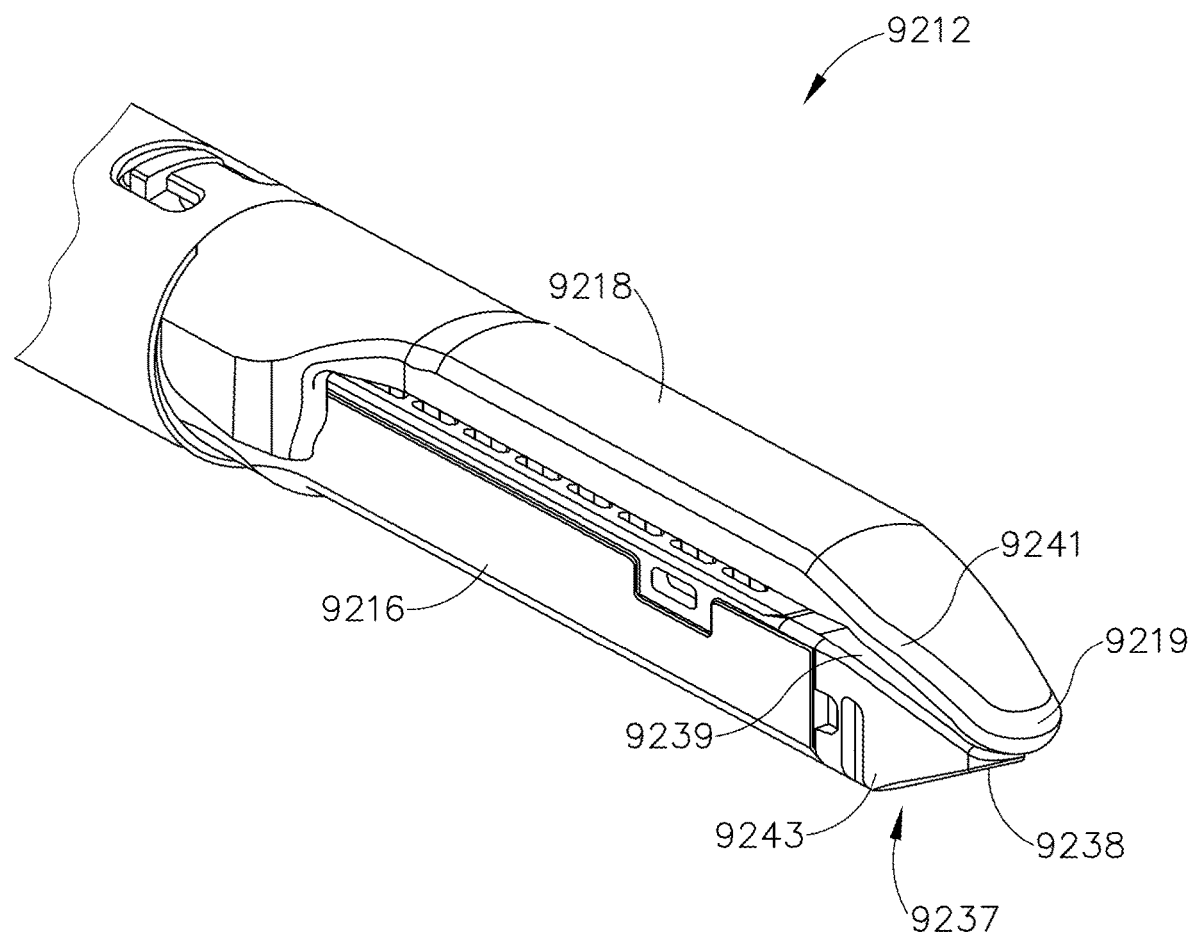
FIG. 74 depicts a perspective view of an alternative version of an end effector with an angled anvil and an angled cartridge.

FIG. 74 depicts an exemplary end effector (9212) comprising an anvil (9218) and a lower jaw (9216). It will be appreciated that end effector (9212) may be used in place of end effector (9012) of instrument (9010). End effector (9212) may be integrally formed with instrument (9010) or in the alternative may be interchangeable with end effector (9012) of instrument (9010).

Anvil (9218) is operable to pivot relative to lower jaw (9216). Anvil (9218) and lower jaw (9216) may clamp tissue (9090) similarly to clamping performed by anvil (9018) and lower jaw (9016) shown in FIG. 67. End effector (9212) further comprises a cartridge (9237) operable to be placed in lower jaw (9216) similarly to cartridge (9037) shown in FIG. 69.

Figure 75:
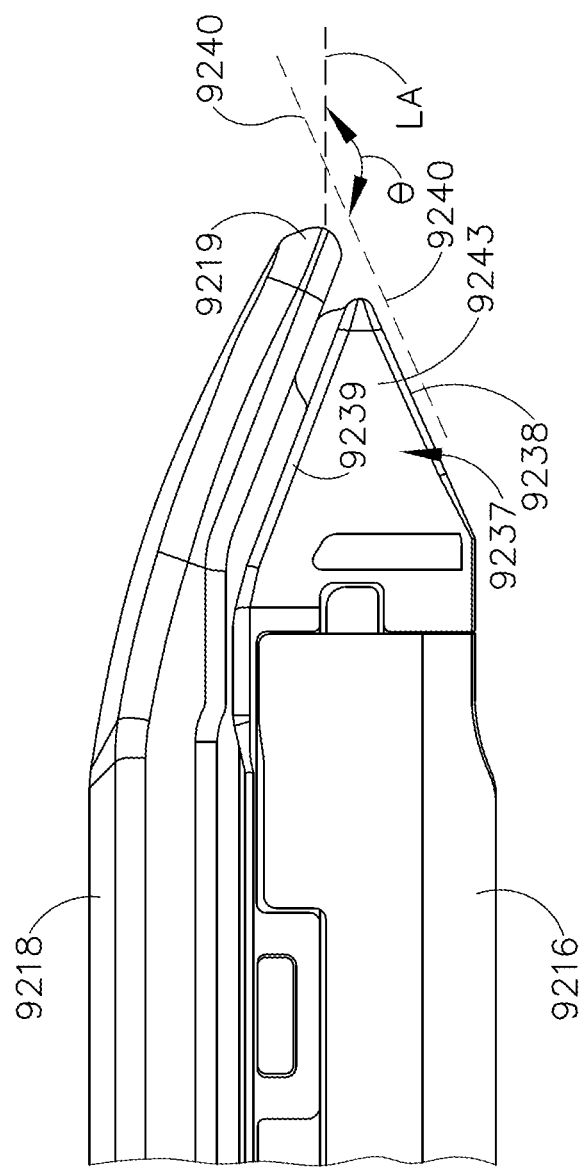
FIG. 75 depicts an enlarged, side view of the end effector of FIG. 74.
Figure 76:
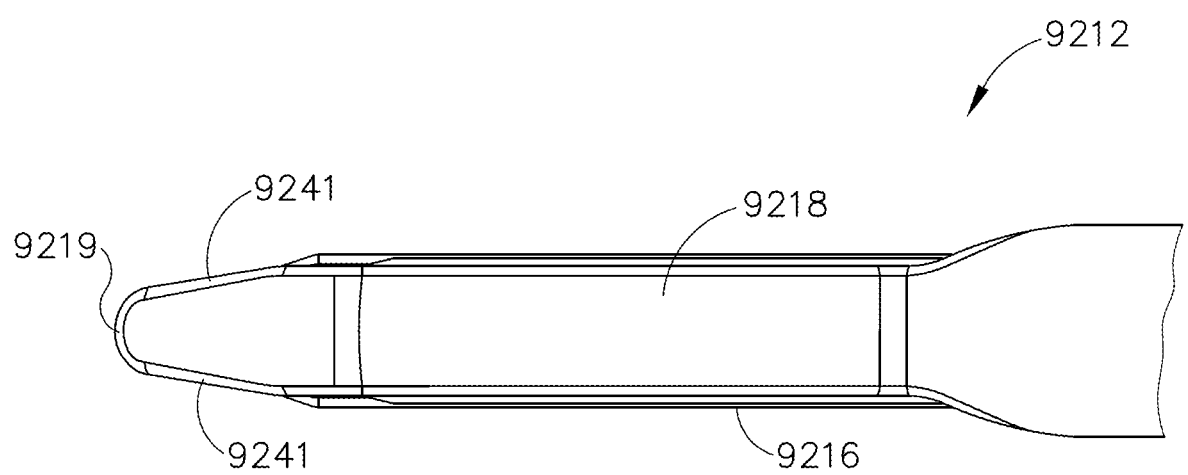
FIG. 76 depicts an enlarged top view of the end effector of FIG. 74.

Anvil (9218) as can be seen in FIGS. 74-76 has an elongated shape where the distal portion of anvil (9218) angles toward cartridge (9237). The distal portion of anvil (9218) angles toward cartridge (9237) such that the distal most tip (9219) of anvil (9218) extends distally longitudinally further than cartridge (9237). Though in some versions, distal tip (9219) may extend to a distance longitudinally equal to cartridge (9237) or proximal relative to the distal most point on cartridge (9237). Furthermore, anvil (9218) angles toward cartridge (9237) through a gentle slope. As seen best in FIG. 76, anvil (9218) includes sides (9241) that taper as they approach the distal most tip (9219) of anvil (9218). By way of example, anvil (9218) is shaped in FIG. 74 similarly to an inverted ski tip. The angled shape of anvil (9218) may provide easier insertion of end effector (9212) into a surgical site. For instance, the gentle slope or inverted ski tip shape of anvil (9218) may provide an atraumatic tissue deflection surface as anvil (9218) contacts or moves through tissue. Such atraumatic tissue deflection may include urging tissue (e.g., a large vessel) proximally into the space between anvil (9218) and lower jaw (9216) as anvil (9218) closes toward lower jaw (9216). Once placed into a surgical site, the angled shape of anvil (9218) may also provide better maneuverability of end effector (9212) and better visibility of the distal end of end effector (9212) in relation to anatomical structures at the surgical site. Other suitable variations of anvil (9218) will be apparent to one of ordinary skill in the art in view of the teachings herein.

Cartridge (9237) is operable to hold staples similar to staples (9047) shown in FIG. 70A for driving into tissue. As shown in FIG. 75, the distal end of cartridge (9237) has a triangular profile. In particular, the distal end of cartridge (9237) comprises an upper tapered surface (9239) and a lower tapered surface (9238). Additionally, the distal end of cartridge (9237) comprises a tapered side surface (9243) on each side. In the present example, each tapered side surface (9243) of cartridge (9237) generally aligns with the taper presented by sides (9241) of anvil (9218). Thus, as shown in FIG. 76, side surfaces (9243) of cartridge (9237) do not extend outwardly from longitudinal axis (LA) of end effector (9212) past sides (9241) of anvil (9218). Upper tapered surface (9239) and lower tapered surface (9238) lead to the distal most end of cartridge (9237). Lower tapered surface (9238) defines a sight line (9240) such that once end effector (9212) is inserted into a surgical site, the user can see along sight line (9240). Sight line (9240) extends along the edge of lower tapered surface (9238). It will be appreciated that the planar shape of lower tapered surface (9238) may be operable to allow the user to visualize and/or nearly visualize the distal tip (9219) of anvil (9218). In particular, sight line (9240) intersects longitudinal axis (LA), which extends longitudinally through end effector (9212), to form a viewing angle ($\theta$).

Viewing angle ($\theta$) may establish the relative visibility that a user has regarding distal tip (9219). In particular, the user can see in front of distal tip (9219) along any line of sight that passes through the intersection of sight line (9240) and longitudinal axis (LA) within viewing angle ($\theta$). For instance, as viewing angle ($\theta$) increases, the user would have greater visibility of the area immediately in front of distal tip (9219) from proximal vantage points; whereas as viewing angle ($\theta$) decreases, the user has less visibility of the area in front of distal tip (9219) from proximal vantage points. In some versions, viewing angle ($\theta$) defines an angle greater than 90 degrees. Additionally, in some versions, viewing angle ($\theta$) defines an angle greater than 135 degrees. Other suitable angles for viewing angle ($\theta$) will be apparent to one of ordinary skill in the art in view of the teachings herein. In the illustrated version, the user generally looks along sight line (9240) or along some other line of sight within viewing angle ($\theta$), thus, the user has visibility along sight line as well as any area within viewing angle ($\theta$). The underside of distal tip (9219) is further slightly rounded to aid in the visibility of the intersection of longitudinal axis (LA) and sight line (9240).

When tissue (9090) is clamped between a closed cartridge (9237) and anvil (9218), the user can look along sight line (9240) or elsewhere within viewing angle ($\theta$) to see, for instance, precisely where anvil (9218) has clamped tissue (9090). Furthermore, the user would be able to determine whether the tissue is completely clamped between anvil (9218) and cartridge (9237) such that tissue does not spill over the end of end effector (9212). The user may be able to also visualize the quality of the clamp between anvil (9218) and cartridge (9237) against tissue (9090). It will be appreciated that in some instances, end effector (9212) may be rotated before, during, or after clamping tissue (9090). As a result, the tapered shape of anvil (9218) may also provide more accessible viewing of distal tip (9219) or substantially adjacent distal tip (9219). The taper of anvil (9218) along with lower tapered surface (9238) of cartridge (9237) may further promote easy insertion of end effector (9212) into tissue in an atraumatic manner. Furthermore, it may be easier to fit end effector (9212) through a trocar or other devices operable to introduce end effector (9212) into a surgical site due to the tapered end of end effector (9212). For instance, once distal tip (9219) is fit into a trocar, lower tapered surface (9238) and the tapered shape of anvil (9218) may provide a lead-in, guiding the rest of end effector (9212) into the trocar. In view of the teachings herein, those of ordinary skill in the art will further appreciate that visibility and maneuverability can be enhanced by the tapered design for both sides (9241) of anvil (9218) and each side (9243) of cartridge (9237).

In addition to the foregoing, end effector (9212) and versions of instrument (9010) incorporating end effector (9212) may be configured and operable in accordance with at least some of the teachings of U.S. Pat. No. 9,186,142, entitled "Surgical Instrument End Effector Articulation Drive with Pinion and Opposing Racks," issued Nov. 17, 2015, the disclosure of which is incorporated by reference herein; U.S. Pat. No. 9,717,497, entitled "Lockout Feature for Movable Cutting Member of Surgical Instrument," issued Aug. 1, 2017, the disclosure of which is incorporated by reference herein; U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pat. No. 9,839,421, entitled "Jaw Closure Feature for End Effector of Surgical Instrument," issued Dec. 12, 2017, the disclosure of which is incorporated by reference herein; U.S. Pat. No. 9,622,746, entitled "Distal Tip Features for End Effector of Surgical Instrument," issued Apr. 18, 2017, the disclosure of which is incorporated by reference herein; U.S. Pat. No. 10,092,292, entitled "Staple Forming Features for Surgical Stapling Instrument," issued Oct. 9, 2018, the disclosure of which is incorporated by reference herein; U.S. Pat. No. 9,795,379, entitled "Surgical Instrument with Multi-Diameter Shaft," issued Oct. 24, 2017, the disclosure of which is incorporated by reference herein; and/or U.S. Pat. No. 9,808,248, entitled "Installation Features for Surgical Instrument End Effector Cartridge," issued Nov. 7, 2017, the disclosure of which is incorporated by reference herein. Further modifications that may be incorporated into end effector (9212) will be described in greater detail below.

XI. Exemplary End Effectors with Bent or Angled Elastically Deformable Anvil Tips In some procedures, it may be necessary to cut along tissue or through tissue where more than one cutting sequence is necessary to complete the procedure—in other words making sequential cuts along a continuous path. In such procedures, this sequential cutting technique can be defined as "marching." With procedures that involve marching, instrument (9010) may be placed at the surgical site, actuated to cut and staple, then removed from the surgical site for installing a new cartridge (9037), and then be placed back at the surgical site again for the next cut and staple along the same path in which the previous cutting and stapling cycle occurred. This process is repeated until the cut and staple procedure is complete. As can be seen in FIGS. 70A-70B and FIG. 73, the distal end configuration of end effector (9012) provides a gap between the distal end of anvil (9018) and the distal end of cartridge (9037). This gap may facilitate marching by providing an atraumatic space for tissue to enter the distal end of end effector (9012) at the beginning of each marching step.

As noted above, the distal end configuration of end effector (9212) is different from the distal end configuration of end effector (9012); with the different configuration of end effector (9212) providing different potential advantages. In particular, the distal end configuration of end effector (9212) may provide improved maneuverability and improved visibility of the relationship between the distal end of end effector (9212) and adjacent anatomical structures. In addition, the distal end configuration of end effector (9212) may provide tissue-gathering effects by urging tissue proximally into the space between anvil (9218) and lower jaw (9216) as anvil (9218) is closed toward lower jaw (9216). However, in versions where all the structures of end effector (9212) are rigid, the bent configuration of distal tip (9219) of anvil (9218) may not lend itself well to marching operations, as distal tip (9219) may impart trauma to tissue that is not gathered into the space between anvil (9218) and lower jaw (9216) as anvil (9218) is closed toward lower jaw (9216). Thus, in versions where all the structures of end effector (9212) are rigid, end effector (9212) may be best suited for cutting and stapling operations (e.g., vessel transection) where all of the tissue that is to be cut and stapled is gathered proximal to distal tip (9219).

In view of the foregoing, it may be desirable to provide a variation of end effectors (9012, 9212) that provides the marching capabilities of end effector (9012), the improved visibility associated with end effector (9212), and the tissue gathering capabilities of end effector (9212), without providing an increased risk of trauma that might otherwise be associated with fully rigid versions of end effector (9212). The following describes several merely illustrative examples of such variations of end effectors (9012, 9212). In the following examples, an anvil has a distal tip that is resiliently biased to assume a bent or angled configuration like distal tip (9219); yet the resiliently biased distal tip is deflectable away from the lower jaw in response to a sufficient load on the distal tip. It will be understood in view of the teachings herein that providing an anvil with an elastically deformable angled distal tip portion can provide an additional level of maneuverability benefits in terms of navigating through tissue to a surgical site. In this manner, the deformable distal tip portion may deflect or deform to promote smooth and atraumatic movement of the end effector through tissue, particularly during marching operations. Additionally, with an anvil having a bias to an angled position when not in a loaded state or contacted by surrounding tissue, enhanced visualization during tissue capture and cutting can be achieved compared to using end effectors with a straight or non-angled anvil. Moreover, an anvil with a distal tip that is biased to an angled position may provide some degree of tissue gathering effects up until reaching a load point that would be associated with marching rather than being associated with simply gathering a relatively small tissue structure between the anvil and lower jaw.

Figure 77:
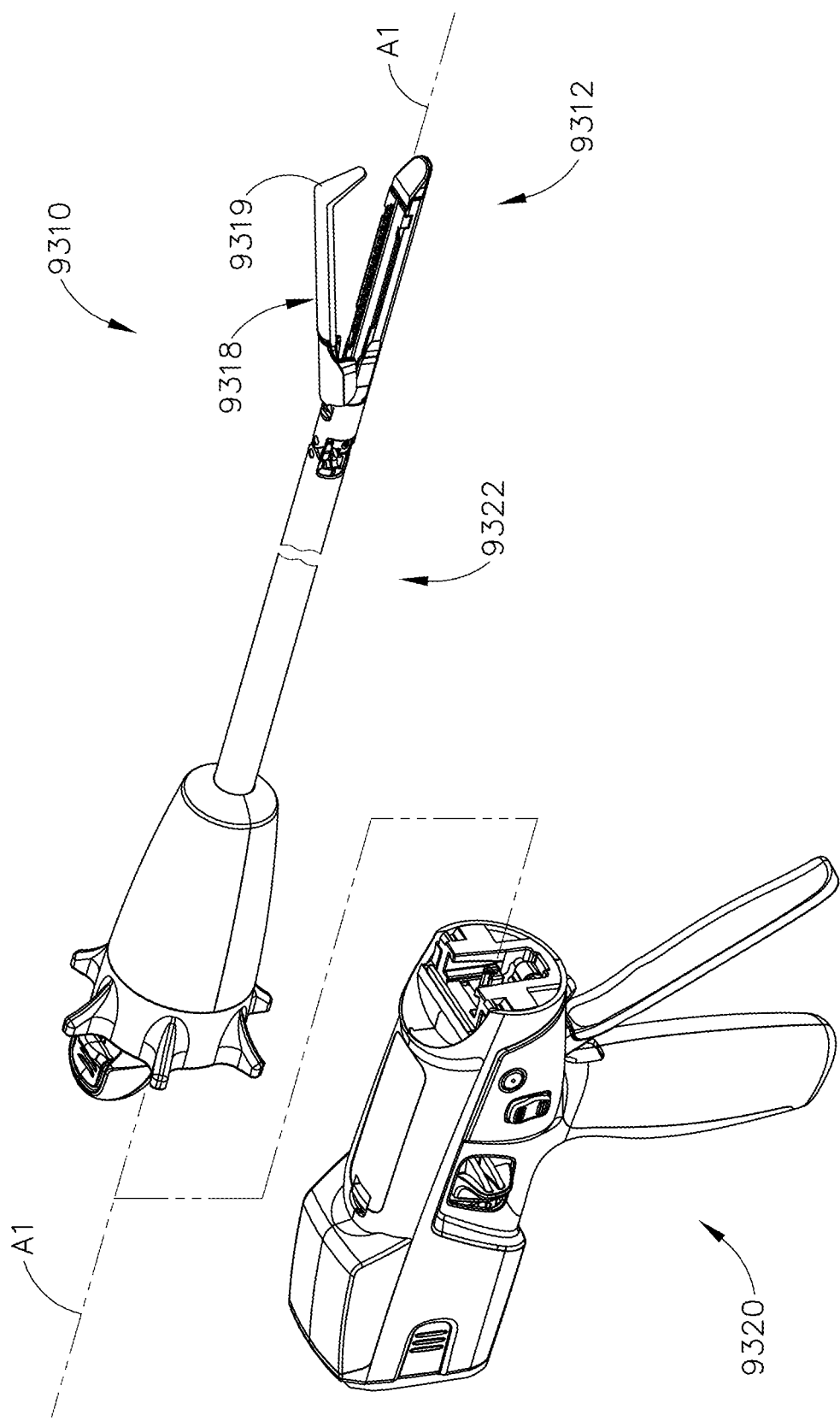
FIG. 77 depicts a perspective view of an exemplary surgical stapling instrument having an end effector with a bent or angled elastically deformable tip section.

FIG. 77 shows another exemplary instrument (9310) configured as a surgical stapler. Instrument (9310) comprises a handle portion (9320) and a shaft (9322). Instrument (9310) has a modular configuration such that shaft (9322) is selectively removable from, and attachable to, handle portion (9320). Instrument (9310) is configured similarly to instrument (9010) such that the operability and use of instrument (9310) is the same as described above for instrument (9010) with the added feature of instrument (9310) being a modular configuration. With its modular configuration, instrument (9310) provides a way to change the end effector. Such a change in the end effector may be made to replace an otherwise worn end effector, or to provide for a different end effector configuration based on the procedure or user preference. In addition to or in lieu of the foregoing, features operable for providing the modular configuration of instrument (9310) may be configured in accordance with at least some of the teachings of U.S. Pub. No. 2017/0086823, entitled "Surgical Stapling Instrument with Shaft Release, Powered Firing, and Powered Articulation," published Mar. 30, 2017, issued as U.S. Pat. No. 10,182,813 on Jan. 22, 2019, the disclosure of which is incorporated by reference herein. Other suitable components, features, and configurations for providing instrument (9310) with a modular configuration will be apparent to those of ordinary skill in the art in view of the teachings herein. Moreover, it will be understood by those of ordinary skill in the art in view of the teachings herein, that instrument (9010) may be modified to incorporate a modular configuration as shown and described with respect to instrument (9310) or other instruments incorporated by reference herein.

In the illustrated example of FIG. 77, instrument (9310) comprises an end effector (9312) having an anvil (9318) that has an angled distal tip (9319). Furthermore, distal tip (9319) of anvil (9318) is elastically deformable. In this manner, and as shown best in FIGS. 78A and 78B, angled distal tip (9319) is operable to elastically deform from a first angled position to a second position. The second position for angled distal tip (9319) may be substantially straight in some versions, but may be angled to a degree (e.g., slightly above or slightly below the longitudinal axis (A1) in other versions. It should be understood that the second position for angled distal tip (9319) may be defined by the characteristics (e.g., thickness, density, etc.) of the tissue that is being captured between anvil (9318) and lower jaw (9016). In the present example, end effector (9312) is provided on shaft (9322) that is detachable from handle portion (9320). By way of example only, shaft (9322) may be detachable from handle portion (9320) in accordance with at least some of the teachings of U.S. Pat. No. 9,913,642, entitled "Surgical Instrument Comprising a Sensor System," issued Mar. 13, 2018, the disclosure of which is incorporated by reference herein. In some other versions, shaft (9322) is not detachable from handle portion (9320).

It will be appreciated that end effector (9312) may be used in place of end effector (9012) shown in FIG. 67. In some versions, end effector (9312) may be integrally formed with shaft (9022) or alternatively may be separately formed and then combined. In some versions, end effector (9312) may be provided for use in robotic systems. In such robotic systems, modular shaft (9322) having end effector (9312) may be attachable to a portion of the robotic system for use such that handle portion (9320) is replaced by components of the robotic system. Still in other examples, end effector (9312) may be adapted for use with a robotic system in a manner where end effector (9312) connects with the robotic system without necessarily connecting the entire modular shaft (9322). In view of the teachings herein, other ways to incorporate an end effector having an angled elastically deformable anvil tip into a user operated or robotic operated instrument will be apparent to those of ordinary skill in the art.

Figure 78A:
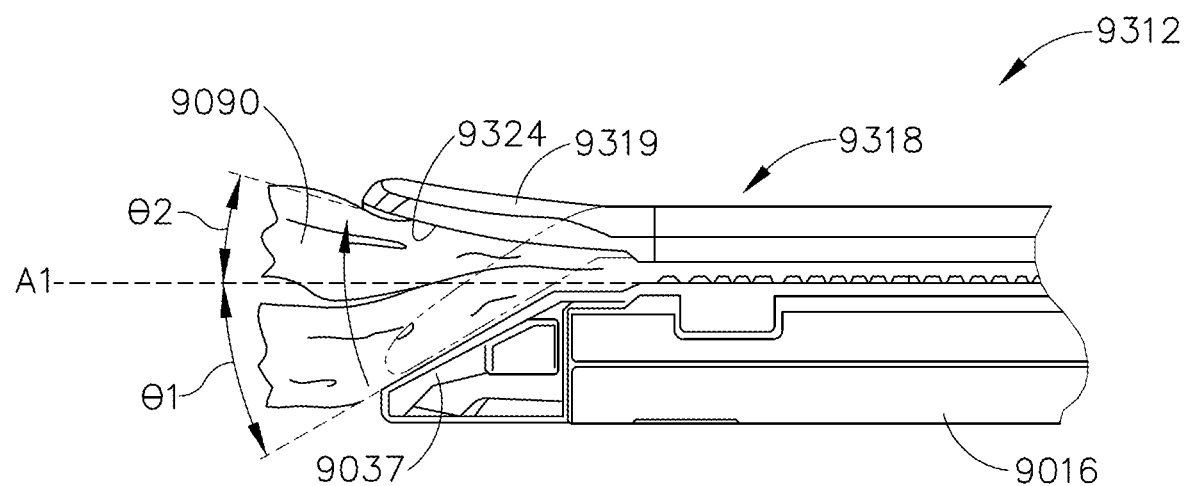
FIG. 78A depicts an enlarged side view of a distal portion of the end effector of FIG. 77.

FIG. 78A shows an enlarged side view of the distal end of end effector (9312). End effector (9312) comprises anvil (9318) and lower jaw (9016) that accepts cartridge (9037) as described above with respect to instrument (9010). Anvil (9318) pivotably rotates toward lower jaw (9016) in the same manner as anvil (9018) as described above with respect to instrument (9010). In this configuration, end effector (9312) is similar to end effector (9012), however, anvil (9318) comprises angled distal tip (9319) that is elastically deformable. As shown in FIG. 78A, tip (9319) is imparted with a bias to an angled position that is shown in FIG. 77 and in phantom in FIG. 78A. Tip (9319) assumes this angled position when end effector (9312) is not clamping tissue and is open, as shown in FIG. 77; or closed without clamping tissue, as shown in phantom in FIG. 78A. In instances when end effector (9312) is in this angled state or position, end effector (9312) can be considered not loaded or in a non-loaded state or position. Conversely when end effector (9312) is clamping tissue, end effector (9312) can be considered loaded or in a loaded state or position.

When closed and not clamping tissue between anvil (9318) and lower jaw (9016), tip (9319) contacts cartridge (9037). In this position, an underside surface (9324) of tip (9319) defines a plane that intersects a longitudinal axis (A1) defined by shaft (9322) to form an angle ($\theta$1). When closed and clamping tissue (9090) between anvil (9318) and lower jaw (9016), underside surface (9324) of tip (9319) contacts tissue (9090). In this position, underside surface (9324) of tip (9319) defines a plane that intersects longitudinal axis (A1) to form an angle ($\theta$2). In the illustrated example of FIG. 78A, angles ($\theta$1, $\theta$2) are relative to longitudinal axis (A1), and the sum of angles ($\theta$1, $\theta$2) represent the range of motion distal tip (9319) undergoes. By way of example only, and not limitation, in some examples angle ($\theta$1) is between about 20 and about 70 degrees, or more particularly between about 30 degrees and about 50 degrees, in a downward direction from longitudinal axis (A1) toward cartridge (9037). By way of example only, and not limitation, in some examples angle ($\theta$2) is between about 0 and about 90 degrees in an upward direction from longitudinal axis (A1) away from cartridge (9037). By way of example only, and not limitation, in some examples the range of motion undergone by tip (9319) is between about 20 degrees and about 110 degrees. The angles described for angles ($\theta$1, $\theta$2) are exemplary only and not limiting. Other suitable angles will be apparent to those of ordinary skill in the art in view of the teachings herein.

Additionally, in some instances longitudinal axis (A1) represents a zero-degree reference and angles relative thereto may be positive or negative. For instance, where an angle is in a downward direction from longitudinal axis (A1) toward cartridge (9037), the angle may be characterized as a negative angle. Similarly, where an angle is in an upward direction from longitudinal axis (A1) away from cartridge (9037), the angle may be characterized as a positive angle. When using these conventions, the range of motion of distal tip (9319) due to deformation can be understood as the sum of the absolute value of the angle when distal tip (9319) is in the position contacting cartridge (9037), and the angle when distal tip (9319) is in the deformed state when clamping tissue.

Figure 78B:
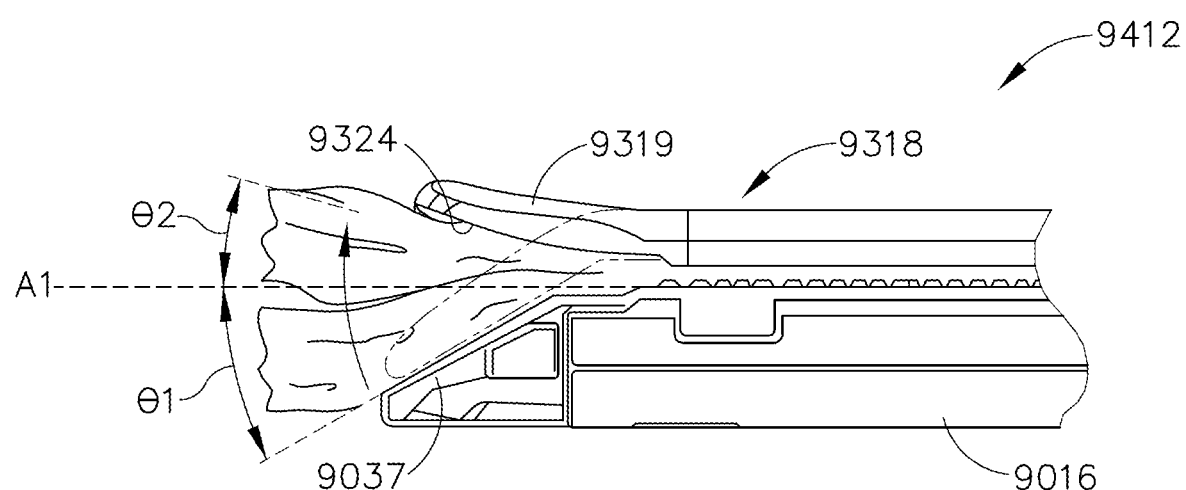
FIG. 78B depicts an enlarged side view of a distal portion of an alternate end effector similar to that of FIG. 77.

FIG. 78B shows another side view of an alternate end effector (9412) similar to end effector (9312) of FIG. 78A. With end effector (9312), when anvil (9318) is in its angled and non-deformed state (as seen in phantom in the view of FIG. 78A), anvil (9318) extends to a point even with or proximal to the distal most end of cartridge (9037). When anvil (9318) is deformed such that it is deflected upwardly, the end of distal tip (9319) extends to a point just distal to the distal most end of cartridge (9037). With end effector (9412), as shown in FIG. 78B, when anvil (9318) is in its angled and non-deformed state (as seen in phantom in the view of FIG. 78B), anvil (9318) extends to a point even with or proximal to the distal most end of cartridge (9037). When anvil (9318) is deformed such that it is deflected upwardly, the end of a distal tip (9319) of anvil (9318) extends to a point even with or proximal to the distal most end of cartridge (9037). In this manner, anvil (9318) of end effector (9412) remains even with or proximal to the distal most end of cartridge (9037) when anvil (9318) is in its angled state or deformed state such that anvil (9318) does not extend past the distal most end of cartridge (9037) whether anvil (9318) is in its angled and non-deformed state or in its deformed state. In some instances, this can be achieved by modifying anvil (9318) such that distal tip (9319) of anvil is shortened in length. In other instances, instruments (9010, 9310) may be modified to provide for a slight proximal retraction of anvil (9318) when clamping. In view of the teachings herein, other ways to modify end effector (9412) as it relates to control of anvil (9318) position, will be apparent to those of ordinary skill in the art.

XII. Additional Exemplary End Effectors for Surgical Staplers

Figure 79:
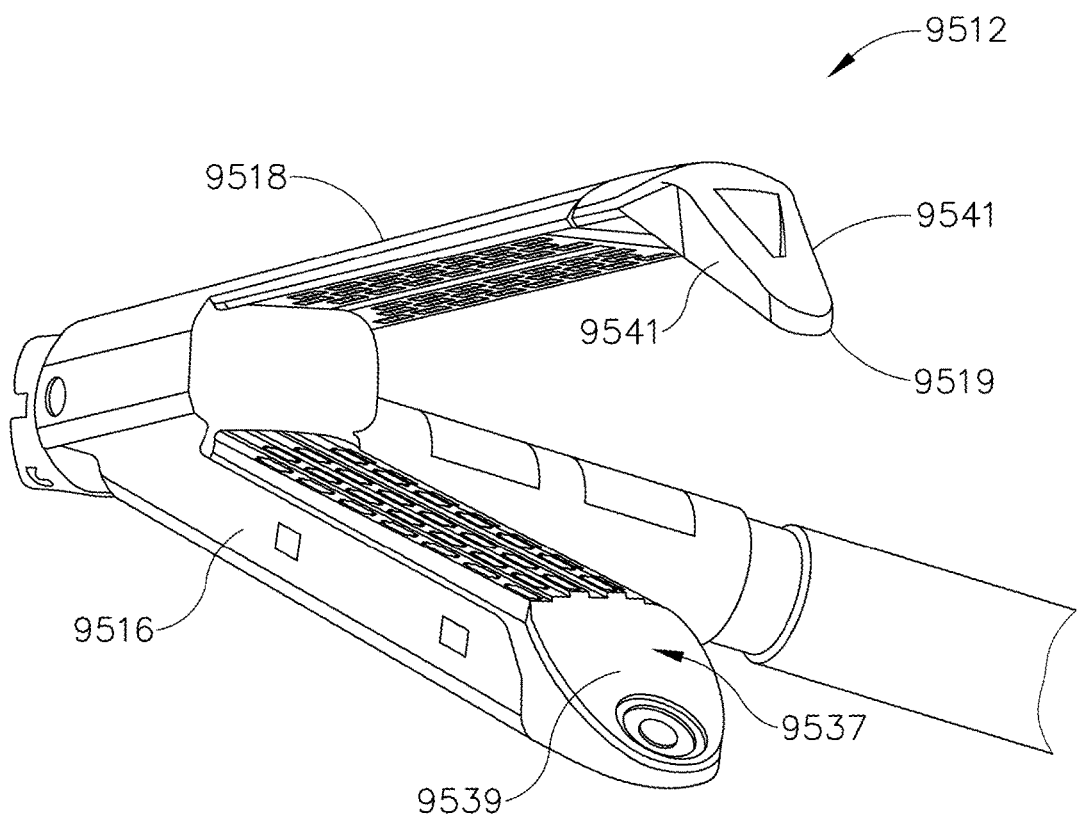
FIG. 79 depicts a perspective view of an alternative version of an end effector with an angled anvil and an angled cartridge.

FIG. 79 illustrates another exemplary end effector (9512) that is configured for use with surgical stapling instruments as described herein. End effector (9512) comprises an anvil (9518) and a lower jaw (9516). It will be appreciated that end effector (9512) may be used in place of end effector (9012) of instrument (9010). End effector (9512) may be integrally formed with instrument (9010) or in the alternative may be interchangeable with end effector (9012) of instrument (9010).

Anvil (9518) is operable to pivot relative to lower jaw (9516). Anvil (9518) and lower jaw (9516) may clamp tissue (9090) similarly to clamping performed by anvil (9018) and lower jaw (9016) shown in FIG. 67. End effector (9512) further comprises a cartridge (9537) operable to be placed in lower jaw (9516) similarly to cartridge (9037) shown in FIG. 69.

Anvil (9518) has an elongated shape where the distal portion of anvil (9518) angles toward cartridge (9537), such that anvil (9518) comprises a curved tip. The distal portion of anvil (9518) angles toward cartridge (9537) such that the distal most tip (9519) of anvil (9518) extends distally longitudinally further than cartridge (9537). Though in some versions, distal tip (9519) may extend to a distance longitudinally equal to cartridge (9537) or proximal relative to the distal most point on cartridge (9537). Furthermore, distal portion of anvil (9518) includes sides (9541) that taper as they approach the distal most tip (9519) of anvil (9518). This shape of anvil (9518) may provide easier insertion of end effector (9512) into a surgical site. For instance, the shape of anvil (9518) may provide an atraumatic tissue deflection surface as anvil (9518) contacts or moves through tissue. Such atraumatic tissue deflection may include urging tissue (e.g., a large vessel) proximally into the space between anvil (9518) and lower jaw (9516) as anvil (9518) closes toward lower jaw (9516). Once placed into a surgical site, the shape of anvil (9518) may also provide better maneuverability of end effector (9512) and better visibility of the distal end of end effector (9512) in relation to anatomical structures at the surgical site. Other suitable variations of anvil (9518) will be apparent to one of ordinary skill in the art in view of the teachings herein.

Cartridge (9537) is operable to hold staples similar to staples (9047) shown in FIG. 70A for driving into tissue. The distal end of cartridge (9537) has a sloped profile. In particular, the distal end of cartridge (9537) comprises an upper tapered surface (9539), which leads to the distal most end of cartridge (9537).

When tissue (9090) is clamped between a closed cartridge (9537) and anvil (9518), the user can look to see where anvil (9518) has clamped tissue (9090). Furthermore, the user can determine whether the tissue is completely clamped between anvil (9518) and cartridge (9537) such that tissue does not spill over the end of end effector (9512). The user may be able to also visualize the quality of the clamp between anvil (9518) and cartridge (9537) against tissue (9090). It will be appreciated that in some instances, end effector (9512) may be rotated before, during, or after clamping tissue (9090). As a result, the shape of anvil (9518) may also provide more accessible viewing of distal tip (9519). The shape of anvil (9518) and cartridge (9537) may further promote easy insertion of end effector (9512) into tissue in an atraumatic manner. Furthermore, it may be easier to fit end effector (9512) through a trocar or other devices operable to introduce end effector (9512) into a surgical site due to the tapered end of end effector (9512). For instance, once distal tip (9519) is fit into a trocar, the shape of anvil (9518) may provide a lead-in, guiding the rest of end effector (9512) into the trocar. In view of the teachings herein, those of ordinary skill in the art will further appreciate that visibility and maneuverability can be enhanced by the tapered design for both sides (9541) of the distal portion of anvil (9518).

Still referring to FIG. 79, by way of example only, and not limitation, in one example of end effector (9512), the curved tip of anvil (9518) may be configured as a dissecting tip for separating tissue. In some such versions, such dissection of tissue may be accomplished using the curved tip of anvil (9518). In such instances, the curved tip of anvil (9518) is a rigid structure without sharp cutting blades or surfaces and dissection occurs by the rigid curved tip separating and/or dissecting tissue that it contacts with sufficient force. In some versions where the curved tip of anvil (9518) is configured as a dissecting tip, the tip of the dissecting tip terminates between the planes defined by the tissue contacting surface and the bottom surface. Also, the tip of the dissecting tip is spaced from a distal end of the cartridge when the end effector is in a closed position. In this manner, the curved tip is configured as a dissecting tip that can separate and/or dissect tissue without requiring engagement or interlocking of the anvil tip with the distal end of the cartridge. Also in this manner, the curved tip is configured as a dissecting tip having a shape such that a user can slide the tip behind certain tissue to separate and/or dissect the tissue it contacts when sufficient force is applied. Of course having the curved tip of anvil (9518) configured as a dissecting tip is not required in all versions of anvil (9518), and accordingly in other versions curved tip of anvil (9518) can be an atraumatic tip or placement tip not configured to sever tissue as described above.

Figure 80:
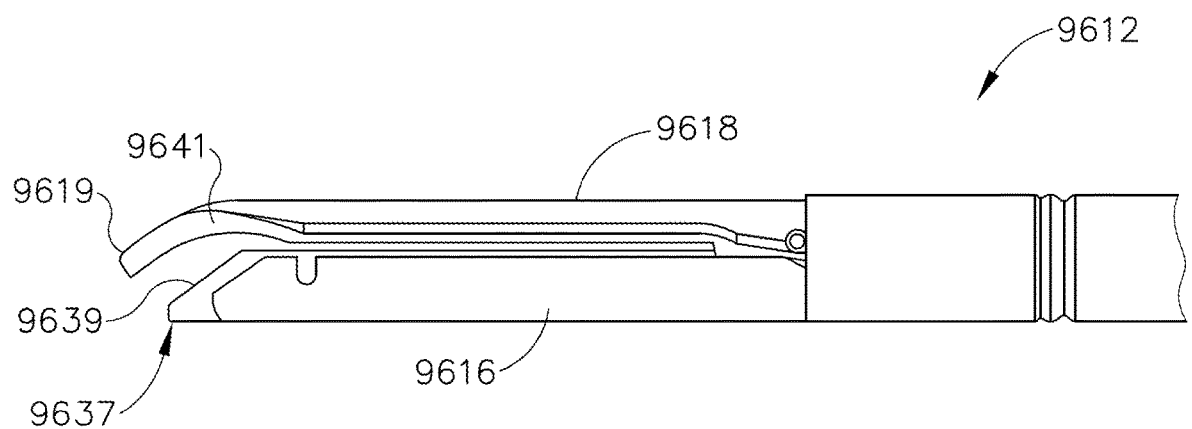
FIG. 80 depicts a perspective view of an alternative version of an end effector with an angled anvil and an angled cartridge.

FIG. 80 illustrates another exemplary end effector (9612) that is configured for use with surgical stapling instruments as described herein. End effector (9612) comprises an anvil (9618) and a lower jaw (9616). It will be appreciated that end effector (9612) may be used in place of end effector (9012) of instrument (9010). End effector (9612) may be integrally formed with instrument (9010) or in the alternative may be interchangeable with end effector (9012) of instrument (9010).

Anvil (9618) is operable to pivot relative to lower jaw (9616). Anvil (9618) and lower jaw (9616) may clamp tissue (9090) similarly to clamping performed by anvil (9018) and lower jaw (9016) shown in FIG. 67. End effector (9612) further comprises a cartridge (9637) operable to be placed in lower jaw (9616) similarly to cartridge (9037) shown in FIG. 69.

Anvil (9618) has an elongated shape where the distal portion of anvil (9618) angles toward cartridge (9637). The distal portion of anvil (9618) angles toward cartridge (9637) such that the distal most tip (9619) of anvil (9618) extends distally longitudinally further than cartridge (9637). Though in some versions, distal tip (9619) may extend to a distance longitudinally equal to cartridge (9637) or proximal relative to the distal most point on cartridge (9637). Furthermore, distal portion of anvil (9618) includes sides (9641) that curve inward as they approach the distal most tip (9619) of anvil (9618). This shape of anvil (9618) may provide easier insertion of end effector (9612) into a surgical site. For instance, the shape of anvil (9618) may provide an atraumatic tissue deflection surface as anvil (9618) contacts or moves through tissue. Such atraumatic tissue deflection may include urging tissue (e.g., a large vessel) proximally into the space between anvil (9618) and lower jaw (9616) as anvil (9618) closes toward lower jaw (9616). Once placed into a surgical site, the shape of anvil (9618) may also provide better maneuverability of end effector (9612) and better visibility of the distal end of end effector (9612) in relation to anatomical structures at the surgical site. Other suitable variations of anvil (9618) will be apparent to one of ordinary skill in the art in view of the teachings herein.

Cartridge (9637) is operable to hold staples similar to staples (9047) shown in FIG. 70A for driving into tissue. The distal end of cartridge (9637) has a sloped profile. In particular, the distal end of cartridge (9637) comprises an upper tapered surface (9639), which leads to the distal most end of cartridge (9637).

When tissue (9090) is clamped between a closed cartridge (9637) and anvil (9618), the user can look to see where anvil (9618) has clamped tissue (9090). Furthermore, the user can determine whether the tissue is completely clamped between anvil (9618) and cartridge (9637) such that tissue does not spill over the end of end effector (9612). The user may be able to also visualize the quality of the clamp between anvil (9618) and cartridge (9637) against tissue (9090). It will be appreciated that in some instances, end effector (9612) may be rotated before, during, or after clamping tissue (9090). As a result, the shape of anvil (9618) may also provide more accessible viewing of distal tip (9619). The shape of anvil (9618) and cartridge (9637) may further promote easy insertion of end effector (9612) into tissue in an atraumatic manner. Furthermore, it may be easier to fit end effector (9612) through a trocar or other devices operable to introduce end effector (9612) into a surgical site due to the tapered end of end effector (9612). For instance, once distal tip (9619) is fit into a trocar, the shape of anvil (9618) may provide a lead-in, guiding the rest of end effector (9612) into the trocar. In view of the teachings herein, those of ordinary skill in the art will further appreciate that visibility and maneuverability can be enhanced by the curved design for both sides (9641) of the distal portion of anvil (9618).

In addition to the foregoing, end effectors (9512, 9612) and versions of instrument (9010) incorporating end effectors (9512, 9612) may be configured and operable in accordance with at least some of the teachings of U.S. Pat. No. 9,186,142, entitled "Surgical Instrument End Effector Articulation Drive with Pinion and Opposing Racks," issued Nov. 17, 2015, the disclosure of which is incorporated by reference herein; U.S. Pat. No. 9,717,497, entitled "Lockout Feature for Movable Cutting Member of Surgical Instrument," issued Aug. 1, 2017, the disclosure of which is incorporated by reference herein; U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pat. No. 9,839,421, entitled "Jaw Closure Feature for End Effector of Surgical Instrument," issued Dec. 12, 2017, the disclosure of which is incorporated by reference herein; U.S. Pat. No. 9,622,746, entitled "Distal Tip Features for End Effector of Surgical Instrument," issued Apr. 18, 2017, the disclosure of which is incorporated by reference herein; U.S. Pat. No. 10,092,292, entitled "Staple Forming Features for Surgical Stapling Instrument," issued Oct. 9, 20018, the disclosure of which is incorporated by reference herein; U.S. Pat. No. 9,795,379, entitled "Surgical Instrument with Multi-Diameter Shaft," issued Oct. 24, 2017, the disclosure of which is incorporated by reference herein; and/or U.S. Pat. No. 9,808,248, entitled "Installation Features for Surgical Instrument End Effector Cartridge," issued Nov. 7, 2017, the disclosure of which is incorporated by reference herein. Further modifications that may be incorporated into end effector (9212) will be described in greater detail below.

XIII. Exemplary Buttress Loading and Application

Figure 81:
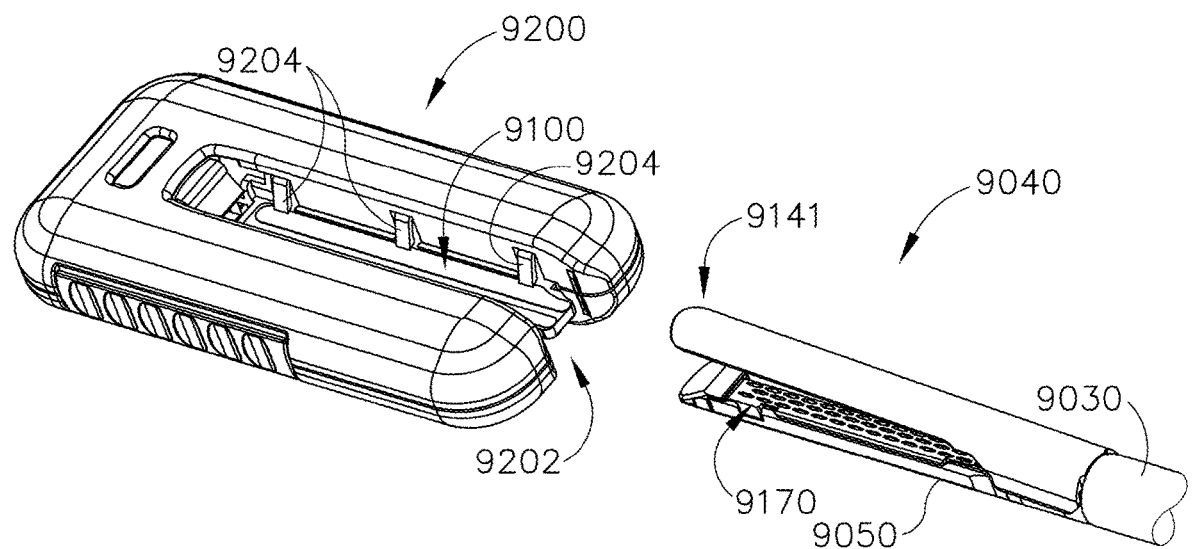
FIG. 81 depicts a perspective view of an exemplary end effector of a surgical stapler and an exemplary buttress assembly applicator, with the end effector approaching the buttress assembly applicator.
Figure 82:
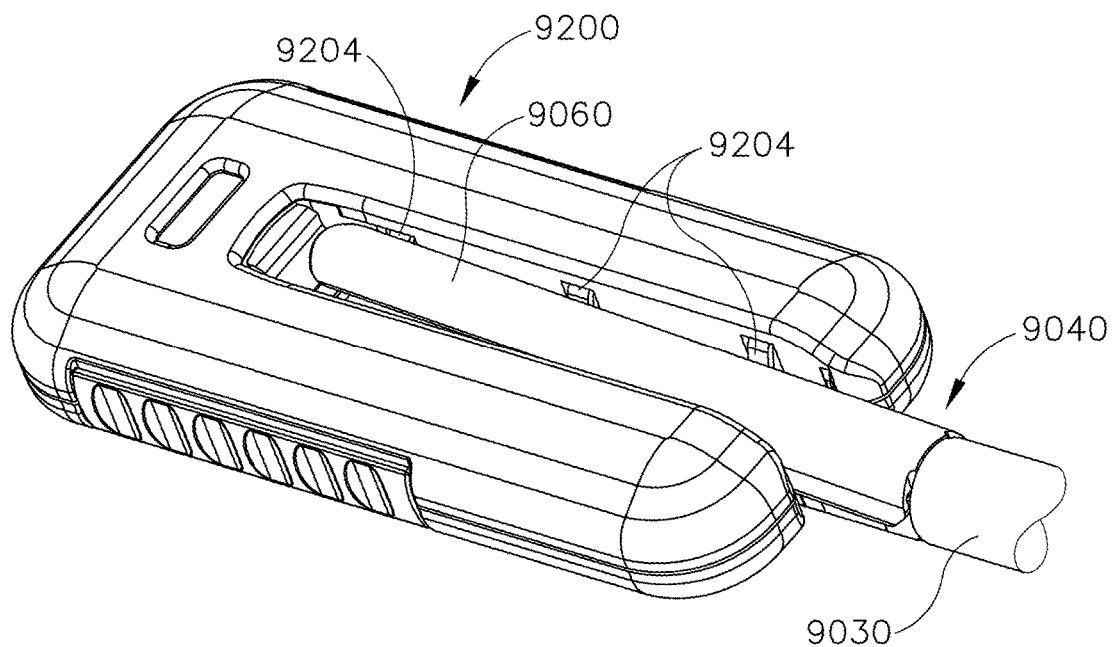
FIG. 82 depicts a perspective view of the end effector and the buttress assembly applicator of FIG. 81, with the buttress assembly applicator positioned in the end effector.

FIGS. 81 and 82 illustrate an exemplary end effector (9040) configured to apply a buttress to a tissue site where a cutting and stapling operation is performed. End effector (9040) includes distal end (9141) and is connected with a shaft assembly (9030). End effector (9040) comprises an anvil (9060), a lower jaw (9050), and a staple cartridge (9170) received by lower jaw (9050). It will be appreciated that end effector (9040) may be used in place of end effector (9012) of instrument (9010). End effector (9040) may be integrally formed with instrument (9010) or in the alternative may be interchangeable with end effector (9012) of instrument (9010).

FIGS. 81 and 82 also illustrate an exemplary buttress applicator (9200). Buttress applicator (9200) is configured to selectively retain buttress assemblies (9100, 9110). In the present example, buttress assembly (9100) is selectively retained on a top side of applicator (9200) and buttress assembly (9110) is selectively retained on a bottom side of applicator (9200). In some other versions, applicator (9200) can be configured such that only one buttress assembly (9100, 9110) is selectively retained by buttress applicator (9200).

Figure 68:
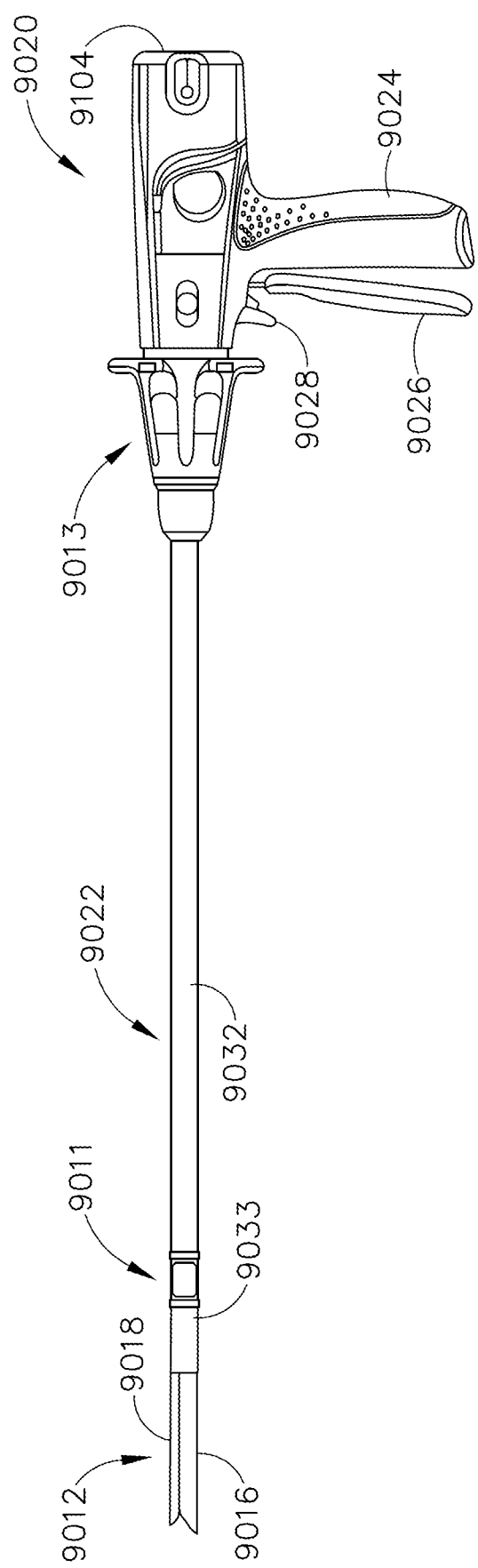
FIG. 68 depicts a side view of the instrument of FIG. 67.
Figure 83:
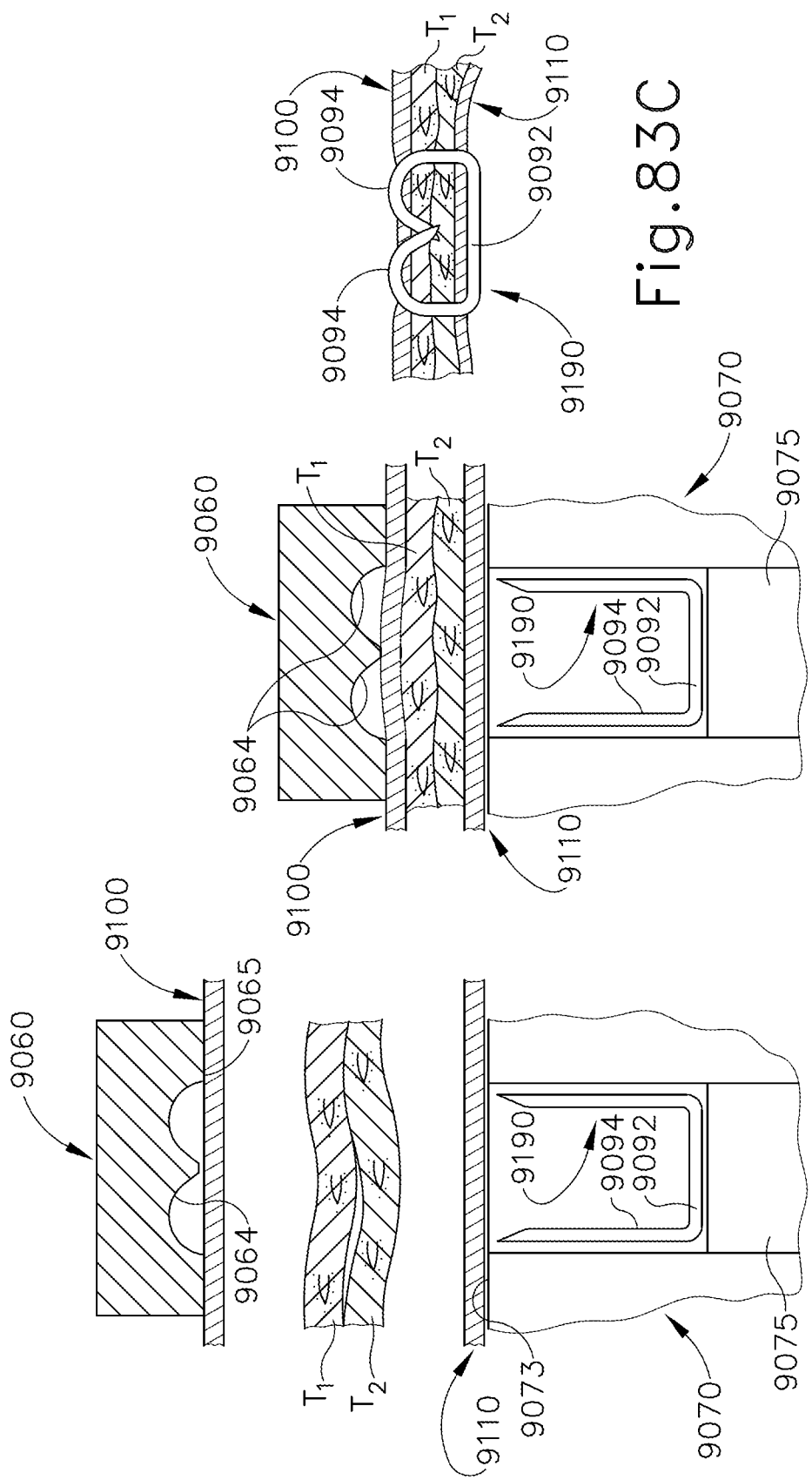
FIG. 83A depicts a cross-sectional end view of a portion of the end effector of FIG. 81 with the buttress assembly of FIG. 81 applied to the end effector, with tissue positioned between the buttresses in the end effector, and with the anvil in an open position.
FIG. 83B depicts a cross-sectional end view of the combined end effector and buttress assembly of FIG. 83A, with tissue positioned between the buttresses in the end effector, and with the anvil in a closed position.
FIG. 83C depicts a cross-sectional view of a staple and the buttress assembly of FIG. 83A having been secured to the tissue by the end effector of FIG. 81.

To use buttress applicator (9200) to load end effector (9040) with buttress assemblies (9100, 9110), the operator would first position applicator (9200) and end effector (9040) such that end effector (9040) is aligned with an open end (9202) of applicator (9200) as shown in FIG. 67. The operator would then advance end effector (9040) distally (and/or retract applicator (9200) proximally) to position buttress assemblies (9100, 9110) between anvil (9060) and staple cartridge (9170) as shown in FIG. 68. In order to load buttress assemblies (9100, 9110) on end effector (9040), the operator may simply close end effector (9040) by pivoting anvil (9060) toward staple cartridge (9170). Closure of end effector (9040) results in the distal ends of anvil (9060) and staple cartridge (9170) bearing against retaining features (9204) of buttress applicator (9200) that are configured to selectively retain buttress assemblies (9100, 9110) with buttress applicator (9200). This contact deflects such retaining features (9204) of buttress applicator (9200) to thereby permit contact between a surface of anvil (9060) and buttress assembly (9100) on one side of buttress applicator (9200), and a surface of staple cartridge (9170) and buttress assembly (9110) on another side of buttress applicator (9200). Buttress assemblies (9100, 9110) comprise an adhesive on their respective surfaces such that with end effector (9040) clamping on both buttress assemblies (9100, 9110), buttress assemblies (9100, 9110) are adhered respectively to an underside of anvil (9060) and a deck surface of staple cartridge (9170). End effector (9040) may then be re-opened (i.e., pivoting anvil (9060) away from staple cartridge (9170) and pulled away from buttress applicator (9200). With retaining features (9204) of applicator (9200) disengaged from buttress assemblies (9100, 9110), end effector (9040) may freely pull buttress assemblies (9100, 9110) away from buttress applicator (9200) as end effector (9040) is pulled away from buttress applicator (9200). With buttress assemblies (9100, 9110) loaded on end effector (9040), end effector (9040) may then be used as described further below with reference to FIGS. 83A-84.

FIGS. 83A-83C show a sequence where an end effector (9040) that has been loaded with buttress assemblies (9100, 9110) is actuated to drive staples (9190) through two apposed layers of tissue ($T_1$, $T_2$), with buttress assemblies (9100, 9110) being secured to the same layers of tissue ($T_1$, $T_2$) by staples (9190). In particular, FIG. 83A shows layers of tissue ($T_1$, $T_2$) positioned between anvil (9060) and staple cartridge (9170), with anvil (9060) in the open position. As shown, anvil (9060) comprises staple forming pockets (9064). Buttress assembly (9100) is adhered, via adhesive, to underside (9065) of anvil (9060); while buttress assembly (9110) is adhered, via adhesive, to deck (9073) of staple cartridge (9170). Layers of tissue ($T_1$, $T_2$) are thus interposed between buttress assemblies (9100, 9110). Next, end effector (9040) is closed, which drives anvil (9060) to the closed position as shown in FIG. 83B. At this stage, layers of tissue ($T_1$, $T_2$) are compressed between anvil (9060) and staple cartridge (9170), with buttress assemblies (9100, 9110) engaging opposite surfaces of tissue layers ($T_1$, $T_2$). End effector (9040) is then actuated, whereby a staple driver (9075) drives staple (9190) through buttress assemblies (9100, 9110) and tissue layers ($T_1$, $T_2$). As shown in FIG. 83C, crown (9092) of driven staple (9190) captures and retains buttress assembly (9110) against layer of tissue ($T_2$). Deformed legs (9094) of staple (9190) capture and retain buttress assembly (9100) against layer of tissue ($T_1$).

Figure 84:
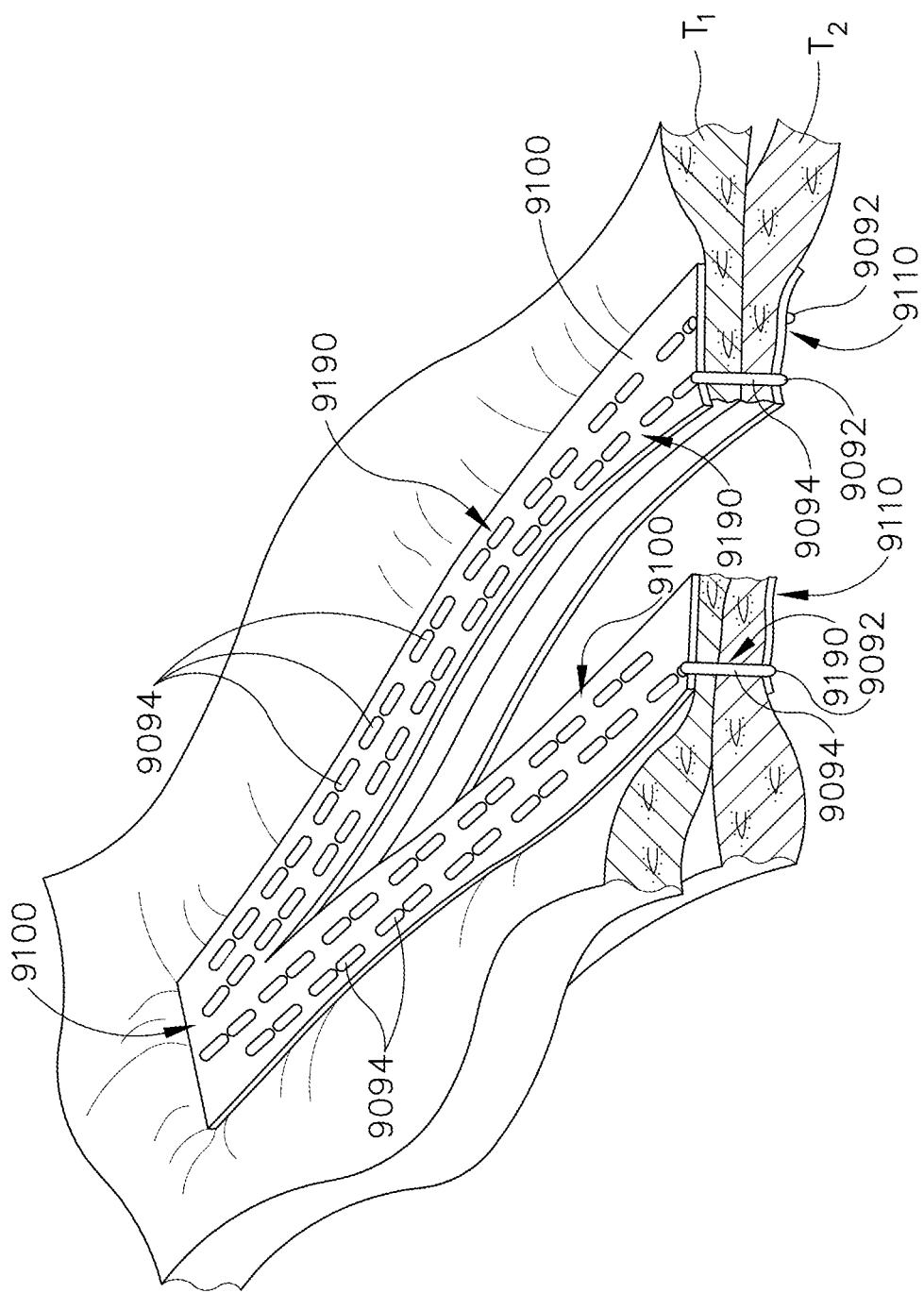
FIG. 84 depicts a perspective view of staples and the buttress assembly of FIG. 83A having been secured to the tissue by the end effector of FIG. 81.

It should be understood that a series of staples (9190) will similarly capture and retain buttress assemblies (9100, 9110) against layers of tissue ($T_1$, $T_2$), thereby securing buttress assemblies (9100, 9110) to tissue ($T_1$, $T_2$) as shown in FIG. 84. As end effector (9040) is pulled away from tissue (9090) after deploying staples (9190) and buttress assemblies (9100, 9110), buttress assemblies (9100, 9110) disengage end effector, such that buttress assemblies (9100, 9110) remain secured to tissue ($T_1$, $T_2$) with staples (9190). Buttress assemblies (9100, 9110) thus provide structural reinforcement to the lines of staples (9190). As can also be seen in FIG. 84, a knife member (not shown) passes through end effector (9040) and in doing so also cuts through a centerline of buttress assemblies (9100, 9110), separating each buttress assembly (9100, 9110) into a corresponding pair of sections, such that each section remains secured to a respective severed region of tissue ($T_1$, $T_2$).

In the foregoing example, buttress assembly (9100) is sized to span across the full width of underside (9065) of anvil (9060), such that a knife member (not shown) cuts through buttress assembly (9100) during actuation of end effector (9040). In some other examples, buttress assembly (9100) is provided in two separate, laterally spaced apart portions, with one portion being disposed on underside (9065) of anvil (9060) on one half of anvil (9060) and another portion being disposed on underside (9065) of anvil (9060) on the other half of anvil (9060). In such versions, the knife member (not shown) does not cut through buttress assembly (9100) during actuation of end effector (9040).

Likewise, buttress assembly (9110) may be sized to span across the full width of deck (9073), such that the knife member (not shown) cuts through buttress assembly (9110) during actuation of end effector (9040). Alternatively, buttress assembly (9110) may be provided in two separate, laterally spaced apart portions, with one portion being disposed on deck (9073) on one half and another portion being disposed on deck (9073) on the other half. In such versions, the knife member (not shown) does not cut through buttress assembly (9110) during actuation of end effector (9040).

In addition to the foregoing, it should also be understood that any of the various buttress assemblies described herein may be further constructed and operable in accordance with at least some of the teachings of U.S. Pat. Pub. No. 2016/0278774, entitled "Method of Applying a Buttress to a Surgical Stapler," published Sep. 29, 2016, issued as U.S. Pat. No. 10,349,939 on Jul. 16, 2019, the disclosure of which is incorporated by reference herein.

XIV. Exemplary Buttress Applier Cartridge Assembly

In some instances, it may be desirable to use an exemplary buttress applier cartridge assembly (9710) as shown in FIG. 85 to equip a surgical instrument with a buttress assembly (9712) for forming staples in tissue with a buttress (9714). In some instances, buttress applier cartridge assembly (9710) may be referred to as a buttress assembly applicator (9710). These terms as used herein should be understood to be interchangeable. Buttress (9714) inhibits the formed staples from pulling through the tissue to thereby reduce a risk of tissue tearing at or near the site of formed staples. In addition to or as an alternative to providing structural support and integrity to a line of staples, buttress (9714) may provide various other kinds of effects such as spacing or gap-filling, administration of therapeutic agents, and/or other effects. Prior to use with the surgical instrument, one or more buttress assemblies (9712) is releasably retained on a buttress applier cartridge (9716), which is configured to deposit one or more buttress assemblies (9712) onto an end effector of a surgical instrument as discussed below.

FIG. 85 shows buttress applier cartridge assembly (9710) including a pair of buttress assemblies (9712) releasably retained on buttress applier cartridge (9716), which supports and protects buttress assemblies (9712) prior to use and further aids with loading buttress assemblies (9712) on surgical instrument (9010) (see FIG. 67). Buttress applier cartridge (9716) of the present example includes an open end (9718) and a closed end (9720). Open end (9718) is configured to receive an end effector such as any of those end effectors described herein, including but not limited to end effectors (9012, 9212, 9312, 9412, 9512, 9612). Buttress applier cartridge (9716) further includes a housing assembly (9724) having an upper housing (9726) and a lower housing (9728), which each generally define a "U" shape to present open end (9718). Various components are interposed between upper and lower housings (9726, 9728). In particular, these components include a chassis (9736) supporting a platform (9730), which is also referred to as a compression layer (9730).

Platform or compression layer (9730) of the present example supports upper buttress assembly (9712) on one side of platform (9730) and lower buttress assembly (9712) on the other side of platform (9730). Platform (9730) is exposed in recesses that are formed between the prongs of the "U" configuration of upper and lower housings (9726,

9728). Thus, upper housing (9726) has an upper gap (9737) extending to the open end (9718) along an upper surface of platform (9730), and lower housing (9728) similarly has a lower gap (9738) extending to the open end (9718) along the lower surface of platform (9730). The location of platform (9730) and buttress assemblies (9712) in such recesses may prevent inadvertent contact between buttress assemblies (9712) and other devices in the operating room. In other words, upper and lower housings (9726, 9728) may provide some degree of physical shielding of buttress assemblies (9712) while buttress assemblies are retained on platform (9730).

Additional features may be combined as applicable with the following example of buttress applier cartridge assembly (9710). Such features are described in U.S. patent application Ser. No. 16/235,473, entitled "Adhesive Distribution on Buttress for Surgical Stapler," filed on Dec. 28, 2018, published as U.S. Pub. No. 2020/0205820 on Jul. 2, 2020, issued as U.S. Pat. No. 11,166,724 on Nov. 9, 2021; U.S. patent application Ser. No. 16/235,488, entitled "Configuration of Buttress for Surgical Stapler," filed on Dec. 28, 2018, published as U.S. Pub. No. 2020/0205821 on Jul. 2, 2020, issued as U.S. Pat. No. 11,166,725 on Nov. 9, 2021; U.S. patent application Ser. No. 16/235,503, entitled "Surgical Stapler Buttress with Tissue In-Growth Promotion," filed on Dec. 28, 2018, published as U.S. Pub. No. 2020/0205822 on Jul. 2, 2020, issued as U.S. Pat. No. 11,432,817 on Sep. 6, 2022; U.S. patent application Ser. No. 16/235,541, entitled "Packaging for Surgical Stapler Buttress," filed on Dec. 28, 2018, published as U.S. Pub. No. 2020/0205824 on Jul. 2, 2020, issued as U.S. Pat. No. 11,432,817 on Sep. 6, 2022; U.S. patent application Ser. No. 16/235,681, entitled "Curved Tip Surgical Stapler Buttress Assembly Applicator with Compression Layer Pocket Feature," filed on Dec. 28, 2018, published as U.S. Pub. No. 2020/0205807 on Jul. 2, 2020, issued as U.S. Pat. No. 11,103,246 on Aug. 31, 2021; U.S. patent application Ser. No. 16/235,670, entitled "Curved Tip Surgical Stapler Buttress Assembly Applicator with Proximal Alignment Feature," filed on Dec. 28, 2018, issued as U.S. Pat. No. 10,905,424 on Feb. 2, 2020; U.S. patent application Ser. No. 29/675,168, entitled "Applicator for Surgical Stapler Buttress," filed on Dec. 28, 2018, issued as U.S. Pat. No. D901,686 on Nov. 10, 2020; U.S. patent application Ser. No. 29/675,170, entitled "Buttress for Surgical Stapler," filed on Dec. 28, 2018, issued as U.S. Pat. No. D933,220 on Oct. 12, 2021; U.S. patent application Ser. No. 29/675,172, entitled "Tray for Surgical Stapler Buttress Applicator," filed on Dec. 28, 2018, issued as U.S. Pat. No. D922,576 on Jun. 15, 2021; U.S. patent application Ser. No. 29/675,197, entitled "Applicator for a Surgical Stapler Buttress," filed on Dec. 28, 2018, issued as U.S. Pat. No. D903,115 on Nov. 25, 2020; and U.S. patent application Ser. No. 29/675,199, entitled "Buttress Assembly for a Surgical Stapler," filed on Dec. 28, 2018, issued as U.S. Pat. No. D932,621 on Oct. 5, 2021, the disclosures of which are hereby incorporated by reference.

A. Exemplary Buttress Assembly

With respect to FIG. 85, upper and lower buttress assemblies (9712) are structurally identical, but for the relative positions of upper and lower buttress assemblies (9712) retained on buttress applier cartridge (9716). Buttress applier cartridge assembly (9710) may thus be used in more than one orientation with surgical instrument (9010) and its respective end effectors that may be combined therewith. It will be appreciated that the following description of upper buttress assembly (9712) similarly applies to lower buttress assembly (9712) but for the respective orientations.

Upper buttress assembly (9712) includes buttress (9714) and an upper adhesive layer (9742). Buttress (9714) of the present example more particularly has a three-layer, polymer construction including a core layer sandwiched between two outer layers to be collectively strong yet flexible to support a line of staples. In the present example, core layer is a polyglactin 910 material, which is manufactured and sold by Ethicon, Inc. of Somerville, New Jersey as VICRYL, whereas each outer layer is a polydioxanone (PDO) film material. Buttress (9714) of the present example is formed by laminating core layer between outer layers under a predetermined pressure, a predetermined temperature, and a predetermine time. Buttress (9714) is further mechanically cut to size thereby inhibiting abrasive edges, such as burrs and/or delamination, that could damage sensitive tissues. It will be appreciated that alternative methods of cutting buttresses (9714), such as a laser cutting or hot knife cutting, may be similarly used.

By way of further example only, each buttress (9714) may comprise one or more of the following: NEOVEIL absorbable PGA felt by Gunze Limited, of Kyoto, Japan; SEAMGUARD polyglycolic acid: trimethylene carbonate (PGA: TMC) reinforcement material by W.L. Gore & Associates, Inc., of Flagstaff, Arizona; PERI-STRIPS DRY with VERITAS Collagen Matrix (PSDV) reinforcement material, by Baxter Healthcare Corporation of Deerfield, Illinois; BIODESIGN biologic graft material by Cook Medical, Bloomington, Indiana; and/or SURGICEL NU-KNIT hemostat material by Ethicon, Inc. of Somerville, New Jersey. Still other suitable materials that may be used to form each buttress (9714) will be apparent to those of ordinary skill in the art in view of the teachings herein.

In addition or in the alternative, each buttress (9714) may comprise a material including, for example, a hemostatic agent such as fibrin to assist in coagulating blood and reduce bleeding at the severed and/or stapled surgical site along tissue. As another merely illustrative example, each buttress (9714) may comprise other adjuncts or hemostatic agents such as thrombin may be used such that each buttress (9714) may assist to coagulate blood and reduce the amount of bleeding at the surgical site. Other adjuncts or reagents that may be incorporated into each buttress (9714) may further include but are not limited to medical fluid or matrix components. Merely illustrative examples of materials that may be used to form each buttress (9714), as well as materials that may be otherwise incorporated into each buttress (9714), are disclosed in U.S. Pub. No. 2016/0278774, entitled "Method of Applying a Buttress to a Surgical Stapler," published Sep. 29, 2016, issued as U.S. Pat. No. 10,349,939 on Jul. 16, 2019, the disclosure of which is incorporated by reference herein. Alternatively, any other suitable materials may be used.

By way of further example only, each buttress (9714) may be constructed in accordance with at least some of the teachings of U.S. Pat. No. 10,123,798, entitled "Tissue Thickness Compensator Comprising Controlled Release and Expansion," issued Nov. 13, 2018, the disclosure of which is incorporated by reference herein; U.S. Pat. Pub. No. 2013/0068816, entitled "Surgical Instrument and Buttress Material," published Mar. 21, 2013, now abandoned, the disclosure of which is incorporated by reference herein; U.S. Pat. No. 9,999,408, entitled "Surgical Instrument with Fluid Fillable Buttress," issued Jun. 19, 2018, the disclosure of which is incorporated by reference herein; U.S. Pat. No. 8,814,025, entitled "Fibrin Pad Matrix with Suspended Heat Activated Beads of Adhesive," issued Aug. 26, 2014, the disclosure of which is incorporated by reference herein; U.S.

Pat. No. 8,899,464, entitled "Attachment of Surgical Staple Buttress to Cartridge," issued Dec. 2, 2014, the disclosure of which is incorporated by reference herein; U.S. Pat. No. 9,492,170, entitled "Device for Applying Adjunct in Endoscopic Procedure," issued Nov. 15, 2016, the disclosure of which is incorporated by reference herein; U.S. Pat. No. 8,998,060, entitled "Resistive Heated Surgical Staple Cartridge with Phase Change Sealant," issued Apr. 7, 2015, the disclosure of which is incorporated by reference herein; U.S. Pat. No. 9,393,018, entitled "Surgical Staple Assembly with Hemostatic Feature," issued Jul. 19, 2016, the disclosure of which is incorporated by reference herein; U.S. Pat. No. 9,101,359, entitled "Surgical Staple Cartridge with Self-Dispensing Staple Buttress," issued Aug. 11, 2015, the disclosure of which is incorporated by reference herein; U.S. Pat. No. 9,198,644, entitled "Anvil Cartridge for Surgical Fastening Device," issued Dec. 1, 2015, the disclosure of which is incorporated by reference herein; U.S. Pat. Pub. No. 2013/0075447, entitled "Adjunct Therapy for Applying Hemostatic Agent," published Mar. 28, 2013, now abandoned, the disclosure of which is incorporated by reference herein; U.S. Pat. No. 9,211,120, entitled "Tissue Thickness Compensator Comprising a Plurality of Medicaments," issued Dec. 15, 2015, the disclosure of which is incorporated by reference herein; U.S. Pat. Pub. No. 2015/0351758, entitled "Adjunct Materials and Methods of Using Same in Surgical Methods for Tissue Sealing," published Dec. 10, 2015, issued as U.S. Pat. No. 10,172,611 on Jan. 8, 2019, the disclosure of which is incorporated by reference herein; U.S. Pat. Pub. No. 2017/0049444, entitled "Implantable Layers for a Surgical Instrument," published Feb. 23, 2017, issued as U.S. Pat. No. 10,835,249 on Nov. 17, 2020, the disclosure of which is incorporated by reference herein; U.S. Pat. Pub. No. 2017/0055986, entitled "Drug Eluting Adjuncts and Methods of Using Drug Eluting Adjuncts," published Mar. 2, 2017, issued as U.S. Pat. No. 10,569,071 on Feb. 25, 2020, the disclosure of which is incorporated by reference herein; U.S. Pat. Pub. No. 2017/0086837, entitled "Compressible Adjunct with Crossing Spacer Fibers," published Mar. 30, 2017, issued as U.S. Pat. No. 10,433,846 on Oct. 8, 2019, the disclosure of which is incorporated by reference herein; and/or U.S. Pat. Pub. No. 2017/0086842, entitled "Method for Applying an Implantable Layer to a Fastener Cartridge," published Mar. 30, 2017, issued as U.S. Pat. No. 11,690,623 on Jul. 4, 2023, the disclosure of which is incorporated by reference herein.

Furthermore, buttress (9714) is configured to be cut by a knife (not shown) from a proximal portion of buttress (9714), along an intermediate portion of buttress (9714), and further through a distal portion of buttress (9714) such that inward edges are adjacent to cut tissue. Buttress (9714) further includes a longitudinally extending pre-cut slit (9744) configured to receive knife (not shown) and aid in separating lateral portions of buttress (9714) as inward edges form therealong.

Upper adhesive layer (9742) is provided on outer layer of buttress (9714) in order to adhere buttress (9714) within end effectors described herein. Adherence of the buttress (9714) can occur through a variety of mechanisms including but not limited to a pressure sensitive adhesive. In the case of pressure sensitive adhesion, adhesion occurs upon the application of at least a predetermined minimum force. In some versions, each adhesive layer (9742) includes a pressure sensitive adhesive material. Examples of various suitable materials that may be used to form adhesive layers (9742) are disclosed in U.S. Pat. Pub. No. 2016/0278774, entitled "Method of Applying a Buttress to a Surgical Stapler," published Sep. 29, 2016, issued as U.S. Pat. No. 10,349,939 on Jul. 16, 2019, the disclosure of which is incorporated by reference herein. Alternatively, any other suitable materials may be used. As shown in the present example, adhesive layer (9742) is applied to form a continuous outer seal to enhance longevity once applied to an end effector.

It should be understood that the term "adhesive," as used herein, may include (but is not limited to) tacky materials and also materials that are pliable or wax-like and adhere to a complex geometry via deformation and conformance. Some suitable adhesives may provide such pliability to adhere to a complex geometry via deformation and conformance without necessarily providing a high initial tack. In some instances, adhesives with lower tackiness may be removed more cleanly from surfaces. Various suitable materials that may be used to form adhesive layers (9742) will be apparent to those of ordinary skill in the art in view of the teachings herein.

B. Exemplary Buttress Applier Cartridge

Figure 86:
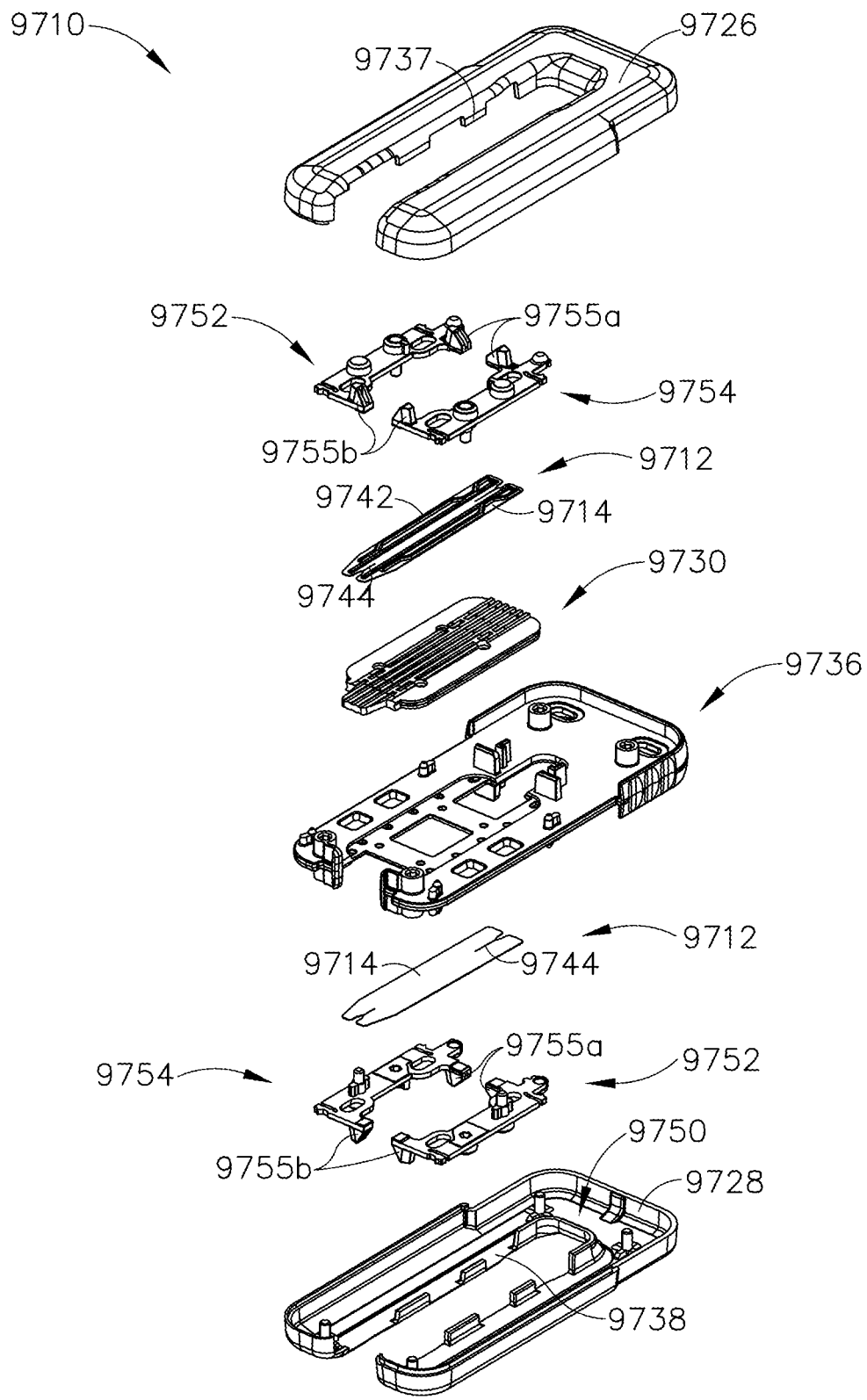
FIG. 86 depicts an exploded perspective view of the buttress assembly applicator of FIG. 85 including a chassis and a platform in addition to a pair of buttress assemblies.

As shown in FIG. 86, buttress applier cartridge (9716) includes chassis (9736) supporting platform (9730) as well as upper and lower housings (9726, 9728) of housing assembly (9724) configured to connect together to define an interior space (9750). An upper left actuator sled (9752) and an upper right actuator sled (9754) are movably connected to an upper face chassis (9736) within interior space (9750), while a lower left actuator sled (9752) and a lower right actuator sled (9754) are movably connected to a lower face of chassis (9736) within interior space (9750). Upper right and left actuator sleds (9752, 9754) retain upper buttress assembly (9712) on platform (9730) in a restraint position, but are configured to move from the restraint position to a release position for depositing the upper buttress assembly (9712) on an end effector, such as any of the end effectors described herein. Similarly, lower right and left actuator sleds (9752, 9754) retain lower buttress assembly (9712) on platform (9730) in the restraint position, but are configured to move from the restraint position to the release position for depositing the lower buttress assembly (9712) on an end effector, such as any of the end effectors described herein. In the present example, left actuator sled (9752) is distinct from right actuator sled (9754) for reasons discussed below in greater detail. Also, upper and lower right actuator sleds (9752) are structurally identical to each other, and upper and lower left actuator sleds (9754) are structurally identical to each other. Thus, upper and lower actuator sleds (9752, 9754) are interchangeable in this respect and any discussion contained herein directed to a pair of upper actuator sleds (9752, 9754) is similarly applicable to a pair of lower actuator sleds (9752, 9754).

Each actuator sled (9752, 9754) includes a pair of arms (9755a, 9755b) extending laterally inward to selectively and releasably secure buttress assemblies (9712) to platform (9730). Arms (9755a, 9755b) may also be referred to as retaining features or retention members, similar to the retaining features (9204) described above with respect to applicator (9200) in FIGS. 81 and 82. In particular, FIG. 86 show arms (9755a, 9755b) positioned such that buttress assemblies (9712) are interposed between the free ends of arms (9755a, 9755b) and platform (9730). Arms (9755a, 9755b) are movable laterally outwardly such that arms (9755a, 9755b) disengage buttress assemblies (9712), thereby enabling buttress assemblies (9712) to be removed from platform (9730). In the present example, arms (9755a, 9755b) are configured to bear against buttress assemblies (9712) in the restraint position, thereby pinching buttress assemblies (9712) against platform (9730). Other suitable ways in which arms (9755a, 9755b) may engage buttress assemblies (9712) will be apparent to those of ordinary skill in the art in view of the teachings herein.

Chassis (9736) is configured to cooperate with upper and lower housings (9726, 9728) to provide a mechanical ground for moving components of buttress applier cartridge (9716) and provide structural support for components of buttress applier cartridge (9716). Chassis (9736) further includes integral gripping features (9756) that are exposed on opposite sides of housing assembly (9724). Gripping features (9756) have a surface geometry configured to promote an operator's grip of buttress applier cartridge (9716) during use of buttress applier cartridge (9716). Various suitable configurations that may be used for gripping features (9756) will be apparent to those of ordinary skill in the art in view of the teachings herein. Similarly, various surface treatments (e.g., elastomeric material, etc.) that may be applied to gripping features (9756) will be apparent to those of ordinary skill in the art in view of the teachings herein.

Figure 87:
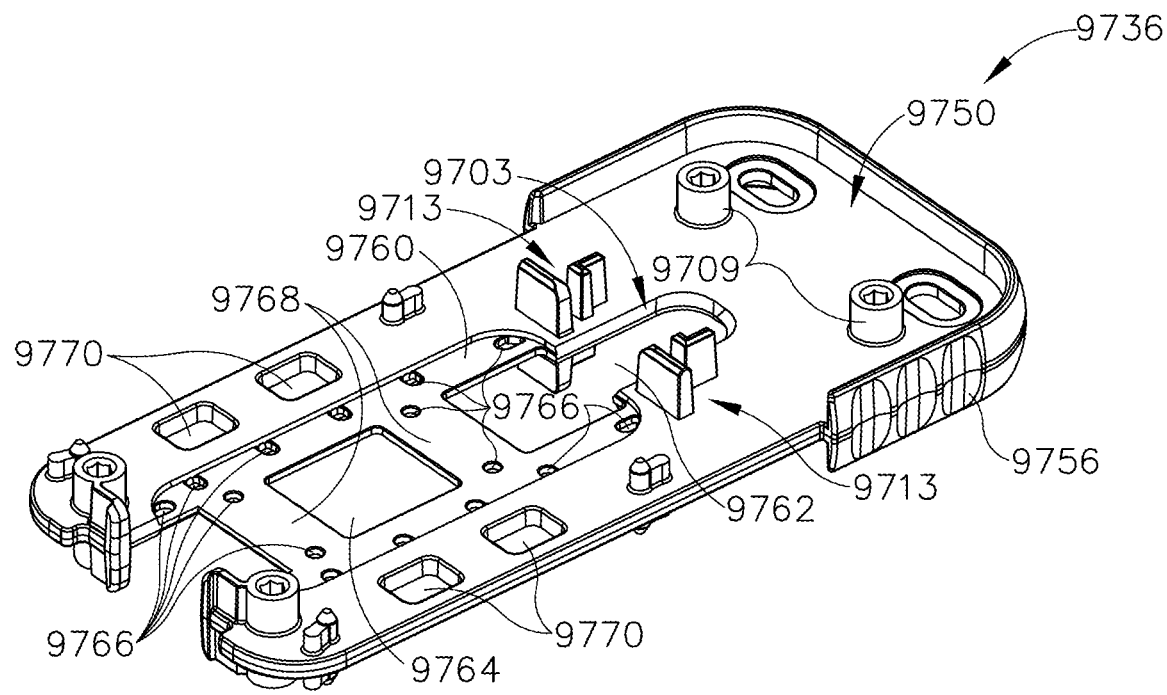
FIG. 87 depicts a front perspective view of the chassis of FIG. 86.

With respect to FIG. 87, platform (9730) is connected to and supported by chassis (9736) to secure platform (9730) relative to upper and lower housing (9726, 9728). In the present example, platform (9730) is unitarily formed and molded to a rigid web portion (9758) including a frame (9760) and defining a plurality of holes (9762, 9764, 9766) configured provide material overlap for mold securement. Holes (9762, 9764, 9766) more particularly include an upper slot (9762) and central slot (9764) that extend through frame (9760) as well as a plurality of through holes (9766) spaced laterally about slot (9762, 9764). Frame (9760) also extends laterally across central slot (9764) at bridge portions (9768) to provide additional structural rigidity to chassis (9736) while providing platform (9730) with sufficient clearance for resilient deformation as discussed below in greater detail. Thereby, slots (9762, 9764) and through holes (9766) receive a resilient, elastomeric material to form and secure the material as platform (9730) to chassis (9736). While the present platform (9730) is molded to chassis (9736), it will be appreciated that platform (9730) may be alternatively secured to chassis (9736), and thus the attachment of platform (9730) to chassis (9736) is not intended to be limited to the particular rigid web portion (9758) and molding as discussed herein. Various suitable materials and structural configurations that may be used to form platform (9730) will be apparent to those of ordinary skill in the art in view of the teachings herein.

Chassis (9736) further includes a plurality of sled clearance holes (9770) arranged in a pair of rows on opposing lateral sides of chassis (9736). Left and right actuator sleds (9752, 9754) connect together on opposing sides of chassis (9736) through such sled clearance holes (9770) to slide inwardly together in connected pairs. Additional details regarding connection and actuation of left and right actuator sleds (9752, 9754) will be discussed below in greater detail. However, it will be appreciated that any such hole through chassis (9736) to provide for fastening clearanceF of left and right actuator sleds (9752, 9754) may be used, and the invention is not intended to be unnecessarily limited to sled clearance holes (9070) as discussed herein.

i. Exemplary Varying Stiffness Platform for Supporting Buttress Assemblies

Figure 88:
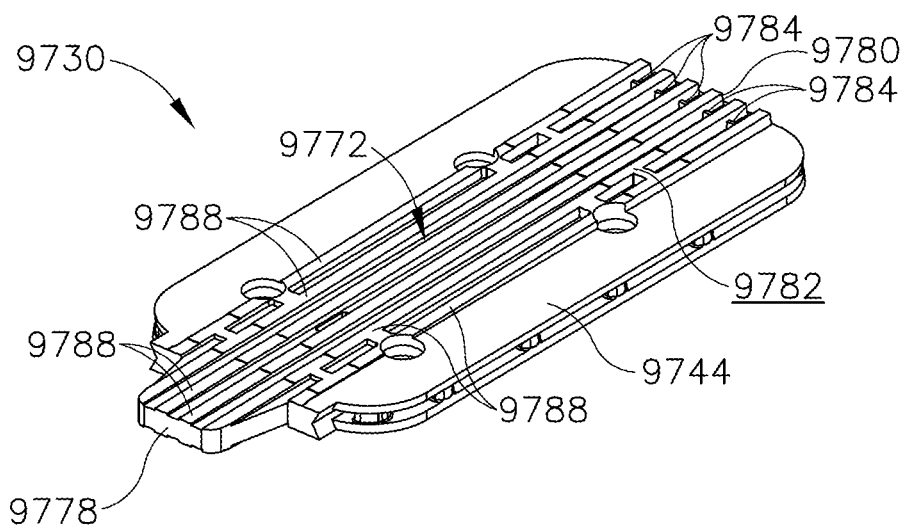
FIG. 88 depicts a front perspective view of the platform of FIG. 86.
Figure 89:
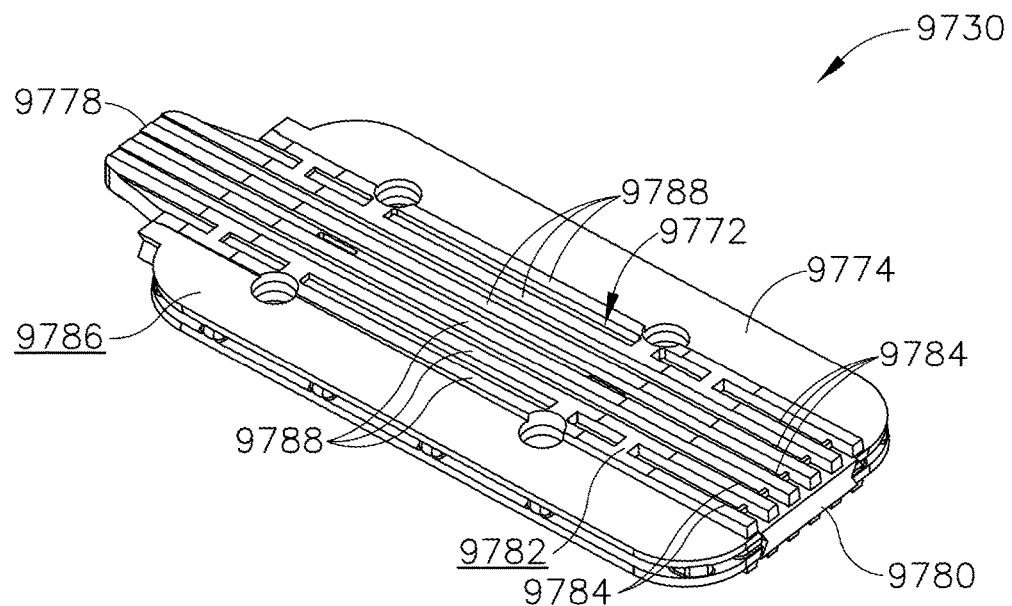
FIG. 89 depicts a rear perspective view of the platform of FIG. 86.
Figure 90:
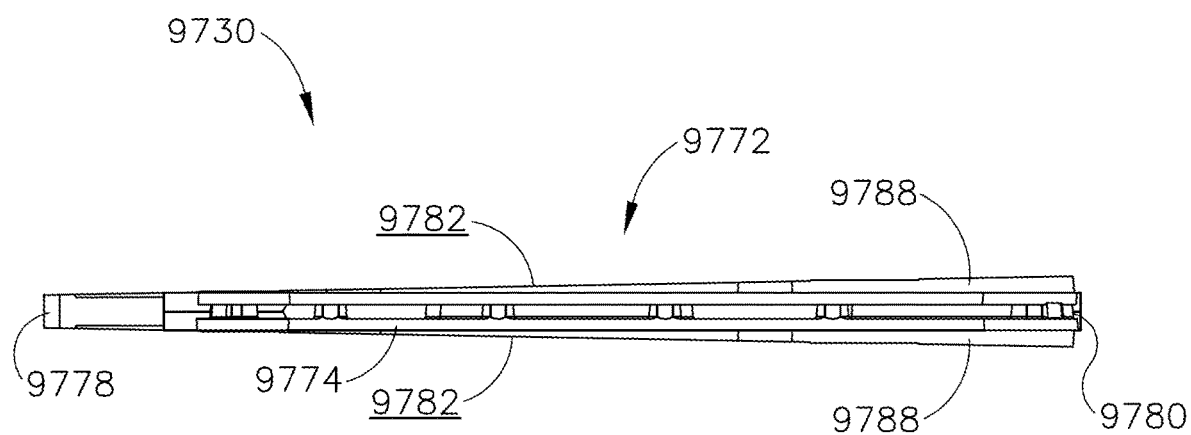
FIG. 90 depicts an elevational side view of the platform of FIG. 86.

FIGS. 88-90 show one example of platform (9730) in additional detail as including a pad (9772) and perimeter region (9774) laterally extending therefrom. Perimeter region (9774) is positioned in within frame (9760) and extends into through holes (9766) to secure pad (9772) to chassis (9736). In some versions, platform (9730) is formed of a material that provides a high coefficient of friction, thereby reducing any tendency that buttress assemblies (9712) might otherwise have to slide along corresponding surfaces of platform (9730). For instance, platform (9730) may comprise a resilient, elastomeric material, such as silicone, to be molded to be formed as securement (9774) and pad (9772). One example silicone material is a 30 Durometer, Shore A silicone. To this end, pad (9772) is formed with varying stiffness along its longitudinal length to simultaneously provide sufficient reactionary forces of at least the predetermined minimum force for adhesion while accommodating a parallel-camber orientation, an over-camber orientation, and an under-camber orientation of an end effector as discussed below in greater detail. As used herein, the term "parallel-camber orientation" refers to an upper jaw and a lower jaw of an end effector being functionally parallel to each other. The term "over-camber orientation" refers to an upper jaw of an end effector being over rotated relative to a lower jaw of an end effector. The term "under-camber orientation" refers to an upper jaw being under rotated relative to a lower jaw of an end effector.

With respect to FIGS. 88 and 89, a resilient proximal end (9778) of pad (9772) has a proximal end stiffness and a proximal transverse depth, whereas a resilient distal end (9780) of pad (9772) has a distal end stiffness and a distal transverse depth. In the present example, proximal end stiffness is generally greater than the distal end stiffness such that initial compression of distal end (9780) requires less compressive force than compression of proximal end (9778). Of course, further compression of distal end (9780) relative to proximal end (9778) may result in distal end stiffness increasing to or even exceeding proximal end stiffness so long as the lesser stiffness of distal end (9780) is included therein for accommodating the over-cambered orientation of an end effector.

In addition, distal transverse depth is greater than proximal transverse depth. Thereby, the greater distal transverse depth effectively props up buttress assembly (9712) for improved engagement with an end effector in the under-camber orientation, but the decreased distal end stiffness allows for greater compression to accommodate an end effector in the over-camber orientation. Pad (9772) of the present example is wedge-shaped having opposing ramp surfaces (9782) continuously tapering together from the distal end (9780) to the proximal end (9778) for accommodating parallel-camber, over-camber, and under-camber orientations along the entire longitudinal length of pad (9772). In some examples, depths and stiffnesses along pad (9772) are configured to receive a full range of over-camber to under-camber orientations based on determined manufacturing tolerances of an end effector.

Pad (9772) shown in FIGS. 88-90 is unitarily formed of a resilient material having a consistent stiffness throughout. Such longitudinally varying stiffness discussed above is thus generated by forming a plurality of reliefs, such as channels (9784), in at least the distal end (9780) to reduce the distal end stiffness relative to the proximal end stiffness. In the present example, channels (9784), such as five channels (9784) are equally spaced laterally apart from each other and longitudinally extend from distal end (9780) to proximal end (9778). Channels (9784) further define varying channel depths in the longitudinal direction along pad (9772). More particularly, upper channels (9784) extend transversely downward from upper ramp surface (9782) to upper base surface (9786), whereas lower channels (9784) extend transversely upward from lower ramp surface (9782) to lower base surface (9786). In turn, a plurality of ribs (9788) are defined between channels (9784) and similarly extend from ramp surfaces (9782) to base surfaces (9786) to support buttress assemblies (9712) and have varying stiffness from the proximal end (9778) to the distal end (9780) on each opposing side of pad (9772).

ii. Exemplary Restraint Features for Retention of Buttress Assemblies on Varying Stiffness Platform FIGS. 86 and 91-94 show restraint features, such as left and right actuator sleds (9752, 9754) discussed briefly above for releasably securing buttress assemblies (9712) to platform (9730) in the restraint position. Each of left and right actuator sleds (9752, 9754) has arms (9755a, 9755b) configured to accommodate varying transverse depths along the longitudinal length of pad (9772). More particularly, arms (9755a, 9755b) include a distal arm (9755a) and a proximal arm (9755b) spaced longitudinally apart from each other and extending laterally inward toward platform (9730). Each distal arm (9755a) and proximal arm (9755b) of left or right actuator sled (9752, 9754) transversely extends toward platform (9730) such that each of distal arm (9755a) and proximal arm (9755b) is offset from the other arms (9755a, 9755b) in the transverse direction. Thereby, distal arm (9755a) and proximal arm (9755b) are transversely spaced from the ramp surface (9782) to trace the contour of the ramp surface (9782).

Figure 91:
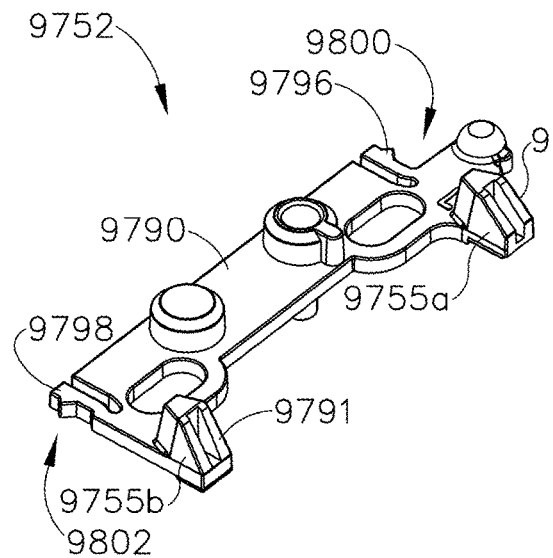
FIG. 91 depicts a top perspective view of a left actuator sled of the buttress assembly applicator of FIG. 86.
Figure 92:
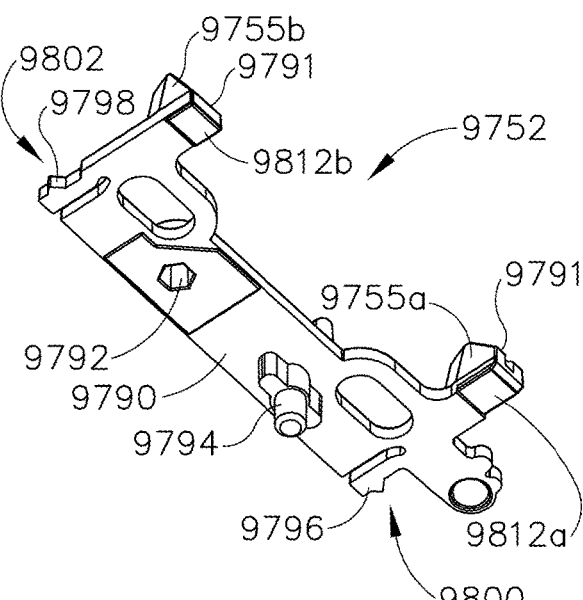
FIG. 92 depicts a bottom perspective view of the left actuator sled of FIG. 91.

With respect to FIGS. 91 and 92, upper left actuator sled (9752) has a longitudinally extending upper left sled body (9790) with distal and proximal arms (9755a, 9755b) laterally extending inward toward the right. Each arm (9755a, 9755b) of left actuator sled (9752) has a cam surface (9791) configured to receive an end effector thereagainst to urge left actuator sled (9752) toward the release position. In addition, a dowel hole (9792) opens downward and is respectively positioned on a portion of upper left sled body (9790). A dowel (9794) extends downward from left sled body (9790) and in longitudinal alignment with outer dowel hole (9792). In order to arrest movement of upper left actuator sled (9752) in the restraint and release positions, a distal cantilever catch (9796) laterally extends to the left from the distal portion of upper left sled body (9790), and a proximal cantilever catch (9798) laterally extends to the left from the proximal portion of upper left sled body (9790). Distal and proximal cantilever catches (9796, 9798) are respectively portions of distal and proximal detent couplings (9800, 9802) discussed below in greater detail.

Figure 93:
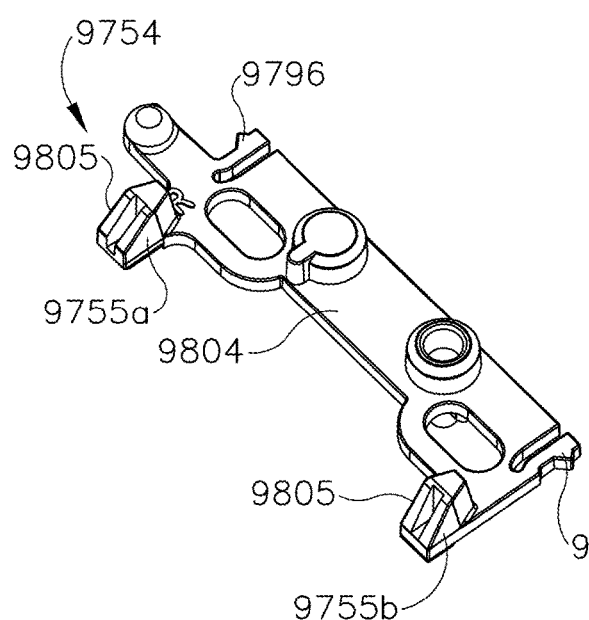
FIG. 93 depicts a top perspective view of a right actuator sled of the buttress assembly applicator of FIG. 86.
Figure 94:
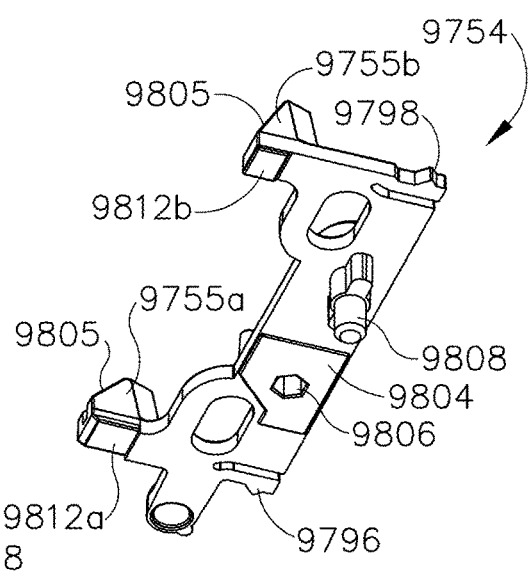
FIG. 94 depicts a bottom perspective view of the right actuator sled of FIG. 93.

With respect to FIGS. 93 and 94, upper right actuator sled (9754) has a longitudinally extending upper right sled body (9804) with distal and proximal arms (9755a, 9755b) laterally extending inward toward the left. Each arm (9755a, 9755b) of right actuator sled (9754) has a cam surface (9805) configured to receive an end effector thereagainst to urge left actuator sled (9752) toward the release position. In addition, a dowel hole (9806) opens downward and is positioned on upper right sled body (9804). A dowel (9808) extends downward from right sled body (9804) and is positioned in longitudinal alignment with inner dowel hole (9806). In order to arrest movement of upper right actuator sled (9754) in the restraint and release positions, another distal cantilever catch (9796) laterally extends to the right from the distal portion of upper right sled body (9804), and another proximal cantilever catch (9796) laterally extends to the right from the proximal portion of upper right sled body (9804). Again, distal and proximal cantilever catches (9796, 9798) are respectively portions of distal and proximal detent couplings (9800, 9802) discussed below in greater detail.

Figure 95:
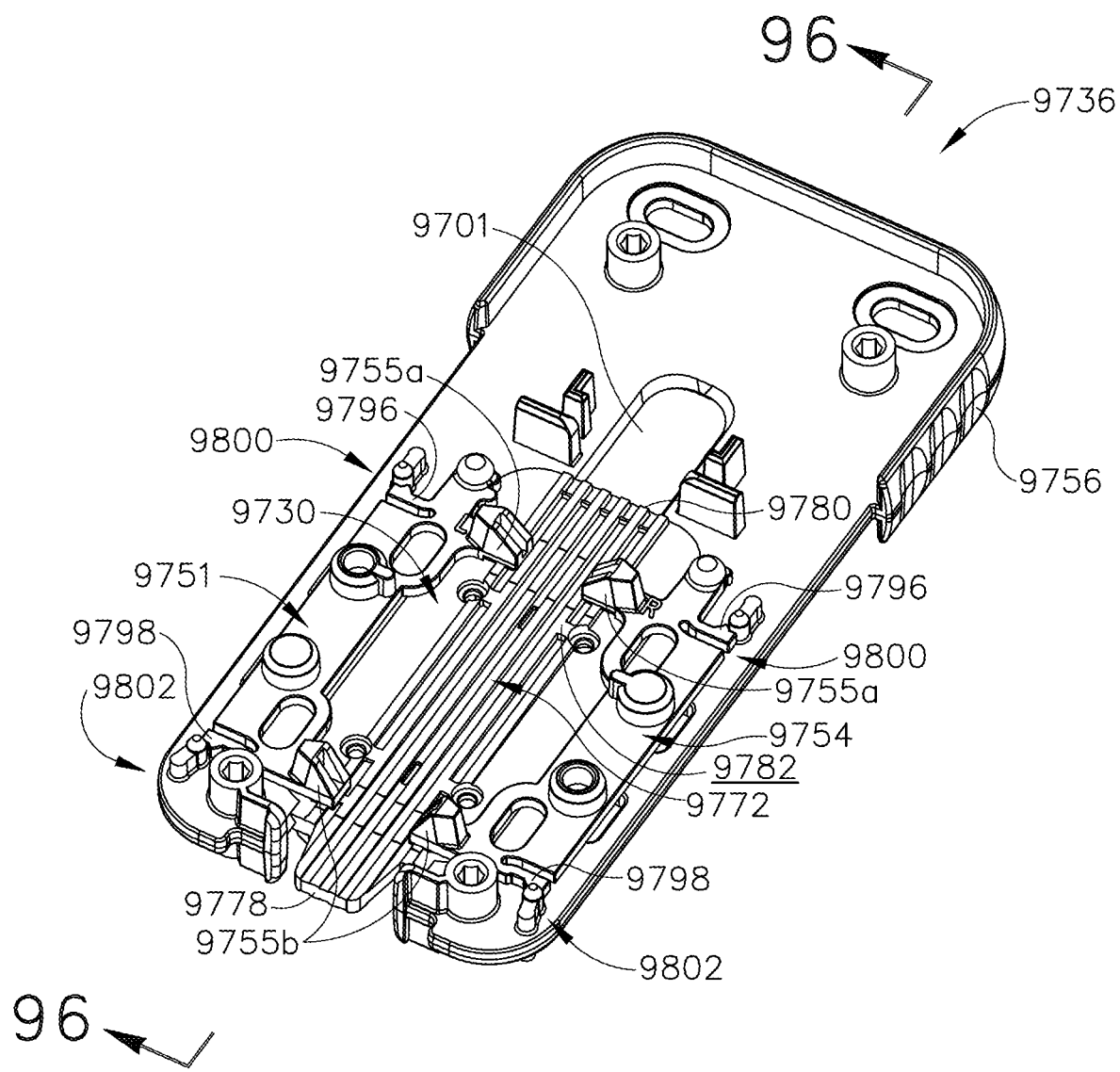
Figure 96:
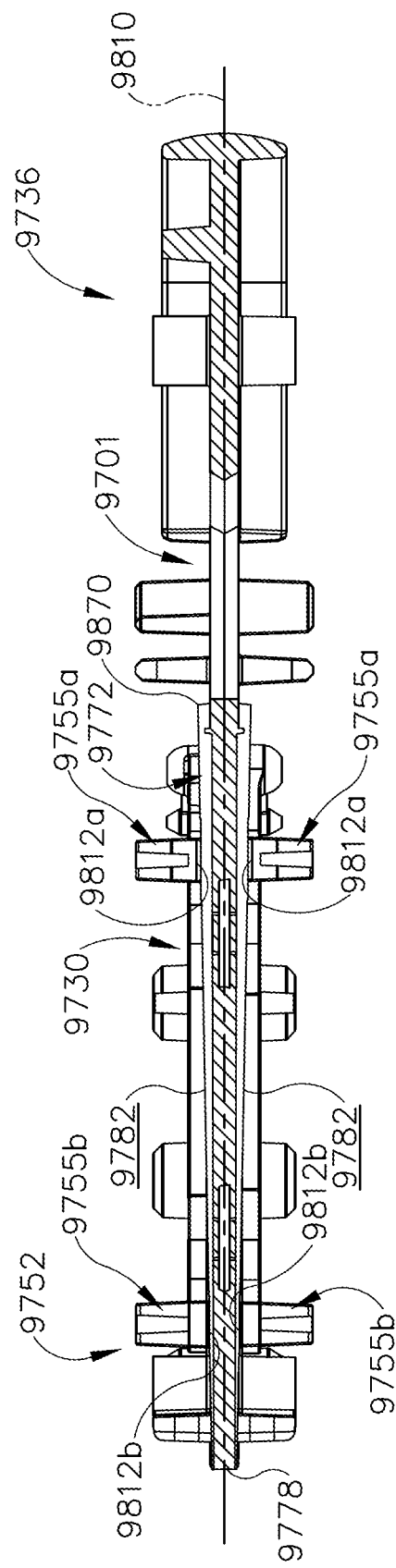

FIG. 86 and FIGS. 95 and 96 show upper right and left actuator sleds (9752, 9754) as discussed above in detail as well as lower right and left actuator sleds (9752, 9754). As briefly discussed above, the description of upper right and left actuator sleds (9752, 9754) similarly applies to lower right and left actuator sleds (9752, 9754) with like features having like numbers, but with reversed transverse directions (e.g. lower, upward, etc.). To this end, upper left actuator sled (9752) and lower right actuator sled (9754) connect together as outer dowel (9808) snaps into outer dowel hole (9792) and inner dowel (9794) snaps into inner dowel hole (9806) with chassis (9736) positioned therebetween. Upper right actuator sled (9754) and lower left actuator sled (9752) similarly connect together as outer dowel (9808) snaps into outer dowel hole (9792) and inner dowel (9794) snaps into inner dowel hole (9806) with chassis (9736) positioned therebetween. Each of inner and outer dowels (9794, 9808) extend through sled clearance holes (9770) to slidably connect left and right actuator sleds (9752, 9754) to chassis (9736).

FIG. 96 shows one example of a pair of distal arms (9755a) and a pair of proximal arms (9755b) respectively having platform (9730) positioned therebetween and tracing opposing ramp surfaces (9782). A central plane (9810) is shown in FIG. 78 bisecting upper and lower portions of buttress applier cartridge (9716) through a central core of platform (9730). Distal arm (9755a) has a distal retention surface (9812a) transversely offset from central plane (9810) a relatively greater distance, and proximal arm (9755b) has a proximal retention surface (9812b) transversely offset from central plane (9810) a relatively lesser distance. Thereby, greater and lesser distances of distal and proximal retention surfaces (9812a, 9812b) trace ramp surfaces (9782) tapering from distal end (9780) of pad (9772) to proximal end (9778) of pad (9772). Thus, distal and proximal retention surfaces (9812a, 9812b) are offset in the transverse direction from each other and from central plane (9810). In the present example, each of distal arm (9755a) and proximal arm (9755b) are transversely spaced from the ramp surface (9782) an equal transverse dimension such that arms (9755a, 9755b) equally trace ramp surfaces (9782) tapering from distal end (9780) of pad (9772) to proximal end (9778) of pad (9772).

Figure 97:
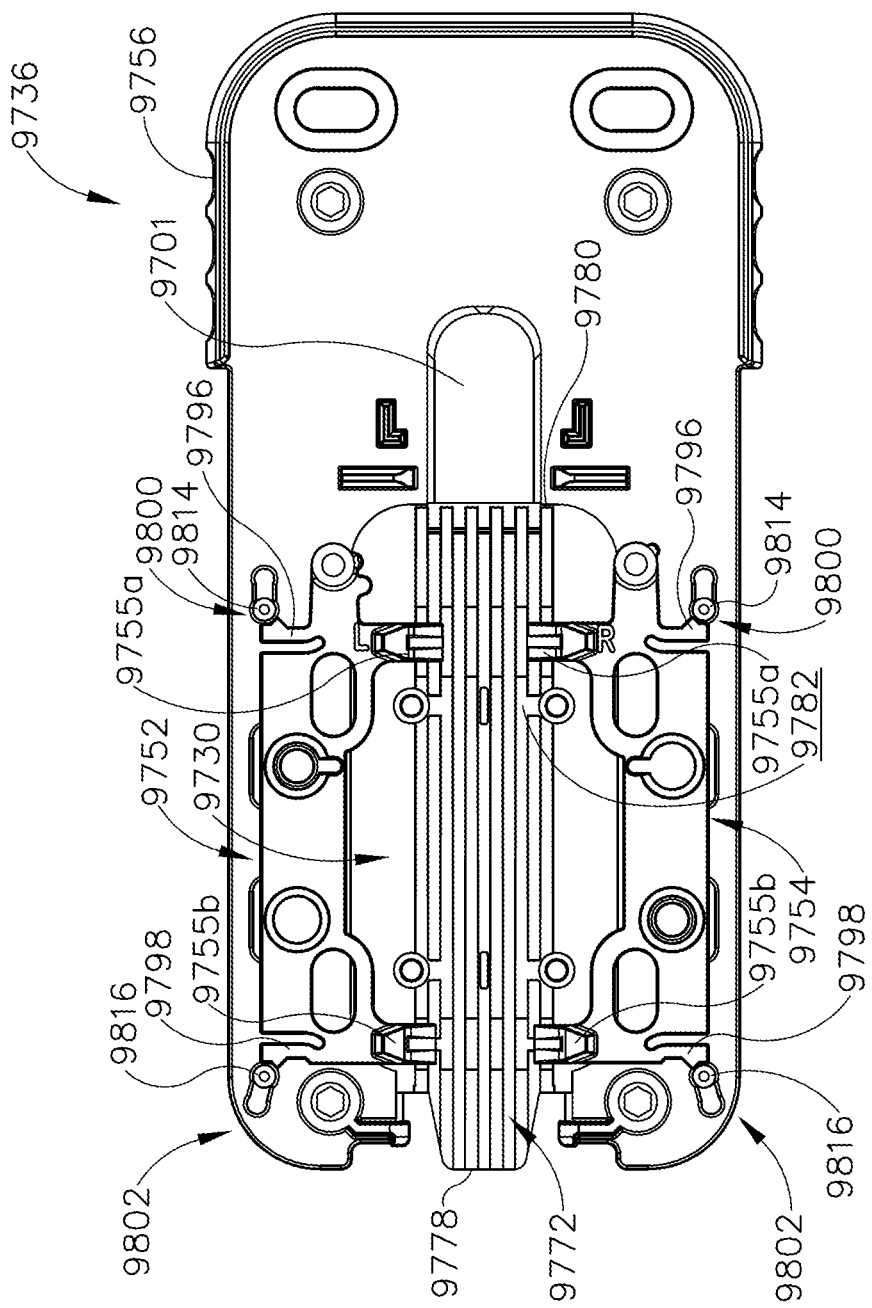
Figure 98:
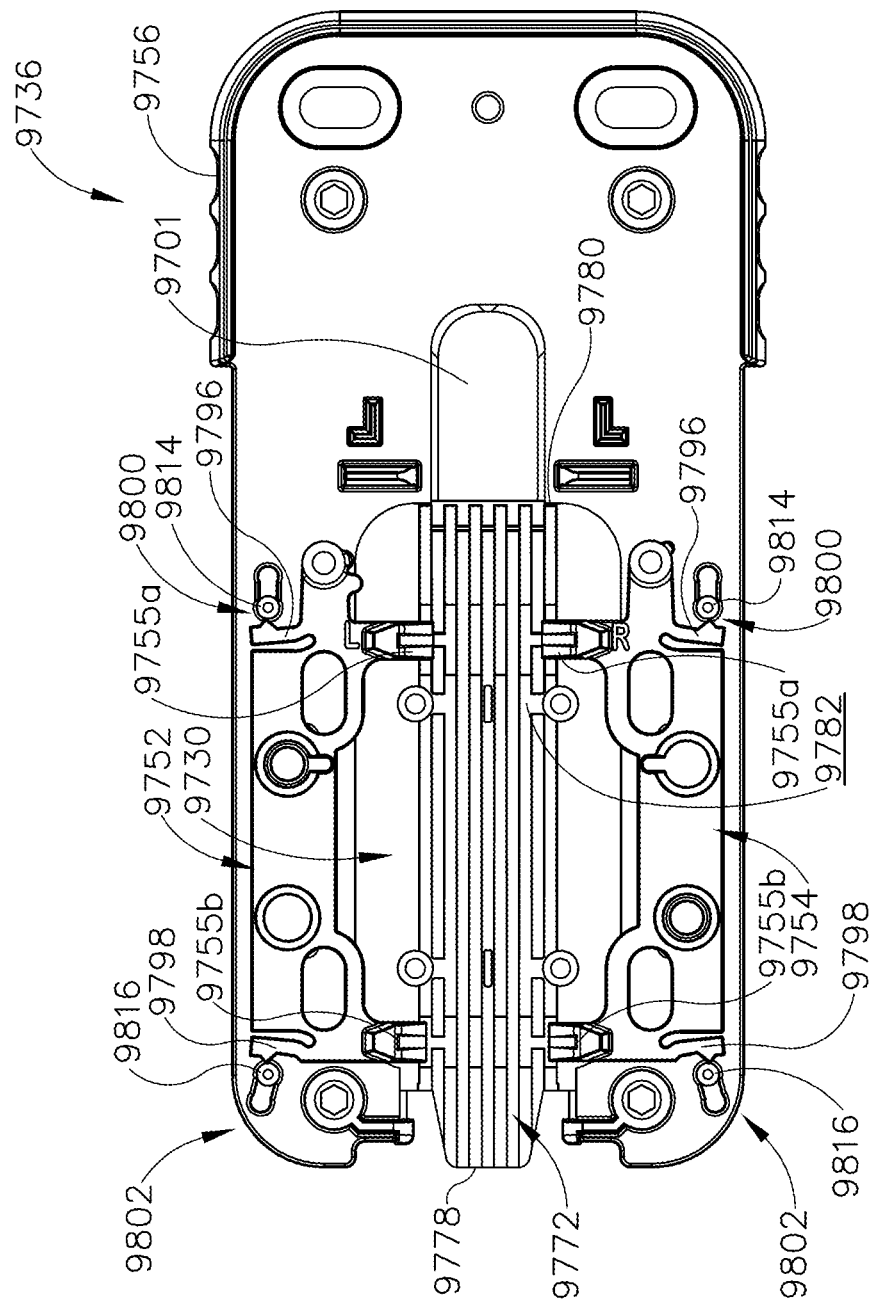
Figure 99:
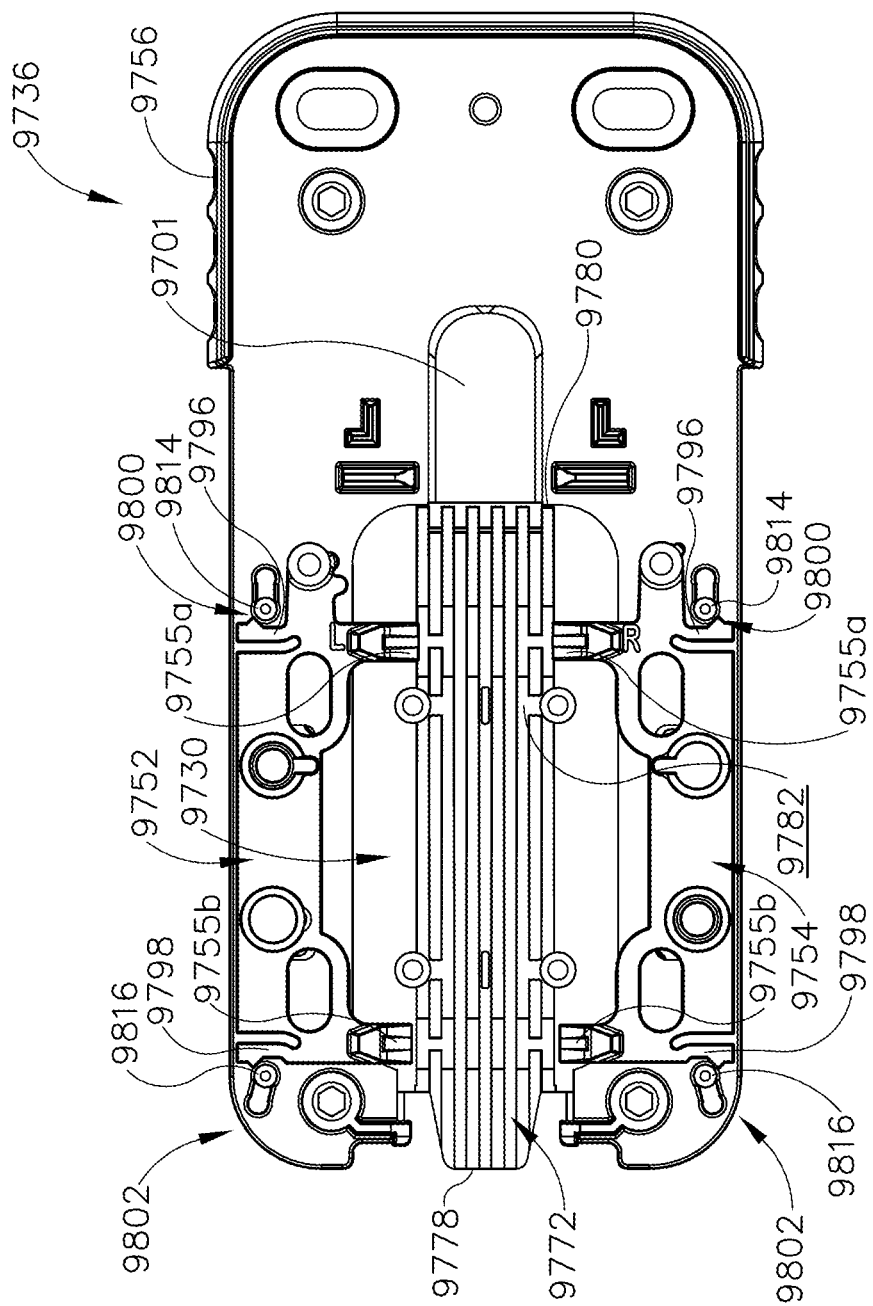

As shown in FIGS. 97-99, left and right actuator sleds (9752, 9754) are respectively urged outward from the restraint position to the release position away from platform to disengage arms (9755a, 9755b) from buttress assemblies (9712) on platform (9730) as discussed herein. More particularly, distal and proximal detent couplings (9800, 9802) releasably connect left and right actuator sleds (9752, 9754) to chassis (9736) to arrest movement of left and right actuator sleds (9752, 9754) in the restraint position and the release position. Distal and proximal detent couplings (9800, 9802) include distal and proximal cantilever catches (9796, 9798) extending from each of left and right actuator sleds (9752, 9754) as discussed briefly above. In addition, distal and proximal detent couplings (9800, 9802) respectively further include distal and proximal ground cams (9814, 9816) extending from chassis (9736) in respective engagement with distal and proximal cantilever catches (9796, 9798).

In the restraint position shown in FIG. 97, each distal cantilever catch (9796) is respectively engaged with each distal ground cam (9814), and each proximal cantilever catch (9798) is respectively engaged with each proximal ground cam (9816) to urge left and right actuator sleds (9752, 9754) inward toward the restraint position. Directing left and right actuator sleds (9752, 9754) outward from the restraint position toward the release position as shown in FIG. 98 resiliently deflects distal and proximal cantilever catches (9796, 9798) as distal and proximal cantilever catches (9796, 9798) follow distal and proximal ground cams (9814, 9816). As distal and proximal cantilever catches (9796, 9798) pass around distal and proximal ground cams (9814, 9816), distal and proximal cantilever catches (9796, 9798) reach a tipping point where distal and proximal cantilever catches (9796, 9798) urge left and right actuator sleds (9752, 9754) to the release position shown in FIG. 99. In the release position, each distal cantilever catch (9796) is respectively engaged with each distal ground cam (9814), and each proximal cantilever catch (9798) is respectively engaged with each proximal ground cam (9816) to urge left and right actuator sleds (9752, 9754) outward toward the release position. Thereby, distal and proximal detent couplings (9800, 9802) effectively hold left and right actuator sleds (9752, 9754) in the release position to inhibit arms (9755a, 9755b) from inadvertently returning inward and catching buttress assembly (9712) upon removal of an end effector as discussed herein.

iii. Exemplary Adhesion of Buttress to Surgical Stapler and Cutting of Buttress Assembly with Tissue As noted above, upper and lower buttress assemblies (9712) include upper and lower adhesive layers (9742) (or other form of adhesive material) to adhere respective buttresses (9714) to an underside of an anvil and deck of a staple cartridge of an end effector. Such adhesive may provide proper positioning of buttress (9714) before and during actuation of an end effector; then allow buttress (9714) to separate from the end effector after the end effector has been actuated, without causing damage to buttress (9714) that is substantial enough to compromise the proper subsequent functioning of buttress (9714). Buttress assemblies (9712) may further incorporate the teachings described in U.S. patent application Ser. No. 16/235,473, entitled "Adhesive Distribution on Buttress for Surgical Stapler," filed on Dec. 28, 2018, published as U.S. Pub. No. 2020/0205820 on Jul. 2, 2020, issued as U.S. Pat. No. 11,166,724 on Nov. 9, 2021, the disclosure of which is hereby incorporated by reference.

By way of example only and not limitation, buttress applier cartridge assembly (9710) can be used to apply buttress assemblies (9712) with end effector (9040) as shown and described with respect to FIGS. 81-84. In such an instance, buttress assemblies (9712) are attached with end effector (9040) in the same manner as described with buttress assemblies (9100, 9110). Moreover, other end effectors described herein can be used in place of end effector (9040) such that buttress applier cartridge assembly (9710) can be used to apply buttress assemblies (9712) with to any of those end effectors. As shown and described above, various end effectors may have a straight configuration, a bent or curved tip configuration where the anvil includes a rigid bent or curved tip, or a bent or curved tip configuration where the anvil includes a deformable bent or curve tip. Despite these different configurations, as will be described further below, buttress applier cartridge assembly (9710) is configured for use with any such configuration end effector.

Furthermore, as mentioned above, buttress applier cartridge assembly (9710) is configured to accommodate alternative camber orientations of an end effector, including parallel-camber, over-camber, and under-camber orientations. As mentioned above, pad (9772) provides sufficient compression such that adhesive layers (9742) of buttresses (9714) completely or at least substantially contact the respect parts of the end effector along their longitudinal length to adhere buttresses (9712) to the end effector whether the end effector is configured with an over-camber orientation, under-camber orientation, or parallel-camber orientation.

iv. Exemplary Opening Feature Accommodating Curved Tip End Effectors

Referring to buttress applier cartridge (9716) as shown in FIGS. 85-99, another feature of buttress applier cartridge (9716) pertains to the ability for buttress applier cartridge (9716) to be used with a variety of end effectors, including those with a bent or curved tip, which could be as part of the anvil or even as part of the cartridge. In this respect, buttress applier cartridge (9716) comprises an opening (9701). Opening (9701) is configured as a space or void where a portion of an end effector can pass through buttress applier cartridge (9716) from a top side or upper side to a bottom side or lower side. As will be described further below, when used with an end effector having a curved tip, opening (9701) allows for the jaws of the end effector to be closed with the curved tip passing through opening (9701) so that the upper jaw and lower jaw of the end effector can close to at least the point where the upper jaw and lower jaw contact buttress assemblies (9712) along its full longitudinal length, or at least substantially along its longitudinal length. At the same time, opening (9701) does not impede or hinder the use of straight tip design end effectors.

Referring now to FIGS. 85 and 95-99, in the present example opening (9701) is defined by chassis (9736) along a distal portion of opening (9701) and lateral sides of opening (9701). Furthermore, opening is defined by platform (9730) along a proximal portion of opening (9701). Thus in the present example, multiple structures or components of buttress applier cartridge (9716) combine to define opening (9701). In some other versions, opening (9701) may be defined by fewer, additional, or other components. Also in the present example, opening (9701) is defined by chassis (9736) and platform (9730) such that opening (9701) comprises a U-shaped opening. In view of the teachings herein, other ways to define opening (9701) to provide for alternate opening shapes will be apparent to those of ordinary skill in the art.

Figure 100:
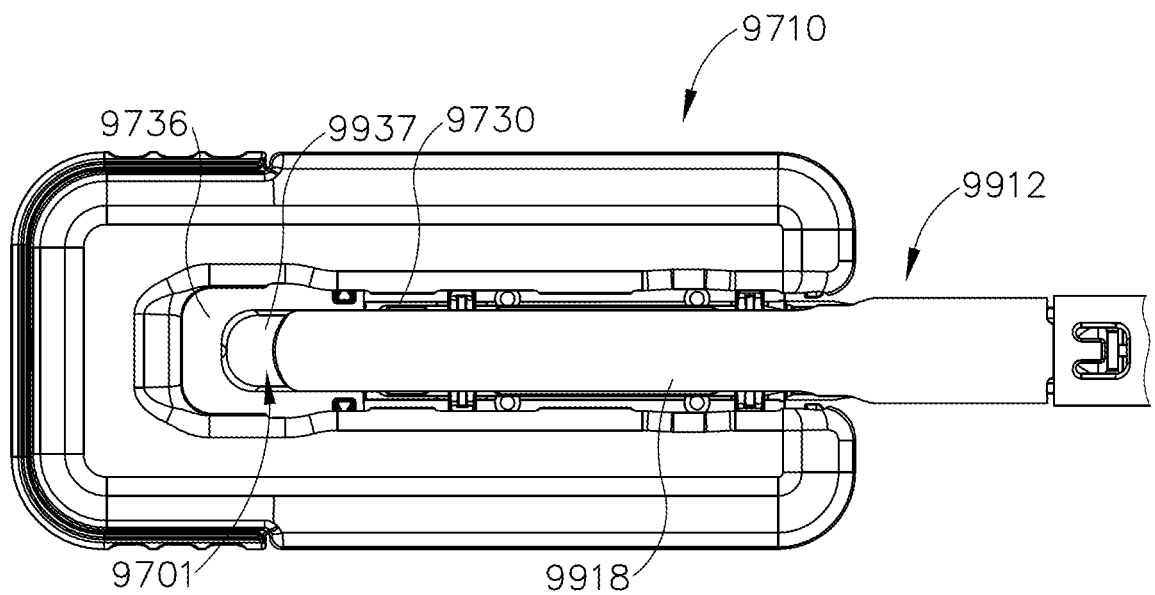
Figure 101:
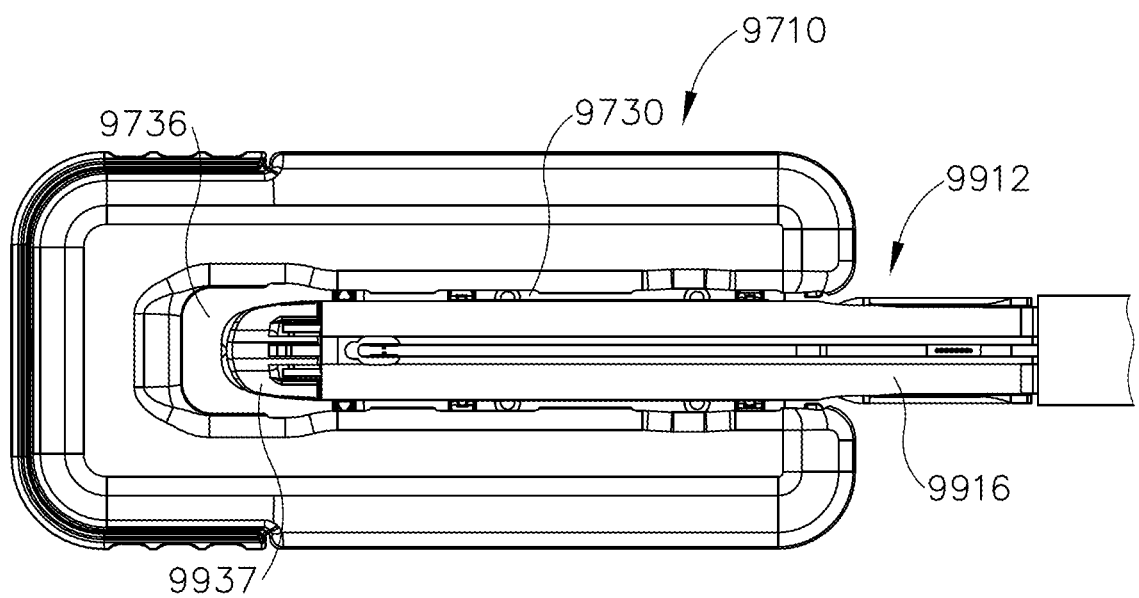

Referring to FIGS. 100 and 101, buttress applier cartridge assembly (9710) is shown used with end effector (9912). End effector (9912) comprises a straight tip configuration, similar to end effectors (9012, 9040) described above. End effector (9912) comprises anvil (9918) and jaw (9916) holding a staple cartridge (9937). As shown in FIG. 100, when end effector (9912) is positioned within buttress applier cartridge assembly (9710) and closed, opening (9701) reveals a portion of cartridge (9937) on the other side of platform (9730). This is the case in this example as end effector (9912) is configured such that cartridge (9937) extends further distally compared to anvil (9918) when end effector (9912) is closed. As shown in FIG. 101, the view from the other side in this configuration shows that opening (9701) is visually blocked by the distal portion of cartridge (9937). Nevertheless, buttress applier cartridge assembly (9710) is configured for use with straight tipped end effectors such as end effectors (9012, 9040, 9912) described herein, among others.

Figure 102:
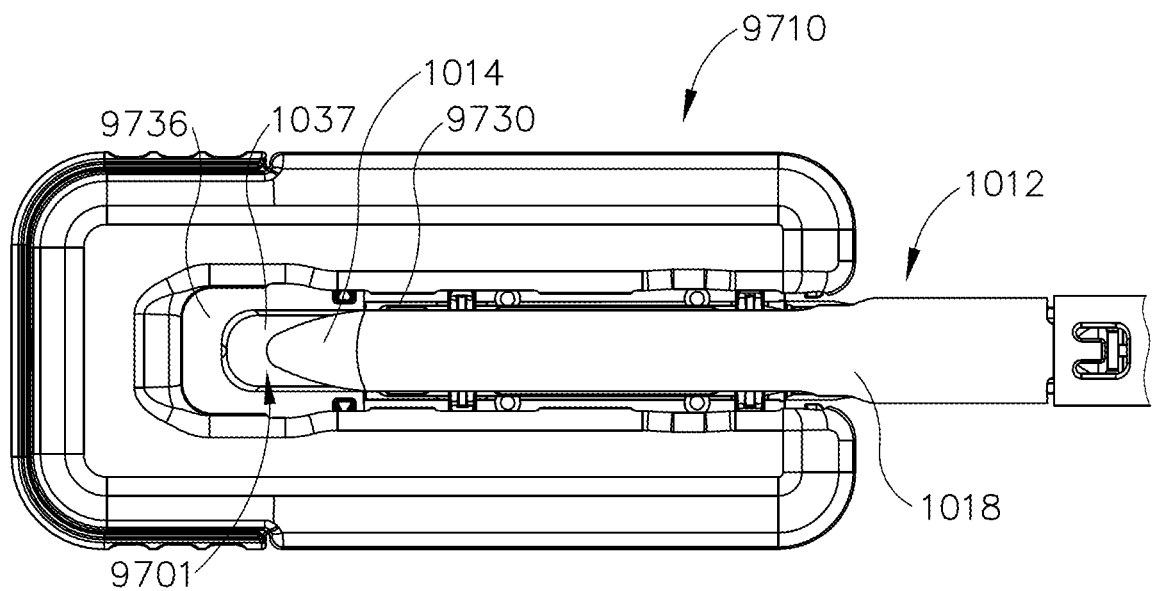
Figure 103:
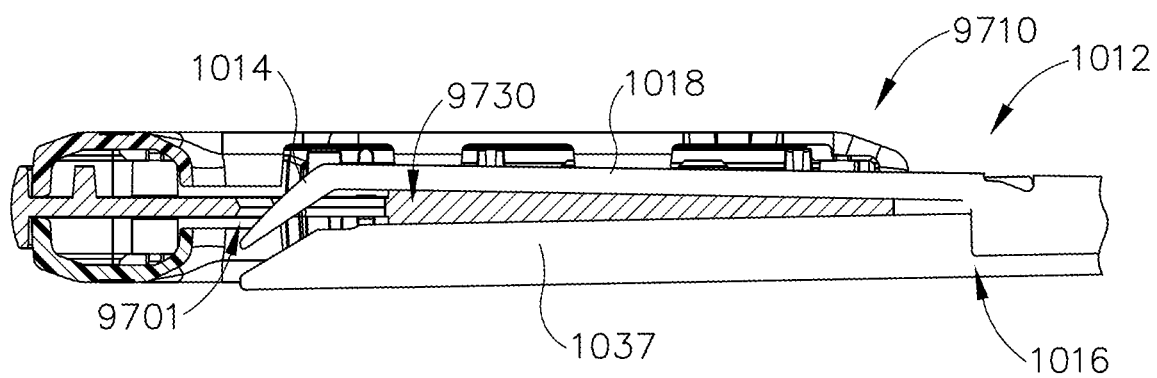

Referring to FIGS. 102 and 103, buttress applier cartridge assembly (9710) is shown used with end effector (1012). End effector (1012) comprises a bent or curved tip configuration, similar to end effectors (9212, 9312, 9412, 9512, 9612) described above. End effector (1012) comprises anvil (1018) and jaw (1016) holding a staple cartridge (1037). As shown in FIG. 102, when end effector (1012) is positioned within buttress applier cartridge assembly (9710) and closed, opening (9701) reveals a portion of cartridge (1037) on the other side of platform (9730). This is the case in this example as end effector (1012) is configured such that cartridge (1037) extends further distally compared to anvil (9918) when end effector (9912) is closed and contacting platform (9730). As shown in FIG. 103, with end effector (1012) closed and contacting platform (9730), a curved tip (1014) of anvil (1018) passes through opening (9701) extending toward cartridge (1037). In the present example, curved tip (1014) is rigid in some versions and deformable in other versions. In either configuration for curved tip (1014), buttress applier cartridge assembly (9710) with opening (9701) accommodates anvil (1018) and curved tip (1014) such that curved tip (1014) extends through opening (9701) when loading buttress assemblies (9712) onto end effector (1012).

v. Exemplary Distal Alignment Feature for Opening Accommodating Curved Tip End Effectors As mentioned above, opening (9701) is defined in part by chassis (9736) along a distal end of opening (9701) and lateral sides of opening (9701). In this manner, chassis (9736) comprises edge (9703) as seen in FIGS. 85 and 87 for example. Edge (9703) extends in a U-shaped manner along a portion of a perimeter of opening (9701) thereby partially defining opening (9701).

Figure 104:
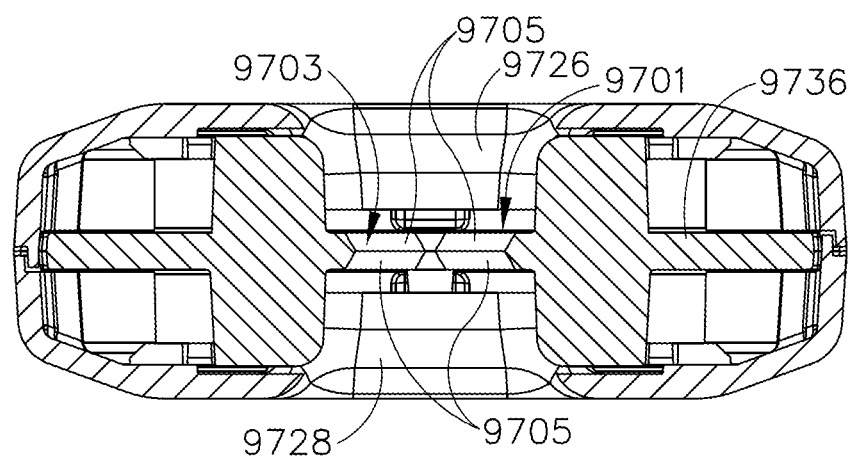

Referring to FIG. 104, opening (9701) comprises alignment features (9705) that are configured to direct a curved tip of an end effector, such as curved tip (1014) of end effector (1012), into and through opening (9701). In addition to directing the curved tip, alignment features (9705) assist in aligning the end effector relative to buttress applier cartridge assembly (9710) so that buttress assemblies (9712) and end effector's jaws are aligned in a parallel or substantially parallel orientation with the end effector's jaws centered or substantially centered relative to buttress assemblies (9712). With this orientation, buttress assemblies (9712) can be adhered to the end effector such that both end effector and buttress assemblies (9712) share a common longitudinal axis.

As shown in FIG. 104, in one example, alignment features (9705) are defined by edge (9703) of opening (9701). Alignment features (9705) comprise tapered surfaces that converge at a center of the thickness of chassis (9736). Moreover, tapered surfaces of alignment features (9705) are oriented or sloped such that when a jaw of an end effector contacts them, the jaw is directed toward the center of opening (9701). As mentioned above, this directing and aligning action not only aligns the curved tip of an end effector but promotes alignment of the end effector as a whole relative to buttress applier cartridge assembly (9710). Furthermore, this alignment action promoted by alignment features (9705) occurs during the clamping of the end effector, as the curved tip extends further through opening (9701) when moving the end effector to the closed position to clamp and contact platform (9730) to ultimately attach buttress assemblies (9712) with the end effector.

In some versions, opening (9701) is sized such that it is narrower than the maximum width of the curved tip of the end effector. By way of example, end effector (1012) has anvil (1018) with curved tip (1014). Curved tip (1014) gradually widens as it extends proximally as shown in FIG. 102. So in such an example, opening (9701) is narrower than the widest portion of curved tip (1014). And when end effector (1012) is closed and clamped on platform (9730), curved tip (1014) will contact edge (9703) of opening (9701). This in turn will cause alignment features (9705) to guide or direct curved tip (1014) and end effector (1012) into alignment with buttresses assemblies (9712) retained on platform (9730) for adhering to end effector (1012). In view of the teachings herein, various sizes and configurations for opening (9701), edge (9703), and alignment features (9705) that can be used with buttress applier cartridge assembly (9710) will be apparent to those of ordinary skill in the art.

Figure 105:
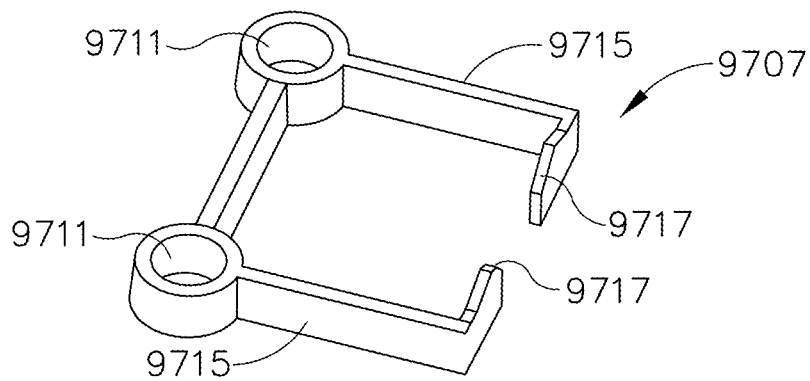
Figure 106:
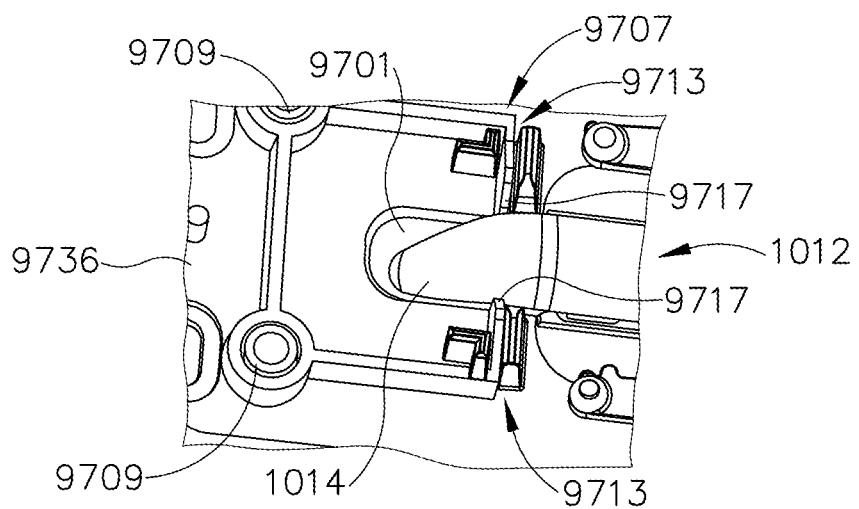

Referring to FIGS. 105 and 106, another exemplary alignment feature (9707) is shown. Alignment feature (9707) is configured to connect with chassis (9736) as shown in FIG. 106. Alignment feature (9707) can be configured to be removable from and/or replaceable with chassis (9736). However, in other versions, alignment feature (9707) can be permanently attached with chassis (9736). In the present example, chassis (9736) comprises a pair of posts (9709) that are configured to engage a pair of bores (9711) of alignment feature (9707). Chassis (9736) further comprises a pair of guides (9713) located proximally from posts (9709). Guides (9713) are each configured to receive end portions of one arm of a pair of lateral arms (9715) of alignment feature (9707) as shown in FIG. 106.

In the present example, arms (9715) of alignment feature (9707) are configured to be resiliently biased and self-centering. In this manner, arms (9715) are configured to deflect outward as an end effector is clamped onto platform (9730). This deflection of arms (9715) allows alignment feature (9707) to be used with end effectors having variation in size and curved tip geometry. Furthermore, with their resilient bias, arms (9715) are configured to guide the curved tip portion of an end effector to a centered orientation relative to opening (9701). In some other versions, arms (9715) and alignment feature (9707) are sized for a specific size or size range for end effectors such that arms (9715) may be rigid and thus not be configured to deflect under clamping forces of the end effector, yet still provide guiding and centering of the end effector by interaction of alignment feature (9707) with a curved tip of the end effector, as described further below.

Arms (9715) of alignment feature (9707) further comprise tapered surfaces (9717) that are configured to contact and interact or engage with a jaw of an end effector such that when a jaw of an end effector contacts them, the jaw is directed or guided toward the center of opening (9701). This directing and aligning action of alignment feature (9707) not only aligns the curved tip of an end effector but promotes alignment of the end effector as a whole relative to buttress applier cartridge assembly (9710).

With opening (9701) and the curved tip end effector, the alignment action promoted by alignment feature (9707) occurs when clamping the end effector, as the curved tip extends further through opening (9701). By way of example, end effectors (9212, 9512, 9612) have respective anvils (9218, 9518, 9618) with curved tips that have tapered sides (9241, 9541, 9641). When end effectors (9212, 9512, 9612), among others, are used with buttress applier cartridge assembly (9710), when clamping end effectors (9212, 9512, 9612) onto platform (9730), tapered surfaces (9717) of alignment feature (9707) contact curved tips of end effectors (9212, 9512, 9612), and further contact tapered sides (9241, 9541, 9641) of end effectors (9212, 9512, 9612) as end effectors (9212, 9512, 9612) are clamped on platform (9730). This contact or engagement causes alignment feature (9707) to guide or direct the curved tips of end effector (9212, 9512, 9612) such that end effectors (9212, 9512, 9612) are guided into alignment with buttresses assemblies (9712) retained on platform (9730) for ultimately adhering to end effectors (9212, 9512, 9612). In view of the teachings herein, other configurations for arms (9715) of alignment feature (9707) that can be used with buttress applier cartridge assembly (9710) will be apparent to those of ordinary skill in the art.

Referring to FIGS. 107 and 108, another exemplary alignment feature (9719) is shown as an anvil alignment rib. Alignment feature (9719) is configured to connect with chassis (9736) as shown in FIG. 107. In the present example, alignment feature (9719) is configured to be secured with or formed with chassis (9736). However, in other versions, alignment feature (9719) can be selectively attached with chassis (9736). In the present example, alignment feature (9719) extends laterally across opening (9701), with ends (9721, 9723) connecting to chassis (9736) on each side of opening (9701). Alignment feature (9719) further extends proximally to distally relative to opening (9701) with a center portion (9725) being located most distally, and connecting with respective side portions (9727, 9729). In this manner, alignment feature (9719) tapers as it extends proximally to distally. Furthermore, center portion (9725) comprises curved portions (9731, 9733) that ultimately connect with side portions (9727, 9729). With this configuration, alignment feature (9719) defines a non-linear decrease in spacing as it spans across opening (9701) and extends proximally to distally.

Alignment feature (9719) also comprises tapered surface (9735) that extends along side portions (9727, 9729) and centered portion (9725). In this manner tapered surface (9735) of alignment feature (9719) extends proximally to distally. Furthermore, tapered surface (9735) is configured to contact tapered sides of curved tip (1014) of an end effector (1012) as end effector (1012) is clamped on platform (9730) as shown in FIGS. 107 and 108. This ultimately guides curved tip (1014) and end effector (1012) into centered alignment with opening (9701) and ultimately with buttress assemblies (9712) retained on platform (9730). As mentioned above, the alignment and guiding of alignment feature (9719) operates in a similar fashion to other alignment features described above where the clamping action of the end effector on platform (9730) promotes contact or engagement of the curved tip of the end effector, and its tapered sides, with alignment feature (9719) and its tapered surface (9735) to center and align the end effector with retained buttress assemblies (9712) on platform (9730). In view of the above description and examples of alignment features, other configurations for one or more alignment features for use with buttress applier cartridge assembly (9710) or other such buttress applicator will be apparent to those of ordinary skill in the art.

XV. Exemplary Alternate Buttress Applier Cartridge with Distal Opening and Alignment Feature for Accommodating Curved Tip End Effectors In other versions of a buttress applier cartridge, an alternate opening, similar to opening (9701) described above, can be incorporated into a buttress applier cartridge to accommodate an end effector having a curved tip. Referring to FIGS. 109-111, buttress applier cartridge assembly (1110) is shown, which is similar to buttress applier cartridge assembly (9710) shown and described above. To that extent, the teachings above with respect to buttress applier cartridge assembly (9710) apply equally to buttress applier cartridge assembly (1110) except for the following differences described below.

Buttress applier cartridge assembly (1110) comprises buttress applier cartridge (1116) having housing assembly (9724), which has upper housing (9726) and lower housing (9728). Buttress applier cartridge (1116) further comprises chassis (1136) and platform (1130). In the present example, housing assembly (9724) defines a channel (1103) that is configured to accommodate an end effector, such as end effector (1012) as shown in FIGS. 110 and 111. As best seen in FIG. 109, platform (1130) is configured to retain buttress assemblies (9712) in the same manner as described above with respect to buttress applier cartridge (9716). In the present example, platform (1130) extends proximally to distally such that the space or area defined by channel (1103) is encompassed by platform (1130). Platform (1130) further includes opening (1101), which is defined by a hole or cut-out in platform (1130). In this manner, opening (1101) is formed in platform (1130), and defined on all sides by platform (1130). Similar to opening (9701) described above, opening (1101) is configured to allow curved tip (1014) of end effector (1012) or another similar end effector to pass through platform (1130) and chassis (1136). In this manner curved tip (1014) extends transversely from one side of combined chassis (1136) and platform (1130) to the other side. Opening (1101) can be configured to be oversized relative to curved tip (1014), undersized relative to curved tip (1014), or equal or substantially equal in size to curved tip (1014). In some cases, platform (1130) comprises a resilient material such that opening (1101) defined by platform (1130) is expandable, for instance when curved tip (1014) extends through opening (1101) and presses against sides of opening (1101). In view of the teachings herein, other configurations for opening (1101) will be apparent to those of ordinary skill in the art.

In addition to opening (1101), similar to platform (9730), platform (1130) is configured to be thicker at its distal portion that is proximal to opening (1101) compared to the proximal portion of platform (1130). In this manner platform (1130) comprises a taper from its distal portion to its proximal portion. Platform (1130) in the present example, also includes a curb (1132) located at its proximal end. Curb (1132) is configured to prevent inadvertent or premature gripping of the jaws of end effector (1012) with platform (1130) and buttress assemblies (9712) prior to end effector (1012) being intentionally clamped onto platform (1130). In other words, curb (1132) is configured to prevent premature substantial contact of the first and second jaws of end effector (1012) with platform (9103) and buttress assemblies (9712) prior to clamping end effector (1012). As shown in FIG. 111, curb (1132) is compressible like platform (1130) such that when end effector (1012) is clamped, curb (1132) compresses and no longer prevents the jaws of end effector (1012) from gripping platform (1130) and thus picking up buttress assemblies (9712).

Referring to FIG. 109, channel (1103) includes a distal portion (9732) that is defined by lateral sides (9734). As shown, distal portion (9732) includes a taper proximally to distally as lateral sides (9734) converge at the distal-most end of distal portion (9732). Accordingly, lateral sides (9734) are configured to guide curved tip (1014) of end effector (1012) toward a centerline of opening (1101) to align end effector (1012) with buttress assemblies (9712) retained on platform (1130). As mentioned above, tapered surfaces may be included on lateral sides (9734) to further facilitate guiding curved tip (1014) of end effector (1012). In view of the teachings herein, additional or other alignment features other than lateral sides (9734) that may be incorporated into buttress applier cartridge (1116) will be apparent to those of ordinary skill in the art.

XVI. Exemplary Alternate Buttress Applier Cartridge for Accommodating Deformable Curved Tip End Effectors In other versions of a buttress applier cartridge, the buttress applier cartridge may be configured for use with curved tip end effectors, but where the curved tips are deformable. In such examples, while an opening like opening (9701) or opening (1101) may be used, an opening may also be omitted. Referring to FIGS. 112-114, buttress applier cartridge assembly (1210) is shown, which is similar to buttress applier cartridge assembly (9710) shown and described above. To that extent, the teachings above with respect to buttress applier cartridge assembly (9710) apply equally to buttress applier cartridge assembly (1210) except for the following differences described below.

Buttress applier cartridge assembly (1210) comprises buttress applier cartridge (1216) having housing assembly (9724), which has upper housing (9726) and lower housing (9728). Buttress applier cartridge (1216) further comprises chassis (1236) and platform (1230). In the present example, housing assembly (9724) defines a channel (1203) that is configured to accommodate an end effector, such as end effector (1312) as shown in FIGS. 112-114. As best seen in FIGS. 112 and 113, platform (1230) is configured to retain buttress assemblies (9712) in the same manner as described above with respect to buttress applier cartridge (9716). In the present example, platform (1230) extends proximally to distally such that the space or area defined by channel (1203) is encompassed by platform (1230). In the present example platform (1230) is a continuous surface, or at least substantially continuous such that curved tip (1314) of end effector (1312) cannot pass through platform (1230). Platform (1230) comprises a proximal end portion (1278) and a distal end portion (1280). Extending further distally from distal end portion (1280), platform (1230) comprises contact portion (1282). Similar to platform (9730), platform (1230) is configured to be compressible and thicker at distal end portion (1280) than proximal end portion (1278). In this manner platform (1230) comprises a taper from distal end portion (1280) to proximal end portion (1278).

Referring to FIG. 112, end effector (1312) is shown within channel (1203) of buttress applier cartridge (1216), but in an unclamped or open state. As shown, when curved tip (1314) touches contact portion (1282) without clamping force, curved tip (1314) does not deform and the jaws of end effector (1312) remain not contacting buttress assemblies (9712). Referring to FIG. 113, when end effector (1312) is clamped, with deformable curved tip (1314), curved tip (1314) deforms so as to deflect or straighten. This deformation occurs because curved tip (1314) contacts or touches contact portion (1282) of platform (1230) instead of passing through an opening as described above with other buttress applier cartridges. The deformation of curved tip (1314) allows sufficient clamping action of end effector (1312) onto platform (1230) such that the jaws of end effector (1312) contact buttress assemblies (9712) so that buttress assemblies are applied to the jaws of end effector (1312). As shown in the clamped state of FIG. 113, center portion (1282) of platform (1230) in the present example is configured to be deflectable. In this manner, contact portion (1282) is resilient so that it remains straight when not subjected to clamping forces from end effector (1312). In other versions center portion (1282) may not be deflectable. However, in some instances where contact portion (1282) is deflectable, some degree of deflection of contact portion (1282) can reduce the stress on the connection of curved tip (1314) with the remainder of the anvil of end effector (1312).

Referring to FIG. 114, end effector (1312) is shown in the clamped state like in FIG. 113. As shown, deformable curved tip (1314), in its deformed state, is slightly expanded in size outward relative to the width of the remainder of end effector (1312). Furthermore, an edge (1205) defining a distal end of channel (1203) of housing assembly (9724) is sized so that housing assembly (9724) is slightly larger than curved tip (1314) in its deformed state when end effector (1312) is clamped. Accordingly, this provides sufficient clearance or space such that a full clamping of end effector (1312) onto platform (1230) can be achieved to transfer buttress assemblies (9712) to the jaws of end effector (1312). In view of the teachings herein, other ways to configured buttress applier cartridge (1216) for use with deformable curved tipped end effectors will be apparent to those of ordinary skill in the art.

XVII. Exemplary Alternate Buttress Applier Cartridge with Proximal Alignment Feature and Distal Opening to Accommodate Curved Tip End Effectors In other versions of a buttress applier cartridge, an alternate opening, similar to opening (9701) described above, can be incorporated into a buttress applier cartridge to accommodate an end effector having a curved tip. Additionally, those buttress applier cartridges described herein can also include one or more alignment features configured to align the end effector of the surgical stapler with the buttress assemblies prior to applying the buttress assemblies to the end effector.

Referring to FIGS. 115-118, buttress applier cartridge assembly (2110) is shown, which is similar to buttress applier cartridge assembly (9710) shown and described above. To that extent, the teachings above with respect to buttress applier cartridge assembly (9710) apply equally to buttress applier cartridge assembly (2110) except for the differences described below. Buttress applier cartridge assembly (2110) comprises buttress applier cartridge (2116) having housing assembly (9724), which has upper housing (9726) and lower housing (9728). In the present example, housing assembly (9724) defines a channel (2103) that is open at a proximal end and configured to accommodate an end effector, such as end effector (1012) as shown in FIGS. 116 and 118.

Buttress applier cartridge (2116) further comprises chassis (2136) and platform (2130). In some examples similar to the configuration for buttress applier cartridge (9716) described above, chassis (2136) is connectable with housing assembly (9724), and platform (2130) is connectable with chassis (2136). In this manner platform (2130) is connectable with housing assembly (9724) indirectly via chassis (2136). Still in other examples buttress applier cartridges (9716, 2116) can be configured such that platform (2136) may be directly connectable with housing assembly (9724).

As best seen in FIG. 115, platform (2130) is configured to retain buttress assemblies (9712) in the same manner as described above with respect to buttress applier cartridge (9716). In the present example, platform (2130) is compressible and also extends proximally to distally such that the space or area defined by channel (2103) is encompassed by platform (2130). Near a distal end of channel (2103), platform (2130) includes opening (2101), which is defined by a hole or cut-out in platform (2130). With this configuration, opening (2101) is located distal to where one or more buttress assemblies (9712) are supported or supportable by platform (2130). In the present example, opening (2101) comprises a U-shaped cut-out. In this manner, opening (2101) is formed in platform (2130), and defined on all sides by platform (2130). Similar to opening (9701) described above, opening (2101) is configured to allow curved tip (1014) of end effector (1012) or another similar end effector to pass through platform (2130) and/or chassis (2136). In this manner curved tip (1014) extends transversely from one side of combined chassis (2136) and platform (2130) to the other side.

Opening (2101) can be configured to be oversized relative to curved tip (1014), undersized relative to curved tip (1014), or equal or substantially equal in size to curved tip (1014). In some cases, such as with U-shaped opening (2101) described here and shown in FIG. 115, platform (2130) comprises a resilient material such that opening (2101) defined by platform (2130) is expandable, for instance when curved tip (1014) extends through opening (2101) and presses against sides of opening (2101). Also in some cases, such as with U-shaped opening (2101), opening (2101) can be configured with a shape that resembles an outline of the shape of curved tip (1014) of end effector (1012). In this way the shape of opening (2101) and curved tip (1014) of end effector (1012) are complementary. In view of the teachings herein, other configurations for opening (2101) will be apparent to those of ordinary skill in the art.

Similar to platform (9730) described above, platform (2130) is configured to be thicker at a distal portion (2180) proximal to opening (2101) compared to a proximal portion (2178) of platform (2130). In this manner platform (2130) comprises a taper from distal portion (2180) to proximal portion (2178). Stated another way, platform (2130) increases in thickness from proximal portion (2178) to distal portion (2180). As shown in the present example of FIG. 115, opening (2101) is located further distally on platform (2130) relative to distal portion (2180). Additionally in the present example, as shown in FIGS. 117 and 118, the portion of platform (2130) with opening (2101) is thinner relative to distal portion (2180).

Referring again to FIG. 116, in defining channel (2103), housing assembly (9724) comprises a V-shaped or U-shaped recess (2105) at the distal end of channel (2103). In this manner, recess (2105) is configured to accommodate distal end or distal tip (1019) of curved tip (1014). Referring again to FIG. 115, in the present example, opening (2101) is located within the area defined by recess (2105). In this manner, buttress applier cartridge (2116) is configured to accommodate curved tip (1014) and distal end (1019) at least with features provided on housing assembly (9724) and platform (2130). In addition to providing space to accommodate distal end (1019) of curved tip (1014) of end effector (1012), in some instances recess (2105) may further assist in guiding or aligning end effector (1012) when clamping end effector (1012) onto platform (2130) such that end effector (1012) can pick-up buttress assemblies (9712). However, as described below, other alignment features or structures can also be provided with buttress applier cartridge (2116) instead of, or in addition to, any alignment provided by recess (2105).

Referring to FIGS. 115, 117, and 118, buttress applier cartridge (2116) also includes an alignment feature (2132) located at a proximal end of buttress applier cartridge (2116). In the present example, alignment feature (2132) comprises a thin rigid portion that extends laterally across the width of channel (2103). In this fashion, alignment features (2132) extends orthogonally relative to the longitudinally extending channel (2103). When end effector (1012) is fully positioned with buttress applier cartridge (2116) as shown in FIG. 117, alignment feature (2132) extends across the cut-line defined by a vertical slot of the end effector where a firing beam travels to sever clamped tissue, the same or similar to vertical slot (9049) and firing beam (9014) of end effector (9012) described above. In some other versions, alignment feature (2132) may extend to a greater or lesser extent laterally across the width of channel (2103) and the cut-line defined by the end effector.

Alignment feature (2132) is configured as a proximal alignment feature. In this way, alignment feature (2132) is configured to engage or contact a proximal edge or one or more tissue stops of the end effector when the end effector is open prior to clamping but fully positioned with buttress applier cartridge (2116) within channel (2103). In some instances, the proximal edge or one or more tissue stops of the end effector may be located on the jaw of the end effector comprising the staple cartridge. In some other instances, the proximal edge or one or more tissue stops of the end effector may be located on the jaw of the end effector comprising the anvil.

As shown in FIGS. 117 and 118, alignment feature (2132) is configured to contact proximal edge (91016) of end effector (1012). In some cases, proximal edge (91016) is operable as a tissue stop such that proximal edge (91016) is prevents over inserting tissue within end effector (1012) to ensure a complete cutting and stapling of the target tissue. In other cases, one or more dedicated tissue stops extend from the end effector, and in such cases alignment feature (2132) is configured to contact such tissue stops. Referring to FIGS. 119 and 120, an end effector (9912) is shown fully positioned with another buttress applier cartridge (2216), which is shown with housing assembly (9724) removed. Alignment feature (2132) is located at the proximal end and extending from platform (2230). Alignment feature (2132) contacts tissue stop (9915) as best seen in FIG. 120.

Referring again to FIGS. 117 and 118, alignment feature (2132) is connectable with platform (2130) and extends proximally from platform (2130). Furthermore, as shown in the present example, alignment feature (2132) is thinner than the adjacent part of platform (2130) from which alignment feature (2132) extends. In this way, alignment feature (2132) is configured to not interfere with the end effector clamping onto platform (2130) to pick-up buttress assemblies (9712). Additionally as shown, alignment feature (2132) is positioned between where buttress assemblies (9712) are supported or supportable by platform (2130). In some versions, alignment feature (2132) comprises a separate rigid structure that connects with platform (2130). However, in other versions, alignment feature (2132) may be a rigid proximal part or end of platform (2130) itself, such that alignment feature (2132) is formed as part of platform (2130).

When an end effector is used with a buttress applier cartridge having alignment feature (2132), alignment feature (2132) guides the end effector to align the end effector relative to the buttress assemblies (9712) supported by the buttress applier cartridge. Thus alignment feature (2132) is configured as a proximal alignment feature that aligns a longitudinal position of the end effector, including aligning the distal part of the end effector.

In the illustrated example of FIGS. 116-118 where end effector (1012) is used with buttress applier cartridge assembly (2110), proximal edge (91016) is used to align longitudinal position of end effector (1012) relative to platform (2130) and buttress assemblies (9712) supported thereon. Additionally, in the present example, alignment feature (2132) is configured to guide curved tip (1014) of end effector (1012) to align curved tip (1014) with opening (2101). In this way, buttress applier cartridge (2116) is configured so that the spacing between opening (2101) and alignment feature (2132) will allow for curved tip (1014) of end effector (1012) to align with opening (2101) when proximal edge (91016) of end effector (1012) contacts alignment feature (2132) prior to clamping end effector (1012) on platform (2130). Furthermore, when subsequently clamping end effector (1012), the alignment of curved tip (1014) with opening (2101) allows at least a portion of curved tip (1014) to extend through or pass through opening (2101). As shown in FIG. 118, when this occurs, opening (2101) deforms such that the portion of platform (2130) around opening (2101) deflects downward away from curved tip (1014) as curved tip (1014) contacts platform (2130) and pushes platform (2130) downward. In view of the teachings herein, other ways to incorporate one or more alignment features with a buttress applier cartridge that align an end effector of a surgical stapler with the buttress applier cartridge, or ways to modify alignment feature (2132) for use with such an end effector will be apparent to those of ordinary skill in the art.

XVIII. Exemplary Alternate Buttress Applier Cartridge with Platform Pocket Feature to Accommodate Curved Tip End Effectors In other versions of a buttress applier cartridge, instead of a hole or opening, similar to opening (9701) described above, a pocket feature can be incorporated into the platform of a buttress applier cartridge to accommodate an end effector having a curved tip. By way of example only and not limitation, several versions of such pocket features are shown and described herein. Furthermore, in view of the teachings herein, other configurations for such pocket features will be apparent to those of ordinary skill in the art.

A. Exemplary Distal Platform U-Shaped Slit

Referring to FIGS. 121-123, buttress applier cartridge assembly (4110) is shown, which is similar to buttress applier cartridge assembly (9710) shown and described above. To that extent, the teachings above with respect to buttress applier cartridge assembly (9710) apply equally to buttress applier cartridge assembly (4110) except for the following differences described below.

Buttress applier cartridge assembly (4110) comprises buttress applier cartridge (4116) having housing assembly (9724), which has upper housing (9726) and lower housing (9728). Buttress applier cartridge (4116) further comprises chassis (9736) and platform (4130). In the present example, housing assembly (9724) defines a channel (4103) that is configured to accommodate an end effector, such as end effector (1012) as shown in FIGS. 122 and 123. Platform (4130) is configured to retain buttress assemblies (9712) in the same manner as described above with respect to buttress applier cartridge (9716). In the present example, platform (4130) extends proximally to distally such that the space or area defined by channel (4103) is encompassed by platform (4130).

Buttress applier cartridge (4116) further includes pocket feature (4100). In the present example, pocket feature (4100) is located distal to where platform (4130) supports buttress assemblies (9712). As shown in FIGS. 122 and 123, pocket feature (4100) is also transversely positioned between where buttress assemblies (9712) are supported on platform (4130). With this positioning, pocket feature (4100) is configured to receive a curved tip of an end effector when clamping the end effector onto platform (4130) as described further below.

In the present example, pocket feature (4100) comprises a slit (4101) formed in platform (4130). Slit (4101) comprises a U-shape in the present example. Similar to opening (9701) described above, slit (4101) is configured to allow curved tip (1014) of end effector (1012) or another similar end effector to pass through platform (4130) and/or chassis (9736). In this manner curved tip (1014) extends transversely from one side of combined chassis (9736) and platform (4130) to the other side. Also, slit (4101) is configured to deform when curved tip (1014) of end effector (1012) passes through pocket feature (4100).

Slit (4101) can be configured to be oversized relative to curved tip (1014), undersized relative to curved tip (1014), or equal or substantially equal in size to curved tip (1014). In some cases, platform (4130) comprises a resilient material such that slit (4101) defined by platform (4130) is expandable, for instance when curved tip (1014) extends through pocket feature (4100) and presses against sides of slit (4101). Also in some cases, slit (4101) can be configured with a shape that resembles an outline of the shape of curved tip (1014) of end effector (1012). In this way the shape of slit (4101) and curved tip (1014) of end effector (1012) are complementary. Additionally, housing assembly (9724) may also comprise a distal portion (9732) of channel (4103) that has a shape that complements curved tip (1014) of end effector (1012) thereby accommodating placement and or guiding curved tip (1014) to slit (4101).

Similar to platform (9730), platform (4130) is configured to be compressible and thicker at a distal portion (4180) that is proximal to slit (4101) compared to a proximal portion (4178) of platform (4130). In this manner platform (4130) comprises a taper from distal portion (4180) to proximal portion (4178). This thickness profile or configuration for platform (4130) compensates for any jaw deflection of the end effector when clamping on platform (4130) to pick-up buttress assemblies (9712). Platform (4130) in the present example, may also include one or more alignment features such as those described in U.S. patent application Ser. No. 16/235,670, entitled "Curved Tip Surgical Stapler Buttress Assembly Applicator with Proximal Alignment Features," filed on Dec. 28, 2018, issued as U.S. Pat. No. 10,905,424 on Feb. 2, 2021; U.S. patent application Ser. No. 16/235,630, entitled "Curved Tip Surgical Stapler Buttress Assembly Applicator with Opening Feature for Curved Tip Alignment," filed on Dec. 28, 2018, published as U.S. Pub. No. 2020/0205826 on Jul. 2, 2020, issued as U.S. Pat. No. 11,272,935 on Mar. 15, 2022, the disclosures of which are hereby incorporated by reference. Additionally, platform (4130) may instead or in addition include one or more features to prevent premature clamping and/or contact of the end effector with the buttress assemblies retained on platform (4130). Examples of such features are described in U.S. patent application Ser. No. 16/235,630, entitled "Curved Tip Surgical Stapler Buttress Assembly Applicator with Opening Feature for Curved Tip Alignment," filed on Dec. 28, 2018, published as U.S. Pub. No. 2020/0205826 on Jul. 2, 2020, issued as U.S. Pat. No. 11,272,935 on Mar. 15, 2022, the disclosure of which is hereby incorporated by reference.

With pocket feature (4100) formed in platform (4130), pocket feature (4100) defines or provides a region (4102) of platform (4130) that comprises a reduced stiffness. Region (4102) is located on and around platform (4130) where pocket feature (4100) is positioned. The reduced stiffness of region (4102) promotes deflection and/or deformation of platform (4130) when region (4102) is contacted by curved tip (1014) of end effector (1012) when clamping end effector (1012) on platform (4130).

Still referring to FIGS. 121-123, U-shaped slit (4101) defines a flap (4104) of platform (4130). Furthermore, slit (4101) is continuous in the present example such that flap (4104) is configured to deflect away from the remainder of platform (4130) when contacted by curved tip (1014) of end effector (1012) when clamping end effector (1012) to platform (4130). With the shape of slit (4101) being U-shaped in the present example, flap (4104) also has a U-shape.

As mentioned above, buttress applier cartridge assembly (4110) includes those features described above with respect to buttress applier cartridge assembly (9710) except for the differences described herein. To this extent, buttress cartridge (4116) comprises actuator sleds (9752, 9754) as shown in FIGS. 86 and 91-94. In the present example, actuator sleds (9752, 9754), which may also be referred to herein as movable sleds (9752, 9754), connect with chassis (9736) in the same manner that actuator sleds (9752, 9754) connect with chassis (9736) as described above. As shown in FIG. 86, actuator sleds (9752, 9754) comprise a first set of actuator sleds (9752, 9754) located or positioned above platform (9736), and a second set of actuator sleds (9752, 9754) located or positioned below platform (9736). Actuator sleds (9752, 9754) each comprise a pair of arms (9755a, 9755b) configured for contact by end effector (1012). This contact drives or pushes actuator sleds (9752, 9754) laterally, which causes arms (9755a, 9755b) to disengage with buttress assemblies (9712) such that buttress assemblies (9712) can be applied to the jaws of end effector (1012).

Referring to the clamping sequence as shown in FIGS. 122 and 123, with pocket feature (4100) of platform (4130), when end effector (1012) is open or not clamped and positioned within channel (4103) of buttress applier cartridge (4116), jaw (1016) of end effector (1012) is positioned close and adjacent to platform (4130), and in a substantially parallel orientation relative to platform (4130). Furthermore, both the distal end of jaw (1016) and the proximal end of jaw (1016) are evenly or substantially evenly spaced from platform (4130). As shown in FIG. 122, with this arrangement, jaw (1016) is positioned to make substantially simultaneous contact with arms (9755a, 9755b) of actuator sleds (9752, 9754) located adjacent to jaw (1016).

At the same time, on the opposite side where anvil (1018) is located, in the positioned but open and not clamped state, anvil (1018) is positioned angled relative to platform (4130). In this fashion, the proximal end of anvil (1018) is positioned closer to platform (4130) while the distal end of anvil (1018) is positioned further from platform (4130). Again as shown in FIG. 122, with this arrangement, anvil (1018) is positioned such that the proximal end of anvil (1018) will make contact with arms (9755a, 9755b) of actuator sleds (9752, 9754) located adjacent to anvil (1018) first, and thereafter the distal end of anvil (1018) will make contact with arms (9755a, 9755b) of actuator sleds (9752, 9754) located adjacent to anvil (1018).

With this configuration, and as shown and understood from the clamping sequence of FIGS. 122 and 123, during positioning and clamping end effector (1012) on platform (4130), the lateral movement of the first set of actuator sleds (9752, 9754) located along the side of platform (4130) adjacent to anvil (1018) differs from the lateral movement of the second set of actuator sleds (9752, 9754) located along the side of platform (4130) adjacent to jaw (1016). For instance, in the present example, clamping end effector (1012) will first fully release buttress assembly (9712) being retained by the second set of actuator sleds (9752, 9754) adjacent jaw (1016), and thereafter fully release buttress assembly (9712) being retained by the first set of actuator sleds (9752, 9754) adjacent anvil (1018). While the above examples illustrate and describe differing lateral movement for actuator sleds (9752, 9754) depending on their position relative to end effector (1012) when clamping, in other versions buttress applier cartridge (4116) can be configured in other ways such that the lateral movement of actuator sleds (9752, 9754) and the release timing of buttress assemblies (9712) for application to end effector (1012) may differ in other ways, or may be substantially the same.

B. Exemplary Distal Platform Perforated Slit

Referring now to FIG. 124, a distal portion of buttress applier cartridge assembly (55110) is shown, which is similar to buttress applier cartridge assemblies (9710, 4110) shown and described above. To that extent, the teachings above with respect to buttress applier cartridge assemblies (9710, 4110) apply equally to buttress applier cartridge assembly (55110) except for the following differences described below.

Buttress applier cartridge assembly (55110) comprises buttress applier cartridge (55116) having housing assembly (9724), chassis (9736), and platform (55130). In the present example, housing assembly (9724) defines a channel (55103) that is configured to accommodate an end effector, such as end effector (1012) as shown in FIGS. 122 and 123. Platform (55130) is configured to retain buttress assemblies (9712) in the same manner as described above with respect to buttress applier cartridges (9716, 4116). In the present example, platform (55130) extends proximally to distally such that the space or area defined by channel (55103) is encompassed by platform (55130).

Buttress applier cartridge (55116) further includes pocket feature (55100). In the present example, pocket feature (55100) is located distal to where platform (55130) supports buttress assemblies (9712). Pocket feature (55100) is also transversely positioned between where buttress assemblies (9712) are supported on platform (55130). With this positioning, pocket feature (55100) is configured to receive a curved tip of an end effector when clamping the end effector onto platform (55130) as described further below.

In the present example, pocket feature (55100) comprises a perforated slit (55101) formed in platform (55130). Slit (55101) is configured to allow curved tip (1014) of end effector (1012) or another similar end effector to deflect platform (55130) when clamping force is applied to end effector (1012). Also, slit (55101) is configured to deform when curved tip (1014) of end effector (1012) press against pocket feature (55100).

Slit (55101) can be configured to be oversized relative to curved tip (1014), undersized relative to curved tip (1014), or equal or substantially equal in size to curved tip (1014). In some cases, platform (55130) comprises a resilient material such that slit (55101) defined by platform (55130) is expandable, for instance when curved tip (1014) contacts and presses against pocket feature (55100). In the present example, perforated slit (55101) extends longitudinally and along a central axis of buttress applier cartridge (55116). However, in some cases, perforated slit (55101) can be configured with a shape that resembles an outline of the shape of curved tip (1014) of end effector (1012). In this way the shape of slit (55101) and curved tip (1014) of end effector (1012) are complementary. Additionally, housing assembly (9724) may also comprise a distal portion (9732) of channel (55103) that has a shape that complements curved tip (1014) of end effector (1012) thereby accommodating placement and or guiding curved tip (1014) to slit (55101).

Similar to platform (9730), platform (55130) is configured to be compressible and thicker at its distal portion that is proximal to slit (55101) compared to its proximal portion. In this manner platform (55130) comprises a taper from its distal portion to its proximal portion. This thickness profile or configuration for platform (55130) compensates for any jaw deflection of the end effector when clamping on platform (55130) to pick-up buttress assemblies (9712). Platform (55130) in the present example, may also include one or more alignment features such as those described in U.S. patent application Ser. No. 16/235,670, entitled "Curved Tip Surgical Stapler Buttress Assembly Applicator with Proximal Alignment Features," filed on Dec. 28, 2018, issued as U.S. Pat. No. 10,905,424 on Feb. 2, 2021; U.S. patent application Ser. No. 16/235,630, entitled "Curved Tip Surgical Stapler Buttress Assembly Applicator with Opening Feature for Curved Tip Alignment," filed on Dec. 28, 2018, published as U.S. Pub. No. 2020/0205826 on Jul. 2, 2020, issued as U.S. Pat. No. 11,272,935 on Mar. 15, 2022, the disclosures of which are hereby incorporated by reference. Additionally, platform (55130) may instead or in addition include one or more features to prevent premature clamping and/or contact of the end effector with the buttress assemblies retained on platform (4130). Examples of such features are described in U.S. patent application Ser. No. 16/235,630, entitled "Curved Tip Surgical Stapler Buttress Assembly Applicator with Opening Feature for Curved Tip Alignment," filed on Dec. 28, 2018, published as U.S. Pub. No. 2020/0205826 on Jul. 2, 2020, issued as U.S. Pat. No. 11,272,935 on Mar. 15, 2022, the disclosure of which is hereby incorporated by reference.

With pocket feature (55100) formed in platform (55130), pocket feature (55100) defines or provides a region (55102) of platform (55130) that comprises a reduced stiffness. Region (55102) is located on and around platform (55130) where pocket feature (55100) is positioned. The reduced stiffness of region (55102) promotes deflection and/or deformation of platform (55130) when region (55102) is contacted by curved tip (1014) of end effector (1012) when clamping end effector (1012) on platform (55130).

As mentioned above, buttress applier cartridge assembly (55110) includes those features described above with respect to buttress applier cartridge assemblies (9710, 4110) except for the differences described herein. To this extent, the description of actuator sleds (9752, 9754) above as it pertains to buttress applier cartridge (4116) applies equally here to buttress applier cartridge (55116).

C. Exemplary Distal Platform T-Shaped Slit

Referring to FIG. 125, buttress applier cartridge assembly (6110) is shown, which is similar to buttress applier cartridge assemblies (9710, 4110) shown and described above. To that extent, the teachings above with respect to buttress applier cartridge assemblies (9710, 4110) apply equally to buttress applier cartridge assembly (6110) except for the following differences described below.

Buttress applier cartridge assembly (6110) comprises buttress applier cartridge (6116) having housing assembly (9724), chassis (9736), and platform (6130). In the present example, housing assembly (9724) defines a channel (6103) that is configured to accommodate an end effector, such as end effector (1012) as shown in FIGS. 122 and 123. Platform (6130) is configured to retain buttress assemblies (9712) in the same manner as described above with respect to buttress applier cartridge (9716). In the present example, platform (6130) extends proximally to distally such that the space or area defined by channel (6103) is encompassed by platform (6130).

Buttress applier cartridge (6116) further includes pocket feature (6100). In the present example, pocket feature (6100) is located distal to where platform (6130) supports buttress assemblies (9712). Pocket feature (6100) is also transversely positioned between where buttress assemblies (9712) are supported on platform (6130). With this positioning, pocket feature (6100) is configured to receive a curved tip of an end effector when clamping the end effector onto platform (6130) as described further below.

In the present example, pocket feature (6100) comprises a slit (6101) formed in platform (6130). Slit (6101) comprises a T-shape in the present example. Similar to opening (9701) described above, slit (6101) is configured to allow curved tip (1014) of end effector (1012) or another similar end effector to pass through platform (6130) and/or chassis (9736). In this manner curved tip (1014) extends transversely from one side of combined chassis (9736) and platform (6130) to the other side. Also, slit (6101) is configured to deform when curved tip (1014) of end effector (1012) passes through pocket feature (6100).

Slit (6101) can be configured to be oversized relative to curved tip (1014), undersized relative to curved tip (1014), or equal or substantially equal in size to curved tip (1014). In some cases, platform (6130) comprises a resilient material such that slit (6101) defined by platform (6130) is expandable, for instance when curved tip (1014) extends through pocket feature (6100) and presses against sides of slit (6101). Also in some cases, slit (6101) can be configured with a shape that resembles an outline of the shape of curved tip (1014) of end effector (1012). In this way the shape of slit (6101) and curved tip (1014) of end effector (1012) are complementary. Additionally, housing assembly (9724) may also comprise a distal portion (9732) of channel (6103) that has a shape that complements curved tip (1014) of end effector (1012) thereby accommodating placement and or guiding curved tip (1014) to slit (6101).

Similar to platform (9730), platform (6130) is configured to be compressible and thicker at its distal portion that is proximal to slit (6101) compared to its proximal portion. In this manner platform (6130) comprises a taper from its distal portion to its proximal portion. This thickness profile or configuration for platform (6130) compensates for any jaw deflection of the end effector when clamping on platform (6130) to pick-up buttress assemblies (9712). Platform (6130) in the present example, may also include one or more alignment features such as those described in U.S. patent application Ser. No. 16/235,670, entitled "Curved Tip Surgical Stapler Buttress Assembly Applicator with Proximal Alignment Features," filed on Dec. 28, 2018, issued as U.S. Pat. No. 10,905,424 on Feb. 2, 2021; U.S. patent application Ser. No. 16/235,630, entitled "Curved Tip Surgical Stapler Buttress Assembly Applicator with Opening Feature for Curved Tip Alignment," filed on Dec. 28, 2018, published as U.S. Pub. No. 2020/0205826 on Jul. 2, 2020, issued as U.S. Pat. No. 11,272,935 on Mar. 15, 2022, the disclosures of which are hereby incorporated by reference. Additionally, platform (6130) may instead or in addition include one or more features to prevent premature clamping and/or contact of the end effector with the buttress assemblies retained on platform (4130). Examples of such features are described in U.S. patent application Ser. No. 16/235,630, entitled "Curved Tip Surgical Stapler Buttress Assembly Applicator with Opening Feature for Curved Tip Alignment," filed on Dec. 28, 2018, published as U.S. Pub. No. 2020/0205826 on Jul. 2, 2020, issued as U.S. Pat. No. 11,272,935 on Mar. 15, 2022, the disclosure of which is hereby incorporated by reference.

With pocket feature (6100) formed in platform (6130), pocket feature (6100) defines or provides a region (6102) of platform (6130) that comprises a reduced stiffness. Region (6102) is located on and around platform (6130) where pocket feature (6100) is positioned. The reduced stiffness of region (6102) promotes deflection and/or deformation of platform (6130) when region (6102) is contacted by curved tip (1014) of end effector (1012) when clamping end effector (1012) on platform (6130).

Still referring to FIG. 125, T-shaped slit (6101) defines a pair of flaps (6104, 6105) of platform (6130). Furthermore, slit (6101) is continuous in the present example such that flaps (6104, 6105) are configured to deflect away from the remainder of platform (6130) when contacted by curved tip (1014) of end effector (1012) when clamping end effector (1012) to platform (6130). With the shape of slit (6101) being T-shaped in the present example, flaps (6104, 6105) each comprise a triangular shape.

As mentioned above, buttress applier cartridge assembly (6110) includes those features described above with respect to buttress applier cartridge assemblies (9710, 4110) except for the differences described herein. To this extent, the description of actuator sleds (9752, 9754) above as it pertains to buttress applier cartridge (4116) applies equally here to buttress applier cartridge (6116).

D. Exemplary Platform Profile

FIG. 126 illustrates an exemplary version of platforms (4130, 55130, 6130) used with respective buttress applier cartridges (4116, 55116, 6116). In particular, FIG. 126 shows a cross-section view, with buttress assemblies (9712) removed, to illustrate a lateral profile of platforms (4130, 55130, 6130). In this example, platforms (4130, 55130, 6130) define a longitudinally extending central region (3500). Central region (3500) defines a central axis (CA) that extends longitudinally along central region (3500) of platforms (4130, 55130, 6130) as indicated in FIG. 121 with reference to platform (4130). As shown in FIG. 126, platforms (4130, 55130, 6130) comprise a smaller thickness along central axis (CA) of central region (3500) compared to the thickness of platforms (4130, 55130, 6130) adjacent to central region (3500).

In addition to central region (3500), platforms (4130, 55130, 6130) further comprise a pair of longitudinally extending outer regions (3501). As shown in FIG. 126, one of outer regions (3501) is located on each side of central region (3500). With this configuration, and as shown in the illustrated version, the thickness of platforms (4130, 55130, 6130) increases as platforms (4130, 55130, 6130) extend laterally from central region (3500) to outer regions (3501). Furthermore, this thickness increase is progressive, showing a gradual increase in thickness the further outward from central region (3500) platforms (4130, 55130, 6130) extends up until at least reaching housing assembly (9724) defining channels (4103, 55103, 6103).

With the above the lateral profile of platforms (4130, 55130, 6130), platforms (4130, 55130, 6130) are configured to accommodate end effectors that may include a portion of a cutting member, such as a translatable knife or firing beam, that extends distally at least some amount such that the cutting member would be positioned over a part of platforms (4130, 55130, 6130) when the end effector is clamped on platforms (4130, 55130, 6130) to pick-up buttress assemblies (9712). In view of the teachings herein, other ways to configure platforms (4130, 55130, 6130) to accommodate various end effectors having various tip configurations including curved tips or having various internal structures such as protruding cutting members or low-height cartridges, etc. will be apparent to those of ordinary skill in the art.

The various buttress applier cartridges described herein may be used with any of the end effectors described herein. By way of example, and not limitation, those features of the buttress applier cartridges that are configured to work with and/or accommodate an end effector having a curved tip make the buttress applier cartridges suitable for use with end effectors having various styles and configurations for the curved tip. For instance, the buttress applier cartridges described herein with features for a curved tip end effector can be used with end effectors where the curved tip may be gradually curved, or where the curved tip may be non-aligned or at an angle relative to the axis of the anvil such that the curved tip has a more angled or bent configuration rather than gradual curve. Also, the buttress applier cartridges with features to accommodate end effectors with a curved tip described herein can be used with, or configured for use with, end effectors where the curved tip portion is spaced from the distal end of the cartridge or terminates at the same or similar point as the distal end of the cartridge. Also, the buttress applier cartridges with features to accommodate end effectors with a curved tip described herein can be used, or configured for use with, end effectors that have curved tips configured for different uses or applications such as atraumatic tips, dissecting tips, visualization tips, placement tips, deflectable or deformable tips, and combinations thereof, etc. In view of the teachings herein, other ways to configure the buttress applier cartridges described herein to work with the end effectors described herein will be apparent to those of ordinary skill in the art.

XIX. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A buttress assembly for reinforcing tissue layers joined by surgical stapling, comprises (a) a buttress comprising a first surface and a second surface, wherein the buttress further comprises a proximal end and a distal end. The buttress defines a longitudinal axis extending between the proximal end and the distal end, wherein the buttress further comprises a center region adjacent to a first edge region on one side of the center region and adjacent to a second edge region on the other side of the center region. The buttress assembly also comprises (b) an adhesive applied to a select one of the first surface and the second surface of the buttress, wherein the adhesive extends continuously from the proximal end of the buttress to the distal end of the buttress. The adhesive is located along the first edge region and the second edge region leaving the center region of the buttress substantially free of the adhesive.

Example 2

The buttress assembly of Example 1, wherein the center region of the buttress comprises one or more slits configured to promote separation of the buttress into halves.

Example 3

The buttress assembly of any one or more of Examples 1 through 2, wherein the adhesive comprises an uneven distribution that comprises more of the adhesive at the distal end of the buttress than at the proximal end of the buttress.

Example 4

The buttress assembly of any one or more of Examples 1 through 3, wherein the adhesive comprises a first bead of the adhesive extending from the proximal end of the buttress to the distal end of the buttress, and wherein the adhesive further comprises a second bead of the adhesive extending from the proximal end of the buttress to the distal end of the buttress.

Example 5

The buttress assembly of Example 4, wherein the first bead of the adhesive partially overlaps the second bead of the adhesive along at least a portion of a length of the buttress.

Example 6

The buttress assembly of any one or more of Examples 4 through 5, wherein the first bead of the adhesive is spaced apart from the second bead of the adhesive along at least a portion of the length of the buttress.

Example 7

The buttress assembly of any one or more of Examples 4 through 6, wherein the second bead of the adhesive extends further proximally than the first bead of the adhesive.

Example 8

The buttress assembly of any one or more of Examples 4 through 7, wherein the first bead of the adhesive and the second bead of the adhesive extend distally to substantially the same extent relative to the buttress.

Example 9

The buttress assembly of any one or more of Examples 4 through 8, wherein the adhesive comprises a third bead of the adhesive extending from the proximal end of the buttress to the distal end of the buttress, and wherein the adhesive further comprises a fourth bead of the adhesive extending from the proximal end of the buttress to the distal end of the buttress.

Example 10

The buttress assembly of any one or more of Examples 4 through 9, wherein the first and the second beads of the adhesive are collectively symmetrical with the third and the fourth beads of the adhesive about the longitudinal axis of the buttress that defines a centerline of the buttress.

Example 11

The buttress assembly of any one or more of Examples 1 through 10, wherein the adhesive comprises a minimum height such that where the adhesive is applied to the buttress the adhesive sits proud of the buttress.

Example 12

The buttress assembly of Example 11, wherein the minimum height of the adhesive is between about 0.254 mm and about 1.27 mm.

Example 13

The buttress assembly of any one or more of Examples 11 through 12, wherein the minimum height of the adhesive is between about 0.4064 mm and about 0.762 mm.

Example 14

The buttress assembly of any one or more of Examples 11 through 13, wherein the minimum height of the adhesive is configured to substantially match a depth of a staple forming pocket of an anvil of an end effector of a surgical stapler.

Example 15

The buttress assembly of any one or more of Examples 11 through 14, wherein the minimum height of the adhesive is configured to substantially match a height of a pocket extender of a staple cartridge of an end effector of a surgical stapler.

Example 16

A buttress assembly for reinforcing tissue layers joined by surgical stapling, comprises (a) a buttress comprising a first surface and a second surface, wherein the buttress further comprises a proximal end and a distal end. The buttress defines a length from the proximal end to the distal end, wherein the buttress defines a longitudinal axis extending between the proximal end and the distal end. The buttress further comprises a center region adjacent to a first edge region on one side of the center region and adjacent to a second edge region on the other side of the center region, wherein the buttress is configured to be cut into substantially equal halves by cutting through the center region. The buttress assembly also comprises (b) an adhesive applied to a select one of the first surface and the second surface of the buttress, wherein the adhesive extends from the proximal end of the buttress to the distal end of the buttress. The adhesive is located along the first edge region and the second edge region leaving the center region of the buttress substantially free of the adhesive, wherein the adhesive comprises an asymmetric distribution along the length of the buttress.

Example 17

The buttress assembly of Example 16, wherein the adhesive on the first edge region and the second edge region changes between areas of greater adhesive and areas of lesser adhesive along the length of the buttress, wherein the areas of greater adhesive on the first edge region are located opposite to the areas of lesser adhesive on the second edge region, and wherein the areas of greater adhesive on the second edge region are located opposite to the areas of lesser adhesive on the first edge region.

Example 18

The buttress assembly of any one or more of Examples 16 through 17, wherein the asymmetric distribution of the adhesive is configured to reduce the force needed for releasing the buttress assembly from a select one of an anvil and a staple cartridge of an end effector of a surgical stapler when opening the end effector.

Example 19

An apparatus for reinforcing tissue layers joined by surgical stapling, comprises (a) a pair of buttress assemblies, each buttress assembly of the pair comprising (i) a buttress comprising a first surface and a second surface, wherein the buttress further comprises a proximal end and a distal end, wherein the buttress defines a length from the proximal end to the distal end, wherein the buttress further comprises a center region adjacent to a first edge region on one side of the center region and adjacent to a second edge region on the other side of the center region, wherein the buttress is configured to be cut into substantially equal halves by cutting through the center region, and (ii) an adhesive applied to a select one of the first surface and the second surface of the buttress, wherein the adhesive extends from the proximal end of the buttress to the distal end of the buttress, wherein the adhesive is located along the first edge region and the second edge region leaving the center region of the buttress substantially free of the adhesive, wherein the adhesive comprises an asymmetric distribution along the length of the buttress having the adhesive on the first edge region and the second edge region changing between areas of greater adhesive and areas of lesser adhesive, wherein the areas of greater adhesive on the first edge region are located opposite to the areas of lesser adhesive on the second edge region, and wherein the areas of greater adhesive on the second edge region are located opposite to the areas of lesser adhesive on the first edge region. The apparatus also comprises (b) each of the buttress assemblies are configured to be positioned in an opposing manner with the adhesive of one of the buttress assemblies facing away from the adhesive of the other of the buttress assemblies, wherein when positioned in the opposing manner, the areas of greater adhesive on one of the buttress assemblies are aligned with the areas of lesser adhesive on the other of the buttress assemblies.

Example 20

The apparatus of Example 19, wherein the center region of the buttress comprises one or more slits configured to promote cutting the buttress into halves.

XX. Miscellaneous

While the terms "buttress" and "buttress assembly" are used throughout this disclosure, it should be understood that the term is not intended to limit the scope of the present invention in any way. For instance, use of the terms "buttress" and "buttress assembly" is not intended to demonstrate contemplation that a "buttress" or "buttress assembly" can only be used to provide structural support to a staple line or serve any other particular purpose. It is contemplated that "buttress" or "buttress assembly" may serve a variety of purposes in addition to or as an alternative to providing structural support to a staple line. The terms "buttress" and "buttress assembly" should therefore be read broadly to include any kind of adjunct to a staple line that serves any suitable purpose.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should also be understood that the teachings herein may be readily combined with various teachings in U.S. Pat. No. D836,198, entitled "Surgical Stapler End Effector with Varying Deck Height and Tissue Gripping Features," issued Dec. 18, 2018, the disclosure of which is incorporated by reference herein. Various suitable ways in which the teachings herein may be combined with the teachings of U.S. Pat. No. D836,198, will be apparent to those of ordinary skill in the art.

It should also be understood that the teachings herein may be readily combined with various teachings in U.S. Pat. No. D833,010, entitled "Circular Surgical Stapler End Effector with Varying Deck Height and Tissue Gripping Features," issued Nov. 6, 2018, the disclosure of which is incorporated by reference herein. Various suitable ways in which the teachings herein may be combined with the teachings of U.S. Pat. No. D833,010, will be apparent to those of ordinary skill in the art.

It should also be understood that the teachings herein may be readily combined with various teachings in U.S. Pat. Pub. No. 2018/0235610, entitled "Surgical Stapler with Insertable Distal Anvil Tip," published Aug. 23, 2018, issued as U.S. Pat. No. 10,729,434 on Aug. 4, 2020, the disclosure of which is incorporated by reference herein. Various suitable ways in which the teachings herein may be combined with the teachings of U.S. Pat. Pub. No. 2018/0235610, issued as U.S. Pat. No. 10,729,434 on Aug. 4, 2020, will be apparent to those of ordinary skill in the art.

It should also be understood that the teachings herein may be readily combined with various teachings in U.S. Pat. Pub. No. 2018/0235611, entitled "Surgical Stapler with Cooperating Distal Tip Features on Anvil and Staple Cartridge," published Aug. 23, 2018, issued as U.S. Pat. No. 10,806,451 on Oct. 20, 2020, the disclosure of which is incorporated by reference herein. Various suitable ways in which the teachings herein may be combined with the teachings of U.S. Pat. Pub. No. 2018/0235611, issued as U.S. Pat. No. 10,806,451 on Oct. 20, 2020, will be apparent to those of ordinary skill in the art.

It should also be understood that the teachings herein may be readily combined with various teachings in U.S. Pat. No. D836,199, entitled "Surgical Stapler with Bent Anvil Tip and Angled Staple Cartridge Tip," issued Dec. 18, 2018, the disclosure of which is incorporated by reference herein. Various suitable ways in which the teachings herein may be combined with the teachings of U.S. Pat. No. D836,199, will be apparent to those of ordinary skill in the art.

It should also be understood that the teachings herein may be readily combined with various teachings in U.S. Pat. Pub. No. 2018/0235619, entitled "Surgical Stapler with Bent Anvil Tip, Angled Staple Cartridge Tip, and Tissue Gripping Features," published Aug. 23, 2018, issued as U.S. Pat. No. 10,758,231 on Sep. 1, 2020, the disclosure of which is incorporated by reference herein. Various suitable ways in which the teachings herein may be combined with the teachings of U.S. Pat. Pub. No. 2018/0235619, issued as U.S. Pat. No. 10,758,231 on Sep. 1, 2020, will be apparent to those of ordinary skill in the art.

It should also be understood that the teachings herein may be readily combined with various teachings in U.S. patent application Ser. No. 16/035,893, entitled "Method of Surgical Stapling with End Effectors Having a Curved Tip," filed Jul. 16, 2018, published as U.S. Pub. No. 2019/0000481 on Jan. 3, 2019, issued as U.S. Pat. No. 11,564,687 on Jan. 31, 2023, the disclosure of which is incorporated by reference herein. Various suitable ways in which the teachings herein may be combined with the teachings of U.S. patent application Ser. No. 16/035,893, published as U.S. Pub. No. 2019/0000481 on Jan. 3, 2019, issued as U.S. Pat. No. 11,564,687 on Jan. 31, 2023, will be apparent to those of ordinary skill in the art.

In addition to the foregoing, it should also be understood that any of the various buttress assemblies described herein may be further constructed and operable in accordance with at least some of the teachings of U.S. Pat. Pub. No. 2016/0278774, entitled "Method of Applying a Buttress to a Surgical Stapler," published Sep. 29, 2016, issued as U.S. Pat. No. 10,349,939 on Jul. 16, 2019, the disclosure of which is incorporated by reference herein; U.S. Pat. Pub. No. 2017/0049444, entitled "Implantable Layers for a Surgical Instrument," published Feb. 23, 2017, issued as U.S. Pat. No. 10,835,249 on Nov. 17, 2020, the disclosure of which is incorporated by reference herein; U.S. Pat. Pub. No. 2017/0086837, entitled "Compressible Adjunct with Crossing Spacer Fibers," published Mar. 30, 2017, issued as U.S. Pat. No. 10,433,846 on Oct. 8, 2019, the disclosure of which is incorporated by reference herein; and U.S. Pat. Pub. No. 2017/0086842, entitled "Method for Applying an Implantable Layer to a Fastener Cartridge," published Mar. 30, 2017, issued as U.S. Pat. No. 11,690,623 on Jul. 4, 2023, the disclosure of which is incorporated by reference herein. Furthermore, in addition to the methods described herein, any of the various buttress assemblies described herein may be applied to end effector (40) in accordance with at least some of the teachings of U.S. Pat. Pub. No. 2017/0056016, entitled "Surgical Stapler Buttress Applicator with End Effector Actuated Release Mechanism," published Mar. 2, 2017, issued as U.S. Pat. No. 10,342,542 on Jul. 9, 2019, the disclosure of which is incorporated by reference herein; U.S. Pat. Pub. No. 2017/0056017, entitled "Surgical Stapler Buttress Applicator with Multi-Zone Platform for Pressure Focused Release," published Mar. 2, 2017, issued as U.S. Pat. No. 10,639,039 on May 5, 2020, the disclosure of which is incorporated by reference herein; U.S. Pat. Pub. No. 2017/0055980, entitled "Surgical Stapler Buttress Applicator with Spent Staple Cartridge Lockout," published Mar. 2, 2017, issued as U.S. Pat. No. 11,039,832 on Jun. 22, 2021, the disclosure of which is incorporated by reference herein; U.S. Pat. Pub. No. 2017/0056018, entitled "Surgical Stapler Buttress Applicator with State Indicator," published Mar. 2, 2017, issued as U.S. Pat. No. 10,349,940 on Jul. 16, 2019, the disclosure of which is incorporated by reference herein; U.S. Pat. Pub. No. 2017/0055982, entitled "Surgical Stapler Buttress Applicator with Multi-Point Actuated Release Mechanism," published Mar. 2, 2017, issued as U.S. Pat. No. 10,342,532 on Jul. 9, 2019, the disclosure of which is incorporated by reference herein; U.S. Pat. Pub. No. 2017/0055981, entitled "Method of Applying a Buttress to a Surgical Stapler End Effector," published Mar. 2, 2017, issued as U.S. Pat. No. 10,166,023 on Jan. 1, 2019, the disclosure of which is incorporated by reference herein; and/or U.S. Pat. Pub. No. 2017/0086842, entitled "Method for Applying an Implantable Layer to a Fastener Cartridge," published Mar. 30, 2017, issued as U.S. Pat. No. 11,690,623 on Jul. 4, 2023, the disclosure of which is incorporated by reference herein. Various suitable ways in which the teachings herein may be combined with various teachings of the above-cited references will be apparent to those of ordinary skill in the art.

It should also be understood that the teachings herein may be readily combined with various teachings in U.S. patent application Ser. No. 16/235,473, entitled "Adhesive Distribution on Buttress for Surgical Stapler," filed on Dec. 28, 2018, published as U.S. Pub. No. 2020/0205820 on Jul. 2, 2020, issued as U.S. Pat. No. 11,166,724 on Nov. 9, 2021, the disclosure of which is incorporated by reference herein. Various suitable ways in which the teachings herein may be combined with the teachings of U.S. patent application Ser. No. 16/235,473 filed on Dec. 28, 2018, published as U.S. Pub. No. 2020/0205820 on Jul. 2, 2020, issued as U.S. Pat. No. 11,166,724 on Nov. 9, 2021, will be apparent to those of ordinary skill in the art.

It should also be understood that the teachings herein may be readily combined with various teachings in U.S. patent application Ser. No. 16/235,488, entitled "Configuration of Buttress for Surgical Stapler," filed on Dec. 28, 2018, published as U.S. Pub. No. 2020/0205821 on Jul. 2, 2020, issued as U.S. Pat. No. 11,166,725 on Nov. 9, 2021, the disclosure of which is incorporated by reference herein. Various suitable ways in which the teachings herein may be combined with the teachings of U.S. patent application Ser. No. 16/235,488 filed on Dec. 28, 2018, published as U.S. Pub. No. 2020/0205821 on Jul. 2, 2020, issued as U.S. Pat. No. 11,166,725 on Nov. 9, 2021, will be apparent to those of ordinary skill in the art.

It should also be understood that the teachings herein may be readily combined with various teachings in U.S. patent application Ser. No. 16/235,522, entitled "Applicator for Surgical Stapler Buttress," filed on—Dec. 28, 2018, published as U.S. Pub. No. 2020/0205823 on Jul. 2, 2020, issued as U.S. Pat. No. 11,116,505 on Sep. 14, 2021, the disclosure of which is incorporated by reference herein. Various suitable ways in which the teachings herein may be combined with the teachings of U.S. patent application Ser. No. 16/235,522-filed on Dec. 28, 2018, published as U.S. Pub. No. 2020/0205823 on Jul. 2, 2020, issued as U.S. Pat. No. 11,116,505 on Sep. 14, 2021, will be apparent to those of ordinary skill in the art.

It should also be understood that the teachings herein may be readily combined with various teachings in U.S. patent application Ser. No. 16/235,522, entitled "Applicator for Surgical Stapler Buttress," filed on Dec. 28, 20218 and issued as U.S. Pat. No. 11,116,505 on Sep. 14, 2021, which is incorporated by reference herein. Various suitable ways in which the teachings herein may be combined with the teachings of U.S. patent application Ser. No. 16/235,522 will be apparent to those of ordinary skill in the art.

It should also be understood that the teachings herein may be readily combined with various teachings in U.S. patent application Ser. No. 16/235,541, entitled "Packaging for Surgical Stapler Buttress," filed on—Dec. 28, 2018, published as U.S. Pub. No. 2020/0205824 on Jul. 2, 2020, issued as U.S. Pat. No. 11,432,817 on Sep. 6, 2022, the disclosure of which is incorporated by reference herein. Various suitable ways in which the teachings herein may be combined with the teachings of U.S. patent application Ser. No. 16/235,541 filed on Dec. 28, 2018, published as U.S. Pub. No. 2020/0205824 on Jul. 2, 2020, issued as U.S. Pat. No. 11,432,817 on Sep. 6, 2022, will be apparent to those of ordinary skill in the art.

It should also be understood that the teachings herein may be readily combined with various teachings in U.S. patent application Ser. No. 29/675,168, entitled "Applicator for Surgical Stapler Buttress," filed on Dec. 28, 2018, issued as U.S. Pat. No. D901,868 on Nov. 10, 2020, the disclosure of which is incorporated by reference herein. Various suitable ways in which the teachings herein may be combined with the teachings of U.S. patent application Ser. No. 29/675,168 filed on Dec. 28, 2018, issued as U.S. Pat. No. D901,868 on Nov. 10, 2020, will be apparent to those of ordinary skill in the art.

It should also be understood that the teachings herein may be readily combined with various teachings in U.S. patent application Ser. No. 29/675,170, entitled "Buttress for Surgical Stapler," filed on—Dec. 28, 2018, issued as U.S. Pat. No. D933,220 on Oct. 12, 2021, the disclosure of which is incorporated by reference herein. Various suitable ways in which the teachings herein may be combined with the teachings of U.S. patent application Ser. No. 29/675,170 filed on Dec. 28, 2018, issued as U.S. Pat. No. D933,220 on Oct. 12, 2021, will be apparent to those of ordinary skill in the art.

It should also be understood that the teachings herein may be readily combined with various teachings in U.S. patent application Ser. No. 29/675,172, entitled "Tray for Surgical Stapler Buttress Applicator," filed on Dec. 28, 2018, issued as U.S. Pat. No. D922,576 on Jun. 15, 2021, the disclosure of which is incorporated by reference herein. Various suitable ways in which the teachings herein may be combined with the teachings of U.S. patent application Ser. No. 29/675,172 filed on Dec. 28, 2018, issued as U.S. Pat. No. D922,576 on Jun. 15, 2021, will be apparent to those of ordinary skill in the art.

It should also be understood that the teachings herein may be readily combined with various teachings in U.S. patent application Ser. No. 16/235,630, entitled "Curved Tip Surgical Stapler Buttress Assembly Applicator with Opening Feature for Curved Tip Alignment," filed on Dec. 28, 2018, published as U.S. Pub. No. 2020/0205826 on Jul. 2, 2020, issued as U.S. Pat. No. 11,272,935 on Mar. 15, 2022; the disclosure of which is incorporated by reference herein. Various suitable ways in which the teachings herein may be combined with the teachings of U.S. patent application Ser. No. 16/235,630, filed on Dec. 28, 2018, published as U.S. Pub. No. 2020/0205826 on Jul. 2, 2020, issued as U.S. Pat. No. 11,272,935 on Mar. 15, 2022, will be apparent to those of ordinary skill in the art.

It should also be understood that the teachings herein may be readily combined with various teachings in U.S. patent application Ser. No. 16/235,670, entitled "Curved Tip Surgical Stapler Buttress Assembly Applicator with Proximal Alignment Features," filed on Dec. 28, 2018, issued as U.S. Pat. No. 10,905,424 on Feb. 2, 2021; the disclosure of which is incorporated by reference herein. Various suitable ways in which the teachings herein may be combined with the teachings of U.S. patent application Ser. No. 16/235,670, filed as Dec. 28, 2018, issued as U.S. Pat. No. 10,905,424 on Feb. 2, 2021, will be apparent to those of ordinary skill in the art.

It should also be understood that the teachings herein may be readily combined with various teachings in U.S. patent application Ser. No. 16/235,681, entitled "Curved Tip Surgical Stapler Buttress Assembly Applicator with Compression Layer Pocket Feature," filed on Dec. 28, 2018, published as U.S. Pub. No. 2020/0205807 on Jul. 2, 2020, issued as U.S. Pat. No. 11,103,243 on Aug. 31, 2021; the disclosure of which is incorporated by reference herein. Various suitable ways in which the teachings herein may be combined with the teachings of U.S. patent application Ser. No. 16/235,681, filed on Dec. 28, 2018, published as U.S. Pub. No. 2020/0205807 on Jul. 2, 2020, issued as U.S. Pat. No. 11,103,243 on Aug. 31, 2021, will be apparent to those of ordinary skill in the art.

It should also be understood that the teachings herein may be readily combined with various teachings in U.S. patent application Ser. No. 29/675,197, entitled "Applicator for a Surgical Stapler Buttress," filed on Dec. 28, 2018, issued as D903,115 on Nov. 25, 2020; the disclosure of which is incorporated by reference herein. Various suitable ways in which the teachings herein may be combined with the teachings of U.S. patent application Ser. No. 29/675,197, filed on Dec. 28, 2018, issued as D903,115 on Nov. 25, 2020, will be apparent to those of ordinary skill in the art.

It should also be understood that the teachings herein may be readily combined with various teachings in U.S. patent application Ser. No. 29/675,199, entitled "Buttress Assembly for a Surgical Stapler," filed on Dec. 28, 2018, issued as U.S. Pat. No. D932,621 on Oct. 5, 2021; the disclosure of which is incorporated by reference herein. Various suitable ways in which the teachings herein may be combined with the teachings of U.S. patent application Ser. No. 29/675,199, filed on Dec. 28, 2018, issued as U.S. Pat. No. D932,621 on Oct. 5, 2021, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System, issued Sep. 30, 2014, the disclosure of which is incorporated by reference herein; U.S. Pat. No. 8,820,605, entitled "Robotically-Controlled Surgical Instrument with Force-Feedback Capabilities," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A buttress assembly for reinforcing tissue layers joined by surgical stapling, wherein the buttress assembly comprises:
   (a) a laminated base material comprising:
      (i) a knitted textile mesh layer comprising a first mesh surface and a second mesh surface, wherein the first mesh surface is configured to contact at least one of the tissue layers joined by the surgical stapling,
      (ii) a first film layer contacting the second mesh surface of the knitted textile mesh layer, wherein the first film layer is configured as an adhesive layer, and
      (iii) a second film layer comprising a first film surface and a second film surface, wherein the first film surface contacts the first film layer, wherein the second film surface is configured to face away from the tissue layers joined by the surgical stapling, wherein the second film layer is configured as an adhesion barrier to prevent tissue from adhering to the second film surface; and
   (b) an adhesive located on the second film surface of the second film layer, wherein the adhesive is configured to provide releasable adhesion of the buttress assembly with an end effector of a surgical stapler,
wherein the knitted textile mesh layer defines a knit pattern, wherein the knit pattern is oriented obliquely relative to a longitudinal axis of the buttress assembly.

2. The buttress assembly of claim 1, wherein the knit pattern comprises a herringbone pattern.

3. The buttress assembly of claim 1, wherein the knitted textile mesh layer comprises polyglactin 910.

4. The buttress assembly of claim 1, wherein the knitted textile mesh layer comprises a multi-filament structure.

5. The buttress assembly of claim 1, wherein the first film layer comprises polydioxanone.

6. The buttress assembly of claim 5, wherein the first film layer has a thickness of about eight micrometers.

7. The buttress assembly of claim 1, wherein the second film layer comprises an absorbable synthetic material.

8. The buttress assembly of claim 7, wherein the second film layer comprises poliglecaprone 25.

9. The buttress assembly of claim 8, wherein the second film layer has a thickness of about ten micrometers.

10. The buttress assembly of claim 1, wherein the laminated base material is formed by laminating the knitted textile mesh layer, the first film layer, and the second film layer together by applying a predetermined pressure and predetermined heat over a predetermined time.

11. The buttress assembly of claim 1, wherein the laminated base material of the buttress assembly comprises cut edges.

12. The buttress assembly of claim 11, wherein the knit pattern is oriented at about 45 degrees relative to the longitudinal axis of the buttress assembly.

13. The buttress assembly of claim 1, wherein the knitted textile mesh layer comprises a plurality of openings that are configured to promote tissue ingrowth.

14. The buttress assembly of claim 1, wherein the adhesive extends continuously from a proximal end of the second film surface to a distal end of the second film surface.

15. A buttress configured for use with an end effector of a surgical stapler, wherein the buttress is further configured for reinforcing a surgically stapled site, the buttress comprising:
   (a) a knitted textile mesh layer comprising a multi-filament absorbable synthetic material, wherein the knitted textile mesh layer defines a plurality of openings, wherein on a first side of the knitted textile mesh layer the plurality of openings is configured to face the surgically stapled site and contact tissue to promote tissue ingrowth, wherein the knitted textile mesh layer comprises polyglactin 910, wherein the knitted textile mesh layer defines a knit pattern, wherein the knit pattern is oriented obliquely relative to a longitudinal axis of the buttress;
   (b) a film layer located opposite to the first side of the knitted textile mesh layer with the exposed plurality of openings, wherein the film layer is configured to face away from the surgically stapled site and prevent tissue adhesions at and around the surgically stapled site, wherein the film layer comprises poliglecaprone 25;
   (c) an adhesive layer positioned between the knitted textile mesh layer and the film layer, wherein the adhesive layer is configured to adhesively bond the knitted textile mesh layer with the film layer to form a laminate, wherein the adhesive layer comprises polydioxanone; and
   (d) an adhesive located on the film layer, wherein the adhesive is configured to provide releasable adhesion of the buttress with the end effector.

16. The buttress of claim 15, wherein the knit pattern comprises a herringbone pattern.

17. A buttress for reinforcing tissue layers joined by surgical stapling, the buttress comprising:
   (a) a knitted textile mesh layer comprising a first mesh surface and a second mesh surface, wherein the first mesh surface is configured to contact at least one of the tissue layers joined by the surgical stapling, wherein the knitted textile mesh layer defines a knit pattern, wherein the knit pattern is oriented obliquely relative to a longitudinal axis of the buttress;
   (b) an adhesive film layer contacting the second mesh surface of the knitted textile mesh layer; and
   (c) an adhesion barrier film layer comprising a first film surface and a second film surface, wherein the first film surface contacts the adhesive film layer, wherein the second film surface is configured to face away from the tissue layers joined by the surgical stapling, wherein the adhesion barrier film layer is configured to prevent tissue from adhering to the second film surface.

18. The buttress of claim 17, wherein the knitted textile mesh layer comprises polyglactin 910, wherein the adhesive film layer comprises polydioxanone, and wherein the adhesion barrier film layer comprises poliglecaprone 25.

19. The buttress of claim 17, further comprising a plurality of longitudinal slits extending through each of the knitted textile mesh layer, the adhesive film layer, and the adhesion barrier film layer for generally dividing the buttress into two equal sections.

20. The buttress of claim 17, wherein the knit pattern comprises a herringbone pattern.

* * * * *